(12) United States Patent
Biel et al.

(10) Patent No.: US 11,147,875 B2
(45) Date of Patent: Oct. 19, 2021

(54) COMPOSITIONS, COMBINATIONS AND RELATED METHODS FOR PHOTOIMMUNOTHERAPY

(71) Applicant: Rakuten Medical, Inc., San Mateo, CA (US)

(72) Inventors: Merrill Biel, Mendota Heights, MN (US); Roger Heim, Del Mar, CA (US); Miguel Garcia-Guzman, San Diego, CA (US)

(73) Assignee: Rakuten Medical, Inc., San Mateo, CA (US)

( * ) Notice: Subject to any disclaimer, the term of this patent is extended or adjusted under 35 U.S.C. 154(b) by 0 days.

(21) Appl. No.: 16/421,409

(22) Filed: May 23, 2019

(65) Prior Publication Data
US 2019/0282696 A1 Sep. 19, 2019

Related U.S. Application Data

(63) Continuation of application No. 15/753,153, filed as application No. PCT/US2016/047640 on Aug. 18, 2016.

(60) Provisional application No. 62/249,085, filed on Oct. 30, 2015, provisional application No. 62/206,776, filed on Aug. 18, 2015.

(51) Int. Cl.
| | | |
|---|---|---|
| A61B 5/00 | (2006.01) | |
| A61B 8/00 | (2006.01) | |
| A61B 10/00 | (2006.01) | |
| A61K 41/00 | (2020.01) | |
| A61K 47/68 | (2017.01) | |
| A61P 35/00 | (2006.01) | |
| A61K 38/18 | (2006.01) | |
| A61K 39/00 | (2006.01) | |

(52) U.S. Cl.
CPC ...... *A61K 41/0071* (2013.01); *A61K 47/6803* (2017.08); *A61K 47/6849* (2017.08); *A61P 35/00* (2018.01); *A61K 38/18* (2013.01); *A61K 41/0057* (2013.01); *A61K 2039/505* (2013.01); *A61K 2300/00* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 3,539,794 A | 11/1970 | Rauhut et al. | |
| 3,710,795 A | 1/1973 | Higuchi et al. | |
| 5,033,252 A | 7/1991 | Carter | |
| 5,052,558 A | 10/1991 | Carter | |
| 5,171,081 A | 12/1992 | Pita et al. | |
| 5,196,005 A * | 3/1993 | Doiron ............... | A61B 18/22 606/7 |
| 5,323,907 A | 6/1994 | Kalveage | |
| 5,494,793 A | 2/1996 | Schindele et al. | |
| 5,585,089 A | 12/1996 | Queen et al. | |
| 6,344,050 B1 | 2/2002 | Chen | |
| 6,534,041 B1 | 3/2003 | Licha et al. | |
| 7,005,518 B2 | 2/2006 | Peng et al. | |
| 7,498,029 B2 | 3/2009 | Hasan et al. | |
| 8,524,239 B2 | 9/2013 | Kobayashi | |
| 8,623,354 B2 | 1/2014 | Brown et al. | |
| 9,358,306 B2 | 6/2016 | Kobayashi | |
| 10,064,943 B2 | 9/2018 | Dilley et al. | |
| 10,295,719 B2 | 5/2019 | Rose et al. | |
| 10,416,366 B2 | 9/2019 | Rose et al. | |
| 10,527,771 B2 | 1/2020 | Rose et al. | |
| 10,537,641 B2 | 1/2020 | Kobayashi | |
| 10,538,590 B2 | 1/2020 | Kobayashi | |
| 10,588,972 B2 | 3/2020 | Kovar | |
| 2001/0044124 A1 | 11/2001 | Bacus | |
| 2004/0120949 A1 | 6/2004 | Adolf et al. | |

(Continued)

FOREIGN PATENT DOCUMENTS

| | | |
|---|---|---|
| CN | 101 023 084 | 8/2007 |
| CN | 102585003 | 7/2012 |

(Continued)

OTHER PUBLICATIONS

Yoon et al. (Clinc. Endosc. 2013, 43, 7-23).*
Van Cutsem et al. (J. Clin. Oncol. 2012, 30, 2861-2868).*
Ali et al., "Dynamic fluorescent imaging with indocyanine green for monitoring the therapeutic effects of photoimmunotherapy," Contrast Media Mol Imaging. (Jul.-Aug. 2014);9(4):276-82.
Amoury et al., "Photoimmunotheranostic agents for triple-negative breast cancer diagnosis and therapy that can be activated on demand," Oncotarget. (2016) 7(34):54925-54936.

(Continued)

*Primary Examiner* — Michael G. Hartley
*Assistant Examiner* — Melissa J Perreira
(74) *Attorney, Agent, or Firm* — Morrison & Foerster LLP

(57) ABSTRACT

Provided herein are conjugates, compositions and methods for use in photoimmunotherapy, such as photoimmunotherapy induced by activation of a phthalocyanine dye conjugated to a targeting molecule that binds a protein on cell, for example, an IR700-antibody conjugate. In some embodiments, the phthalocyanine-dye conjugate can be activated by irradiation with near-infrared light. Features of the conjugates, compositions and methods, including the dose of the conjugate, provide various advantages, such as lower toxicity and/or improved efficacy. In some embodiments, also provided is a dual label phthalocyanine-dye conjugate in which the targeting molecule is conjugated to an additional fluorescent dye, which can be used for photoimmunotherapy while, for example, also exhibiting improved performance for imaging or detection. Also provided are therapeutic methods using the conjugates and compositions for treatment of diseases and conditions, including tumors or cancers.

29 Claims, 27 Drawing Sheets

Specification includes a Sequence Listing.

(56) References Cited

U.S. PATENT DOCUMENTS

| | | |
|---|---|---|
| 2004/0171827 A1 | 9/2004 | Peng et al. |
| 2005/0157292 A1 | 7/2005 | Saitoh et al. |
| 2006/0231107 A1 | 10/2006 | Glickman et al. |
| 2007/0020272 A1 | 1/2007 | Hasan |
| 2007/0133086 A1 | 6/2007 | Wilhelm et al. |
| 2008/0073566 A1 | 3/2008 | Frangioni |
| 2008/0095699 A1 | 4/2008 | Zheng et al. |
| 2008/0253960 A1 | 10/2008 | Zheng et al. |
| 2010/0255057 A1 | 10/2010 | Hyde et al. |
| 2011/0082412 A1 | 4/2011 | Hyde et al. |
| 2012/0010558 A1 | 1/2012 | Kobayashi |
| 2012/0070377 A1 | 3/2012 | Yahioglu et al. |
| 2012/0070853 A1* | 3/2012 | Johansen ......... G01N 33/57419 435/7.92 |
| 2012/0171290 A1 | 7/2012 | Pierre |
| 2012/0263651 A1 | 10/2012 | Widen et al. |
| 2013/0287688 A1 | 10/2013 | Jain |
| 2013/0336995 A1 | 12/2013 | Kobayashi et al. |
| 2014/0050662 A1 | 2/2014 | Ho |
| 2014/0120119 A1 | 5/2014 | Kobayashi |
| 2014/0309578 A1 | 10/2014 | Anvari |
| 2014/0314778 A1 | 10/2014 | Alavattam |
| 2015/0343060 A1 | 12/2015 | Kovar |
| 2015/0343084 A1 | 12/2015 | Dilley |
| 2015/0374819 A1 | 12/2015 | Kovar |
| 2016/0256564 A2 | 1/2016 | Kobayashi et al. |
| 2016/0345834 A1* | 12/2016 | Hasan ................ A61B 1/00009 |
| 2017/0122853 A1 | 5/2017 | Kobayashi et al. |
| 2018/0113246 A1 | 4/2018 | Rose et al. |
| 2018/0113247 A1 | 4/2018 | Rose et al. |
| 2018/0236076 A1 | 8/2018 | Kobayashi et al. |
| 2018/0239074 A1 | 8/2018 | Rose et al. |
| 2018/0250405 A1 | 9/2018 | Biel et al. |
| 2018/0339048 A1 | 11/2018 | Dilley et al. |
| 2019/0015510 A1 | 1/2019 | Makings et al. |
| 2019/0070296 A1 | 3/2019 | Wang et al. |
| 2019/0365897 A1 | 12/2019 | Garcia-Guzman et al. |
| 2020/0085950 A1 | 3/2020 | Kobayashi et al. |
| 2020/0095331 A1 | 3/2020 | Kobayashi et al. |
| 2020/0166690 A1 | 5/2020 | Rose et al. |
| 2020/0179514 A1 | 6/2020 | Kovar |

FOREIGN PATENT DOCUMENTS

| | | |
|---|---|---|
| CN | 103 781 495 | 5/2014 |
| CN | 104 203 286 | 12/2014 |
| DE | 19717904 | 10/1998 |
| EP | 1512963 | 3/2005 |
| JP | 2003284757 | 10/2003 |
| JP | 2003344284 | 12/2003 |
| JP | 2006515892 | 6/2006 |
| JP | 2006517230 | 7/2006 |
| JP | 2007155722 | 6/2007 |
| JP | 2014523907 | 9/2014 |
| JP | 2017524002 | 8/2017 |
| WO | WO 2001057495 | 8/2001 |
| WO | WO 2003011106 | 2/2003 |
| WO | WO 2003083811 | 10/2003 |
| WO | WO 2004/038378 | 5/2004 |
| WO | WO 2004067038 | 8/2004 |
| WO | WO 2004071571 | 8/2004 |
| WO | WO 2005099689 | 10/2005 |
| WO | WO 2006092598 | 9/2006 |
| WO | WO 2008120134 | 10/2008 |
| WO | WO 2008152424 | 12/2008 |
| WO | WO 2009038776 | 3/2009 |
| WO | WO 2009092062 | 7/2009 |
| WO | WO 2010047611 | 4/2010 |
| WO | WO 2010085651 | 7/2010 |
| WO | WO 2010121163 | 10/2010 |
| WO | WO 2011025950 | 3/2011 |
| WO | WO 2011038006 | 3/2011 |
| WO | WO 2012076631 | 6/2012 |
| WO | WO 2012082118 | 6/2012 |
| WO | WO 2013009475 | 1/2013 |
| WO | WO 2013044156 | 3/2013 |
| WO | WO 2013080187 | 6/2013 |
| WO | WO 2013/139391 | 9/2013 |
| WO | WO 2014084394 | 6/2014 |
| WO | WO 2014089247 | 6/2014 |
| WO | WO 2014120974 | 8/2014 |
| WO | WO 2014127365 | 8/2014 |
| WO | WO 2014/160497 | 10/2014 |
| WO | WO 2014168950 | 10/2014 |
| WO | WO 2014176284 | 10/2014 |
| WO | WO 2015042325 | 3/2015 |
| WO | WO 2015057692 | 4/2015 |
| WO | WO 2015061247 | 4/2015 |
| WO | WO 2015/120198 | 8/2015 |
| WO | WO 2015175750 | 11/2015 |
| WO | WO 2015187651 | 12/2015 |
| WO | WO 2015187677 | 12/2015 |
| WO | WO 2016022896 | 2/2016 |
| WO | WO 2017027247 | 2/2017 |
| WO | WO 2017031363 | 2/2017 |
| WO | WO 2018080952 | 5/2018 |
| WO | WO 2018156815 | 8/2018 |
| WO | WO 2019009941 | 1/2019 |
| WO | WO 2019/036249 | 2/2019 |
| WO | WO2019232478 A1 | 12/2019 |
| WO | WO 2020/205623 | 10/2020 |
| WO | WO 2021/021882 | 2/2021 |

OTHER PUBLICATIONS

Anonymous, "Near Infrared Light for the Treatment of Painful Peripheral Neuropathy," U.S. National Institutes of Health, Aug. 2, 2012, XP002686617, retrieved from the internet: URL:http://clinicaltrials.gov/ct2/show/NCT00125268, retrieved on Nov. 7, 2011.

Ballou et al., "Tumor labeling in vivo using cyanine-conjugated monoclonal antibodies." Cancer Immunol Immunother. Oct. 1995;41(4):257-63.

Barrett et al., "In vivo diagnosis of epidermal growth factor receptor expression using molecular imaging with a cocktail of optically labeled monoclonal antibodies," Clin Cancer Res. Nov. 15, 2007;13(22 Pt 1):6639-48.

Berger et al., "Phase I safety and pharmacokinetic study of CT-011, a humanized antibody interacting with PD-1, in patients with advanced hematologic malignancies," Clin Cancer Res (2008) 14:3044-3051.

Blank et al., "Contribution of the PD-L1/PD-1 pathway to T-cell exhaustion: an update on implications for chronic infections and tumor evasion," Cancer Immunol Immunother (2007) 56(5):739-745.

Brahmer et al., "Safety and Activity of Anti—PD-L1 Antibody in Patients with Advanced Cancer," N Engl J Med (2012) 366:2455-2465.

Carcenac et al., "Internalisation enhances photo-induced cytotoxicity of monoclonal antibody-phthalocyanine conjugates." British Journal of Cancer, Nov. 30, 2001, vol. 85, No. 11, pp. 1787-1793.

Carter et al., "Identification and Validation of Cell Surface Antigens for Antibody Targeting in Oncology," Endocr Relat Cancer 11:659-687, 2004.

Chen et al., "Tumor vascular permeabilization by vascular-targeting photosensitization: effects, mechanism, and therapeutic implications," Clin Cancer Res. 12:917-923, 2006.

Chopra, "IRDye 700DX-Labeled annexin V," Molecular Imaging and Contrast Agent Database (MICAD) [Internet]. Bethesda (MD): National Center for Biotechnology Information (US); 2004-2013. Oct. 27, 2009 [updated Dec. 17, 2009].

de Boer et al., "A standardized light-emitting diode device for photoimmunotherapy," J Nucl Med. (Nov. 2014);55(11):1893-8.

de Boer et al., "Biodistribution Study of Intravenously Injected Cetuximab- IRDye700DX in Cynomolgus Macaques," Mol Imaging Biol. (Apr. 2016);18(2):232-42.

Del Governatore et al., "Experimental Photoimmunotherapy of Hepatic Metastases of Colorectal Cancer with a 17.1A Chlorine6 Immunoconjugate," Cancer Res. 60:4200-4205, 2000.

(56) References Cited

OTHER PUBLICATIONS

Denis et al., "Synthesis, bioanalysis and biodistribution of photosensitizer conjugates for photodynamic therapy," Bioanalysis (2013) 5:1099-1114.
Dixit et al., "Transferrin Receptor-Targeted Theranostic Gold Nanoparticles for Photosensitizer Delivery in Brain Tumors," Nanoscale, (2015) 7(5):1782-1790.
Duska et al., "Combination Photoimmunotherapy and Cisplatin: Effects on Human Ovarian Cancer Ex Vivo," J Nat Cancer Inst. 91:1557-1563, 1999.
Eisenhauer et al., "New response evaluation criteria in solid tumours: revised RECIST guideline (version 1.1)," Eur J Cancer (2009) 45(2):228-247.
Elliott et al., "Direct characterization of arterial input functions by fluorescence imaging of exposed carotid artery to facilitate kinetic analysis," Mol Imaging Biol. (Aug. 2014);16(4):488-94.
Finger et al., "The human PD-1 gene: complete cDNA, genomic organization, and developmentally regulated expression in B cell progenitors," Gene (1997) 197(1-2):177-187.
Fracasso et al., "A Phase 1 Escalating Single-Dose and Weekly Fixed-Dose Study of Cetuximab: Pharmacokinetic and Pharmacodynamic Rationale for Dosing," Clin Cancer Res (2007) 13(3):986-996.
Gajewski et al., Current Protocols in Immunology (2001) 20.4.1-20.4.18 by John Wiley & Sons, Inc., 2001.
Gao et al., "In vivo cancer targeting and imaging with semiconductor quantum dots," Nat Biotechnol. Aug. 2004;22(8):969-76.
Gildener-Leapman et al., "Promising systemic immunotherapies in head and neck squamous cell carcinoma," Oral Oncol (2013) 49(12):1089-1096.
Gleysteen et al., "Fluorescently Labeled Cetuximab to Evaluate Head and Neck Cancer Response to Treatment," Cancer Biology & Therapy. 2007 6(8):e1-e5.
Gleysteen et al., "Update on Aspyrian Trial: Study of RM-1929 and Photoimmunotherapy in Patients with Recurrent Head and Neck Cancer," Abstract, submitted for 2017 Combined Otolaryngology Spring Meetings, American Head and Neck Cancer Society, Apr. 26, 2017, San Diego, CA, available online at: https://www.researchposters.com/display_posters.aspx?page=eposter&code=COSM2017.
Gleysteen et al., "Update on Aspyrian Trial: Study of RM-1929 and Photoimmunotherapy in Patients with Recurrent Head and Neck Cancer," Poster, Presented at 2017 Combined Otolaryngology Spring Meetings, American Head and Neck Cancer Society, Apr. 26, 2017, San Diego, CA, available online at https://www.researchposters.com/Posters/COSM/COSM2017/B043.pdf.
Green et al., "Mitochondria and Apoptosis," Science (1998) 281(5381):1309-1312.
Greish, K., "Enhanced permeability and retention of macromolecular drugs in solid tumors: a royal gate for targeted anticancer nanomedicines," J Drug Target. 15:457-464, 2007.
Hanaoka et al., "Glypican-3 targeted human heavy chain antibody as a drug carrier for hepatocellular carcinoma therapy," Mol Pharm. (Jun. 1, 2015);12(6):2151-7.
Hanaoka et al., "Photoimmunotherapy of hepatocellular carcinoma-targeting Glypican-3 combined with nanosized albumin-bound paclitaxel," Nanomedicine (Lond). (2015);10(7):1139-47.
Heukers et al., "Nanobody-photosensitizer conjugates for targeted photodynamic therapy," Nanomedicine (2014) 10:14441-51.
Hiroshima et al., "Photoimmunotherapy Inhibits Tumor Recurrence After Surgical Resection on a Pancreatic Cancer Patient-Derived Orthotopic Xenograft (PDOX) Nude Mouse Model," Ann Surg Oncol. (Dec. 2015);22 Suppl 3:S1469-74.
Iqbal et al., "Phthalocyanine-Biomolecule Conjugated Photosensitizers for Targeted Photodynamic Therapy and Imaging," Current Drug Metabolism, (2015) 16(9):816-832.
Ishida et al., "Trastuzumab-Based Photoimmunotherapy Integrated with Viral HER2 Transduction Inhibits Peritoneally Disseminated HER2-Negative Cancer," Mol Cancer Ther. (Mar. 2016);15(3):402-11.
Ito et al., "Combination photoimmunotherapy with monoclonal antibodies recognizing different epitopes of human epidermal growth factor receptor 2: an assessment of phototherapeutic effect based on fluorescence molecular imaging," Oncotarget. (Mar. 22, 2016);7(12):14143-52.
Ito et al., "Molecular targeted photoimmunotherapy for HER2-positive human gastric cancer in combination with chemotherapy results in improved treatment outcomes through different cytotoxic mechanisms," BMC Cancer. (Jan. 25, 2016);16:37.
Jia et al., "Cannabinoid CB2 receptor as a new phototherapy target for the inhibition of tumor growth," Mol Pharm. (Jun. 2, 2014);11(6):1919-29.
Jing et al., "Imaging and Selective Elimination of Glioblastoma Stem Cells with Theranostic Near-Infrared-Labeled CD133-Specific Antibodies," Theranostics. (Apr. 12, 2016);6(6):862-74.
Kijanka et al., "Optical imaging of pre-invasive breast cancer with a combination of VHHs targeting CAIX and HER2 increases contrast and facilitates tumour characterization," EJNMMI Res. (2016) 6(1):14.
Kines et al., "HPV Based Photodynamic Therapy: A New Approach for Anti-Cancer Therapy," J. Immunol. 192(1): Supplement 206.8, 2014.
Kirveliene et al., "Schedule-Dependent Interaction Between Doxorubicin and mTHPC-Mediated Photodynamic Therapy in Murine Hepatoma In Vitro and In Vivo," Cancer Chemother. Pharmacol. 57:65-72, 2005.
Kishimoto et al., "Evaluation of oxygen dependence on in vitro and in vivo cytotoxicity of photoimmunotherapy using IR-700-antibody conjugates," Free Radic Biol Med. (Aug. 2015);85:24-32.
Kobayashi, "Activatable Fluorescent Imaging Probes for Cancer Detection and Diagnosis," Abstract presented at the American Chemical Society meeting in San Francisco, 2014.
Kobayashi, "Near infrared photoimmunotherapy: A new cancer therapy kills cancer cells with exposure of harmless near infrared light," Poster Presentation, at NEST Conference, Tokyo, Japan, Apr. 2018.
Kochuparambil et al., "A Phase 1, Multicenter, Open-label, Dose-escalation, Combination Study of RM-1929 and Photoimmunotherapy in Patients with Recurrent Head and Neck Cancer," Abstract, Annals of Oncology, vol. 28, Issue suppl_5, Sep. 1, 2017, mdx374.008, Published: Sep. 18, 2017, available online at: https://doi.org/10.1093/annonc/mdx374.008.
Kochuparambil et al., "A Phase 1, Multicenter, Open-label, Dose-escalation, Combination Study of RM-1929 and Photoimmunotherapy in Patients with Recurrent Head and Neck Cancer," Poster, Presented at 2017 European Society for Medical Oncology, Sep. 8-12, 2017, Madrid, Spain.
Kovar et al., "A Systematic Approach to the Development of Fluorescent Contrast Agents for Optical Imagining of Mouse Cancer Models," Anal. Biochem. 367: 1-12, 2007.
Kroemer et al., "Immunogenic Cell Death in Cancer Therapy," Annual Review of Immunology (2013) 31:51-72.
Licor, "High Photostability of IRDye® 700DX," Retrieved on Aug. 23, 2018. Retrieve on https://www.licor.com/bio/products/reagents/irdye/700dx/photostability.html.
Lin et al., "Comparison of Cherenkov excited fluorescence and phosphorescence molecular sensing from tissue with external beam irradiation," Phys Med Biol. (May 21, 2016);61(10):3955-68.
Lipson et al., "Durable cancer regression off-treatment and effective reinduction therapy with an anti-PD-1 antibody," Clin Cancer Res (2013) 19(2):462-468.
Maawy et al., "Near infra-red photoimmunotherapy with anti-CEA-IR700 results in extensive tumor lysis and a significant decrease in tumor burden in orthotopic mouse models of pancreatic cancer," PLoS One. (Mar. 23, 2015);10(3):e0121989.
Maawy et al., "Photoimmunotherapy lowers recurrence after pancreatic cancer surgery in orthotopic nude mouse models," J Surg Res. (Jul. 2015);197(1):5-11.
Master et al. "A Cell-targeted Photodynamic Nanomedicine Strategy for Head & Neck Cancers," Mol. Pharm., (2013) 6:1988-1997.
Maya et al., "Synthesis, Aggregation Behavior and Nonlinear Absorption Properties of Lead Phthalocyanines Substituted with Siloxane Chains," J Materials Chem. 13: 1603-1613, 2003.

(56) References Cited

OTHER PUBLICATIONS

McHugh et al., "The role of suppressor T cells in regulation of immune responses." J Allergy Clin Immunol. Nov. 2002;110(5):693-702.

Menzies et al., "New combinations and immunotherapies for melanoma: latest evidence and clinical utility," Ther Adv Med Oncol (2013) 5:278-285.

Mitchell et al., "Comparison of Two Infrared Devices in Their Effectiveness in Reducing Symptoms Associated with RLS," Physiother. Theory Pract. 27:352-359, 2011.

Mitsunaga et al., "Abstract 3618: Target-Specific Photo-Activatable Immunotherapy (PIT) for Cancer Based on a Monoclonal Antibody-Photosensitizer Conjugate," in Proceedings of the 102nd Annual Meeting of the American Association for Cancer Research; Apr. 2-6, 2011; Orlando, FL. Philadelphia (PA): AACR; Cancer Res. 71:3618, 2011.

Mitsunaga et al., "Cancer cell-selective in vivo near infrared photoimmunotherapy targeting specific membrane molecules," Nat Med. (Nov. 6, 2011);17(12):1685-91.

Mitsunaga et al., "Immediate in vivo target-specific cancer cell death after near infrared photoimmunotherapy," BMC Cancer. (Aug. 8, 2012);12:345.

Mitsunaga et al., "Near-infrared theranostic photoimmunotherapy (PIT): repeated exposure of light enhances the effect of immunoconjugate," Bioconjug Chem. (Mar. 21, 2012);23(3):604-9.

Moore et al., "Photoimmunotherapy of residual disease after incomplete surgical resection in head and neck cancer models," Cancer Med. (Jul. 2016);5(7):1526-34.

Nagaya et al., "Host Immunity Following Near-Infrared Photoimmunotherapy Is Enhanced with PD-1 Checkpoint Blockade to Eradicate Established Antigenic Tumors," Cancer Immunol Res. 7:401-413, 2019.

Nagaya et al., "Improved micro-distribution of antibody-photon absorber conjugates after initial near infrared photoimmunotherapy (NIR-PIT)," J Control Release. (Jun. 28, 2016);232:1-8.

Nagaya et al., "Near infrared photoimmunotherapy of B-cell lymphoma," Mol Oncol. (Jul. 29, 2016). 10(9):1404-1414.

Nagaya et al., "Near infrared photoimmunotherapy targeting bladder cancer with a canine anti-epidermal growth factor receptor (EGFR) antibody," Oncotarget 9:19026-19038, 2018.

Nagaya et al., "Near Infrared Photoimmunotherapy Targeting EGFR Positive Triple Negative Breast Cancer: Optimizing the Conjugate-Light Regimen," PLoS One. (Aug. 27, 2015);10(8):e0136829.

Nagaya et al., "Near infrared photoimmunotherapy with an anti-mesothelin antibody," Oncotarget. (Apr. 26, 2016);7(17):23361-9.

Nagaya et al., "Near infrared photoimmunotherapy with avelumab, an antiprogrammed death-ligand 1 (PD-L1) antibody," Oncotarget 8:8807-8817, 2017.

Nagaya et al., "Syngeneic Mouse Models of Oral Cancer Are Effectively Targeted by Anti-CD44-Based NIR-PIT," Mol Cancer Res. 15:1667-1677, 2017.

Nakajima et al., "Improving the efficacy of Photoimmunotherapy (PIT) using a cocktail of antibody conjugates in a multiple antigen tumor model," Theranostics. (Apr. 23, 2013);3(6):357-65.

Nakajima et al., "Real-time monitoring of in vivo acute necrotic cancer cell death induced by near infrared photoimmunotherapy using fluorescence lifetime imaging," Cancer Res. (Sep. 15, 2012);72(18):4622-8.

Nakajima et al., "The effects of conjugate and light dose on photo-immunotherapy induced cytotoxicity," BMC Cancer. (May 30, 2014);14:389.

Nakamura et al., "MR imaging biomarkers for evaluating therapeutic effects shortly after near infrared photoimmunotherapy," Oncotarget. Mar. 29, 2016;7(13):17254-64.

Nowis et al., "The influence of photodynamic therapy on the immune response," Photodiagnosis Photodyn Ther. Dec. 2005;2(4):283-98.

Ogawa et al., "In vivo molecular imaging of cancer with a quenching near-infrared fluorescent probe using conjugates of monoclonal antibodies and indocyanine green," Cancer Res. Feb. 15, 2009;69(4):1268-72.

Olejko et al., "An ion-controlled four-color fluorescent telomeric switch on DNA origami structures," Nanoscale. (May 21, 2016);8(19):10339-47.

Ott et al., "CTLA-4 and PD-1/PD-L1 Blockade: New Immunotherapeutic Modalities with Durable Clinical Benefit in Melanoma Patients," Clin Cancer Res (2013) 19:5300-5309.

Pardoll, "The blockade of immune checkpoints in cancer immunotherapy," Nature Reviews Cancer (2012) 12:252-264.

Peng et al., "A nonfluorescent, broad-range quencher dye for Förster resonance energy transfer assays," Anal Biochem. (May 15, 2009);388(2):220-8.

Peng et al., "Phthalocyanine dye as an extremely photostable and highly fluorescent near-infrared labeling reagen," Proc SPIE Int Soc Opt Eng. vol. 6097, 60970E (2006).

Radvanyi et al., "Antagonist Antibodies to PD-1 and B7-H1 (PD-L1) in the Treatment of Advanced Human Cancer—Letter," Clin Cancer Research (2013) 19:5541.

Robert et al., "What is the role of cytotoxic T lymphocyte-associated antigen 4 blockade in patients with metastatic melanoma?" Oncologist (2009) 14(8):848-861.

Rosenthal et al., "In Vivo Detection of Head and Neck Cancer Orthotopic Xenografts by Immunofluorescence," Laryngoscope 116: 1636-1641, 2006.

Samkoe et al., "High vascular delivery of EGF, but low receptor binding rate is observed in AsPC-1 tumors as compared to normal pancreas," Mol Imaging Biol. (Aug. 2012);14(4):472-9.

Sano et al., "Acute cytotoxic effects of photoimmunotherapy assessed by 18F-FDG PET," J Nucl Med. (May 2013);54(5):770-5.

Sano et al., "The effect of photoimmunotherapy followed by liposomal daunorubicin in a mixed tumor model: a demonstration of the super-enhanced permeability and retention effect after photoimmunotherapy," Mol Cancer Ther. (Feb. 2014);13(2):426-32.

Sano et al., "Markedly Enhanced Permeability and Retention Effects Induced by Photo-Immunotherapy of Tumors," ACS Nano. (Jan. 22, 2013); 7:717-724.

Sato et al., "Comparative effectiveness of light emitting diodes (LEDs) and Lasers in near infrared photoimmunotherapy," Oncotarget. (Mar. 22, 2016);7(12):14324-35.

Sato et al., "Near infrared photoimmunotherapy for lung metastases," Cancer Lett. (Aug. 28, 2015);365(1):112-21.

Sato et al., "Near infrared photoimmunotherapy in the treatment of disseminated peritoneal ovarian cancer," Mol Cancer Ther. (Jan. 2015);14(1):141-50.

Sato et al., "Near infrared photoimmunotherapy in the treatment of pleural disseminated NSCLC: preclinical experience," Theranostics. (Mar. 19, 2015);5(7):698-709.

Sato et al., "Photoimmunotherapy of gastric cancer peritoneal carcinomatosis in a mouse model," PLoS One. (Nov. 17, 2014);9(11):e113276.

Sato et al., "Photoimmunotherapy: comparative effectiveness of two monoclonal antibodies targeting the epidermal growth factor receptor," Mol Oncol. (May 2014);8(3):620-32.

Sato et al., "Photoinduced Ligand Release from a Silicon Phthalocyanine Dye Conjugated with Monoclonal Antibodies: A Mechanism of Cancer Cell Cytotoxicity after Near-Infrared Photoimmunotherapy," ACS Cent Sci. 4:1559-1569, 2018.

Sato et al., "Selective cell elimination in vitro and in vivo from tissues and tumors using antibodies conjugated with a near infrared phthalocyanine," RSC Adv. (Mar. 3, 2015);5(32):25105-25114.

Sato et al., "Spatially selective depletion of tumor-associated regulatory T cells with near-infrared photoimmunotherapy." Sci Transl Med. Aug. 17, 2016;8(352):352ra110.

Savellano et al., "Multiepitope HER2 Targeting Enhances Photoimmunotherapy of HER2-Overexpressing Cancer Cells with Pyropheophorbide-a Immunoconjugates," Cancer Res. 65:6371-6379, 2005.

Scully et al., "Application of Fluorescence Lifetime Imaging Microscopy to the Investigation of Intracellular PDT Mechanisms," Bio imaging 5 :9-18, 1997.

(56) References Cited

OTHER PUBLICATIONS

Serebrovskaya et al., "Targeting Cancer Cells by Using an Antireceptor Antibody-Photo sensitizer Fusion Protein," Proc Nat A cad Sci. 106:9221-9225, 2009.
Shimoyama et al., "Viral transduction of the HER2-extracellular domain expands trastuzumab-based photoimmunotherapy for HER2-negative breast cancer cells," Breast Cancer Res Treat. (Feb. 2015);149(3):597-605.
Shinohara et al., "Structure and chromosomal localization of the human PD-1 gene (PDCD1)," Genomics (1994) 23(3):704-706.
Shirasu et al., "Potent and specific antitumor effect of CEA-targeted photoimmunotherapy," Int J Cancer. (Dec. 1, 2014);135(11):2697-710.
Snyder et al., "Photodynamic therapy: a means to enhanced drug delivery to tumors," Cancer Res. 63:8126-8131, 2003.
Soukos et al., "Epidermal Growth Factor Receptor-Targeted Immunophotodiagnosis and Photoimmunotherapy of Oral Precancer in Vivo," Cancer Res. 61 :4490-4496, 2001.
Specenier et al., "Cetuximab: its unique place in head and neck cancer treatment," Biologics (2013) 7:77-90.
Steele et al., "Suppressor deletion therapy: selective elimination of T suppressor cells in vivo using a hematoporphyrin conjugated monoclonal antibody permits animals to reject syngeneic tumor cells." Cancer Immunol Immunother. 1988;26(2):125-31.
Steiner et al., "Efficient Selection of DARPins with Sub-nanomolar Affinities using SRP Phage Display," J Mol Biol (2008) 382(5):1211-1227.
Sugiyama et al., "Anti-CCR4 mAb selectively depletes effector-type FoxP3+CD4+ regulatory T cells, evoking antitumor immune responses in humans." Proc Natl Acad Sci U S A. Oct. 29, 2013;110(44):17945-50.
Supplementary materials from Mitsunaga et al., "Cancer Cell-Selective in Vivo Near Infrared Photomimmunotherapy Targeting Specific Membrane Molecules," Nat. Med. 17:1685-1691, 2011.
Tamaskovic et al., "Designed ankyrin repeat proteins (DARPins) from research to therapy," Methods Enzymol (2012) 503:101-134.
Therasse et al., "New guidelines to evaluate the response to treatment in solid tumors. European Organization for Research and Treatment of Cancer, National Cancer Institute of the United States, National Cancer Institute of Canada," J Natl Cancer Inst (2000)92(3):205-216.
Topalian et al., "Safety, Activity, and Immune Correlates of Anti—PD-1 Antibody in Cancer," N Engl J Med (2012) 366:2443-2454.
Tynan et al., "Multicolour single molecule imaging in cells with near infra-red dyes," PLoS One. (2012);7(4):e36265.
van Dongen et al., "Photosensitizer-Antibody Conjugates for Detection and Therapy of Cancer," Adv Drug Deliv Rev. 56:31-52, 2004.
van Driel et al., "EGFR targeted nanobody-photosensitizer conjugates for photodynamic therapy in a pre-clinical model of head and neck cancer," J Control Release. (May 10, 2016);229:93-105.
von Felbert et al., "A specific photoimmunotheranostics agent to detect and eliminate skin cancer cells expressing EGFR," J Cancer Res Clin Oncol. (May 2016);142(5):1003-11.
Vrouenraets et al., "Targeting of aluminum (III) phthalocyanine tetrasulfonate by use of internalizing monoclonal antibodies: improved efficacy in photodynamic therapy." Cancer Research, Mar. 1, 2001, vol. 61, No. 5, pp. 1970-1975.
Wada et al., "Sequencing CTLA-4 blockade with cell-based immunotherapy for prostate cancer," J Transl Med (2013) 11:89.
Waite and Roth, "Nanoscale drug delivery systems for enhanced drug penetration into solid tumors: current progress and opportunities," Crit Rev Biomed Eng. 40:21-41, 2012.
Wang et al., "Theranostic Agents for Photodynamic Therapy of Prostate Cancer by Targeting Prostate-Specific Membrane Antigen," Mol Cancer Ther. (Aug. 2016);15(8):1834-44.
Watanabe et al., "Photoimmunotherapy targeting prostate-specific membrane antigen: are antibody fragments as effective as antibodies?," J Nucl Med. (Jan. 2015);56(1):140-4.

Weber, "Review: anti-CTLA-4 antibody ipilimumab: case studies of clinical response and immune-related adverse events," Oncologist (2007) 12(7):864-872.
Wessels et al., "Advances in cellular, subcellular, and nanoscale imaging in vitro and in vivo," Cytometry A:77:667-676, 2010.
Whiteside, "The tumor microenvironment and its role in promoting tumor growth," Oncogene (2008) 27(45):5904-5912.
Xu et al., "Antibody Conjugated Magnetic Iron Oxide Nanoparticles for Cancer Cell Separation in Fresh Whole Blood," Biomaterials 32:9758-9765, 2011.
Zhang et al., "Target-selective phototherapy using a ligand-based photosensitizer for type 2 cannabinoid receptor," Chem Biol. (Mar. 20, 2014);21(3):338-44.
Zhang et al., "Tumor mitochondria-targeted photodynamic therapy with a translocator protein (TSPO)-specific photosensitizer," Acta Biomater. (Dec. 2015);28:160-70.
Zhu et al., "Visualization of P53264-2n/HLA-A *0201 Complexes Naturally Presented on Tumor Cell Surface by a Multimeric Soluble Single-Chain T Cell Receptor," J Immunol. 176:3223-3232, 2006.
Zinn et al., "IND-Directed Safety and Biodistribution Study of Intravenously Injected Cetuximab-IRDye800 in Cynomolgus Macaques." Molecular Imaging Biology, Feb. 5, 2015, vol. 17, No. 1, pp. 49-57.
Zuluaga et al., "Combination of Photodynamic Therapy With Anti-Cancer Agents," Curr Med Chem. 15:1655-1673, 2008.
Sanchez-Barcelo et al., "Recent Patents on Light Based Therapies: Photodynamic Therapy, Photothermal Therapy and Photoimmunotherapy," Recent Patents on Endocrine, Metabolic & Immune Drug Discovery (2014) 8: 1-8.
Serebrovskaia et al., "Genetically Encoded Photoimmunosensitizer," abstract (in English); Bioorg. Khim. 2011 37 (1):137-44.
Clinical Trial Identifier NCT02422979, first posted on Apr. 22, 2015. Last updated on Sep. 20, 2019.
U.S. Appl. No. 17/057,589, filed Nov. 20, 2020, by Manibusan et al. (Copy not provided). (Copy not submitted herewith pursuant to the waiver of 37 C.F. R. § 1.98(a)(2)(iii) issued by the Office on Sep. 21, 2004).
Butcher et al., "Visible Light," Tour of the Electromagnetic Spectrum, National Aeronautics and Space Administration, 2016, available at https://smd-prod.s3.amazonaws.com/science-pink/s3fs-public/atoms/files/Tour-of-the-EMS-TAGGED-v7_0.pdf.
Doane et al., "Observation and Photophysical Characterization of Silicon Phthalocyanine J-Aggregate Dimers in Aqueous Solutions," Chem Eur J. 20:8030-8039, 2014.
Dougherty et al., "Photodynamic Therapy," J Natl Cancer Inst. 90:889-905, 1998.
Jeong et al., "Indium gallium nitride-based ultraviolet, blue, and green lightemitting diodes functionalized with shallow periodic hole patterns," (2017) Scientific Reports 7:45726.
Li et al., "Structural basis for inhibition of the epidermal growth factor receptor by cetuximab," Cancer Cell Apr. 2005;7(4):301-11.
Li-Cor, "IRDye® Infrared Dyes: Advancing Discovery with Infrared Imaging," 2010.
Maruoka et al., "Combined CD44- and CD25-targeted Near-Infrared Photoimmunotherapy to Selectively Kill Cancer and Regulatory T cells in Syngeneic Mouse Cancer Models," Cancer Immunol Res. 8:345-355, 2020.
New Pharmacology (New Yakurigaku), Nankodo Co., Ltd., 2012, the third impression of the revised sixth edition, p. 558-559. (including English translation).
Rosas-Arellano et al., "A simple solution for antibody signal enhancement in immunofluorescence and triple immunogold assays," Histochem Cell Biol (2016) 146:421-430.
Supplementary materials from Gao et al., "In vivo cancer targeting and imaging with semiconductor quantum dots," Nat Biotechnol. Aug. 2004;22(8):969-76.
Turner et al., Administration of substances to laboratory animals: routes of administration and factors to consider. J Am Assoc Lab Anim Sci. 2011;50(5):600-613.
Zhang et al., "Inhibition of tumor growth and metastasis by photoimmunotherapy targeting tumor-associated macrophage in a sorafenib-resistant tumor model," Biomaterials (Jan. 2016); vol. 84, pp. 1-12.

(56) References Cited

OTHER PUBLICATIONS

Blaudszun et al., "A photosensitizer delivered by bispecific antibody redirected T lymphocytes enhances cytotoxicity against EpCAM-expressing carcinoma cells upon light irradiation," J Control Release (2015) 197:58-68.

EC—PDT probe "Machinery and equipment 31 Medical ablation device," Apr. 2017 revision (No. 6 edition). English translation included.

Gao et al., "Enhanced Anti-Tumor Efficacy through a Combination of Integrin αvβ6-Targeted Photodynamic Therapy and Immune Checkpoint Inhibition," Theranostics (2016) 6(5):627-637

Kabolizadeh et al., "The role of cetuximab in the management of head and neck cancers," Exp Opin Biol Ther (2012) 12(4):517-528.

Meading et al., "Boosting tumor-specific immunity using PDT," Cancer (2016) 8:91.

Moreira et al., "Targeted Therapy in Head and Neck Cancer: An Update on Current Clinical Developments in Epidermal Growth Factor Receptor-Targeted Therapy and Immunotherapies," Drugs (2017) 77:843-857.

Package Insert of Cetuximab, "Anti-malignant tumor agent Anti-human EGFR Monochrome antibody," Revised Mar. 2021 (2nd edition) English translation included.

Sekkat et al., "Like a bolt from the Blue: Phthalocyanines in Biomedical Optics," Molecules (2012) 17:98-144.

Van Cutsem et al., "Cetuximab and chemotherapy as initial treatment for metastatic colorectal cancer," The New England Journal of Medicine (2009) 360:1408-1417.

Wagner-Rousset et al., "Antibody-drug conjugate model fast characterization by LC-MS following IdeS proteolytic digestion," mAbs (2014) 6(1):173-184.

Wolina, "Cetuximab in non-melanoma skin cancer," Exp Opin Biol Ther (2012) 12(7):949-956.

* cited by examiner

COMPOSITIONS, COMBINATIONS AND RELATED METHODS FOR PHOTOIMMUNOTHERAPY

CROSS-REFERENCE TO RELATED APPLICATIONS

This application is a continuation of U.S. application Ser. No. 15/753,153 filed on Feb. 15, 2018 which is a U.S. National Phase Application of International Application No. PCT/US2016/047640, filed Aug. 18, 2016, which claims priority from U.S. provisional application No. 62/206,776, filed Aug. 18, 2015, entitled "Combination Therapy with Photoimmunotherapy and Related Methods" and from U.S. provisional application No. 62/249,085 filed Oct. 30, 2015 entitled "Compositions and Methods for Photoimmuotherapy" the contents of each of which are incorporated by reference in their entirety.

INCORPORATION BY REFERENCE OF SEQUENCE LISTING

The present application is being filed with a Sequence Listing in electronic format. The Sequence Listing is provided as a file entitled 751702000401 seqlist.txt, created May 22, 2019, which is 9,934 bytes in size. The information in electronic format of the Sequence Listing is incorporated by reference in its entirety.

FIELD

The present disclosure relates to conjugates, compositions and methods for use in photoimmunotherapy, such as photoimmunotherapy induced by activation of a phthalocyanine dye conjugated to a targeting molecule that binds a protein on cell, for example, an IR700-antibody conjugate. The present disclosure also relates to combination therapies for use in combination with photoimmunotherapy, such as photoimmunotherapy induced by activation of a phthalocyanine dye conjugated to a targeting molecule that targets a tumor cell, for example, an IR700-antibody conjugate. In some embodiments, the phthalocyanine-dye conjugate can be activated by irradiation with near-infrared light. Features of the conjugates, compositions, combinations and methods, including the dose of the conjugate, provide various advantages, such as lower toxicity and/or improved efficacy. In some embodiments, the disclosure also relates to a dual label phthalocyanine-dye conjugate in which the targeting molecule is conjugated to an additional fluorescent dye, which can be used for photoimmunotherapy while, for example, also exhibiting improved performance for imaging or detection. The disclosure also provides therapeutic methods using the conjugates, compositions and combinations for treatment of diseases and conditions, including tumors or cancers.

BACKGROUND

Various therapies are available for treating disease, such as cancer. For example, photoimmunotherapy (PIT) is a method that uses a photosensitizer conjugated to an antibody or other targeting molecule to target a cell surface protein in order to permit the targeted killing of specific cells. In some cases, PIT can selectively target disease cells, such as tumor cells, and thereby selectively kill such cells without damaging healthy cells. Improved strategies are needed to improve photoimmunotherapy methods, for example, to increase the efficacy of treatment. Provided are compositions and methods that meet such needs.

SUMMARY

Provided in some embodiments is a method of treating a disease or condition in a subject containing using photoimmunotherapy (PIT). In some embodiments, the method includes administering to the subject having a disease or condition a conjugate containing a phthalocyanine dye linked to a targeting molecule, such as an antibody or an antigen-binding fragment thereof, that binds to a protein on the surface of a cell present in the microenvironment of a lesion associated with the disease or condition. In some embodiments, the conjugate is administered to effect a systemic exposure that is no more than 75% of the total therapeutically effective systemic exposure of the antibody or antigen-binding fragment that is not so conjugated for treating the same disease or condition as described at the label approved for commercialization by the regulatory agencies (e.g. FDA, EMA, PDMA). In some embodiments, after administering the conjugate, the lesion is irradiated at a wavelength of 500 to 900 nm at a dose of at least 1 J cm$^{-2}$ or 1 J/cm of fiber length thereby treating the tumor in the subject. In some embodiments, the wavelength for irradiation is 600 nm to 850 nm, such as 660 nm to 740 nm.

In some embodiments, the conjugate is administered in a dosing schedule in which: the administration of the conjugate is performed only one time as a single injection or infusion; or the dosing schedule does not include a subsequent dose of the conjugate; or the dosing schedule does not include a subsequent dose of the targeting molecule, e.g., a macromolecule, that is not so conjugated.

In some embodiments, the conjugate is administered systemically. In some embodiments, the conjugate is administered intravenously.

In some embodiments, the conjugate is administered to effect a systemic exposure (AUC) that is no more than 60%, no more than 50%, no more than 40% or no more than 30% of the therapeutically effective systemic exposure of the antibody or antigen-binding fragment that is not so conjugated for treating the same disease or condition.

In some embodiments, the disease or condition is a tumor, whereby the antibody or an antigen-binding fragment binds to a molecule on the surface of a cell present in the tumor microenvironment and the tumor is irradiated.

Provided in some embodiments is a method of treating a disease or condition in a subject using photoimmunotherapy (PIT) wherein the systemic exposure as measured by the average area under the plasma conjugate concentration-time curve from time 0 to infinity (AUC[0-inf] or $AUC_{0-\infty}$) for a patient population, such as a sample patient population after administration of the conjugate is between or between about 250 µg/mL*h and 100,000 µg/mL*h, between or between about 500 µg/mL*h and 50,000 µg/mL*h, between or between about 500 µg/mL*h and 18,000 µg/mL*h, or between or between about 500 µg/mL*h and 10,000 µg/mL*h. In some embodiments, the systemic exposure as measured by the average area under the plasma conjugate concentration-time curve from time 0 to infinity (AUC[0-inf] or $AUC_{0-\infty}$) for a patient population, such as a sample patient population after administration of the conjugate is no more than 100,000 µg/mL*h, no more than 75,000 µg/mL*h, no more than 50,000 µg/mL*h, no more than 40,000 µg/mL*h, no more than 30,000 µg/mL*h, no more than 20,000 µg/mL*h, no more than 10,000 µg/mL*h, no more than 5,000 µg/mL*h, or no more than 2,500 µg/mL*h.

In some embodiments, the systemic exposure as measured by the average area under the plasma conjugate concentration-time curve from time 0 to 24 hours (AUC[0-24] or $AUC_{0-24}$) for a patient population, such as a sample patient population after administration of the conjugate is between or between about 100 μg/mL*h and 25,000 μg/mL*h, between or between about 200 μg/mL*h and 10,000 μg/mL*h, between or between about 500 μg/mL*h and 5,000 μg/mL*h; or the systemic exposure as measured by the average area under the plasma conjugate concentration-time curve from time 0 to 24 hours (AUC[0-24] or $AUC_{0-24}$) for a patient population, such as a sample patient population after administration of the conjugate is no more than 25,000 μg/mL*h, no more than 15,000 μg/mL*h, no more than 10,000 μg/mL*h, no more than 5,000 μg/mL*h, no more than 2,500 μg/mL*h, no more than 1,000 μg/mL*h, or no more than 500 μg/mL*h.

In some embodiments, the conjugate is administered in a dosage range that is at least about 10 mg/m$^2$ (body surface area of the subject), at least about 50 mg/m$^2$ or at least about 75 mg/m$^2$ and is no more than 5000 mg/m$^2$, no more than 2000 mg/m$^2$, no more than 1000 mg/m$^2$. In some embodiments, the conjugate is administered in a dosage range that is no more than 500 mg/m$^2$, no more than 250 mg/m$^2$, or no more than 200 mg/m$^2$. In some embodiments, the conjugate is administered at a dosage that is between or between about 100 mg/m$^2$ and 1500 mg/m$^2$ or 150 mg/m$^2$ and 750 mg/m$^2$. In some embodiments, the conjugate is administered at a dosage that is or is about 160 mg/m$^2$, 320 mg/m$^2$, 640 mg/m$^2$ or 1280 mg/m$^2$.

In some embodiments, the targeting molecule is an antibody or an antigen-binding antibody fragment. In some embodiments, the antibody is an antigen-binding antibody fragment that is a Fab, a single $V_H$ domain, a single chain variable fragment (scFv), a multivalent scFv, a bispecific scFv or an scFv-CH3 dimer.

In some embodiments, the lesion is irradiated at a wavelength of 690±50 nm or at a wavelength of or about 690±20 nm. In some embodiments, the lesion is irradiated at a dose of from or from about 2 J cm$^{-2}$ to about 400 J cm$^{-2}$ or from or from about 2 J/cm fiber length to about 500 J/cm fiber length. In some embodiments, the lesion is irradiated at a dose of at least or at least about 2 J cm$^2$, 5 J cm$^2$, 10 J cm$^{-2}$, 25 J cm$^{-2}$, 50 J cm$^{-2}$, 75 J cm$^{-2}$, 100 J cm$^2$, 150 J cm$^{-2}$, 200 J cm$^{-2}$, 300 J cm$^{-2}$, 400 J cm$^{-2}$, or 500 J cm$^{-2}$; or the lesion is irradiated at a dose of at least or at least about 2 J/cm fiber length, 5 J/cm fiber length, 10 J/cm fiber length, 25 J/cm fiber length, 50 J/cm fiber length, 75 J/cm fiber length, 100 J/cm fiber length, 150 J/cm fiber length, 200 J/cm fiber length, 250 J/cm fiber length, 300 J/cm fiber length, 400 J/cm fiber length or 500 J/cm fiber length.

In some embodiments, the irradiation is carried out or effected between or between about 30 minutes and 96 hours after administering the conjugate. In some embodiments, the conjugate is administered in a dosing schedule in which the administration of the conjugate is performed only one time as a single injection or infusion. In some embodiments, the conjugate is administered in a dosing schedule in which the dosing schedule does not contain a subsequent dose of the conjugate. In some embodiments, the conjugate is administered in a dosing schedule in which the dosing schedule does not contain a subsequent dose of the targeting molecule that is not so conjugated. In some embodiments, the dosing schedule is repeated.

In some embodiments, the conjugate is administered systemically. In some embodiments, the conjugate is administered intravenously.

In some embodiments, the phthalocyanine dye has a maximum absorption wavelength from or from about 600 nm to about 850 nm.

In some embodiments, the phthalocyanine dye is linked directly or indirectly to the targeting molecule. In some embodiments, the phthalocyanine dye includes the formula:

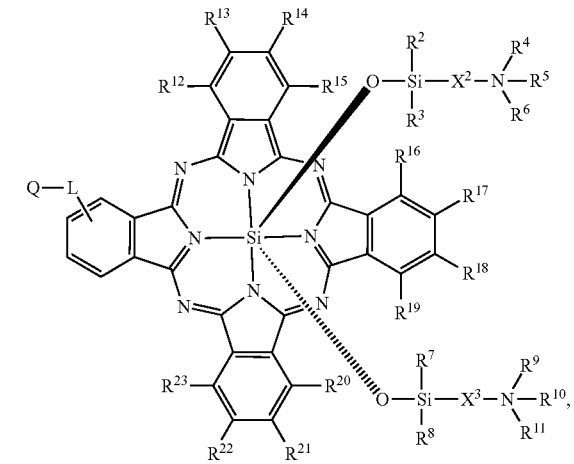

wherein:

L is a linker;

Q is a reactive group for attachment of the dye to the targeting molecule;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ include a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from hydrogen, halogen, optionally substituted alkylthio, optionally substituted alkylamino and optionally substituted alkoxy; and $X^2$ and $X^3$ are each independently $C_1$-$C_{10}$ alkylene, optionally interrupted by a heteroatom.

In some embodiments, the phthalocyanine dye includes the formula:

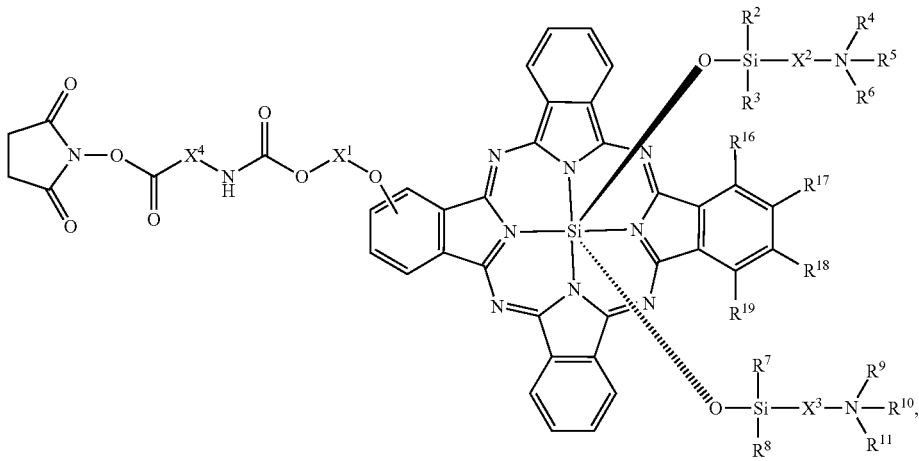

wherein:

$X^1$ and $X^4$ are each independently a $C_1$-$C_{10}$ alkylene optionally interrupted by a heteroatom;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ includes a water soluble group; and $R^{16}$, $R^{17}$, $R^{18}$ and $R^{19}$ are each independently selected from hydrogen, halogen, optionally substituted alkylthio, optionally substituted alkylamino and optionally substituted alkoxy.

In some embodiments, the phthalocyanine dye includes IRDye 700DX (IR700).

In some embodiments, the cell surface protein is selected from among ACTHR, endothelial cell Anxa-1, aminopetidase N, anti-IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CD133, CD7, CD15, CD34, CD44, CD206, CD271, CEA (CarcinoEmbryonic Antigen), CGRP, chemokine receptors, cell-surface annexin-1, cell-surface plectin-1, Cripto-1, CRLR, CXCR2, CXCR4, DCC, DLL3, E2 glycoprotein, EGFR, EGFRvIII, EMR1, Endosialin, EP2, EP4, EpCAM, EphA2, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like) like), G-protein coupled receptors of the Family C (Metabotropic Glutamate Receptor-like), GD2, GP100, GP120, Glypican-3, hemagglutinin, Heparin sulfates, HER1, HER2, HER3, HER4, HMFG, HPV 16/18 and E6/E7 antigens, hTERT, IL11-R, IL-13R, ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/HABP1), p75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family (e.g., P2X1-5), mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP (e.g., TRPV1-6, TRPA1, TRPC1-7, TRPM1-8, TRPP1-5, TRPML1-3), TSH receptor, VEGF receptors (VEGFR1 or Flt-1, VEGFR2 or FLK-1/KDR, and VEGF-3 or FLT-4), voltage-gated ion channels, VPAC1, VPAC2, Wilms tumor 1, Y1, Y2, Y4, and Y5.

In some embodiments, the cell surface protein is selected from among HER1/EGFR, HER2/ERBB2, CD20, CD25 (IL-2Ra receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, and SK-1 antigen.

In some embodiments, the cell surface protein is selected from among CD25, PD-1 (CD279), PD-L1 (CD274, B7-H1), PD-L2 (CD273, B7-DC), CTLA-4, LAG3 (CD223), TIM3 (HAVCR2), 4-1BB (CD137, TNFRSF9), CXCR2, CXCR4 (CD184), CD27, CEACAM1, Galectin 9, BTLA, CD160, VISTA (PD1 homologue), B7-H4 (VCTN1), CD80 (B7-1), CD86 (B7-2), CD28, HHLA2 (B7-H7), CD28H, CD155, CD226, TIGIT, CD96, Galectin 3, CD40, CD40L, CD70, LIGHT (TNFSF14), HVEM (TN-FRSF14), B7-H3 (CD276), Ox40L (TNFSF4), CD137L (TNFSF9, GITRL), B7RP1, ICOS (CD278), ICOSL, KIR, GAL9, NKG2A (CD94), GARP, TL1A, TNFRSF25, TMIGD2, BTNL2, Butyrophilin family, CD48, CD244, Siglec family, CD30, CSF1R, MICA (MHC class I polypeptide-related sequence A), MICB (MHC class I polypeptide-related sequence B), NKG2D, KIR family (Killer-cell immunoglobulin-like receptor, LILR family (Leukocyte immunoglobulin-like receptors, CD85, ILTs, LIRs), SIRPA (Signal regulatory protein alpha), CD47 (IAP), Neuropilin 1 (NRP-1), a VEGFR, and VEGF.

In some embodiments, the antibody or an antigen-binding fragment is selected from among cetuximab, panitumumab, zalutumumab, nimotuzumab, Tositomomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Basiliximab, nivolumab, pembrolizumab, pidilizumab, MK-3475, BMS-936559, MPDL3280A, ipilimumab, tremelimumab, IMP321, BMS-986016, LAG525, urelumab, PF-05082566, TRX518, MK-4166, dacetuzumab, lucatumumab, SEA-CD40, CP-870, CP-893, MEDI6469, MEDI6383, MEDI4736, MOXR0916, AMP-224, PDR001, MSB0010718C, rHIgM12B7, Ulocuplumab, BKT140, Varlilumab (CDX-1127), ARGX-110, MGA271, lirilumab (BMS-986015, IPH2101), IPH2201, AGX-115, Emactuzumab, CC-90002 and MNRP1685A or is an antigen-binding fragment thereof.

In some embodiments, the conjugate is selected from among cetuximab-IR700, panitumumab-IR700, zalutumumab-IR700, nimotuzumab-IR700, Tositomomab-IR700, Rituximab-IR700, Ibritumomab tiuxetan-IR700, Daclizumab-IR700, Gemtuzumab-IR700, Alemtuzumab-IR700, CEA-scan Fab fragment-IR700, OC125-IR700, ab75705-IR700, B72.3-IR700, Bevacizumab-IR700, Basiliximab-IR700, nivolumab-IR700, pembrolizumab-IR700, pidilizumab-IR700, MK-3475-IR700, BMS-936559-IR700, MPDL3280A-IR700, ipilimumab-IR700, tremelimumab-IR700, IMP321-IR700, BMS-986016-IR700, LAG525-IR700, urelumab-IR700, PF-05082566-IR700, TRX518-IR700, MK-4166-IR700, dacetuzumab-IR700, lucatumumab-IR700, SEA-CD40-IR700, CP-870-IR700, CP-893-IR700, MEDI6469-IR700, MEDI6383-IR700, MEDI4736-IR700, MOXR0916-IR700, AMP-224-IR700, PDR001-IR700, MSB0010718C-IR700, rHIgM12B7-IR700, Ulocuplumab-IR700, BKT140-IR700, Varlilumab-IR700, ARGX-110-IR700, MGA271-IR700, lirilumab-IR700, IPH2201-IR700, AGX-115-IR700, Emactuzumab-IR700, CC-90002-IR700 and MNRP1685A-IR700.

In some embodiments, the targeting molecule is an antibody that is cetuximab or is an antigen-binding fragment thereof or the conjugate is cetuximab-IR700.

In some embodiments, the average area under the plasma conjugate concentration-time curve from time 0 to infinity (AUC[0-inf] or $AUC_{0-\infty}$) for a patient population, such as a sample patient population after administration of the conjugate is between or between about 500 g/mL*h and 18,000 μg/mL*h, between or between about 500 μg/mL*h and 10,000 μg/mL*h, between or between about 500 μg/mL*h and 5,000 μg/mL*h, or between or between about 500 g/mL*h and 2,500 μg/mL*h. In some embodiments, the average area under the plasma conjugate concentration-time curve from time 0 to 24 hours (AUC[0-24] or $AUC_{0-24}$) for a patient population, such as a sample patient population after administration of the conjugate is between or between about 500 μg/mL*h and 8,000 μg/mL*h, between or between about 500 g/mL*h and 5,000 μg/mL*h, between or between about 500 μg/mL*h and 2,000 μg/mL*h or between or between about 1000 μg/mL*h and 4,000 μg/mL*h.

In some embodiments, the conjugate is administered in a dosage range that is between or between about 75 mg/m$^2$ (body surface area of the subject) and 1500 mg/m$^2$, between or between about 75 mg/m$^2$ and 1000 mg/m$^2$, between or between about 75 mg/m$^2$ and 500 mg/m$^2$ or between or between about 75 mg/m$^2$ and 225 mg/m$^2$. In some embodiments, the conjugate is administered in a dosage range that is at least about or is about 160 mg/m$^2$, 320 mg/m$^2$, 640 mg/m$^2$ or 1280 mg/m$^2$.

Provided in some embodiments is a method of treating a disease lesion in a subject, that includes: a) intravenously administering to a subject having a lesion associated with a disease or condition a cetuximab-IR700 conjugate, wherein the conjugate is administered in an amount that is or is about 640 mg/m$^2$; and b) after administering the conjugate, irradiating the lesion at a wavelength of 690±20 nm at a dose of at least or about at least or about 50 J cm$^{-2}$ or 100 J/cm of fiber length, thereby treating the disease or condition in the subject.

In some embodiments, the conjugate is administered in a dosing schedule in which: the administration of the conjugate is performed only one time as a single injection or infusion; or the dosing schedule does not include a subsequent dose of the conjugate; or the dosing schedule does not include a subsequent dose of the targeting molecule that is not so conjugated.

In some embodiments, the irradiation is carried out 24 hours±3 hours, such as 24 hours±2 hours, after administering the conjugate.

In some embodiments, the lesion is a tumor and the disease or condition is a tumor or a cancer.

In some embodiments, the lesion is a tumor that is a superficial tumor. In some embodiments, the tumor is less than 10 mm thick. In some embodiments, irradiation is carried out using a microlens-tipped fiber for surface illumination. In some embodiments, the light irradiation dose is from or from about 5 J/cm$^2$ to about 200 J/cm$^2$.

Provided in some embodiments is a method for treating a superficial tumor with photoimmunotherapy, that includes illuminating an superficial tumor in a subject with a microlens-tipped fiber for surface illumination with a light dose of from or from about 5 J/cm$^2$ to about 200 J/cm$^2$, wherein the tumor is associated with a phototoxic agent that includes a targeting molecule bound to a cell surface molecule of the tumor. In some embodiments, the light irradiation dose is or is about 50 J/cm$^2$.

In some embodiments, the lesion is a tumor that is an interstitial tumor. In some embodiments, the tumor is greater than 10 mm deep or is a subcutaneous tumor. In some embodiments, irradiation is carried out using cylindrical diffusing fibers that includes a diffuser length of 0.5 cm to 10 cm and spaced 1.8±0.2 cm apart. In some embodiments, the light irradiation dose is from or from about 20 J/cm fiber length to about 500 J/cm fiber length.

Provided in some embodiments is a method for treating an interstitial tumor with photoimmunotherapy, that includes illuminating an interstitial tumor in a subject with cylindrical diffusing fibers that includes a diffuser length of 0.5 cm to 10 cm and spaced 1.8±0.2 cm apart with a light dose of or about 100 J/cm fiber length or with a fluence rate of or about 400 mW/cm, wherein the tumor is associated with a phototoxic agent that includes a targeting molecule bound to a cell surface molecule of the tumor.

In some embodiments, the light irradiation dose is from or from about 50 J/cm fiber length to about 300 J/cm fiber length. In some embodiments, the light irradiation dose is or is about 100 J/cm fiber length.

In some embodiments, the tumor is greater than 10 mm deep or is a subcutaneous tumor. In some embodiments, the cylindrical diffusing fibers are placed in a catheter positioned in the tumor 1.8±0.2 cm apart. In some embodiments, the catheter is optically transparent.

In some embodiments, greater than 6 hours prior to illuminating the tumor, the subject has been administered the phototoxic agent that includes the targeting molecule, wherein the phototoxic agent associates with the tumor. In some embodiments, the phototoxic agent has been previously administered to the subject greater than or greater than about 12 hours, 24 hours, 26 hours, 48 hours, 72 hours or 96 hours prior to illuminating the tumor. In some embodiments, the phototoxic agent is a phthalocyanine dye-targeting molecule conjugate. In some embodiments, the phthalocyanine dye is IR700.

In some embodiments, in any of the methods for treating provided herein, the dosing schedule is repeated, whereby steps (a) and (b) are repeated. In some embodiments, the dosing schedule is repeated if residual lesion remains after a prior treatment with the conjugate. In some embodiments, the method additionally includes assessing the subject for the presence of a residual lesion and if residual lesion remains repeating the dosing schedule. In some embodiments, the dosing schedule is repeated if a residual lesion remains at a time that is more than or about or 1 week, 2 weeks, 3 weeks, 4 weeks, 2 months, 6 months or 1 year after initiation of the prior administration of the conjugate. In some embodiments, the dosing schedule is repeated if a residual lesion remains at or about 4 weeks after initiation of the prior administration of the conjugate.

In some embodiments, the conjugate contains 1 to 100, 1 to 10 or 2 to 5 phthalocyanine dye molecules per targeting molecule.

In some embodiments, the method does not contain administration of an additional therapeutic agent or anti-cancer treatment. In some embodiments, the method contains administration of an additional therapeutic agent or anti-cancer treatment. In some embodiments, the anti-cancer treatment contains radiation therapy.

In some embodiments, the additional therapeutic agent is an anti-cancer agent or an immune modulating agent. In some embodiments, the additional therapeutic agent is an immune modulating agent is an immune checkpoint inhibitor. In some embodiments, the immune checkpoint inhibitor specifically binds a molecule selected from among CD25, PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28 and VISTA. In some embodiments, the immune checkpoint inhibitor is and antibody or antigen-binding fragment, a small molecule or a polypeptide. In some embodiments, the immune checkpoint inhibitor is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MEDI4736, MOXR0916, AMP-224, and MSB001078C, or is an antigen-binding fragment thereof.

In some embodiments, the immune modulating agent is administered prior to irradiating the lesion or tumor. In some embodiments, the immune modulating agent is administered greater than or greater than about 30 minutes, 1 hour, 2 hours, 6 hours, 12 hours, 24 hours, 48 hours, 96 hours, one week, two weeks, three weeks or one month prior to irradiating the tumor.

In some embodiments, the provided methods include continued administration of the immune modulating agent subsequent to the irradiation three times a week, two times a week, once every week, once every two weeks, once every three weeks or once a month.

Provided in some embodiments is a method of treating a tumor in a subject that includes: a) administering to a subject an immune modulating agent; b) administering to the subject a therapeutically effective amount of a conjugate that includes a phthalocyanine dye linked to a targeting molecule capable of binding to a molecule on the surface of a cell present in the microenvironment of a tumor; and c) greater than 12 hours after administering the immune modulating agent, irradiating the tumor at a wavelength that renders the conjugate cytotoxic, thereby treating the tumor. In some embodiments, the immune modulating agent is administered greater than or greater than about 24 hours, 48 hours, 96 hours, one week, two weeks, three weeks or one month prior to irradiating the tumor.

In some embodiments, the conjugate binds to a protein on the surface of a cell present in the microenvironment of the tumor. In some embodiments of the provided methods, step c) of irradiating the tumor is carried out either i) after administration of the immune modulating agent and after administration of the conjugate or ii) only after administration of the conjugate.

In some embodiments, the conjugate is administered prior to, simultaneously or subsequently to administration of the immune-modulating agent. In some embodiments, the conjugate is administered after administering the immune modulating agent but prior to irradiating the tumor. In some embodiments, the conjugate is administered from or from about 12 hours to 48 hours prior to irradiating the tumor and the immune modulating agent is administered from or from about 12 hours to about 1 month prior to irradiating the tumor.

In some embodiments, the immune modulating agent is an immune checkpoint inhibitor. In some embodiments, the immune checkpoint inhibitor specifically binds a molecule selected from among CD25, PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28 and VISTA. In some embodiments, the immune checkpoint inhibitor is and antibody or antigen-binding fragment, a small molecule or a polypeptide. In some embodiments, the immune checkpoint inhibitor is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MEDI4736, MOXR0916, AMP-224, and MSB001078C, or is an antigen-binding fragment thereof of any of the foregoing.

In some embodiments, the immune modulating agent that is a demethylating agent that upregulates expression of a tumor associated antigen (TAA) or is a cytokine.

In some embodiments, the provided methods include continued administration of the immune modulating agent subsequent to the irradiation three times a week, two times a week, once every week, once every two weeks, once every three weeks or once a month.

Provided in some embodiments is a method of treating a tumor in a subject that includes: a) administering to a subject an immune modulating agent that enhances the expression of a molecule on the surface of a cell present in the microenvironment of the tumor; b) administering to the subject a therapeutically effective amount of a conjugate that includes a phthalocyanine dye linked to a targeting molecule that is capable of binding to the cell surface molecule; and c) greater than 5 minutes after administering the conjugate, irradiating the tumor at a wavelength that renders the conjugate cytotoxic, thereby treating the tumor.

In some embodiments, the immune modulating agent is a cytokine or is an agent that induces increased expression of a cytokine in the tumor microenvironment. In some embodiments, the cytokine is interferon gamma.

In some embodiments, the molecule on the surface of the cells is selected from CD25, PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28 and VISTA. In some embodiments, the molecule on the surface of the cell is PD-L1.

In some embodiments, the targeting molecule is an immune checkpoint inhibitor.

In some embodiments, the targeting molecule is an antibody or antibody fragment, a small molecule or a polypeptide. In some embodiments, the targeting molecule is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MED14736, MOXR0916, AMP-224, and MSB001078C, or is an antigen-binding fragment thereof of any of the foregoing.

Provided in some embodiments is a method of treating a tumor in a subject that includes: a) administering to a subject a conjugate that includes a phthalocyanine dye linked to a targeting molecule capable of binding a cell surface molecule on a cell in the microenvironment of the tumor; b) greater than 5 minutes after administering the conjugate, irradiating the tumor at a wavelength that renders the conjugate cytotoxic, wherein the treatment of the tumor with the conjugate followed by light irradiation increases the presence of immunosuppressive cells in the tumor or increases the expression of immunosuppressive markers at the tumor; and c) administering to the subject a therapeutically effective amount of an immune modulating agent capable of reducing the amount or activity of immunosuppressive cells in the tumor or capable of blocking the activity of the immunosuppressive marker or reducing the activity of a tumor promoting cell in the tumor or capable of blocking the activity of the tumor promoting marker.

In some embodiments, the phthalocyanine dye is a first dye and the immune modulating agent includes a conjugate that includes a second phthalocyanine dye conjugated to an immune modulating agent capable of binding to the immunosuppressive cell or a tumor promoting cell. In some embodiments, the first and second phthalocyanine dye is the same or different.

In some embodiments, the immune modulating agent is an immune checkpoint inhibitor. In some embodiments, the immune modulating agent specifically binds a molecule selected from among CD25, PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28 and VISTA.

In some embodiments, the immune modulating agent is an antibody or antibody fragment, a small molecule or a polypeptide.

In some embodiments, the immune modulating agent is not an anti-CTLA4 antibody.

In some embodiments, the immune modulating agent is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MED14736, MOXR0916, AMP-224, and MSB001078C, or is an antigen-binding fragment thereof of any of the foregoing.

Provided in some embodiments is a method of treating a tumor in a subject that includes: a) administering to a subject a conjugate that includes a phthalocyanine dye linked to a targeting targeting molecule capable of binding to a molecule on the surface of a cell present in the microenvironment of the tumor; b) greater than 5 minutes after administering the conjugate, irradiating the tumor at a wavelength that renders the conjugate cytotoxic, wherein the treatment of the tumor with the conjugate followed by light irradiation primes activation of immune cells; and c) administering to the subject a therapeutically effective amount of an immune modulating agent capable of increasing the activity of the immune cell.

In some embodiments, the immune cell is an antigen presenting cell. In some embodiments, the immune cell is a dendritic cell. In some embodiments, the immune modulating agent is selected from among GM-CSF, CpG-ODN (CpG oligodeoxynucleotides), lipopolysaccharide (LPS), monophosphoryl lipid A (MPL), alum, recombinant *Leishmania* polyprotein, imiquimod, MF59, poly I:C, poly A:U, type 1 IFN, Pam3Cys, Pam2Cys, complete freund's adjuvant (CFA), alpha-galactosylceramide, RC-529, MDF2β, Loxoribine, anti-CD40 agonist, SIRPa antagonist, AS04, AS03, Flagellin, Resiquimod, DAP (diaminopimelic acid), MDP (muramyl dipeptide) and CAF01 (cationic adjuvant formulation-01). In some embodiments, the immune modulating agent is a Toll-like receptor (TLR) agonist, an adjuvant or a cytokine. In some embodiments, the immune modulating agent is a TLR agonist and the TLR agonist is TLR agonist is a TLR4 agonist, a TLR7 agonist, a TLR8 agonist, or a TLR9 agonist. In some embodiments, the TLR agonist is selected from among triacylated lipoprotein, diacylated lipopeptide, lipoteichoic acid, peptidoglycan, zymosan, Pam3CSK4, dsRNA, polyI:C, Poly G10, Poly G3, CpG, 3M003, flagellin, lipopolysaccharide (LPS) *Leishmania* homolog of eukaryotic ribosomal elongation and initiation factor 4a (LeIF), MEDI9197, SD-101, and imidazoquinoline TLR agonists.

In some embodiments, the immune modulating agent is a cytokine and the cytokine is IL-4, TNF-α, GM-CSF or IL-2. In some embodiments, the immune modulating agent is administered prior to, simultaneously with or after the irradiation. In some embodiments, the immune modulating agent is administered no more than 5 minutes, 30 minutes, 60 minutes, 2 hours, 6 hours, 12 hours or 24 hours after the irradiation. In some embodiments, the immune modulating agent is administered no more than 5 minutes, 30 minutes, 60 minutes, 2 hours, 6 hours, 12 hours or 24 hours before the irradiation.

In some embodiments, the targeting molecule binds to molecule or protein directly or indirectly. In some embodiments, the targeting molecule is a second binding molecule that binds to a first binding molecule, said first binding molecule being capable of binding to the molecule or protein. In some embodiments, the targeting molecule is a secondary antibody.

In some embodiments, the phthalocyanine dye has a maximum absorption wavelength from or from about 600 nm to about 850 nm.

In some embodiments, the phthalocyanine dye is covalently or non-covalently linked to the targeting molecule. In some embodiments, the phthalocyanine dye includes a linker that includes a reactive group for attachment of the dye to the targeting molecule.

In some embodiments, the phthalocyanine dye includes the formula:

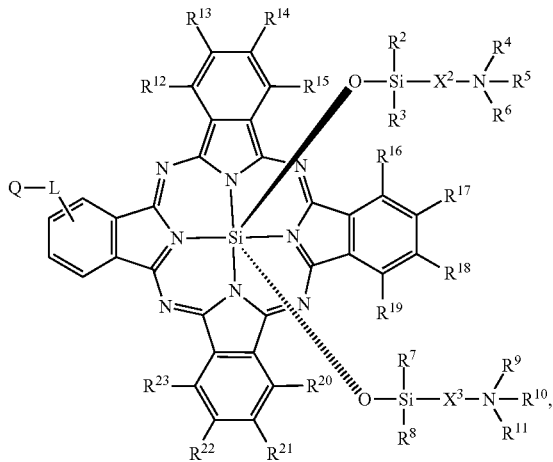

wherein:

L is a linker;

Q is a reactive group for attachment of the dye to the targeting molecule;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^1$ includes a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from hydrogen, halogen, optionally substituted alkylthio, optionally substituted alkylamino and optionally substituted alkoxy; and $X^2$ and $X^3$ are each independently $C_1$-$C_{10}$ alkylene, optionally interrupted by a heteroatom.

In some embodiments, the phthalocyanine dye includes the formula:

wherein:

$X^1$ and $X^4$ are each independently a $C_1$-$C_{10}$ alkylene optionally interrupted by a heteroatom;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ includes a water soluble group; and $R^{16}$, $R^{17}$, $R^{18}$ and $R^{19}$ are each independently selected from hydrogen, halogen, optionally substituted alkylthio, optionally substituted alkylamino and optionally substituted alkoxy.

In some embodiments, the phthalocyanine dye includes IRDye 700DX (IR700).

In some embodiments, the conjugate is administered at a dose from or from about 50 mg/m² to about 5000 mg/m², from about 250 mg/m² to about 2500 mg/m², from about 750 mg/m² to about 1250 mg/m² or from about 100 mg/m² to about 1000 mg/m².

In some embodiments, the tumor is a cancer. In some embodiments, the cancer is a cancer located at the head and neck, breast, liver, colon, ovary, prostate, pancreas, brain, cervix, bone, skin, eye, bladder, stomach, esophagus, peritoneum, or lung. In some embodiments, the tumor is a sarcoma or carcinoma. In some embodiments, the tumor is a carcinoma that is a squamous cell carcinoma, basal cell carcinoma or adenocarcinoma. In some embodiments, the tumor is a carcinoma that is a carcinoma of the bladder, pancreas, colon, ovary, lung, breast, stomach, prostate, cervix, esophagus or head and neck.

In some embodiments, the tumor is irradiated at a wavelength of 600 nm to 850 nm at a dose of at least 1 J cm⁻² or at least 1 J/cm fiber length. In some embodiments, the tumor is irradiated at a wavelength of 690 nm±50 nm or at a wavelength of or about 690±20 nm.

In some embodiments, the method reduces the size or volume of the tumor by at least 30%, at least 40%, at least 50%, at least 60%, at least 70%, at least 80% at least 90% or more within one month of the irradiation compared to the size or volume of the tumor prior to the administration and irradiation.

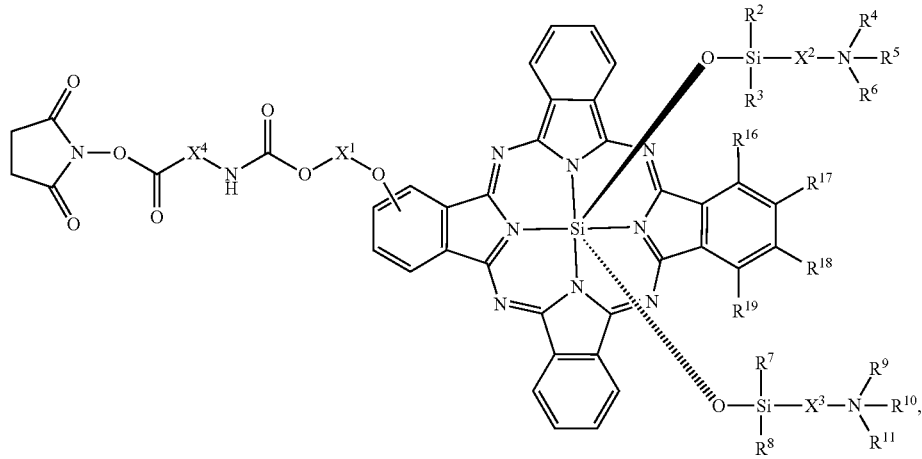

In some embodiments, the method of PIT treatment using the phthalocyanine dye conjugate, such as in accord with any of the methods above or provided herein, results in an improvement of a disorder- or cancer-related parameter in a population of treated subjects compared to a similarly situated population of subjects treated with the antibody or antigen-binding antibody fragment that is not conjugated. In some embodiments, the parameter is selected from one or more of: a) objective response rate (ORR); b) progression free survival (PFS); c) overall survival (OS); d) reduction in toxicity; e) tumor response; or f) quality of life.

In some embodiments, the parameter is improved by at least 10%, at least 20%, at least 30%, at least 40%, at least 50%, at least 60%, at least 70%, at least 80%, at least 90%, at least 100% or more.

In some embodiments, the method of PIT treatment using the phthalocyanine dye conjugate, such as in accord with any of the methods above or provided herein, results in an objective response rate (ORR) that is at least 15%, at least 25%, at least 50%, at least 55%, at least 60%, at least 65%, at least 70%, at least 75%, at least 80%, at least 85%, at least 90%, at least 95% or more in a population of treated subjects.

In some embodiments, the conjugate contains a phthalocyanine dye as a first dye and further contains a second fluorescent dye linked to the targeting molecule that is different than the first dye. In some embodiments, the second fluorescent dye exhibits one or more spectral properties selected from among fluorescent quantum yield in water, extinction coefficient, Stokes shift, absorption and emission at long wavelength and photostability that is greater compared to the corresponding spectral property of the first dye. In some embodiments, the lesion or tumor emits a fluorescence signal from the second fluorescent dye to effect detection of the presence of the conjugate at the lesion or tumor in the subject. In some embodiments, the provided method further includes imaging the lesion or tumor in the subject by irradiating or illuminating the tumor at a wavelength capable of being absorbed by the second dye.

In some embodiments, the first dye is IR700. In some embodiments, the second dye is not IR700. In some embodiments, the second dye is selected from among hydroxycoumarin, Cascade Blue, Dylight 405, Pacific Orange, Alexa Fluor 430, Fluorescein, Oregon Green, Alexa Fluor 488, BODIPY 493, 2.7-Diochlorofluorescien, ATTO 488, Chromeo 488, Dylight 488, HiLyte 488, Alexa Fluor 555, ATTO 550, BODIPY TMR-X, CF 555, Chromeo 546, Cy3, TMR, TRITC, Dy547, Dy548, Dy549, HiLyte 555, Dylight 550, BODIPY 564, Alexa Fluor 568, Alexa Fluor 594, Rhodamine, Texas Red, Alexa Fluor 610, Alexa Fluor 633, Dylight 633, Alexa Fluor 647, APC, ATTO 655, CF633, CF640R, Chromeo642, Cy5, Dylight 650, Alexa Fluor 680, IRDye 680, Alexa Fluor 700, Cy 5.5, ICG, Alexa Fluor 750, Dylight 755, IRDye 750, Cy7, Cy7.5, Alexa Fluor 790, Dylight 800, IRDye 800, Qdot® 525, Qdot® 565, Qdot® 605, Qdot® 655, Qdot® 705 and Qdot® 800.

In some embodiments, the first dye is IR700 and the conjugate contains 1 to 10 or 1 to 5 second dye molecules per targeting molecule.

In some embodiments, the second dye exhibits a Stokes shift that is greater than 15 nm, greater than 20 nm, greater than 30 nm, greater than 40 nm, greater than 50 nm, greater than 60 nm, greater than 70 nm, greater than 80 nm, greater than 90 nm or greater than 100 nm.

In some embodiments, the second dye has a quantum yield in water that is greater than 10%, greater than 15%, greater than 20% or greater than 25%, greater than 30%, greater than 40%, greater than 50% or greater.

In some embodiments, the second dye has an absorption and emission wavelength in the spectrum between or between about 650 nm and 950 nm, between or between about 700 nm and 1000 nm, or between or between about 1000 nm and 1700 nm.

In some embodiments, the first dye and second dye do not exhibit an overlapping emission and absorption spectra. In some embodiments, the second dye is selected from among ICG, IRDye 680, Alexa Fluor 750, Dylight 755, IRDye 750, Cy7.5, Alexa Fluor 790, Dylight 800 and IRDye 800. In some embodiments, the second dye is Alexa Fluor 488, IRDye 680, IRDye 800 or Dylight 755.

In some embodiments, the method further includes irradiating or illuminating the tumor at a wavelength capable of being absorbed by the second dye, thereby imaging the subject. In some embodiments, the irradiation or illumination of the tumor is performed with a device selected from among a hand-held ultraviolet lamp, a mercury lamp, a xenon lamp, a laser, a laser diode or an imaging device. In some embodiments, the LED imaging device contains a near-infrared (NIR) diode.

Provided in some embodiments is a composition containing a conjugate containing a phthalocyanine dye linked to an antibody or antigen-binding antibody fragment that binds to a molecule on the surface of a cell present in the microenvironment of a lesion, such as the tumor microenvironment. In some embodiments, the composition is formulated for single dosage administration of the conjugate in an amount that is between or between about 100 mg and 1200 mg. In some embodiments, the composition is formulated for single dosage administration of an amount between or between about 100 mg and 500 mg or between or between about 200 mg and 400 mg. In some embodiments, the composition is formulated for single dosage administration of an amount between or between about 500 mg and 1500 mg, 800 mg and 1200 mg or 1000 mg and 1500 mg.

In some embodiments, the volume of the composition is between or between about 10 mL and 500 mL or 50 mL and 250 mL. In some embodiments, the volume of the composition is at least 10 mL, 20 mL, 30 mL, 40 mL, 50 mL, 75 mL, 100 mL, 150 mL, 200 mL, 250 mL, 300 mL, 400 mL or 500 mL. In some embodiments, the volume of the composition is between or between about 10 mL and 1000 mL or 50 mL and 500 mL; or the volume of the composition is at least 10 mL, 20 mL, 30 mL, 40 mL, 50 mL, 75 mL, 100 mL, 150 mL, 200 mL, 250 mL, 300 mL, 400 mL, 500 mL or 1000 mL.

Provided in some embodiments is an article of manufacture, including a plurality of sealable containers, each individually containing a fraction of a single administration dose of a composition containing a conjugate containing a phthalocyanine dye linked to an antibody or antigen-binding antibody fragment that binds to a molecule on the surface of a cell present in the microenvironment of a lesion, such as the tumor microenvironment. In some embodiments, the combined amount of the conjugate in the plurality of sealable containers is between or between about 100 mg and 1500 mg, or 100 mg and 1200 mg. In some embodiments, the article of manufacture contains packaging material and a label or package insert containing instructions for combining the contents of the plurality of vials to prepare a single dosage formulation of the composition.

In some embodiments, the combined amount of the conjugate in the plurality of sealable containers is between or between about 100 mg and 1200 mg. In some embodiments, the combined amount of the conjugate in the plurality of sealable container is between or between about 100 mg and 500 mg, between or between about 200 mg and 400 mg, between or between about 500 mg and 1500 mg, between or between about 800 mg and 1200 mg or between or between about 1000 mg and 1500 mg.

In some embodiments, the lesion is a tumor.

Provided in some embodiments is a conjugate, that includes a phthalocyanine dye linked to an antibody or antigen-binding fragment that is an immune modulating agent. In some embodiments, the immune modulating agent is an immune checkpoint inhibitor.

In some embodiments, the immune modulating agent is an antibody or antigen binding fragment that binds to the surface of a tumor, tumor cell or cancer cell. In some embodiments, the immune modulating agent specifically binds a molecule selected from among CD25, PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28 and VISTA. In some embodiments the immune modulating agent is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MED14736, MOXR0916, AMP-224, and MSB001078C, or is an antigen-binding fragment thereof of any of the foregoing. In some embodiments, the immune modulating agent is an antibody or antibody fragment that binds to PD-L1.

In some embodiments, the immune modulating agent is an antibody selected from BMS-935559, MEDI4736, MPDL3280A and MSB0010718C, or an antigen-binding fragment thereof.

Provided in some embodiments is a conjugate that contains a targeting molecule linked to at least a first and second fluorescent dye. In some embodiments, the first fluorescent dye is a phthalocyanine dye capable of exhibiting phototoxicity.

In some embodiments, the conjugate has the formula:

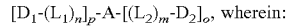

[D$_1$-(L$_1$)$_n$]$_p$-A-[(L$_2$)$_m$-D$_2$]$_o$, wherein:

A is a targeting molecule that can bind to a molecule on the surface of a cell;

L$_1$ and L$_2$ are each an independently selected linker, which can be the same or different;

n and m are independently 1 or 2;

D$_1$ is a first dye that is the phthalocyanine dye capable of exhibiting phototoxicity;

D$_2$ is a second dye that is a fluorescent dye, wherein D$_2$ is different than D$_1$;

p is 1 to 10; and o is 1 to 10.

In some embodiments, the targeting molecule is an antibody or an antigen-binding antibody fragment.

In some embodiments, the cell surface molecule contains an antigen, a polypeptide, a lipid, or a carbohydrate or a combination of these molecules.

In some embodiments, the cell surface molecule is selected from among ACTHR, endothelial cell Anxa-1, aminopetidase N, anti-IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CD133, CD7, CD15, CD34, CD44, CD206, CD271, CEA (CarcinoEmbryonic Antigen), CGRP, chemokine receptors, cell-surface annexin-1, cell-surface plectin-1, Cripto-1, CRLR, CXCR2, CXCR4, DCC, DLL3, E2 glycoprotein, EGFR, EGFRvIII, EMR1, Endosialin, EP2, EP4, EpCAM, EphA2, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like) like), G-protein coupled receptors of the Family C (Metabotropic Glutamate Receptor-like), GD2, GP100, GP120, Glypican-3, hemagglutinin, Heparin sulfates, HER1, HER2, HER3, HER4, HMFG, HPV 16/18 and E6/E7 antigens, hTERT, IL11-R, IL-13R, ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/HABP1), p75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family (e.g., P2X1-5), mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP (e.g., TRPV1-6, TRPA1, TRPC1-7, TRPM1-8, TRPP1-5, TRPML1-3), TSH receptor, VEGF receptors (VEGFR1 or Flt-1, VEGFR2 or FLK-1/KDR, and VEGF-3 or FLT-4), voltage-gated ion channels, VPAC1, VPAC2, Wilms tumor 1, Y1, Y2, Y4, and Y5.

In some embodiments, the cell surface molecule is selected from among HER1/EGFR, HER2/ERBB2, CD20, CD25 (IL-2Ra receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, and SK-1 antigen.

In some embodiments, the cell surface molecule is selected from among CD25, PD-1 (CD279), PD-L1 (CD274, B7-H1), PD-L2 (CD273, B7-DC), CTLA-4, LAG3 (CD223), TIM3 (HAVCR2), 4-1BB (CD137, TNFRSF9), CXCR2, CXCR4 (CD184), CD27, CEACAM1, Galectin 9, BTLA, CD160, VISTA (PD1 homologue), B7-H4 (VCTN1), CD80 (B7-1), CD86 (B7-2), CD28, HHLA2 (B7-H7), CD28H, CD155, CD226, TIGIT, CD96, Galectin 3, CD40, CD40L, CD70, LIGHT (TNFSF14), HVEM (TNFRSF14), B7-H3 (CD276), Ox40L (TNFSF4), CD137L (TNFSF9, GITRL), B7RP1, ICOS (CD278), ICOSL, KIR, GAL9, NKG2A (CD94), GARP, TL1A, TNFRSF25, TMIGD2, BTNL2, Butyrophilin family, CD48, CD244, Siglec family, CD30, CSF1R, MICA (MHC class I polypeptide-related sequence A), MICB (MHC class I polypeptide-related sequence B), NKG2D, KIR family (Killer-cell immunoglobulin-like receptor, LILR family (Leukocyte immunoglobulin-like receptors, CD85, ILTs, LIRs), SIRPA (Signal regulatory protein alpha), CD47 (IAP), Neuropilin 1 (NRP-1), a VEGFR, and VEGF.

In some embodiments, the targeting molecule is an antibody or an antigen-binding fragment that is selected from among cetuximab, panitumumab, zalutumumab, nimotuzumab, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Basiliximab, nivolumab, pembrolizumab, pidilizumab, MK-3475, BMS-936559, MPDL3280A, ipilimumab, tremelimumab, IMP321, BMS-986016, LAG525, urelumab, PF-05082566, TRX518, MK-4166, dacetuzumab, lucatumumab, SEA-CD40, CP-870, CP-893, MEDI6469, MEDI6383, MEDI4736, MOXR0916, AMP-224, PDR001, MSB0010718C, rHIgM12B7, Ulocuplumab, BKT140, Varlilumab (CDX-1127), ARGX-110, MGA271, lirilumab (BMS-986015, IPH2101), IPH2201, AGX-115, Emactuzumab, CC-90002 and MNRP1685A or is an antigen-binding fragment thereof.

In some embodiments, the targeting molecule is not or does not include a nanocarrier. In some embodiments, the targeting molecule is not or does not include a virus-like particle, a nanoparticle, a liposome, a quantum dot, or a combination thereof.

wherein:
L is a linker;
Q is a reactive group for attachment of the dye to the targeting molecule;
$R^2$, $R^3$, $R^7$, and $R^8$ are each independently selected from optionally substituted alkyl and optionally substituted aryl;
$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ contains a water soluble group;
$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from hydrogen, halogen, optionally substituted alkylthio, optionally substituted alkylamino and optionally substituted alkoxy; and
$X^2$ and $X^3$ are each independently $C_1$-$C_{10}$ alkylene, optionally interrupted by a heteroatom.

In some embodiments, the first dye that is a phthalocyanine dye contains the formula:

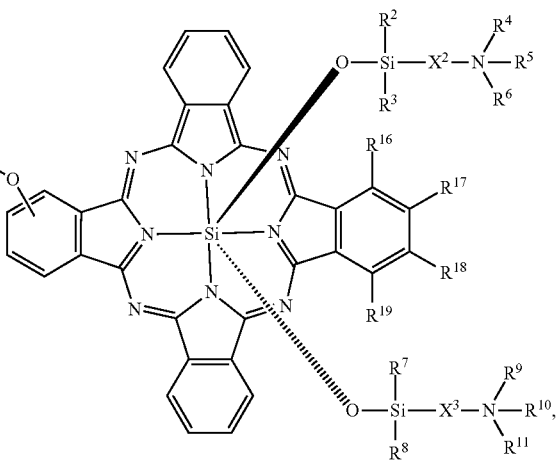

In some embodiments, the first dye that is a phthalocyanine dye that has a maximum absorption wavelength from or from about 600 nm to about 850 nm.

In some embodiments, the first dye that is a phthalocyanine dye contains the formula:

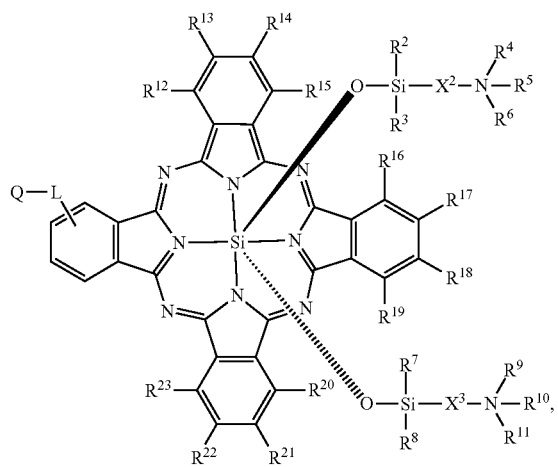

wherein:
$X^1$ and $X^4$ are each independently a $C_1$-$C_{10}$ alkylene optionally interrupted by a heteroatom;
$R^2$, $R^3$, $R^7$, and $R^8$ are each independently selected from optionally substituted alkyl and optionally substituted aryl;
$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ contains a water soluble group; and
$R^{16}$, $R^{17}$, $R^{18}$ and $R^{19}$ are each independently selected from hydrogen, halogen, optionally substituted alkylthio, optionally substituted alkylamino and optionally substituted alkoxy.

In some embodiments, the first dye that is a phthalocyanine dye contains IRDye 700DX (IR700).

In some embodiments, the second fluorescent dye exhibits one or more spectral properties selected from among fluorescent quantum yield in water, extinction coefficient, Stokes shift, absorption and emission at long wavelength and photostability that is greater compared to the corresponding spectral property of the first dye.

In some embodiments, the second dye is not IR700. In some embodiments, the second dye is selected from among hydroxycoumarin, Cascade Blue, Dylight 405, Pacific Orange, Alexa Fluor 430, Fluorescein, Oregon Green, Alexa Fluor 488, BODIPY 493, 2.7-Diochlorofluorescien, ATTO 488, Chromeo 488, Dylight 488, HiLyte 488, Alexa Fluor 555, ATTO 550, BODIPY TMR-X, CF 555, Chromeo 546, Cy3, TMR, TRITC, Dy547, Dy548, Dy549, HiLyte 555, Dylight 550, BODIPY 564, Alexa Fluor 568, Alexa Fluor 594, Rhodamine, Texas Red, Alexa Fluor 610, Alexa Fluor 633, Dylight 633, Alexa Fluor 647, APC, ATTO 655, CF633, CF640R, Chromeo642, Cy5, Dylight 650, Alexa Fluor 680, IRDye 680, Alexa Fluor 700, Cy 5.5, ICG, Alexa Fluor 750, Dylight 755, IRDye 750, Cy7, Cy7.5, Alexa Fluor 790, Dylight 800, IRDye 800, Qdot® 525, Qdot® 565, Qdot® 605, Qdot® 655, Qdot® 705 and Qdot® 800.

In some embodiments, the first dye is IR700 and the conjugate contains 1 to 10 or 1 to 5 second dye molecules per targeting molecule.

In some embodiments, the second dye exhibits a Stokes shift that is greater than 15 nm, greater than 20 nm, greater than 30 nm, greater than 40 nm, greater than 50 nm, greater than 60 nm, greater than 70 nm, greater than 80 nm, greater than 90 nm or greater than 100 nm.

In some embodiments, the second dye has a quantum yield in water that is greater than 10%, greater than 15%, greater than 20% or greater than 25%, greater than 30%, greater than 40%, greater than 50% or greater.

In some embodiments, the second dye has an absorption and emission wavelength in the spectrum between or between about 650 nm and 950 nm, between or between about 700 nm and 1000 nm, between or between about 1000 nm and 1700 nm.

In some embodiments, the first dye and second dye do not exhibit an overlapping emission and absorption spectra.

In some embodiments, the second dye is selected from among ICG, IRDye 680, Alexa Fluor 750, Dylight 755, IRDye 750, Cy7.5, Alexa Fluor 790, Dylight 800 and IRDye 800. In some embodiments, the second dye is Alexa Fluor 488, IRDye 680, IRDye 800 or Dylight 755.

Provided in some embodiments is a composition, containing any of the conjugates described herein. In some embodiments, the composition further contains a pharmaceutically acceptable excipient.

Provided in some embodiments is a method of treating a disease or condition in a subject that includes: a) administering to the subject a therapeutically effective amount of any of the conjugates or compositions described herein, wherein the conjugate binds to a cell present in the microenvironment of a lesion associated with a disease or condition; and b) after administering the conjugate, irradiating the lesion at one or more wavelengths to induce phototoxic activity of the conjugate, thereby treating the disease or condition.

Provided in some embodiments is a method of treating a disease or a condition, such as a tumor in a subject using photoimmunotherapy (PIT), that includes administering to the subject a therapeutically effective amount of any of the conjugates or compositions described herein. In some embodiments, the method includes irradiating the tumor at a wavelength of 660 nm to 740 nm at a dose of at least 1 J cm$^{-2}$ or 1 J/cm of fiber length, thereby treating the disease or condition in the subject.

Provided in some embodiments is a method of treating a disease or condition in a subject that includes: a) administering to the subject a therapeutically effective amount of of any of the conjugates or compositions described herein, wherein the conjugate binds to a cell present in the microenvironment of a lesion associated with a disease or condition; and b) after administering the conjugate, irradiating the lesion at one or more wavelengths to induce phototoxic activity of the first dye of the conjugate and a fluorescent signal of the second dye of the conjugate.

In some embodiments, the provided methods include irradiating the lesion at a wavelength that is from or from about 400 to about 900 nm at a dose of at least 1 J cm$^{-2}$ or 1 J/cm of fiber length. In some embodiments, the provided methods include irradiating the lesion with a single wavelength. In some embodiments, the provided methods include irradiating the lesion at two different wavelengths, simultaneously or sequentially, wherein one wavelength induces the phototoxic activity and the other wavelength induces the fluorescent signal.

In some embodiments, the disease or condition is a tumor.

In some embodiments, the provided methods include irradiating the tumor at a wavelength of 660 nm to 740 nm and at a dose of at least 1 J cm$^{-2}$, thereby treating the tumor in the subject.

In some embodiments, the tumor is a cancer. In some embodiments, the cancer is a cancer located at the head and neck, breast, liver, colon, ovary, prostate, pancreas, brain, cervix, bone, skin, eye, bladder, stomach, esophagus, peritoneum, or lung. In some embodiments, the tumor is a sarcoma or carcinoma. In some embodiments, the tumor is a carcinoma that is a squamous cell carcinoma, basal cell carcinoma or adenocarcinoma. In some embodiments, the tumor is a carcinoma that is a carcinoma of the bladder, pancreas, colon, ovary, lung, breast, stomach, prostate, cervix, esophagus or head and neck.

In some embodiments, prior to administration of the conjugate, the targeting molecule is administered to the subject. In some embodiments, the targeting molecule is administered up to 96 hours prior to administration of the conjugate. In some embodiments, the targeting molecule is administered at a dose within a range from or from about 10 mg/m$^2$ to about 500 mg/m$^2$. In some embodiments, the targeting molecule is an antibody or antigen binding fragment, such as cetuximab. In some examples, cetuximab is administered to the subject prior to the administration of the conjugate.

BRIEF DESCRIPTION OF THE DRAWINGS

FIG. 5A shows cells death after PIT using single-labeled panitumumab-IR700 conjugate. FIG. 5B shows cell death after PIT using a dual-labeled panitumumab-IR700-Alexa-488 conjugate.

DETAILED DESCRIPTION

I. Photoimmunotherapy Methods

Figure 1:
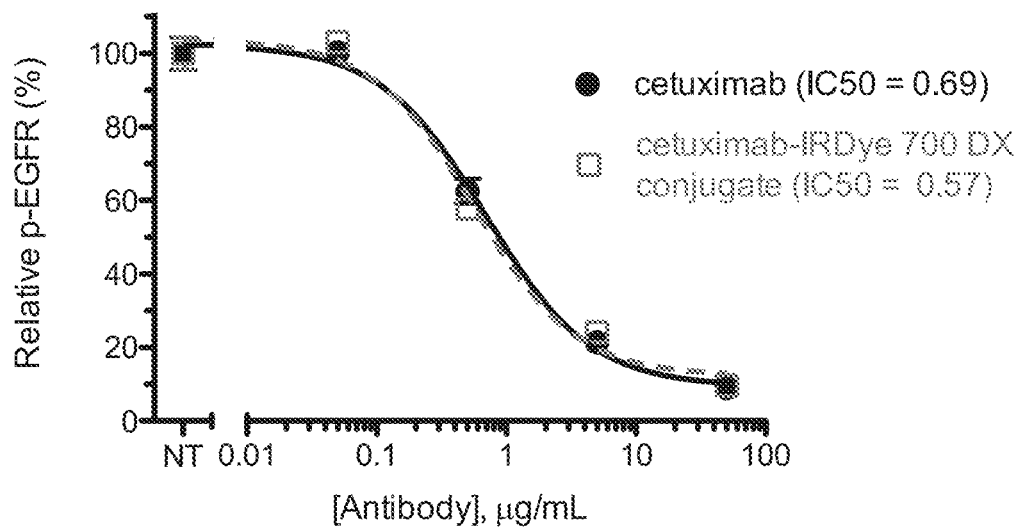
FIG. 1 shows the dose response curves of cetuximab and cetuximab-IRDye 700DX conjugate for the inhibition of EGFR phosphorylation in A431 cells.

Provided herein are conjugates, compositions, combinations and methods related to photoimmunotherapy (PIT). Photoimmunotherapy is a molecular targeted therapy that utilizes a target-specific photosensitizer based on phthalocyanine dye, such as a near infrared (NIR) phthalocyanine dye (e.g., IR700), conjugated to a targeting molecule targeting a protein, such as a cell surface protein on a cell in a disease or condition, such as a cell in a tumor. For example, in some cases a phthalocyanine dye-conjugate used in photoimmunotherapy can include conjugation to a monoclonal antibody (mAb) targeting a cell surface protein receptor or receptor expressed on a cell in the environment of a disease lesion, such as a tumor microenvironment, which can include tumor cells and other infiltrating cells. In some embodiments, activation of the dye-conjugate by irradiation with absorbing light, such as NIR light, excites the photosensitizer and results in cell killing, thereby reducing or eliminating the lesion (e.g., tumor) and treating the disease or condition. In some cases, the use of light in the NIR range leads to deeper tissue penetration resulting in successful eradication of tumors after only a single dose of external NIR light irradiation.

Generally, targeted phototoxicity appears to be primarily dependent on binding of the dye-conjugate to the cell membrane via the specific targeting targeting molecule (e.g., a macromolecule, such as an antibody). For example, studies using an exemplary antibody-IR700 molecule indicate that the conjugate must be bound to the cellular membrane to be active, and that cell killing does not require intracellular localization to be effective (see, e.g., U.S. Pat. No. 8,524,239 and U.S. published application No. US20140120119). Photo-activation of the conjugate-bound cells results in rapid cell death and necrosis.

Typically, PIT results in cell death primarily of those cells to which the phthalocyanine-dye conjugate, such as IR700-antibody conjugate, binds after the cells are irradiated with NIR, while cells that do not express the cell surface protein recognized by the targeting molecule (e.g., antibody) are not killed in significant numbers. Thus, because the therapy is targeted specifically to disease cells, such as cells in a tumor, its effects are highly selective to disease tissue compared to healthy tissue or cells. For example, although a targeted photosensitizer can be distributed throughout the body, it is only active where intense light is applied, reducing the likelihood of off-target effects. This is in contrast to non-PIT-based methods in which the activity of similar therapeutic targeting molecules (e.g., therapeutic antibodies) that are not conjugated to a photosensitizer (e.g., IR700) cannot be localized, thereby resulting in significant risks of off-target side effects. In some embodiments, the phototoxic agent is a phthalocyanine dye-targeting molecule conjugate. In some embodiments, the phthalocyanine dye is IR700.

In some embodiments, the provided methods involve administering the phthalocyanine dye-targeting molecule conjugate (e.g., IR700-antibody conjugate) in a dosage amount to achieve an exposure that is far lower than the exposure that would otherwise be required to achieve a therapeutic effect of the targeting molecule (e.g., antibody) that is not conjugated to a phthalocyanine dye. Since PIT requires binding of the conjugated targeting molecule (e.g., antibody) to a cell surface protein to mediate cell killing, it was believed that receptor occupancy would be a factor that would be correlated with the extent of PIT activity. Thus, it was believed that a similar, or even higher, systemic exposure of the conjugate would be necessary to ensure exposure at the site of the lesion (e.g., tumor) to achieve sufficient cell killing as would be required to achieve a clinically acceptable therapeutic effect of the targeting molecule (e.g., antibody) that was not so conjugated (i.e. not conjugated to the photosensitizer, e.g., IR700). For example, the dose of Erbitux® (cetuximab) approved by the Food and Drug Administration (FDA) to treat Head and Neck cancer is an initial dose of 400 mg/m$^2$ followed by a weekly administration of 250 mg/m$^2$. The average systemic exposure (AUC, e.g., $AUC_{0-inf}$ or AUC[0-inf]) in a sample patient population resulting from single dosage administration of Erbitux at 400 mg/m$^2$ is about 24,620 µg*h/mL and the total systemic exposure for a one (1)-month treatment (initial dose of 400 mg/m$^2$ followed by weekly administration of 250 mg/m$^2$) is estimated to be about 60,056 µg*h/mL (cumulative systemic exposures of the four weekly doses in 1 month, 1×24,620+ 3×11,812 µg*h/mL) (Fracasso et al. (2007) Clin. Cancer. Res., 13:986).

It is found herein, however, that cell killing by PIT could be observed following single dosage administration of an amount of cetuximab-IR700 conjugate that achieved a mean systemic exposure of only about 1810 µg/mL*h ($AUC_{0-inf}$) or 770+/−47.5 ($AUC_{0-24}$) in a sample patient population. This amount is up to or about 13.6-fold than the systemic exposure observed following the clinical therapeutic doses of Erbitrux® at 400 mg/m$^2$ described above. Further, as shown in Example 2, the results showed that the average systemic exposure ($AUC_{0-24}$) in a sample patient population even at a higher dose of 640 mg/m$^2$ was approximately 15% of the AUC for 400 mg/m$^2$ Erbitux® (3,690 vs. 24,740 µg/mL*h, respectively). The results further showed that in patients with head and neck cancer (which included patients that had failed other treatments), there was a 100% objective response rate (ORR) to the single dosage treatment (all patients exhibited a complete or partial response to the treatment), demonstrating a rapid and robust response that was surprising considering the low systemic exposure. By comparison, the ORR of subjects treated with Erbitux® monotherapy is usually about 15% or below, even with the multiple doses required for continuous exposure.

Further, most treatments with Erbitux® involve combination therapy with one or more chemotherapeutic or other anti-cancer treatments. As an example, in one reported study, the increase of ORR by cetuximab in combination with chemotherapy compared to chemotherapy alone is only about 16%, which is similar to the ORR provided by cetuximab monotherapy (see, e.g., Specenier and Vermorken (2013) Biologics, 7:77-90).

Thus, the provided methods are based on observations that the potency of a phthalocyanine dye-targeting molecule conjugate (e.g., IR700-antibody conjugate) for mediating PIT and cell killing is sufficiently high even when the systemic exposure of the conjugate is low. Thus, the provided methods include administration of the conjugate at doses that achieve a systemic exposure that is a fraction of the exposure of a clinical dose in humans of the corresponding therapeutictargeting molecule (e.g., therapeutic antibody) when it is not so conjugated to a phthalocyanine dye (e.g., IR700). In some embodiments, the clinical dose in humans of a therapeutic molecule is a dose as described at the label approved for commercialization by regulatory agencies (e.g. FDA, EMA, PDMA). In some embodiments, the low systemic exposure achieved by such doses of the phthalocyanine dye-targeting molecule conjugate means that the systemic exposure of the targeting molecule is not sufficiently high to exhibit pharmacologic activity, unless PIT is induced by exposure of the conjugate to light. Since irradiation with a dose of light can be localized to the disease lesion (e.g., tumor), the provided methods can achieve selective cell killing only of the disease lesion (e.g., tumor) while avoiding unwanted or undesired off-target activity.

Besides the potency of the response provided by the PIT methods provided herein, the provided methods also are particularly advantageous for treating disease or conditions (e.g., tumors) in which existing therapies, such as existing antibody therapies, are prone to result in adverse off-target side effects. For example, in some cases, it is difficult to achieve strong anti-cancer activity in the range of safety using therapies involving immune modulating agents. In some cases, this is because such immune modulating agents inhibit (or enhance) mechanisms that are the same mechanisms in which our body uses to fight autoimmunity. As a result, in many cases, dosing with immune modulating agents can result in significant therapeutic side effects. For safety of many immune modulating agents (and other therapeutic antibodies), the acceptable doses compromise therapeutic efficacy, must be administered in a dosage cycle to achieve or maintain a continuous threshold systemic exposure and/or must be administered in combination with other chemotherapeutic or anti-cancer agents that risk even greater adverse side effects. The provided methods solve these problems because PIT-based conjugates containing therapeutic targeting molecules, including immune modulating agents and other anti-tumor antibody molecules, can be administered at doses that avoid or minimize high systemic exposure, while also permitting selective cell killing at the site of the disease or lesion. Thus, the advantage of low dosing and/or low systemic exposure is significant for achieving safety.

In some embodiments, the fluorescent properties of the phthalocyanine dye also permits monitoring of the PIT therapy using any of a number of imaging or other method capable of detecting fluorescent signal. In some embodiments, evaluation of fluorescence, such as by imaging, can be used to monitor the upload or presence of the conjugate at the lesion (e.g., tumor) prior to PIT. In some embodiments, evaluation of fluorescence, such as by imaging, can be used to illuminate the lesion (e.g., tumor) to ensure PIT is directed at the site of the lesion (e.g., tumor). In some embodiments, evaluation of fluorescence can use used in the surgical setting where the margins of the lesion (e.g., tumor) can be visualized with fluorescence and then residual cancer cells in the margins can be killed with PIT.

In some embodiments, the conjugate further contains an additional fluorescent dye in addition to the phthalocyanine dye (e.g., IR700). For example, in some cases, IR700 is not among the most ideal dyes for imaging because, for example, it exhibits one or more spectral properties that may not be as suitable to ensure specific and efficient fluorescent labeling. In some aspects, other fluorophores commonly used to label proteins can exhibit a higher fluorescent quantum yield, a larger Stokes shift, a larger extinction coefficient at the excitation wavelength and/or a longer wavelength for deeper tissue penetration. Thus, in some embodiments, a dual-label conjugate is provided in which a targeting molecule (e.g., antibody or antigen-binding antibody fragment) is conjugated to a first dye that is a phthalocyanine dye (e.g., IR700) and also is conjugated to another second fluorescent dye that exhibits one or more properties from among a higher quantum yield, larger Stokes shift, larger extinction coefficient and/or longer wavelength that is improved or better as compared to the first dye. In some embodiments, the dual-label conjugate can be used to both monitor PIT therapy as described above and also to treat with PIT by activating the phthalocyanine dye, such as activating IR700. In some embodiments, the first and second dye are selected to minimize energy transfer between them, for example, the first and second dye are selected to avoid or minimize overlapping emission and absorption spectra.

In some embodiments, also provided herein are combination therapies for use in concert with photoimmunotherapy for treating a disease or condition in a subject. In some embodiments, the combination therapy can be used in methods for treating a tumor or cancer. In some embodiments, the combination of photoimmunotherapy and administration of an additional therapeutic agent, such as an immune modulating agent, anti-cancer agent or other agent, can increase the efficacy of treating the tumor, which, in some cases, can increase the therapeutic outcome or survival of the treated subject.

In some aspects, the provided combination therapy methods exploit the cytotoxic killing and/or lysis effects induced by PIT to enhance therapeutic outcomes in connection with tumor therapy. In particular aspects, one or more additional therapeutic agents can be administered to a subject having a tumor prior to completing PIT, which occurs by light irradiation to activate the phthalocyanine dye-conjugate. In some embodiments, the prior administration of the additional therapeutic agent can prime the tumor microenvironment to be more responsive to the PIT or to the additional therapeutic agent following the subsequent irradiation of the tumor.

For example, in one embodiment, an additional therapeutic agent can be an immune modulating agent, which, in some aspects, is administered prior to irradiation in order to enhance the immune response to PIT-induced tumor-associated agents released from lysed cells. In another example, an additional therapeutic agent can be an anti-cancer agent, which, in some aspects, is administered prior to irradiation to increase systemic availability of the anti-cancer agent to enhance delivery or uptake of the anti-cancer agent into the tumor area in response to changes in tumor permeability induced by PIT. In some embodiments, the enhanced therapeutic outcome from the combination therapy can result in an increased reduction in tumor size (e.g., tumor volume or weight) or an increased or longer survival of the subject compared to methods involving treatment with either therapy alone. In some embodiments, the therapeutic effect of the combination therapy can be synergistic compared to treatment methods involving treatment with the phthalocyanine dye-conjugate/PIT alone or treatments involving the additional therapeutic agent alone, such as treatments with only the immune modulating agent or only the anti-cancer agent.

A. Conjugates Containing a Phthalocyanine Dye and Targeting Molecule

The methods, compositions and combinations provided herein include a conjugate containing a photosensitizer, such as a phthalocyanine dye, for example IR700, and a targeting molecule (e.g., antibody or an antigen binding fragment of an antibody) that binds to a cell surface protein. In some embodiments, binding of the targeting molecule that is conjugated to the photosensitizer, such as a phthalocyanine dye (e.g., IR700), to the cell surface protein permits the targeting of the conjugate to cells involved in a disease or condition, such as a tumor or cancer, infection, inflammatory disease or condition, neuronal disease or condition or other diseases or conditions. In some embodiments, the targeted cells (e.g., cells expressing the cell surface protein capable of being bound by the targeting molecule) are present in the microenvironment of a lesion associated with the disease or condition, for example, the cells are present in a tumor microenvironment. In some embodiments, cell targeting increases the efficacy of PIT induced upon local irradiation of the lesion (e.g., tumor) of the subject at a wavelength that is absorbed by the phthalocyanine dye (e.g., a near-infrared (NIR) wavelength), since cell killing is selective to those cells in which the dye-targeting molecule conjugate is bound.

In some embodiments, the phthalocyanine dye conjugates for use in the combination therapy provided herein include a dye molecule conjugated to a targeting molecule via a linker group. In one aspect, the conjugate is of Formula I:

$$A\text{-}[(L)_n\text{-}D]_p \qquad (I)$$

wherein:
  A is a targeting molecule that can bind to cells or tissues;
  L is an independently selected linker for each p;
  n is 1 or 2;
  D is an independently selected hydrophilic phthalocyanine dye for each p; and
  p is independently 1, 2, 3, 4, 5 or greater than 5, such as up to 1000. For example, p can be 1 to 1000, such as generally 1 to 10 or 2 to 5.

In some embodiments, the phthalocyanine dye conjugate is produced by a method or process in which the phthalocyanine dye-targeting molecule conjugate, such as an IR700-targeting molecule (e.g., IR700-antibody) conjugate, is prepared under light-protected conditions. In some embodiments, the method includes 1) preparing or providing a phthalocyanine dye and a targeting molecule; 2) contacting the targeting molecule and phthalocyanine dye under conditions to generate the conjugate with minimal exposure of the dye; and 3) formulating, purifying and/or isolating the conjugate to produce a composition containing the drug substance, where one or more of the steps, such as in some cases all of the steps, are performed with minimal exposure of the dye or the conjugate containing the dye to environmental light. In some embodiments, the phthalocyanine dye-targeting molecule conjugate, such as an IR700-targeting molecule (e.g., IR700-antibody) conjugate, is a conjugate, or is prepared using methods for producing a conjugate, as described in U.S. Application No. 62/206,774, which is incorporated by reference herein.

1. Phathalocyanine Dye

Phthalocyanines are a group of photosensitizer compounds having the phthalocyanine ring system. Phthalocyanines are azaporphyrins that contain four benzoindole groups connected by nitrogen bridges in a 16-membered ring of alternating carbon and nitrogen atoms (i.e., $C_{32}H_{16}N_8$) which form stable chelates with metal and metalloid cations. In these compounds, the ring center is occupied by a metal ion (either a diamagnetic or a paramagnetic ion) that may, depending on the ion, carry one or two ligands. In addition, the ring periphery may be either unsubstituted or substituted. The synthesis and use of a wide variety of phthalocyanines in photodynamic therapy are described in International Publication WO 2005/099689 and U.S. Pat. No. 7,005,518.

In some embodiments, phthalocyanines strongly absorb red or near IR radiation with absorption peaks falling between about 600 nm and 810 nm, which, in some cases, allow deep penetration of tissue by the light. Phthalocyanines are generally photostable. This photostability is typically advantageous in pigments and dyes and in many of the other applications of phthalocyanines.

In some embodiments, the phthalocyanine dye is water soluble and contains a luminescent fluorophore moiety having at least one aqueous-solubilizing moiety. In some embodiments, the aqueous solubilizing moiety contains silicon. In some embodiments, the phthalocyanine dye has a core atom such as Si, Ge, Sn, or Al. In some embodiments, the phthalocyanine dye exists as a single core isomer, essentially free of other isomers. In some embodiments, the phthalocyanine dye contains a linker that has a reactive or activatable group, which is able to form a bond between the linker and targeting molecule. In some embodiments, the phthalocyanine dye can be tailored to fluoresce at a particular wavelength.

In some embodiments, the phthalocyanine dye contains a linker, i.e., is a linker-phthalocyanine dye moiety (L-D). In some embodiments, the linker contains a reactive group. In some embodiments, the phthalocyanine dye is of Formula Ia:

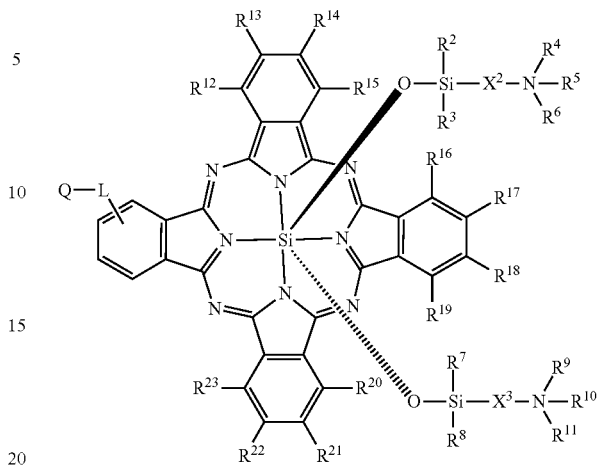

(Ia)

wherein

L is selected from a direct link, or a covalent linkage;

Q is a reactive group or an activatable group that can be part of the linker L, and is any group that can react to form a bond between L and the targeting molecule A;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$, if present, are each independently selected from hydrogen, optionally substituted alkyl, optionally substituted alkanoyl, optionally substituted alkoxycarbonyl, optionally substituted alkylcarbamoyl, or a chelating ligand, wherein at least one of $R^4$, $R^5$, $R^6$, $R^9$, $R^{10}$, and $R^{11}$ comprises a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each functional groups that can be independently selected from hydrogen, halogen, optionally substituted alkylthio, optionally substituted alkylamino or optionally substituted alkoxy;

or in an alternative embodiment, at least one of i) $R^{13}$ and $R^{14}$, and the carbons to which they are attached, or ii) $R^{17}$ and $R^{18}$, and the carbons to which they are attached, or iii) $R^{21}$ and $R^{22}$, and the carbons to which they are attached, join to form a fused ring; and $X^2$ and $X^3$ are each independently $C_1$-$C_{10}$ alkylene, optionally interrupted by a heteroatom.

In some embodiments, L is a covalent linkage. In some embodiments, the covalent linkage is linear or branched, cyclic or heterocyclic, saturated or unsaturated, having 1-60 atoms, such as 1-45 atoms or 1-25 atoms. In some cases, such atoms can be selected from C, N, P, O, and S. In some embodiments, L can have additional hydrogen atoms to fill valences (in addition to the 1-60 atoms). Generally, the linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds.

In some embodiments, L is of the formula —$R^1$—Y—$X^1$—$Y^1$—, wherein $R^1$ is a bivalent radical or direct link; Y and $Y^1$ are each independently selected from t a direct link, oxygen, an optionally substituted nitrogen, or sulfur; and $X^1$ is selected from t a direct link and $C_1$-$C_{10}$ alkylene optionally interrupted by an atom. Bivalent radicals include, but are not limited to, optionally substituted alkylene, optionally substituted alkyleneoxycarbonyl, optionally substituted alkylenecarbamoyl, optionally substituted alkylenesulfonyl, and optionally substituted arylene.

Exemplary $R^1$ substituents include, but are not limited to, optionally substituted alkylene, optionally substituted alkyleneoxycarbonyl, optionally substituted alkylenecarbamoyl, optionally substituted alkylenesulfonyl, optionally substituted alkylenesulfonylcarbamoyl, optionally substituted arylene, optionally substituted arylenesulfonyl, optionally substituted aryleneoxycarbonyl, optionally substituted arylenecarbamoyl, optionally substituted arylenesulfonylcarbamoyl, optionally substituted carboxyalkyl, optionally substituted carbamoyl, optionally substituted carbonyl, optionally substituted heteroarylene, optionally substituted heteroaryleneoxycarbonyl, optionally substituted heteroarylenecarbamoyl, optionally substituted heteroarylenesulfonylcarbamoyl, optionally substituted sulfonylcarbamoyl, optionally substituted thiocarbonyl, a optionally substituted sulfonyl, and optionally substituted sulfinyl.

In some embodiments, Q contains a reactive group for optional attachment to a material, such as a targeting molecule. As used herein, the term "reactive group" means a moiety on the compound that is capable of chemically reacting with the functional group on a different material (e.g., targeting molecule) to form a linkage, such as a covalent linkage. Typically, the reactive group is an electrophile or nucleophile that can form a covalent linkage through exposure to the corresponding functional group that is a nucleophile or electrophile, respectively. Alternatively, the reactive group is a photoactivatable group, and becomes chemically reactive only after illumination with light of an appropriate wavelength. Typically, the conjugation reaction between the reactive dye and the targeting molecule to be conjugated results in one or more atoms of the reactive group Q incorporated into a new linkage attaching the dye to the conjugated targeting molecule.

In some embodiments, Q contains a reactive group that is reactive with a carboxyl group, an amine, or a thiol group on the targeting molecule. Suitable reactive groups include, but are not limited to, an activated ester, an acyl halide, an alkyl halide, an anhydride, a carboxylic acid, a carbodiimide, a carbonate, a carbamate, a haloacetamide (e.g., iodoacetamide), an isocyanate, an isothiocyanate, a maleimide, an NHS ester, a phosphoramidite, a platinum complex, a sulfonate ester and a thiocyanate for optional attachment to the targeting molecule. In some embodiments, the reactive groups are reactive with a carboxyl group, an amine, or a thiol group on a targeting molecule. In some embodiments, the reactive group is a sulfhydryl-reactive chemical group such as maleimide, haloacetyl, and pyridyl disulfide. In some embodiments, the reactive group is amine-reactive. In some embodiments, the reactive group is an NHS ester.

In some embodiments, $R^2$, $R^3$, $R^7$, and $R^8$ are each optionally substituted alkyl such as optionally substituted methyl, ethyl, or isopropyl groups.

In some embodiments, at least one of $R^4$, $R^5$, $R^6$, $R^9$, $R^{10}$, and $R^{11}$ contains a water soluble group. For example, the alkyl portion of $R^4$, $R^5$, $R^6$, $R^9$, $R^{10}$, and $R^{11}$ is substituted with a water soluble substituent. As used herein, "water soluble group" refers to a group comprising one or more polar and/or ionic substituents that improves the solubility of the overall molecule in aqueous media. In some cases, at least two of $R^4$, $R^5$, $R^6$, $R^9$, $R^{10}$, and $R^{11}$ comprise water soluble groups. In other embodiments, three or more comprise water soluble groups. Water soluble groups include, but are not limited to, a carboxylate ($-CO_2$) group, a sulfonate ($-SO_3$) group, a sulfonyl ($-SO_2$) group, a sulfate ($-SO_{4-2}$) group, a hydroxyl ($-OH$) group, a phosphate ($-OPO_{3-2}$) group, a phosphonate ($-PO_{3-2}$) group, an amine ($-NH_2$) group and an optionally substituted quaternized nitrogen with each having an optional counter ion.

Suitable counter ions include, but are not limited to, sodium, potassium, calcium, ammonium, organic amino salt, or magnesium salt, or a similar salt. Preferably, the counter ion is a biologically acceptable counter ion.

In some embodiments, the nitrogen atom(s) to which $R^4$, $R^5$, $R^6$, $R^9$, $R^{10}$, and $R^{11}$ are attached can be trivalent or tetravalent.

In some embodiments, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each hydrogen.

In some embodiments, $X^2$ and $X^3$ are each independently selected from $C_1$-$C_{10}$ alkylene optionally interrupted by an atom. In some embodiments, the nitrogens appended to $X^2$ and/or $X^3$ can be optionally quaternized.

In some embodiments, the phthalocyanine dye is of Formula Ib:

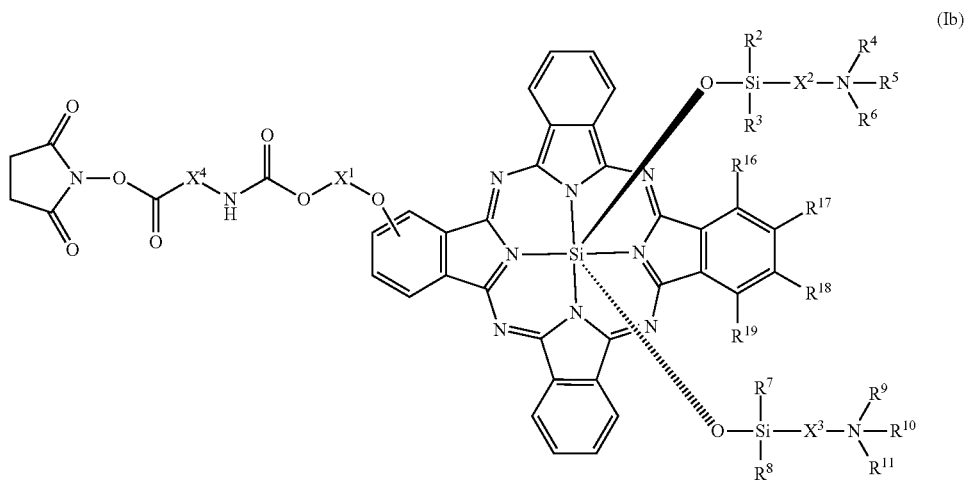

(Ib)

wherein $X^1$ and $X^4$ are each independently a $C_1$-$C_{10}$ alkylene optionally interrupted by a heteroatom; and $R^2$, $R^3$, $R^4$, $R^5$, $R^6$, $R^7$, $R^8$, $R^9$, $R^{10}$, $R^{11}$, $R^{16}$, $R^{17}$, $R^{18}$, $R^{19}$, $X^2$, and $X^3$ are as defined herein.

In some embodiments, the phthalocyanine dye containing the reactive group is IR700 NHS ester, such as IRDye 700DX NHS ester (Li-Ccor 929-70010, 929-70011). Thus, in some embodiments, the dye is a compound having the following formula:

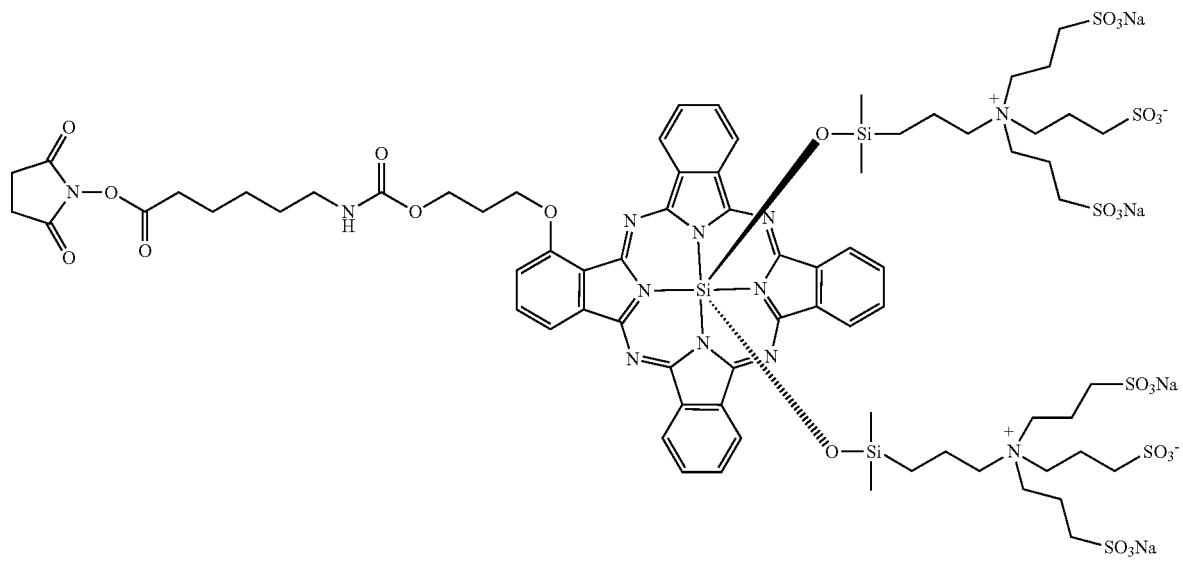

Chemical Formula: $C_{74}H_{96}N_{12}Na_4O_{27}S_6Si_3$
Exact Mass: 1952.37
Molecular Weight: 1954.22
IRDye 700DX NHS Ester In some embodiments, the reactive group is an NHS ester. In some embodiments, the reactivity of the NHS ester can be adjusted by varying the length of the alkylene group of $X^4$, between the NHS ester and carbamate functionality. In some embodiments, the length of the alkylene group of $X^4$ between the NHS ester and the carbamate functionality is inversely proportional to the NHS ester reactivity. In some embodiments, $X^4$ is $C_5$-alkylene. In other embodiments, $X^4$ is $C_3$-alkylene. In some embodiments, $X^1$ is $C_6$-alkylene. In other embodiments, $X^1$ is $C_3$-alkylene.

In some embodiments, the phthalocyanine dye has an overall electronic charge of zero. This charge neutrality can in certain instances by obtained with one or more optional counterions, or quaternized nitrogens.

In some embodiments, the phthalocyanine dye has sufficient solubility in aqueous solutions that once it is attached to a soluble targeting molecule, the targeting molecule retains its solubility. In some embodiments, the dye also is soluble in organic media (e.g., DMSO or DMF).

In some embodiments, the phthalocyanine dye has a maximum light absorption in the near infrared (NIR range). In some embodiments, the phthalocyanine dye has a maximum light absorption wavelength between 400 nm and 900 nm, such as between 600 nm and 850 nm, such as between 680 nm and 850 nm, for example at approximately 690 nm±50 nm or 690±20 nm. In some embodiments, the phthalocyanine dye can be excited efficiently by commercially available laser diodes that emit light at these wavelengths.

For purposes herein, the term "IR700," "IRDye 700DX," or variations thereof refer to the above formula when the dye is conjugated to a targeting molecule via its reactive group. Generally, IR700 has several favorable chemical properties. Amino-reactive IR700 is a relatively hydrophilic dye and can be covalently conjugated with an antibody using the NHS ester of IR700. Typically, IR700 also has more than 5-fold higher extinction coefficient ($2.1\times10^5$ M-cm$^{-1}$ at the absorption maximum of 689 nm), than conventional photosensitizers such as the hematoporphyrin derivative Photofrin® ($1.2\times10^3$ M$^{-1}$ cm$^{-1}$ at 630 nm), meta-tetrahydroxyphenylchlorin; Foscan® ($2.2\times10^4$ M$^{-1}$ cm$^{-1}$ at 652 nm), and mono-L-aspartylchlorin e6; NPe6/Laserphyrin® ($4.0\times10^4$ M$^{-1}$ cm$^{-1}$ at 654 nm).

The phthalocyanine dyes described herein can be made with commercially available starting material. The core structure is synthesized by condensation of two or more different diiminoisoindolines. Synthetic strategies using different dinitriles or diiminoisoindolines can lead to various degrees of substitution of the phthalocyanine and/or distribution of regioisomers. Exemplary synthetic schemes for generating the dyes are described in U.S. Pat. No. 7,005,518.

In some embodiments, in any of the methods provided herein, the targeting molecule (e.g. antibody) is linked directly or indirectly to the phthalocyanine dye (e.g. IR700). In some embodiments, the targeting molecule (e.g. antibody) is linked, directly or indirectly, to the phthalocyanine dye (e.g. IR700) via a covalent bond or a non-covalent interaction. In some embodiments, the covalent or non-covalent interactions or linkage is direct or indirect. In some embodiments, the attachment includes an indirect link, such as through a linker (e.g. such as any of the exemplary linkers described above), binding moiety or domain or reactive group. In some embodiments, the linkage includes a direct interaction between the targeting molecule and a phthalocyanine dye (e.g., IR700). In other embodiments, one or both of the targeting molecule and the phthalocyanine dye are linked to one or more linkers, and the interaction is indirect, e.g., between a linker attached to one of the molecules and another molecule, or between two linkers, each attached to the targeting molecule or the phthalocyanine dye.

In some embodiments, the phathalocyanine dye is non-covalently linked to or associated with the targeting molecule. For example, the phathalocyanine dye forms a complex with the targeting molecule via a non-covalent interaction. In some embodiments, the phthalocyanine dye (e.g. IR700) contains a moiety or domain capable of non-covalently interacting with an attachment group of the targeting molecule. In some embodiments, the method includes incubating or binding the phthalocyanine dye (e.g. IR700) with the targeting molecule (e.g. antibody) to form a non-covalent interaction between the dye and the targeting molecule. In some examples, the non-covalent interaction between the targeting molecule and the phthalocyanine dye include, for example, electrostatic interactions, van der Waals force, hydrophobic interactions, n-effects, ionic interactions, hydrogen bonding, halogen bonding and/or combinations thereof, or any interactions that depend on one or more of the forces. In some embodiments, the targeting molecule and the phthalocyanine dye are linked using or using interactions that mimic non-covalent molecular interactions such as, for example, ligand-receptor interaction, antibody-antigen interaction, avidin-biotin interaction, streptavidin-biotin interaction, histidine-divalent metal ion interaction (e.g., Ni, Co, Cu, Fe), interactions between multimerization (e.g., dimerization) domains, glutathione S-transferase (GST)-glutathione interaction and/or any combination thereof.

In some embodiments, a non-covalent interaction moiety or domain is attached to or is a part of the targeting molecule, and forms a non-covalent interaction, e.g. a complex, with the phthalocyanine dye (e.g. IR700). In other embodiments, non-covalent interaction molecule or domain is attached to or is a part of the phthalocyanine dye molecule, and forms a non-covalent interaction e.g. a complex, with the targeting molecule. In some embodiments, the method includes incubating or contacting a targeting molecule conjugated to biotin (e.g. antibody-biotin, such as a cetuximab-biotin) and the phthalocyanine dye conjugated to an avidin or analog thereof or a streptavidin or analog thereof, including monomeric forms thereof (e.g. monomeric avidin-IR700 or monomeric streptavidin-IR700). By virtue of the non-covalent interaction between avidin, streptavidin or analogs thereof and biotin, in some embodiments, the phthalocyanine dye (e.g. IR700) forms a non-covalent complex with the targeting molecule.

2. Targeting Molecule

In some embodiments, the phthalocyanine dye is conjugated to a targeting molecule via a reactive group of the dye molecule. In some embodiments, the targeting molecule is one that is able to target the conjugate to a cell or pathogen, for example, by binding to a cell surface molecule (e.g. cell surface receptor) on the cell or pathogen. In some embodiments, the targeting molecule, e.g., a macromolecule, can selectively bind to a desired cell type, cells with a particular phenotype, or cells displaying one or more cell surface markers or antigens. In some cases, the targeting molecule binds to a cell that is a cancer cell, a tumor cell, an inflammatory cell, an immune cell, a neuron, a stem cell, a proliferating cell, or a cell in a hyperplasia. In some cases, the targeting molecule binds to a pathogen or a pathogen infected cell. In some embodiments, the cell is an inflammatory cell, such a leukocyte, for example, a neutrophil, an eosinophil, a basophil, a lymphocyte, or a monocyte. In some embodiments, the cell is an immune cell, such as a T cell, a B cell, a Natural Killer (NK) cell, a dendritic cell, a macrophage or a neutrophil. In some embodiments, the cell is a neuron that is a peripheral nervous system neuron or a central nervous system neuron, such as a nociceptor, for example, thermal nociceptors, mechanical nociceptors, chemical nociceptors or polymodal nociceptors. In some cases, the targeting molecule binds to a pathogen or a pathogenic cell, such as a virus, bacterium, fungus, biofilm or other prokaryotic cell system. In some embodiments, the targeting molecule binds to a pathogen that is a gram-negative or gram-positive bacterium.

In some embodiments, the targeting molecule (e.g., antibody) of the phthalocyanine dye conjugate bind to a protein on the surface of a cell or cells present in a microenvironment of a lesion that is associated with or present as a result of a disease or condition. For example, in some embodiments, the conjugate binds to a protein on the surface of a cell or cells present in a tumor microenvironment associated with or present in a tumor. In some embodiments, the conjugate binds to a protein present the extracellular matrix in the microenvironment of the tumor.

As used herein, a "cell present in the microenvironment of a lesion" refers to any cell present in the cellular environment associated with a lesion, a disease or a disorder, such as any cell present in or immediately adjacent to a tumor, such as cells present in a tumor microenvironment, or the extracellular matrix in the tumor microenvironment.

As used herein, a "cell present in a tumor microenvironment" refers to any cell present in the cellular environment in which the tumor exists, such as any cell present in or immediately adjacent to the tumor, including the proliferating tumor cells (e.g., cancer cells), the tumor stroma, blood vessels, infiltrating inflammatory cells (e.g., immune cells) and a variety of associated tissue cells (e.g., fibroblasts). Thus, it is understood that reference to the tumor refers not only to the tumor cells, which can include malignant or cancer cells, but also to other cells present in the tumor microenvironment that regulate the growth of the tumor, including immune cells. In some cases, immune cells present in a tumor microenvironment can include T lymphocytes, including regulatory T lymphocytes (Treg), dendritic cells, natural killer (NK) cells, B cells, macrophages and other immune cells (Whiteside (2008) Oncogene, 27:5904-5912). It is recognized that, in some aspects, many non-cancerous cells present in and around the tumor can regulate the proliferation, angiogenesis, invasion and/or metastasis of tumor cells, thereby promoting the growth of the tumor. Thus, in some cases, targeting such non-cancerous cells, such as immune cells (e.g., T cells, such as regulatory T cells), present in a tumor can be an effective therapy for killing a tumor by PIT.

Generally, cancerous cells contain antigens associated with a tumor that should be recognized by the immune system. Typically, in an active immune system, immune cells, such as cytotoxic T cells, attack and eradicate these cancerous cells. Under normal physiological conditions, the T cell-mediated immune response is initiated by antigen recognition by the T cell receptor (TCR) and is regulated by a balance of co-stimulatory and inhibitory signals (e.g., immune checkpoint proteins). In particular, CD4+ and CD8+ T cells expressing a TCR can become activated upon recognition of antigenic peptides presented on antigen-presenting cells on major histocompatibility complex (MHC) class I or class II molecules, respectively. In some aspects, activated CD8+ cells, or cytotoxic T cells, can kill tumor cells expressing the antigen, which can be helped by the presence of CD4+ T cells.

In the case of tumors, however, the tumor microenvironment has mechanisms to suppress the immune system, thereby evading immune recognition and preventing or reducing killing of tumor cells. For example, in some cases, immune checkpoint proteins can be dysregulated in tumors, thereby resulting in a suppression of the immune response in the tumor microenvironment as a mechanism of evading the immune system. In some cases, tumor-infiltrating lymphocytes can include Tregs (e.g., CD4+CD25+ T cells), which are cells that are capable of suppressing proliferation of other T cells in the microenvironment (Whiteside, TL (2008) Oncogene, 27:5904-5912). In some cases, other mechanisms can act to inhibit access of immune cells to tumor antigens, thereby also contributing to the tumors ability to evade the immune system.

In some embodiments, the targeting molecule is a targeting molecule that binds to a cell surface protein on a tumor or cancer cell. In some embodiments, the targeting molecule binds to a cell surface protein on an immune cell or other non-cancerous cell present in a tumor microenvironment. In some embodiments, the targeting molecule binds to a cell surface protein on the surface of a T lymphocyte, such as a Treg, a dendritic cell, a natural killer (NK) cell, a B cell, a macrophage or other immune cell that is present in a tumor microenvironment. In some cases, the tumor or cancer is located at the head and neck, breast, liver, colon, ovary, prostate, pancreas, brain, cervix, bone, skin, eye, bladder, stomach, esophagus, peritoneum, or lung.

Exemplary of targeting molecules, such as targeting molecules that target a tumor or cancer, include, but are not limited to, any as described in published international PCT appl. Nos. WO2014120974, WO2014176284, WO2015042325, U.S. Pat. No. 8,524,239 or U.S. patent publication No. US20140120119.

Exemplary targeting molecules include, but are not limited to, a protein, a glycoprotein, an antibody, an antibody fragment, an antigen, an antigen binding fragment, a peptide, a polypeptide, a small molecule, a polymeric synthetic molecule, a polymeric nanoparticle, a liposome, an enzyme substrate, a hormone, a neurotransmitter, a cell metabolite, a viral particle, a viral capsid, a viral nanoparticle, a bacterial particle, a marker, a cell, a hapten, an avidin, a streptavidin, a monomeric streptavidin, a biotin, a carbohydrate, an oligosaccharide, a polysaccharide, a nucleic acid, a deoxy nucleic acid, a fragment of DNA, a fragment of RNA, nucleotide triphosphates, acyclo terminator triphosphates, or PNA.

In some embodiments, the targeting molecule is an amino acid, peptide, protein, tyramine, polysaccharide, ion-complexing moiety, nucleoside, nucleotide, oligonucleotide, psoralen, drug, hormone, lipid, lipid assembly, polymer, polymeric microparticle, a biological cell, or virus. In some embodiments, the targeting molecule is an antigen, steroid, vitamin, drug, metabolite, toxin, environmental pollutant, nucleic acid polymer, carbohydrate, lipid, or glass, plastic or other non-biological polymer. In some embodiments, the targeting molecules is a cell, cellular system, cellular fragment, or subcellular particle, e.g., a virus particle, bacterial particle, virus component, biological cell (such as animal cell, plant cell, bacteria, yeast, or protist), or cellular component. In some embodiments, reactive dyes may label functional groups at the cell surface, in cell membranes, organelles, or cytoplasm.

In some embodiments, the targeting molecule targets or binds to an antigen, such as any structural substance that serves as a target capable of being bound by the targeting molecule. In some embodiments, the antigen is or is comprised as part of a cell surface molecule, such as a protein, e.g., a receptor, that is expressed on a cell surface. In some embodiments, for example, the antigen is or is comprised as part of a molecule expressed on the surface of a cell present in a tumor, including any cell present in the tumor microenvironment. Examples of cell surface molecules include, but are not limited to, an antigen, peptides, lipids, polysaccharides, carbohydrate, or nucleic acids containing antigenic determinants, such as those recognized by an immune cell. In some examples, an antigen includes a tumor-specific peptide (such as one found on the surface of a cancer cell) or immunogenic fragment thereof. In some embodiments, the targeting molecule is an antibody or an antigen-binding antibody fragment thereof.

In some embodiments, the cell surface molecule can be ACTHR, endothelial cell Anxa-1, aminopetidase N, anti-IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CD133, CD7, CD15, CD34, CD44, CD206, CD271, CEA (CarcinoEmbryonic Antigen), CGRP, chemokine receptors, cell-surface annexin-1, cell-surface plectin-1, Cripto-1, CRLR, CXCR2, CXCR4, DCC, DLL3, E2 glycoprotein, EGFR, EGFRvIII, EMR1, Endosialin, EP2, EP4, EpCAM, EphA2, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like) like), G-protein coupled receptors of the Family C (Metabotropic Glutamate Receptor-like), GD2, GP100, GP120, Glypican-3, hemagglutinin, Heparin sulfates, HER1, HER2, HER3, HER4, HMFG, HPV 16/18 and E6/E7 antigens, hTERT, IL11-R, IL-13R, ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/HABP1), p75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family (e.g., P2X1-5), mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP (e.g., TRPV1-6, TRPA1, TRPC1-7, TRPM1-8, TRPP1-5, TRPML1-3), TSH receptor, VEGF receptors (VEGFR1 or Flt-1, VEGFR2 or FLK-1/KDR, and VEGF-3 or FLT-4), voltage-gated ion channels, VPAC1, VPAC2, Wilms tumor 1, Y1, Y2, Y4, or Y5.

In some embodiments, the targeting molecule is a binding partner, such as a ligand, capable of binding to a cell surface molecule, such as a cell surface protein, e.g., a cell surface receptor. In some embodiments, the targeting molecule is selected from adrenocorticotropic hormone (ACTH), angiotensin II, atrial natriuretic factor (ANF), bombesin, bradykinin, brain derived neurotropihic factor (BDNF), bone morphogenetic protein 2 (BMP-2), bone morphogenetic protein 6 (BMP-6), bone morphogenetic protein 7 (BMP-7), calcitonin, cardiotrophin 1 (BMP-2), CD22, CD40, cholecystokinin (CCK), ciliary neurotrophic factor (CNTF), CCL1-CCL28, CXCL1-CXCL17, XCL1, XCL2, CX3CL1, cripto 1 binding peptide, vascular endothelial cell growth factor (VEGF), epidermal growth factor (EGF), endothelin 1, endothelin 1/3, FAS-ligand, fibroblast growth factor 1 (FGF-1), fibroblast growth factor 2 (FGF-2), fibroblast growth factor 4 (FGF-4), fibroblast growth factor 5 (FGF-5), fibroblast growth factor 6 (FGF-6), fibroblast growth factor 1 (FGF-7), fibroblast growth factor 1 (FGF-10), Flt-3, gastrin, gastrin releasing peptide (GRP), granulocyte colony-stimulating factor (G-CSF), granulocyte macrophage stimulating factor (GM-CSF), glucagon like peptide (GLP-1), hepatocyte growth factor (HGF), interferon alpha (IFN-α), interferon beta (IFN-b), interferon gamma (IFNg), insulin-like growth factor 1 (IGF-1), insulin-like growth factor 2 (IGF-2), interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 7 (IL-8), interleukin 9 (IL-9), interleukin 10 (IL-10), interleukin 11 (IL-11), interleukin 12 (IL-12), interleukin 13 (IL-13), interleukin 15 (IL-15), interleukin 17 (IL-17), interleukin 19 (IL-19), luteinizing hormone (LH), luteinizing-releasing hormone (LHRH), macrophage colony-stimulating factor (M-CSF), monocyte chemotactic protein 1 (MCP-1), macrophage inflammatory protein 3a (MIP-3a), macrophage inflammatory protein 3b (MIP-3b), nerve growth factor (NGF), neuromedin B, neurotrophin 3 (NT-3), neurotrophin 4 (NT-4), neurotensin, neuropeptide Y, oxytocin, pituitary adenylate cyclase activating peptide (PACAP), platelet derived growth factor AA (PDGF-AA), platelet derived growth factor AB (PDGF-AB), platelet derived growth factor BB (PDGF-BB), platelet derived growth factor CC (PDGF-CC), platelet derived growth factor DD (PDGF-DD), netrin-1 (NTN1), netrin-2 (NTN2), netrin-4 (NTN4), netrin-G1 (NTNG1) and netrin-G2 (NTNG2), ephrin A1 (EFNA1), ephrin A2 (EFNA2), ephrin A3 (EFNA3), ephrin A4 (EFNA4), ephrin A5 (EFNA5), semaphorin 3A (SEMA3A), semaphorin 3B (SEMA3B), semaphorin 3C (SEMA3C), semaphorin 3D (SEMA3D), semaphorin 3F (SEMA3F), semaphorin 3G (SEMA3G), semaphorin 4A (SEMA4A), semaphorin 4B (SEMA4B), semaphorin 4C (SEMA4C), semaphorin 4D (SEMA4D), semaphorin 4F (SEMA4F), semaphorin 4G (SEMA4G), semaphorin 5A (SEMA5A), semaphorin 5B (SEMA5B), semaphorin 6A (SEMA6A), semaphorin 6B (SEMA6B), semaphorin 6D (SEMA6D), semaphorin 7A (SEMA7A), SLIT1, SLIT2, SLIT3, SLIT and NTRK-like family, member 1 (SLITRK1), SLIT and NTRK-like family, member 2 (SLITRK2), SLIT and NTRK-like family, member 3 (SLITRK3), SLIT and NTRK-like family, member 4 (SLITRK4), SLIT and NTRK-like family, member 5 (SLITRK5), SLIT and NTRK-like family, member 6 (SLITRK6), prostaglandin E2 (PGE2), RANTES, Somatostatin-14, Somatostatin-28, stem cell factor (SCF), stromal cell derived factor 1 (SDF-1), substance P, thyroid stimulating hormone (TSH), transforming growth factor alpha (TGF-α), transforming growth factor beta (TGF-b), tumor necrosis factor alpha (TNF-α), thrombin, vasoactive intestinal peptide (VIP), Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16, Sonic hedgehog, Desert hedgehog, and Indian hedgehog, or is a binding fragment thereof that is capable of binding to its cognate cell surface molecule, such as a cell surface protein, e.g., cell surface receptor.

In some embodiments, the targeting molecule can be an immune modulating agent, which can bind to a cell surface molecule or protein on an immune cell to either suppress or activate the body's immune response. In some embodiments, binding of the immune modulating agent to the cell surface molecule or protein can stimulate an immune response to a tumor and/or a pathogen, such as by inhibiting immune suppression or by enhancing immunostimulation. In some embodiments, the cell surface molecule or protein can be CD25, PD-1 (CD279), PD-L1 (CD274, B7-H1), PD-L2 (CD273, B7-DC), CTLA-4, LAG3 (CD223), TIM3 (HAVCR2), 4-1BB (CD137, TNFRSF9), CXCR2, CXCR4 (CD184), CD27, CEACAM1, Galectin 9, BTLA, CD160, VISTA (PD1 homologue), B7-H4 (VCTN1), CD80 (B7-1), CD86 (B7-2), CD28, HHLA2 (B7-H7), CD28H, CD155, CD226, TIGIT, CD96, Galectin 3, CD40, CD40L, CD70, LIGHT (TNFSF14), HVEM (TNFRSF14), B7-H3 (CD276), Ox40L (TNFSF4), CD137L (TNFSF9, GITRL), B7RP1, ICOS (CD278), ICOSL, KIR, GAL9, NKG2A (CD94), GARP, TL1A, TNFRSF25, TMIGD2, BTNL2, Butyrophilin family, CD48, CD244, Siglec family, CD30, CSF1R, MICA (MHC class I polypeptide-related sequence A), MICB (MHC class I polypeptide-related sequence B), NKG2D, KIR family (Killer-cell immunoglobulin-like receptor, LILR family (Leukocyte immunoglobulin-like receptors, CD85, ILTs, LIRs), SIRPA (Signal regulatory protein alpha), CD47 (IAP), Neuropilin 1 (NRP-1), a VEGFR or VEGF. In some example, the targeting molecule is an antibody or antigen-binding fragment that is an immune modulating agent. In some embodiments, the immune modulating agent is an immune checkpoint inhibitor.

In some embodiments, the cell surface molecule can be HER1/EGFR, HER2/ERBB2, CD20, CD25 (IL-2Rα receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, or SK-1 antigen.

In some embodiments, the targeting molecule is an antibody or an antigen-binding antibody fragment that specifically binds to an antigen that is or is part of a cell surface molecule expressed on the surface of a cell. Included among such antibodies are antibodies or antigen-binding antibody fragments capable of binding to a cell surface molecule, such as a cell surface protein, e.g., cell surface receptor, described herein. In some cases, the antibody can bind to an antigen of a protein expressed on a cell in a tumor, including a tumor-specific protein.

In some embodiments, the targeting molecule binds to an antigen or protein directly or indirectly. For example, in some embodiments, the targeting molecule is a second binding molecule that binds to a first binding molecule which is capable of binding to the antigen or protein. For example, the targeting molecule is a secondary antibody, which binds to a first binding molecule, e.g., a primary antibody, capable of binding the protein or antigen, e.g., a cell surface protein or a cell surface receptor. Thus, in some embodiments, the dye is conjugated to a secondary antibody.

An "antibody" is a polypeptide ligand comprising at least a light chain and/or heavy chain immunoglobulin variable region that specifically recognizes and binds an epitope of an antigen. Generally, antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. The term antibody includes intact antibodies and antigen-binding antibody fragments that exhibit antigen-binding, such as Fab fragments, Fab' fragments, F(ab)'$_2$ fragments, single chain Fv proteins ("scFv"), and disulfide stabilized Fv proteins ("dsFv"). An scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as modified forms of immunoglobulins, chimeric antibodies, for example, humanized murine antibodies, and heteroconjugate antibodies, such as bispecific antibodies. See also, *Pierce Catalog and Handbook,* 1994-1995 (Pierce Chemical Co., Rockford, Ill.); Kuby, J., *Immunology,* 3$^{rd}$Ed., W.H. Freeman & Co., New York, 1997.

Typically, a naturally occurring immunoglobulin has heavy (H) chains and light (L) chains interconnected by disulfide bonds. There are two types of light chain, lambda (k) and kappa (κ). There are five main heavy chain classes, or isotypes, which determine the functional activity of an antibody molecule: IgM, IgD, IgG, IgA and IgE.

Each heavy and light chain contains a constant region and a variable region, also known as "domains." In combination, the heavy and the light chain variable regions generally specifically bind the antigen. Light and heavy chain variable regions may contain a "framework" region interrupted by three hypervariable regions, also called "complementarity-determining regions" or "CDRs." The extent of the framework region and CDRs has been defined (see, Kabat et al., *Sequences of Proteins of Immunological Interest,* U.S. Department of Health and Human Services, 1991, which is hereby incorporated by reference). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are typically responsible for binding to an epitope of an antigen. The CDRs of each chain are typically referred to as CDR1, CDR2, and CDR3, numbered sequentially starting from the N-terminus, and are also generally identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Antibodies with different specificities, such as different combining sites for different antigens, have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. Other antibody fragments or multispecific antibodies formed from antibody fragments include a multivalent scFv, a bispecific scFv or an scFv-CH3 dimer. Antibody fragments can be made by various techniques, including but not limited to proteolytic digestion of an intact antibody as well as production by recombinant host cells.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs, which generally confer antigen binding, from another species, such as a murine antibody that specifically binds mesothelin.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In some embodiments, the CDRs are from the donor immunoglobulin in a humanized immunoglobulin. Constant regions need not be present, but if they are, they may be substantially identical to human immunoglobulin constant regions, such as at least about 85-90%, such as about 95% or more identical. Hence, parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and CDRs from a human immunoglobulin. In some embodiments, the framework and the CDRs are from the same originating human heavy and/or light chain amino acid sequence. However, frameworks from one human antibody can be engineered to include CDRs from a different human antibody. Parts of a human immunoglobulin may be substantially identical to corresponding parts of natural human immunoglobulin sequences.

"Specifically binds" refers to the ability of a molecule, such as an antibody or antigen-binding fragment, to specifically bind an antigen, such as a tumor-specific antigen, relative to binding to unrelated proteins, such as non-tumor proteins, for example β-actin. In some embodiments, a molecule, such as an antibody or fragment, including a molecule, such as an antibody or fragment, attached to a phthalocyanine dye molecule, specifically binds to a target, such as a cell surface protein, with a binding constant that is at least $10^3$ $M^{-1}$ greater, $10^4 M^{-1}$ greater or $10$ $M^{-1}$ greater than a binding constant for other molecules in a sample or subject. In some embodiments, a molecule, such as an antibody or fragments thereof, has an equilibrium association constant ($K_A$) of greater than or equal to about $10^6$ $M^{-1}$, greater than or equal to about $10^7$ $M^{-1}$, greater than or equal to about $10^8$ $M^{-1}$, or greater than or equal to about $10^9$ $M^{-1}$, $10^{10} M^{-1}$, $10^{11}$ $M^{-1}$ or $10^{12}$ $M^{-1}$. Antibodies also can be characterized by an equilibrium dissociation constant ($K_D$) of $10^{-6}$ M, $10^{-7}$ M, $10^{-8}$ M, $10^{-10}$ M, $10^{-11}$ M or $10^{-12}$ M or lower. In some embodiments, an equilibrium dissociation constant ($K_D$) can be 1 nM or less. Affinity constants, such as $K_D$ or $K_A$, can be estimated empirically or affinities can be determined comparatively, e.g. by comparing the affinity of one antibody and another antibody for a particular antigen. For example, such affinities can be readily determined using techniques known in the art, such as, for example, by competitive ELISA (enzyme-linked immunosorbent assay) or using a surface-plasmon resonance device, such as the Biacore T100 (available from Biacore, Inc., Piscataway, N.J), a radioimmunoassay using radiolabeled target antigen, or by another method known to the skilled artisan.

In some embodiments, the phthalocyanine dye (e.g., IR700) is conjugated to an antibody or an antigen-binding antibody fragment. For example, in some aspects, the phthalocyanine dye-targeting molecule conjugate is an IR700-antibody conjugate. Exemplary antibodies to which the phthalocyanine dye (e.g., IR700) can be conjugated to include, but are not limited to, cetuximab, panitumumab, zalutumumab, nimotuzumab, trastuzumab, Ado-trastuzumab emtansine, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Afatinib, Axitinib, Bosutinib, Cabozantinib, Ceritinib, Crizotinib, Dabrafenib, Dasatinib, Erlotinib, Everolimus, Ibrutinib, Imatinib, Lapatinib, Lenvatinib, Nilotinib, Olaparib, Palbociclib, Pazopanib, Pertuzumab, Ramucirumab, Regorafenib, Ruxolitinib, Sorafenib, Sunitinib, Temsirolimus, Trametinib, Vandetanib, Vemurafenib, Vismodegib, Basiliximab, Ipilimumab, Nivolumab, pembrolizumab, MPDL3280A, Pidilizumab (CT-011), MK-3475, BMS-936559, MPDL3280A, tremelimumab, IMP321, BMS-986016, LAG525, urelumab, PF-05082566, TRX518, MK-4166, dacetuzumab, lucatumumab, SEQ-CD40, CP-870, CP-893, MEDI6469, MEDI6383, MOXR0916, AMP-224, MSB0010718C, MEDI4736, PDR001, rHIgM12B7, Ulocuplumab, BKT140, Varlilumab (CDX-1127), ARGX-110, MGA271, lirilumab (BMS-986015, IPH2101), IPH2201, AGX-115, Emactuzumab, CC-90002 and MNRP1685A or an antibody-binding fragment thereof.

In some embodiments, the targeting molecule is a tissue-specific homing peptide. For example, in some embodiments, the homing polypeptide can contain the sequence of amino acids set forth in any of SEQ ID NOS: 1-52. In some embodiments, the targeting molecule is an RGD polypeptide, such as an iRGD polypeptide, a Lyp-1 polypeptide, a cripto-1 binding polypeptide, a somatostatin receptor binding polypeptide, or a prohibitin binding polypeptide, a NGR polypeptide, or an iNGR polypeptide.

In some embodiments, the targeting molecule is a viral particle, such as a virus-like particle, a viral-like nanoparticle, or a viral capsid. In some embodiments, the targeting molecule is a viral-like nanoparticle. In some embodiments, the viral-like nanoparticle is assembled from L1 capsid proteins. In some embodiments, the viral-like nanoparticle is assembled from a combination of L1 and L2 capsid proteins. In some embodiments, the targeting molecule and bind to and infect cells. In some embodiments, the targeting molecule is one described in WO2015042325.

In some embodiments, a virus-like particle (VLP) refers to an organized capsid-like structure, such as roughly spherical or cylindrical in shape, that comprises self-assembling ordered arrays of L1 or L1 and L2 capsomers and does not include a viral genome. In some embodiments, virus-like particles are morphologically and antigenically similar to authentic virions, but they lack viral genetic material, such as viral nucleic acid, rendering the particles noninfectious. A VLP may be used to deliver to a recipient cell an agent, such as prophylactic agent, therapeutic agent or diagnostic agent, or an enclosed circular or linear DNA or RNA molecule.

In some embodiments, VLPs may have modified immunogenicity and/or antigenicity with respect to the wild type VLPs. The VLPs may, for example, be assembled from capsomers having a variant capsid protein with modified immunogenicity and/or antigenicity. In some embodiments, a variant capsid protein with modified immunogenicity and/or antigenicity is one that is modified naturally or synthetically, such as mutated, substituted, deleted, pegylated or inserted, at an amino acid to reduce or prevent recognition of the capsid protein by pre-existing, such as endogenous, viral serotype-specific antibodies. A variant capsid protein may be a human papillomavirus (HPV) L1 variant, a non-human papillomavirus L1 variant, or a papillomavirus L1 variant based on a combination of amino acids from different HPV serotypes.

In some embodiments, a VLP is a papilloma virus VLP. The VLP may be a human papilloma virus VLP, such as derived from a virus that can infect human, while in other embodiments, the VLP may be a non-human papilloma virus VLP. Examples of non-human VLPs include those derived from, without limitation, bovine papilloma viruses, murine papilloma viruses, cotton-rabbit papilloma viruses and macaque or rhesus papilloma virus particles. In some embodiments, the VLPs are bovine papilloma virus viral-like nanoparticles, such as type 1 viral-like nanoparticles, such as assembled from BPV L1 capsid proteins or a combination of BPV L1 and BPV L2 capsid proteins.

In some embodiments, a capsid protein refers to a protein monomer, several of which form a capsomer oligomer. In some embodiments, a capsomer refers to the basic oligomeric structural unit of a viral capsid, which is an outer covering of protein that protects the genetic material of a virus. Capsid proteins may include in some embodiments, papillomavirus L1 major capsid proteins and papillomavirus L2 minor capsid proteins. In some embodiments, the VLPs contain only L1 capsid proteins, while in other embodiments, the VLPs contain a mixture, or combination, of L1 and L2 capsid proteins.

In some embodiments, the percentage of L1 capsid proteins in a virus-like particle is greater than the percentage of L2 capsid proteins in the virus-like particle. For example, in some embodiments, the percentage of L1 capsid proteins in a virus-like particle is 80% to 100% of the total number of capsid proteins in the virus-like particle. In some embodiments, the percentage of L1 capsid proteins in a virus-like particle is at least or is about 80%, 85%, 90%, 91%, 92%, 93%, 94%, 95%, 96%, 97%, 98%, 99% or 100%. In some embodiments, the percentage of L2 capsid proteins in a virus-like particle is 1% to 25% of the total number of capsid proteins in the virus-like particle. For example, in some embodiments, the percentage of L2 capsid proteins in a virus-like particle is at least or about 1%, 2%, 3%, 4%, 5%, 6%, 7%, 8%, 9%, 10%, 11%, 12%, 13%, 14%, 15%, 16%, 17%, 18%, 19% or 20%.

In some embodiments, a virus-like particle contains 12 to 72 L2 proteins. In some embodiments, a virus-like particle contains 360 L1 proteins and 12 to 72 L2 proteins. In some embodiments, capsid proteins assemble into viral-like nanoparticles having a diameter of 20 to 60 nm. For example, capsid proteins may assemble into viral-like nanoparticles having a diameter of at least or about 20, 25, 30, 35, 40, 45, 50, 55 or 60 nm.

In some embodiments, the targeting molecule is not or does not include a nanocarrier. In some embodiments, the targeting molecule is not or does not include a virus-like particle, a nanoparticle, a liposome, a quantum dot, or a combination thereof.

In some embodiments, the targeting molecule is a DARPin (designed ankyrin repeat protein). Typically, DARPins are derived from natural ankyrin repeat proteins and bind to proteins including e.g., human receptors, cytokines, kinases, human proteases, viruses and membrane proteins (Molecular Partners AG Zurich Switzerland; see Chapter 5. "Designed Ankyrin Repeat Proteins (DARPins): From Research to Therapy", Methods in Enzymology, vol 503: 101˜134 (2012); and "Efficient Selection of DARPins with Sub-nanomolar Affinities using SRP Phage Display", J. Mol. Biol. (2008) 382, 1211-1227, the entire disclosures of which are hereby incorporated by reference. In some embodiments, the DARPin is an antibody mimetic protein having high specificity and high binding affinity to a target protein, which is prepared via genetic engineering. In some embodiments, DARPins have a structure comprising at least 2 ankyrin repeat motifs, for example, comprising at least 3, 4 or 5 ankyrin repeat motifs. The DARPins can have any suitable molecular weight depending on the number of repeat motifs. For example, the DARPins including 3, 4 or 5 ankyrin repeat motifs may have a molecular weight of about 10 kDa, about 14 kDa, or about 18 kDa, respectively.

In some embodiments, the DARPin includes a core part that provides structure and a target binding portion that resides outside of the core and binds to a target. In some embodiments, the structural core includes a conserved amino acid sequence and the target binding portion includes an amino acid sequence that differs depending on the target.

In some embodiments, the conjugate contains a number of dye residues per targeting molecule that is from or from about 1 to about 1000, such as from or from about 1 to about 100, from or from about 1 to about 50, from or from about 1 to about 25, from or from about 1 to about 10, from or from about 1 to about 5. In some embodiments, the ratio of dye molecules to targeting molecule is or is about 2:1, 3:1, 4:1, 5:1, 10:1, 15:1, 20:1, 25:1, 50:1, 75:1, 100:1, 150:1, 200:1, 250:1, 300:1, 350:1, 400:1, 450:1, 500:1, 550:1, 600:1, 650:1, 700:1, 750:1, 800:1, 850:1, 900:1, 950:1 or 1000:1, or is between or between about any two of such values. In some embodiments, the targeting molecule may contain up to 2, 3, 4, 5, 6, 7, 8, 9, 10, 15, 20, 50, 75, 100, 150, 200, 250, 300, 350, 400, 450, 500, 550, 600, 650, 700, 750, 800, 850, 900, 950 or 1000 dye molecules. In some embodiments, the targeting molecule may contain more than 1000 dye molecules or less than 10 dye molecules.

In some embodiments, such as when the targeting molecule is a polypeptide, such as an antibody or antigen-binding antibody fragment, the number of dye molecule per targeting molecule can be from or from about 2 to about 5, such as from or from about 2 to about 4, for example about 3 or 3. In some embodiments, for example where the targeting molecule is a nanoparticle, such as a virus-like particle (VLP), the number of dye molecules to targeting molecule can be from or from about 10 to about 1000, 10 to about 500, 50 to about 500, or 50 to about 1000. Thus, in some embodiments, the targeting molecule may contain about 10 to about 1000 dye molecules.

In some embodiments, such as where the targeting molecule is a VLP, more than one dye molecule may be conjugated to a single capsid protein. For example, a single capsid protein, such as LI or L2 capsid protein, may be conjugated to 1 to 5, such as 1, 2, 3, 4 or 5, dye molecules. Thus, more than one amino acid of a capsid protein may be conjugated to a dye molecule. In some embodiments, a single capsid protein may be conjugated to 1 to 2, 1 to 3, or 2 to 3 dye molecules. Thus, a dye molecule may be conjugated to 1, 2, 3, 4 or 5 different amino acids, such as lysine, arginine and/or histidine, or other amino acid, of a single capsid protein. 3. Additional Dye for Imaging In some embodiments, the conjugate optionally can include an additional dye such that the targeting molecule can be conjugated to two or more different fluorescent dyes. For example, provided is a conjugate containing a targeting molecule conjugated to a first dye that is a phthalocyanine dye, such as any described above, e.g., IR700, and a second fluorescent dye that is different than the first dye. In one aspect, the conjugate is of Formula (II):

$$[D_1\text{-}(L_1)_n]_p\text{-}A\text{-}[(L_2)_m\text{-}D_2]_o \qquad (II)$$

wherein:
A is a targeting molecule that can bind to cells or tissues;
$L_1$ and $L_2$ are each an independently selected linker for each o or p, wherein each $L_1$ and $L_2$ are as defined above for L;
n and m are independently 1 or 2;
$D_1$ is an independently selected hydrophilic phthalocyanine dye for each p, wherein $D_1$ is as defined above for D;
$D_2$ is an independently selected fluorescent dye for each o; and
p and o are independently 1, 2, 3, 4, 5 or greater than 5, such as up to 1000. For example, p and o can each independently be 1 to 1000, such as generally 1 to 10 or 2 to 5.

In some embodiments, the first dye $D_1$ is a phthalocyanine dye, such as a near infrared (NIR) phthalocyanine dye, such as any of the dyes described above. In some embodiments, the phthalocyanine dye is or comprises a photosensitizer compound such that it is capable of exhibiting phototoxic activity upon irradiation with near-infrared light. In some embodiments, $D_1$ is IR700.

In some embodiments, the second dye $D_2$ is selected to offer better fluorescence for visualization than the first dye $D_1$ (e.g., IR700). Thus, in some aspects, the compound of formula II is used for both fluorescence imaging and photoimmunotherapy. For example, irradiating the lesion or tumor emits a fluorescence signal from the second fluorescent dye to effect detection of the presence of the conjugate at the lesion or tumor in the subject. In some embodiments, the conjugate can be used to both monitor the binding of the dye to the target site (e.g., tumor) with fluorescence imaging of $D_2$ and to eradicate cells associated with a disease or condition, e.g., cells of a tumor, using photoimmunotherapy by activation of $D_1$ (e.g., IR700). In some embodiments, the second dye $D_2$ exhibits one or more spectral properties selected from among fluorescent quantum yield (e.g., in water), extinction coefficient, Stokes shift, absorption and emission at long wavelength, and photostability that is greater compared to the corresponding spectral property of $D_1$. In some embodiments, $D_2$ is not IR700.

In some embodiments, the additional dye $D_2$ is a fluorescent dye. In some embodiments, $D_2$ can be, but is not limited to, hydroxycoumarin, Cascade Blue, Dylight 405 Pacific Orange, Alexa Fluor 430, Fluorescein, Oregon Green, Alexa Fluor 488, BODIPY 493, 2,7-Diochlorofluorescien, ATTO 488, Chromeo 488, Dylight 488, HiLyte 488, Alexa Fluor 532, Alexa Fluor 555, ATTO 550, BODIPY TMR-X, CF 555, Chromeo 546, Cy3, TMR, TRITC, Dy547, Dy548, Dy549, HiLyte 555, Dylight 550, BODIPY 564, Alexa Fluor 568, Alexa Fluor 594, Rhodamine, Texas Red, Alexa Fluor 610, Alexa Fluor 633, Dylight 633, Alexa Fluor 647, APC, ATTO 655, CF633, CF640R, Chromeo642, Cy5, Dylight 650, Alexa Fluor 680, IRDye 680, Alexa Fluor 700, Cy5.5, ICG, Alexa Fluor 750, Dylight 755, IRDye 750, Cy7, Cy7.5, Alexa Fluor 790, Dylight 800, IRDye 800, Qdot® 525, Qdot® 565, Qdot® 605, Qdot® 655, Qdot® 705, or Qdot® 800.

In some embodiments, $D_2$ absorbs light and emits fluorescence at longer wavelengths where tissue autofluorescence is low, essentially absent or eliminated or is absent or eliminated. Thus, in some aspects, $D_2$ facilitates a deep tissue penetration of imaging. In some embodiments, $D_2$ is a near-infrared (NIR) dye that has an absorption and emission wavelength in the NIR spectrum between or between about 650 and 1450 nm, such as between or between about 650 and 900 nm, between or between about 700 and 1000 nm, or between or between about 750 and 950 nm. In some embodiments, $D_2$ is a second near-infrared (NIR-II) dye that has an absorption and emission wavelength in the NIR-II spectrum between or between about 1000 and 1700 nm, such as between or between about 1000 and 1400 nm. In some embodiments, $D_2$ is a dye that has an absorption and emission wavelength in the visible spectrum between or between about 300 and 750 nm, such as between or between about 400 and 600 nm or between or between about 400 and 700 nm. In some embodiments, the targeting molecule conjugate contains two dyes with different emission and excitation wavelengths. In some embodiments, the additional dye has long wavelength excitation and emission properties. In some embodiments, any of the provided methods can further comprise imaging the lesion or tumor in the subject by irradiating or illuminating the tumor at a wavelength capable of being absorbed by the second dye.

In some embodiments, the additional dye has a large extinction coefficient at the excitation wavelength. In some embodiments, $D_2$ has a extinction coefficient in water of above about 10,000 $Mol^{-1}$ $cm^{-1}$, such as above about 25,000 $Mol^{-1}$ $cm^{-1}$, above about 50,000 $Mol^{-1}$ $cm^{-1}$, above about 75,000 $Mol^{-1}$ $cm^{-1}$, above about 100,000 $Mol^{-1}$ $cm^{-1}$, above about 150,000 $Mol^{-1}$ $cm^{-1}$, above about 200,000 $Mol^{-1}$ $cm^{-1}$, above about 250,000 $Mol^{-1}$ $cm^{-1}$, or above about 300,000 $Mol^{-1}$ $cm^{-1}$.

In some embodiments, the second dye $D_2$ has a higher fluorescent quantum yield when conjugated to proteins than does the first dye $D_1$. In some embodiments, the additional dye has a high fluorescent quantum yield in water. In some embodiments, the second dye $D_2$ has a quantum yield in water that is greater than 5%, such as great than 10%, greater than 15%, greater than 20% or greater than 25%, greater than 30%, greater than 40%, or greater than 50% or greater.

In some embodiments, the second dye $D_2$ has a large Stokes shift (difference between $EX_{max}$ and $EM_{max}$). In some embodiments, the additional dye $D_2$ exhibits a Stokes shift that is greater than 15 nm, 20 nm, 25 nm, such as great than 30 nm, greater than 40 nm, greater than 50 nm, greater than 60 nm, greater than 70 nm, greater than 80 nm, greater than 90 nm or greater than 100 nm.

In some embodiments, the additional dye $D_2$ can be ICG, IRDye 680, Alexa Fluor 750, Dylight 755, IRDye 750, Cy7.5, Alexa Fluor 790, Dylight 800, or IRDye 800. In some embodiments, the additional dye $D_2$ can be ICG, IRDye 680, Alexa Fluor 750, Dylight 755, IRDye 750, Cy7.5, Alexa Fluor 790, Dylight 800, or IRDye 800. In some embodiments, the additional dye $D_2$ can be Alexa Fluor 488, IRDye 680, IRDye 800 or Dylight 755.

In some embodiments, the conjugate contains a number of second dye, $D_2$, residues per targeting molecule that is from or from about 1 to about 1000, such as from or from about 1 to about 100, from or from about 1 to about 50, from or from about 1 to about 25, from or from about 1 to about 10, or from or from about 1 to about 5. In some embodiments, the ratio of second dye molecules to targeting molecule is or is about 2:1, 3:1, 4:1, 5:1, 10:1, 15:1, 20:1, 25:1, 50:1, 75:1, 100:1, 150:1, 200:1, 250:1, 300:1, 350:1, 400:1, 450:1, 500:1, 550:1, 600:1, 650:1, 700:1, 750:1, 800:1, 850:1, 900:1, 950:1 or 1000:1, or is between or between about any two of such values. In some embodiments, the ratio of second dye molecules to targeting molecule is 1 to 10 or 1 to 5 second dye molecules per targeting molecule.

II. Pharmaceutical Compositions and Articles of Manufacture

Provided herein are pharmaceutical compositions containing a phthalocyanine-dye targeting molecule conjugate (e.g., IR700-antibody conjugate). In some embodiments, the compositions can be used in methods of PIT as described herein. The phthalocyanine dye-targeting molecule conjugate, for example, IR700-antibody conjugate. In some embodiments, the compositions can be provided in combination with another therapeutic agent (e.g., an immune modulating agent or anti-cancer agent). In some embodiments, the phthalocyanine dye-targeting molecule conjugate and other therapeutic agent, such as one or both of an immune modulating agent or anti-cancer agent, can be packaged as an article of manufacture as separate compositions for administration together, sequentially or intermittently. The combinations can be packaged as a kit.

1. Compositions, Formulations and Dosage Forms

In some embodiments, the compounds, such as conjugate, can be formulated in a pharmaceutically acceptable buffer, such as that containing a pharmaceutically acceptable carrier or vehicle. Generally, the pharmaceutically acceptable carriers or vehicles, such as those present in the pharmaceutically acceptable buffer, are can be any known in the art. Remington's Pharmaceutical Sciences, by E. W. Martin, Mack Publishing Co., Easton, Pa., 19th Edition (1995), describes compositions and formulations suitable for pharmaceutical delivery of one or more therapeutic compounds.

Pharmaceutically acceptable compositions generally are prepared in view of approvals for a regulatory agency or other agency prepared in accordance with generally recognized pharmacopeia for use in animals and in humans.

Pharmaceutical compositions can include carriers such as a diluent, adjuvant, excipient, or vehicle with which the compound is administered. Examples of suitable pharmaceutical carriers are described in "Remington's Pharmaceutical Sciences" by E. W. Martin. Such compositions will contain a therapeutically effective amount of the compound, generally in purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Water is a typical carrier when the pharmaceutical composition is administered intravenously. Saline solutions and aqueous dextrose and glycerol solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acacia, gelatin, glucose, molasses, polvinylpyrrolidine, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. A composition, if desired, also can contain minor amounts of wetting or emulsifying agents, or pH buffering agents, for example, acetate, sodium citrate, cyclodextrin derivatives, sorbitan monolaurate, triethanolamine sodium acetate, triethanolamine oleate, and other such agents.

In some embodiments, pharmaceutical preparation can be in liquid form, for example, solutions, syrups or suspensions. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). In some cases, pharmaceutical preparations can be presented in lyophilized form for reconstitution with water or other suitable vehicle before use.

In some embodiments, the nature of the pharmaceutically acceptable buffer, or carrier, depends on the particular mode of administration being employed. For instance, in some embodiments, parenteral formulations may comprise injectable fluids that include pharmaceutically and physiologically acceptable fluids such as water, physiological saline, balanced salt solutions, aqueous dextrose, or glycerol as a vehicle. In some embodiments, for solid compositions, for example powder, pill, tablet, or capsule forms, non-toxic solid carriers can include, for example, pharmaceutical grades of mannitol, lactose, starch, or magnesium stearate. In addition to biologically-neutral carriers, pharmaceutical compositions to be administered can in some embodiments contain minor amounts of non-toxic auxiliary substances, such as wetting or emulsifying agents, preservatives, and pH buffering agents, for example sodium acetate or sorbitan monolaurate.

The compounds can be formulated into suitable pharmaceutical preparations such as solutions, suspensions, tablets, dispersible tablets, pills, capsules, powders, sustained release formulations or elixirs, for oral administrate, as well as transdermal patch preparation and dry powder inhalers. Typically, the compounds are formulated into pharmaceutical compositions using techniques and procedures well known in the art (see e.g., Ansel Introduction to Pharmaceutical Dosage Forms, Fourth Edition, 1985, 126). Generally, the mode of formulation is a function of the route of administration.

Compositions can be formulated for administration by any route known to those of skill in the art including intramuscular, intravenous, intradermal, intralesional, intraperitoneal injection, subcutaneous, intratumoral, epidural, nasal, oral, vaginal, rectal, topical, local, otic, inhalational, buccal (e.g., sublingual), and transdermal administration or any route. Other modes of administration also are contemplated. Administration can be local, topical or systemic depending upon the locus of treatment. Local administration to an area in need of treatment can be achieved by, for example, but not limited to, local infusion during surgery, topical application, e.g., in conjunction with a wound dressing after surgery, by injection, by means of a catheter, by means of a suppository, or by means of an implant.

Parenteral administration, generally characterized by injection, either subcutaneously, intramuscularly, intratumorally, intravenously or intradermally is contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain an activator in the form of a solvent such as pH buffering agents, metal ion salts, or other such buffers. The pharmaceutical compositions also may contain other minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) also is contemplated herein. The percentage of active compound contained in such parenteral compositions is highly dependent on the specific nature thereof, as well as the activity of the compound and the needs of the subject.

Injectables are designed for local and systemic administration. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous. If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers, which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate.

If administered intravenously, suitable carriers include physiological saline or phosphate buffered saline (PBS), and solutions containing thickening and solubilizing agents, such as glucose, polyethylene glycol, and polypropylene glycol and mixtures thereof.

The composition can be formulated for single dosage administration or for multiple dosage administration. The agents can be formulated for direct administration. The composition can be provided as a liquid or lyophilized formulation. Where the composition is provided in lyophilized form it can be reconstituted just prior to use by an appropriate buffer, for example, a sterile saline solution.

Compositions also can be administered with other biologically active agents, either sequentially, intermittently or in the same composition. Administration also can include controlled release systems including controlled release formulations and device controlled release, such as by means of a pump.

The most suitable route in any given case depends on a variety of factors, such as the nature of the disease, the progress of the disease, the severity of the disease and the particular composition which is used. For example, compositions are administered sytemically, for example, via intravenous administration. Subcutaneous methods also can be employed, although increased absorption times can be necessary to ensure equivalent bioavailability compared to intravenous methods.

Pharmaceutical compositions can be formulated in dosage forms appropriate for each route of administration. Pharmaceutically and therapeutically active compounds and derivatives thereof are typically formulated and administered in unit dosage forms or multiple dosage forms. Each unit dose contains a predetermined quantity of therapeutically active compound sufficient to produce the desired therapeutic effect, in association with the required pharmaceutical carrier, vehicle or diluent. Unit dosage forms, include, but are not limited to, tablets, capsules, pills, powders, granules, sterile parenteral solutions or suspensions, and oral solutions or suspensions, and oil water emulsions containing suitable quantities of the compounds or pharmaceutically acceptable derivatives thereof. Unit dose forms can be contained ampoules and syringes or individually packaged tablets or capsules. Unit dose forms can be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses that are not segregated in packaging. Generally, dosage forms or compositions containing active ingredient in the range of 0.005% to 100% with the balance made up from non-toxic carrier can be prepared. Pharmaceutical compositions can be formulated in dosage forms appropriate for each route of administration.

The concentration of the pharmaceutically active compound is adjusted so that an injection provides an effective amount to produce the desired pharmacological effect. The exact dose depends on the age, weight and condition of the patient or animal as is known in the art. The unit-dose parenteral preparations are packaged in an ampoule, a vial or a syringe with a needle. The volume of liquid solution or reconstituted powder preparation, containing the pharmaceutically active compound, is a function of the disease to be treated and the particular article of manufacture chosen for package. All preparations for parenteral administration must be sterile, as is known and practiced in the art. In some embodiments, the compositions can be provided as a lyophilized powder, which can be reconstituted for administration as solutions, emulsions and other mixtures. They may also be reconstituted and formulated as solids or gels. The lyophilized powders can be prepared from any of the solutions described above.

The sterile, lyophilized powder can be prepared by dissolving a phthalocyanine dye-targeting molecule conjugate in a buffer solution. The buffer solution may contain an excipient which improves the stability of other pharmacological components of the powder or reconstituted solution, prepared from the powder.

In some embodiments, subsequent sterile filtration of the solution followed by lyophilization under standard conditions known to those of skill in the art provides the desired formulation. Briefly, the lyophilized powder is prepared by dissolving an excipient, such as dextrose, sorbitol, fructose, corn syrup, xylitol, glycerin, glucose, sucrose or other suitable agent, in a suitable buffer, such as citrate, sodium or potassium phosphate or other such buffer known to those of skill in the art. Then, a selected enzyme is added to the resulting mixture, and stirred until it dissolves. The resulting mixture is sterile filtered or treated to remove particulates and to ensure sterility, and apportioned into vials for lyophilization. Each vial can contain a single dosage (1 mg-1 g, generally 1-100 mg, such as 1-5 mg) or multiple dosages of the compound. The lyophilized powder can be stored under appropriate conditions, such as at about 4° C. to room temperature. Reconstitution of this lyophilized powder with a buffer solution provides a formulation for use in parenteral administration. The precise amount depends upon the indication treated and selected compound. Such amount can be empirically determined.

In some embodiments, the pH of the composition is between or between about 6 and 10, such as between or between about 6 and 8, between or between about 6.9 and 7.3, such as about pH 7.1. In some embodiments, the pH of the pharmaceutically acceptable buffer is at least or about 5, at least or about 6, at least or about 7, at least or about 8, at least or about 9 or at least or about 10, or is 7.1.

The compositions can be formulated for single dosage administration or for multiple dosage administration. The agents can be formulated for direct administration.

In some embodiments, the compositions provided herein are formulated in an amount for direct administration of the active compound, such as phthalocyanine dye-targeting molecule conjugate, in a range from or from about 0.01 mg to about 3000 mg, from about 0.01 mg to about 1000 mg, from about 0.01 mg to about 500 mg, from about 0.01 mg to about 100 mg, from about 0.01 mg to about 50 mg, from about 0.01 mg to about 10 mg, from about 0.01 mg to about 1 mg, from about 0.01 mg to about 0.1 mg, from about 0.1 mg to about 2000 mg, from about 0.1 mg to about 1000 mg, from about 0.1 mg to about 500 mg, from about 0.1 mg to about 100 mg, from about 0.1 mg to about 50 mg, from about 0.1 mg to about 10 mg, from about 0.1 mg to about 1 mg, from about 1 mg to about 2000 mg, from about 1 mg to about 1000 mg, from about 1 mg to about 500 mg, from about 1 mg to about 100 mg, from about 1 mg to about 10 mg, from about 10 mg to about 2000 mg, from about 10 mg to about 1000 mg, from about 10 mg to about 500 mg, from about 10 mg to about 100 mg, from about 100 mg to about 2000 mg, from about 100 mg to about 1000 mg, from about 100 mg to about 500 mg, from about 500 mg to about 2000 mg, from about 500 mg to about 1000 mg, and from about 1000 mg to about 3000 mg. In some embodiments, the volume of the composition can be 0.5 mL to 1000 mL, such as 0.5 mL to 100 mL, 0.5 mL to 10 mL, 1 mL to 500 mL, 1 mL to 10 mL, such as at least or about at least or about or 0.5 mL, 1 mL, 2 mL, 3 mL, 4 mL, 5 mL, 6 mL, 7 mL, 8 mL, 9 mL, 10 mL, 15 mL, 20 mL, 30 mL, 40 mL, 50 mL or more. For example, the composition is formulated for single dosage administration of an amount between or between about 100 mg and 500 mg, or between or between about 200 mg and 400 mg. In some embodiments, the composition is formulated for single dosage administration of an amount between or between about 500 mg and 1500 mg, 800 mg and 1200 mg or 1000 mg and 1500 mg. In some embodiments, the volume of the composition is between or between about 10 mL and 1000 mL or 50 mL and 500 mL; or the volume of the composition is at least 10 mL, 20 mL, 30 mL, 40 mL, 50 mL, 75 mL, 100 mL, 150 mL, 200 mL, 250 mL, 300 mL, 400 mL, 500 mL or 1000 mL.

In some embodiments, the entire vial contents of the formulations can be withdrawn for administration, or can be divided up into a plurality of dosages for multiple administrations. Upon withdrawal of an amount of drug for administration, the formulation can be further diluted if desired, such as diluted in water, saline (e.g., 0.9%) or other physiological solution.

In some embodiments, also provided are compositions containing an immune modulating agent or anti-cancer agent, which can be prepared in accord with known or standard formulation guidelines, such as described above. In some embodiments, the immune modulating agent, anti-cancer agent and/or phthalocyanine dye-targeting molecule conjugate (e.g., IR700-targeting molecule, such as IR700-antibody conjugate) are formulated as separate compositions. In some embodiments, the immune modulating agent is provided as a separate composition from the phthalocyanine dye-targeting molecule conjugate, and the two compositions are administered separately. In some embodiments, the anti-cancer agent is provided as a separate composition from the phthalocyanine dye-targeting molecule conjugate, and the two compositions are administered separately. The compositions can be formulated for parenteral delivery (i.e. for systemic delivery). For example, the compositions or combination of compositions are formulated for subcutaneous delivery or for intravenous delivery. The agents, such as a phthalocyanine dye-targeting molecule conjugate, an immune modulating agent, and/or an anti-cancer agent can be administered by different routes of administration. 3 Packaging and Articles of Manufacture Also provided are articles of manufacture containing packaging materials, any pharmaceutical compositions or combinations provided herein, and a label that indicates that the compositions and combinations are to be used for treatment of cancers. Exemplary articles of manufacture are containers including single chamber and dual chamber containers. The containers include, but are not limited to, tubes, bottles and syringes. The containers can further include a needle for subcutaneous administration.

In some embodiments, the agents can be provided separately for packaging as articles of manufacture. In some embodiments, the article of manufacture contains pharmaceutical compositions containing the phthalocyanine dye-targeting molecule conjugate, such as a IR700-antibody conjugate, and the immune modulatory agent. In some embodiments, the article of manufacture contains pharmaceutical compositions containing the phthalocyanine dye-targeting molecule conjugate (e.g., IR700-antibody conjugate) and an anti-cancer agent. In some embodiments, the article of manufacture contains pharmaceutical compositions containing the phthalocyanine dye-targeting molecule conjugate (e.g., IR700-antibody conjugate), the immune modulatory agent, and a further anti-cancer agent.

The articles of manufacture provided herein contain packaging materials. Packaging materials for use in packaging pharmaceutical products are well known to those of skill in the art. See, for example, U.S. Pat. Nos. 5,323,907, 5,052, 558 and 5,033,252, each of which is incorporated herein in its entirety. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. The choice of package depends on the agents. In general, the packaging is non-reactive with the compositions contained therein.

The components can be packaged in the same of different container. For example, in some embodiments, the components are separately packaged in the same container. Generally, examples of such containers include those that have an enclosed, defined space that contains the phthalocyanine dye-targeting molecule conjugate, and a separate enclosed, defined space containing the other components or component such that the subsequent areas are separated to permit the components to be separately administered. Any container or other article of manufacture is contemplated, so long as the agents are separated from the other components prior to administration. For suitable embodiments see e.g., containers described in U.S. Pat. Nos. 3,539,794 and 5,171,081. In some embodiments, a plurality of containers are provided, each separately containing a phthalocyanine dye-targeting molecule conjugate, an immune modulating agent or an anti-cancer agent. In such examples, the plurality of containers can be packaged together as a kit.

In some embodiments, a container containing the phthalocyanine dye-targeting molecule conjugate is contained in a light-protected container. In some embodiments, the container is a vial, such as a depyrogenated, glass vial. In some embodiments, the container, such as a vial, blocks light of a particular wavelength, such as a wavelength of light that is absorbed by the dye or dye-targeting molecule conjugate. In some embodiments, the conjugate is protected from light using containers that protect contents from light, or certain wavelengths or intensities of light. For example, in some embodiments, the container has a light transmittance of no more than 50%, no more than 40%, no more than 30%, no more than 20%, no more than 10%, no more than 5%, or no more than 1%. In some embodiments, the container protects from transmittance of light having a wavelength between or between about 500 nm and 725 nm, such as between or between about 650 nm and 725 nm, or does not transmit an intensity of light greater than 700 lux, 600 lux, 500 lux, 400 lux, 300 lux, 200 lux, or 100 lux. In some embodiments, the container is green, amber, translucent, opaque, or is wrapped in an opaque material, such as a foil, such as aluminum foil. In some embodiments, the container is sterile or depyrogenated.

In some embodiments, the conjugates are provided in a plurality of sealable containers. For example, the containers can each individually comprising a fraction of a single administration dose of a composition containing a conjugate that includes a phthalocyanine dye linked to a targeting molecule. In some embodiments, the combined amount of the conjugate in the plurality of sealable containers is between or between about 100 mg and 1500 mg, or 100 mg and 1200 mg. In some embodiments, the combined amount of the conjugate in the plurality of sealable container is between or between about 100 mg and 500 mg, between or between about 200 mg and 400 mg, between or between about 500 mg and 1500 mg, between or between about 800 mg and 1200 mg or between or between about 1000 mg and 1500 mg.

In some embodiments, the article of manufacture contains packaging material and a label or package insert containing instructions for combining the contents of the plurality of vials to prepare a single dosage formulation of the composition.

In some embodiments, the containers are further packaged to protect the contents from light. In some embodiments, a packaging system is provided that includes an internal packaging material comprising a container comprising the phthalocyanine dye-targeting molecule conjugate (e.g., IR700-targeting molecule conjugate, such as IR700-antibody conjugate), and optionally a container containing an immune modulating agent or anti-cancer agent. In some embodiments, the internal packaging material has a light transmittance of less than 20%, such as less than 15%, less than 10%, less than 5%, or less than 1%. In some embodiments, the packaging system includes an external packaging material comprising the internal packaging material. In some embodiments, the external packaging material has a light transmittance of less than 20%, such as less than 15%, less than 10%, less than 5%, or less than 1%. In some embodiments, the internal or external packaging material includes an opaque foil, such as aluminum foil. In some embodiments, the secondary packaging material is an aluminum pouch. In some embodiments, the external packaging material comprises cardboard.

In some embodiments, the internal and/or external packaging material is suitable for storage of the conjugate. In some embodiments, the internal and/or external packaging material is suitable for shipping of the conjugate.

Selected compositions including articles of manufacture thereof also can be provided as kits. Kits can include a pharmaceutical composition described herein and an item for administration provided as an article of manufacture. The kit can, optionally, include instructions for application including dosages, dosing regimens and instructions for modes of administration. Kits also can include a pharmaceutical composition described herein and an item for diagnosis.

In some embodiments, the compositions used for administration of agents, such as the phthalocyanine dye-targeting molecule conjugate contain an effective amount of each agent along with conventional pharmaceutical carriers and excipients appropriate for the type of administration contemplated.

In some embodiments, a single dosage amount of the agent, such as the phthalocyanine dye-targeting molecule conjugate, is comprised within a single container, such as a container in which the agent is stored. In some embodiments, a single dosage amount of the agent is comprised in a plurality of containers. Thus, in some embodiments, a plurality of containers, such as vials, are combined, in a container to be used for administration of the agent, such as an intravenous (IV) bag. In some embodiments, the container used for administration, such as IV bag, is prepared by opening one or a plurality of containers comprising the agent and placing the contents in the bag, such as until a desired dose of the agent for administration, e.g., infusion, is achieved. During the preparation of the administration container, such as IV bag, light precautions were taken to avoid exposure of the agent to light, such as the various light precautions described herein.

III. Methods of Treatment

In some embodiments, provided are methods for using and uses of the compositions containing a phthalocyanine-dye targeting molecule conjugate (e.g., IR700-targeting molecule conjugate, such as IR700-antibody conjugate) for PIT. In some embodiments, the phthalocyanine-dye targeting molecule conjugate targets to a cell or pathogen associated with a disease or condition, such as via binding to a cell surface protein or cell surface receptor expressed on a cell. Such methods and uses include therapeutic methods and uses, for example, involving administration of the molecules to a subject having a disease, condition or disorder followed by irradiation to achieve photoimmunotherapy (PIT), thereby resulting in photolysis of such cells or pathogens to effect treatment of the disease or disorder. In some embodiments, the methods can be used for treating a tumor or a cancer, whereby an administered phthalocyanine-dye targeting molecule conjugate (IR700-targeting molecule conjugate, such as IR700-antibody conjugate) is targeted to a cell associated with a tumor, thereby resulting in photolysis of such cell and, in some cases, resulting in treatment of the tumor. Uses include uses of the compositions in such methods and treatments, and uses of such compositions in the preparation of a medicament in order to carry out such therapeutic methods. In some embodiments, the methods and uses thereby treat the disease or condition or disorder, such as a tumor or cancer, in the subject.

In some embodiments, the methods include administration of a phthalocyanine dye-targeting molecule conjugate (e.g., IR-700 antibody conjugate) to the subject under conditions in which, generally, a cell targeted for killing is contacted with the conjugate. In some embodiments, the methods result in the binding of the targeting molecule (e.g., antibody) portion of the conjugate to a cell surface protein associated with a tumor or cancer. After contacting or administering the conjugate, a local area of the subject containing the targeted cells, e.g., a cell or cells associated with a tumor, is exposed or irradiated with light absorbed by the dye, generally NIR light, thereby activating the conjugate to effect specific cell killing. In some embodiments, irradiation is performed at a wavelength of 600 nm to 850 nm at a dose of at least 1 J cm$^{-2}$ or at least 1 J/cm of fiber length. In some embodiments, the methods of administering a phthalocyanine dye-targeting molecule conjugate (e.g., IR-700 antibody conjugate) include methods described in U.S. Pat. No. 8,524,239 or U.S. publication No. US2014/0120119.

A. Tumors and Subjects to be Treated

In some embodiments, the lesion is a tumor. In some embodiments, the tumor is a cancer. In some embodiments, the cancer is a cancer of the head and neck, breast, liver, colon, ovary, prostate, pancreas, brain, cervix, bone, skin, lung, or blood. In some embodiments, cancer may include a malignant tumor characterized by abnormal or uncontrolled cell growth. Other features that may be associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. Metastatic disease may refer to cancer cells that have left the original tumor site and migrated to other parts of the body, for example via the bloodstream or lymph system. In some embodiments, a cell targeted by the disclosed methods is a cancer cell or an immune cell. In some embodiments, the cancer cell is a cancer stem cell. In some embodiments, a cell targeted by the disclosed methods is a cell that is a cancer cell, a tumor cell, an inflammatory cell, an immune cell, a neuron, a stem cell, a proliferating cell, or a cell in a hyperplasia.

The target cell can be a cell that is not desired or whose growth is not desired, such as a tumor or cancer cell. In some embodiments, the cells can be growing in culture, or present in a mammal to be treated, such as a subject with cancer. Any target cell can be treated with the claimed methods. In some embodiments, the target cell expresses a cell surface protein that is not substantially found on the surface of other normal cells. In some embodiments, an antibody can be selected that specifically binds to such protein, and a phthalocyanine dye-antibody conjugate may be generated for that protein. In some embodiments, the cell surface protein is a tumor-specific protein. In some embodiments, the cell surface protein is CD25, which can be used to target cells associated with undesired transplant rejection.

In some embodiments, the tumor cell is a cancer cell, such as a cell in a subject with cancer. Exemplary cells that can be targeted in the disclosed methods include cells of the following tumors: a liquid tumor such as a leukemia, including acute leukemia (such as acute lymphocytic leukemia, acute myelocytic leukemia, and myeloblastic, promyelocytic, myelomonocytic, monocytic and erythroleukemia), chronic leukemias (such as chronic myelocytic (granulocytic) leukemia and chronic lymphocytic leukemia), polycythemia vera, lymphoma, Hodgkin's disease, non-Hodgkin's lymphoma, multiple myeloma, Waldenstrom's macroglobulinemia, heavy chain disease). In some embodiments, the cell is a solid tumor cell, such as a sarcoma or carcinoma, fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer, ovarian cancer, prostate cancer, hepatocellular carcinomna, lung cancer, colorectal cancer, squamous cell carcinoma, basal cell carcinoma, adenocarcinoma, for example adenocarcinoma of the pancreas, colon, ovary, lung, breast, stomach, prostate, cervix, or esophagus, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, CNS tumors, such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma. In some embodiments, the cancer is a squamous cell carcinoma of the head and neck.

Exemplary tumors, such as cancers, that can be treated with the claimed methods include solid tumors, such as breast carcinomas, such as lobular and duct carcinomas, sarcomas, carcinomas of the lung, such as non-small cell carcinoma, large cell carcinoma, squamous carcinoma, and adenocarcinoma, mesothelioma of the lung, colorectal adenocarcinoma, stomach carcinoma, prostatic adenocarcinoma, ovarian carcinoma, such as serous cystadenocarcinoma and mucinous cystadenocarcinoma, ovarian germ cell tumors, testicular carcinomas and germ cell tumors, pancreatic adenocarcinoma, biliary adenocarcinoma, hepatocellular carcinoma, bladder carcinoma, including, for instance, transitional cell carcinoma, adenocarcinoma, and squamous carcinoma, renal cell adenocarcinoma, endometrial carcinomas, including, for instance, adenocarcinomas and mixed Mullerian tumors (carcinosarcomas), carcinomas of the endocervix, ectocervix, and vagina, such as adenocarcinoma and squamous carcinoma of each of same, tumors of the skin, such as squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma, esophageal carcinoma, carcinomas of the nasopharynx and oropharynx, including squamous carcinoma and adenocarcinomas of same, salivary gland carcinomas, brain and central nervous system tumors, including, for example, tumors of glial, neuronal, and meningeal origin, tumors of peripheral nerve, soft tissue sarcomas and sarcomas of bone and cartilage, and lymphatic tumors, including B-cell and T-cell malignant lymphoma. In some embodiments, the tumor is an adenocarcinoma.

The methods can also be used to treat liquid tumors, such as a lymphatic, white blood cell, or other type of leukemia. In some embodiments, the tumor treated is a tumor of the blood, such as a leukemia, for example acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, and adult T-cell leukemia, lymphomas, such as Hodgkin's lymphoma and non-Hodgkin's lymphoma, and myelomas.

In some embodiments, the conjugate is targeted to a protein expressed on the surface of a lesion or on the surface of a cell present in the microenvironment of the lesion. For example, in some embodiments, the conjugate is targeted to a protein expressed on the surface of a cell in the tumor or on the surface of a cell in the microenvironment of the tumor. Exemplary of such cell surface proteins are any as described herein, including those described above.

In some embodiments, the protein on the cell surface of the target cell to be targeted is not present in significant amounts on other cells. For example, the cell surface protein can be a receptor that is only found on the target cell type.

In some embodiments, the protein expressed in the tumor, e.g., tumor-specific protein, can be HER1/EGFR, HER2/ERBB2, CD20, CD25 (IL-2Rα receptor), CD33, CD52, CD133, CD206, CEA, cancer antigen 125 (CA125), alpha-fetoprotein (AFP), Lewis Y, TAG72, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, SK-1 antigen or PD-L1. In some embodiments, the tumor-specific protein is PD-L1, HER1/EGFR, HER2, CD20, CD25, CD33, CD52, prostate specific membrane antigen (PSMA), EpCAM, EphA2, CD206, CD44, CD133, Mesothelin, Glypican-3, or carcinoembryonic antigen (CEA). Other cell surface proteins include any as described above.

In some embodiments, the cell surface protein is associated with a tumor, such as is a tumor-specific protein or tumor-specific antigen, such as members of the EGF receptor family (e.g., HER1, 2, 3, and 4) and cytokine receptors (e.g., CD20, CD25, IL-13R, CD5, CD52, etc.). In some embodiments, tumor specific proteins are those proteins that are unique to cancer cells or are much more abundant on them, as compared to other cells, such as normal cells. For example, HER2 is generally found in breast cancers, while HER1 is typically found in adenocarcinomas, which can be found in many organs, such as the pancreas, breast, prostate and colon.

Exemplary proteins associated with a tumor that can be found on a target cell, and to which targeting molecule, e.g. antibody or antibody fragment, specific for that protein can be used to formulate a phthalocyanine dye-antibody conjugate, include but are not limited to: any of the various MAGEs (Melanoma-Associated Antigen E), including MAGE 1, MAGE 2, MAGE 3, and MAGE 4, any of the various tyrosinases, mutant ras, mutant p53, p97 melanoma antigen, human milk fat globule (HMFG) which may be associated with breast tumors, any of the various BAGEs (Human B melanoma-Associated Antigen E), including BAGE1 and BAGE2, any of the various GAGEs (G antigen), including GAGE1, GAGE2-6, various gangliosides, and CD25.

Other proteins associated with a tumor include the HPV 16/18 and E6/E7 antigens associated with cervical cancers, mucin (MUC1)-KLH antigen which may be associated with breast carcinoma, CEA (carcinoembryonic antigen) which may be associated with colorectal cancer, gp100 which may be associated with for example melanoma, MART1 antigens which may be associated with melanoma, cancer antigen 125 (CA125, also known as mucin 16 or MUC16) which may be associated with ovarian and other cancers, alpha-fetoprotein (AFP) which may be associated with liver cancer, Lewis Y antigen which may be associated with colorectal, biliary, breast, small-cell lung, and other cancers, tumor-associated glycoprotein 72 (TAG72) which may be associated with adenocarcinomas, and the PSA antigen which may be associated with prostate cancer.

Other exemplary proteins associated with a tumor further include, but are not limited to, PMSA (prostate membrane specific antigen), which may be associated with solid tumor neovasculature, as well prostate cancer, HER-2 (human epidermal growth factor receptor 2) which may be associated with breast cancer, ovarian cancer, stomach cancer and uterine cancer, HER-1 which may be associated with lung cancer, anal cancer, and gliobastoma as well as adenocarcinomas, NY-ESO-1 which may be associated with melanoma, sarcomas, testicular carcinomas, and other cancers, hTERT (aka telomerase), proteinase 3, and Wilms tumor 1 (WT-1).

In some embodiments, the protein associated with a tumor is CD52 and may be associated with chronic lymphocytic leukemia, CD33 and may be associated with acute myelogenous leukemia, or CD20 and may be associated with Non-Hodgkin lymphoma.

Thus, the disclosed methods can be used to treat any cancer that expresses a tumor-specific protein. In some embodiments, the tumor therapeutic is an antibody, an antigen binding fragment, a protein, a glycoprotein, a peptide, a polypeptide, a virus, a viral capsid, or a viral particle.

In some embodiments, the tumor therapeutic is an antibody or an antigen binding fragment.

In some embodiments, the subject is a human or non-human mammal. In some embodiments, the subject is a human or veterinary subject, such as a mouse. In some embodiments, the subject is a mammal, such as a human, who has cancer, or is being treated for cancer. In some embodiments the disclosed methods are used to treat a subject who has a tumor, such as a tumor described herein. In some embodiments, the tumor has been previously treated, such as surgically or chemically removed, and the disclosed methods are used subsequently to kill any remaining undesired tumor cells that may remain in the subject.

The disclosed methods can be used to treat any mammalian subject, such as a human, who has a tumor, such as a cancer, or has had such previously removed or treated. Subjects in need of the disclosed therapies can include human subjects having cancer, wherein the cancer cells express a tumor-specific protein on their surface that can specifically bind to phthalocyanine dye-targeting molecule conjugate. For example, the disclosed methods can be used as initial treatment for cancer either alone, or in combination with radiation or other chemotherapy. The disclosed methods can also be used in patients who have failed previous radiation or chemotherapy. Thus, in some embodiments, the subject is one who has received other therapies, but those other therapies have not provided a desired therapeutic response. The disclosed methods can also be used in patients with localized and/or metastatic cancer.

In some embodiments, the method includes selecting a subject that will benefit from the disclosed therapies, such as selecting a subject having a tumor that expresses a cell surface protein, such as a tumor-specific protein, that can specifically bind to a phthalocyanine dye-targeting molecule conjugate. For example, if the subject is determined to have a breast cancer that expresses HER1, the subject may be selected to be treated with an anti-HER1-IR700 molecule, such as cetuximab-IR700.

B. Dosage and Administration

The compositions provided herein containing a phthalocyanine dye-targeting molecule conjugate (e.g., IR700-antibody conjugate) are administered in amounts that are sufficient to exert a therapeutically useful effect. Typically, the active agents are administered in an amount that does not result in undesirable side effects of the patient being treated, or that minimizes or reduces the observed side effects as compared to dosages and amounts required for single treatment with one of the above agents.

Methods of determining optimal dosages of a phthalocyanine dye-targeting molecule conjugate (e.g., IR700-antibody conjugate) to a patient in need thereof, either alone or in combination with one or more other agents, may be determined by standard dose-response and toxicity studies that are well known in the art.

The amount of a therapeutic agent, such as the phthalocyanine dye-targeting molecule conjugate (e.g., IR700-antibody conjugate) that is administered to a human or veterinary subject will vary depending upon a number of factors associated with that subject, for example the overall health of the subject. In some embodiments, an effective amount of the agent can be determined by varying the dosage of the product and measuring the resulting therapeutic response, such as the regression of a tumor. In some embodiments, effective amounts can be determined through various in vitro, in vivo or in situ immunoassays. In some embodiments, the disclosed agents can be administered in a single dose, or in several doses, as needed to obtain the desired response. In some embodiments, the effective amount is dependent on the source applied, the subject being treated, the severity and type of the condition being treated, and the manner of administration.

In some embodiments, a therapeutically effective amount is an amount of a composition that alone, or together with an additional therapeutic agent, such as a chemotherapeutic agent, is sufficient to achieve a desired effect in a subject, or in a cell, being treated with the composition. The effective amount of the therapeutic agent, such as the phthalocyanine dye-targeting molecule conjugate (e.g., IR700-antibody conjugate) can be dependent on several factors, including, but not limited to the subject or cells being treated, the particular therapeutic agent, and the manner of administration of the therapeutic composition. In some embodiments, a therapeutically effective amount or concentration is one that is sufficient to prevent advancement, such as metastasis, delay progression, or to cause regression of a disease, or which is capable of reducing symptoms caused by the disease, such as cancer. In some embodiments, a therapeutically effective amount or concentration is one that is sufficient to increase the survival time of a patient with a tumor.

In some embodiments, a therapeutically effective dose of the conjugate is between or between about 10 mg/m$^2$ and 5000 mg/m$^2$, such as between or between about 10 mg/m$^2$ and 3000 mg/m$^2$, 10 mg/m$^2$ and 1500 mg/m$^2$, 10 mg/m$^2$ and 750 mg/m$^2$, 10 mg/m$^2$ and 500 mg/m$^2$, 10 mg/m$^2$ and 250 mg/m$^2$, 10 mg/m$^2$ and 200 mg/m$^2$, 10 mg/m$^2$ and 100 mg/m$^2$, 10 mg/m$^2$ and 75 mg/m$^2$, 10 mg/m$^2$ and 50 mg/m$^2$, 10 mg/m$^2$ and 25 mg/m$^2$, 25 mg/m$^2$ and 5000 mg/m$^2$, 25 mg/m$^2$ and 3000 mg/m$^2$, 25 mg/m$^2$ and 1500 mg/m$^2$, 25 mg/m$^2$ and 750 mg/m$^2$, 25 mg/m$^2$ and 500 mg/m$^2$, 25 mg/m$^2$ and 250 mg/m$^2$, 25 mg/m$^2$ and 200 mg/m$^2$, 25 mg/m$^2$ and 100 mg/m$^2$, 25 mg/m$^2$ and 75 mg/m$^2$, 25 mg/m$^2$ and 50 mg/m$^2$, 50 mg/m$^2$ and 5000 mg/m$^2$, 50 mg/m$^2$ and 3000 mg/m$^2$, 50 mg/m$^2$ and 1500 mg/m$^2$, 50 mg/m$^2$ and 750 mg/m$^2$, 50 mg/m$^2$ and 500 mg/m$^2$, 50 mg/m$^2$ and 250 mg/m$^2$, 50 mg/m$^2$ and 200 mg/m$^2$, 50 mg/m$^2$ and 100 mg/m$^2$, 50 mg/m$^2$ and 75 mg/m$^2$, 75 mg/m$^2$ and 5000 mg/m$^2$, 75 mg/m$^2$ and 3000 mg/m$^2$, 75 mg/m$^2$ and 1500 mg/m$^2$, 75 mg/m$^2$ and 1000 mg/m$^2$, 75 mg/m$^2$ and 750 mg/m$^2$, 75 mg/m$^2$ and 500 mg/m$^2$, 75 mg/m$^2$ and 250 mg/m$^2$, 75 mg/m$^2$ and 225 mg/m$^2$, 75 mg/m$^2$ and 200 mg/m$^2$, 75 mg/m$^2$ and 100 mg/m$^2$, 100 mg/m$^2$ and 5000 mg/m$^2$, 100 mg/m$^2$ and 3000 mg/m$^2$, 100 mg/m$^2$ and 1500 mg/m$^2$, 100 mg/m$^2$ and 750 mg/m$^2$, 100 mg/m$^2$ and 500 mg/m$^2$, 100 mg/m$^2$ and 250 mg/m$^2$, 100 mg/m$^2$ and 200 mg/m$^2$, 100 mg/m$^2$ and 150 mg/m$^2$, 150 mg/m$^2$ and 5000 mg/m$^2$, 150 mg/m$^2$ and 3000 mg/m$^2$, 150 mg/m$^2$ and 1500 mg/m$^2$, 150 mg/m$^2$ and 750 mg/m$^2$, 150 mg/m$^2$ and 500 mg/m$^2$, 150 mg/m$^2$ and 250 mg/m$^2$, 150 mg/m$^2$ and 200 mg/m$^2$, 200 mg/m$^2$ and 5000 mg/m$^2$, 200 mg/m$^2$ and 3000 mg/m$^2$, 200 mg/m$^2$ and 1500 mg/m$^2$, 200 mg/m$^2$ and 750 mg/m$^2$, 200 mg/m$^2$ and 500 mg/m$^2$, 200 mg/m$^2$ and 250 mg/m$^2$, 250 mg/m$^2$ and 5000 mg/m$^2$, 250 mg/m$^2$ and 3000 mg/m$^2$, 250 mg/m$^2$ and 1500 mg/m$^2$, 250 mg/m$^2$ and 750 mg/m$^2$, 250 mg/m$^2$ and 500 mg/m$^2$, 500 mg/m$^2$ and 5000 mg/m$^2$, 500 mg/m$^2$ and 3000 mg/m$^2$, 500 mg/m$^2$ and 1500 mg/m$^2$, 500 mg/m$^2$ and 750 mg/m$^2$, 750 mg/m$^2$ and 5000 mg/m$^2$, 750 mg/m$^2$ and 3000 mg/m$^2$, 750 mg/m$^2$ and 1500 mg/m$^2$, 1500 mg/m$^2$ and 5000 mg/m$^2$, 1500 mg/m$^2$ and 3000 mg/m$^2$, and 3000 mg/m$^2$ and 5000 mg/m$^2$. In some embodiments, the therapeutically effective dose of the conjugate is no more than 10 mg/m$^2$, 50 mg/m$^2$, 75 mg/m$^2$, 100 mg/m$^2$, 150 mg/m$^2$, 200 mg/m$^2$, 225 mg/m$^2$, 250 mg/m$^2$, 300 mg/m$^2$, 400 mg/m$^2$, 500 mg/m$^2$, 600 mg/m$^2$, 700 mg/m$^2$, 800 mg/m$^2$, 900 mg/m$^2$, 1000 mg/m$^2$, 1250 mg/m$^2$, 1500 mg/m$^2$, 2000 mg/m$^2$, 2500 mg/m$^2$, 3000 mg/m$^2$, 3500 mg/m$^2$, 4000 mg/m$^2$, 4500 mg/m$^2$, or 5000 mg/m$^2$. In some embodiments, the dose is from or from about 50 mg/m$^2$ to about 5000 mg/m$^2$, from about 250 mg/m$^2$ to about 2500 mg/m$^2$, from about 750 mg/m$^2$ to about 1250 mg/m$^2$ or from about 100 mg/m$^2$ to about 1000 mg/m$^2$. In some embodiments, the dose is or is about 160 mg/m$^2$, 320 mg/m$^2$, 640 mg/m$^2$ or 1280 mg/m$^2$.

In some embodiments, a therapeutically effective dose of the conjugate is between or between about 0.25 mg/kg and 150 mg/kg, 0.25 mg/kg and 100 mg/kg, 0.25 mg/kg and 75 mg/kg, 0.25 mg/kg and 60 mg/kg, 0.25 mg/kg and 50 mg/kg, 0.25 mg/kg and 25 mg/kg, 0.25 mg/kg and 10 mg/kg, 0.25 mg/kg and 7.5 mg/kg, 0.25 mg/kg and 5.0 mg/kg, 0.25 mg/kg and 2.5 mg/kg, 0.25 mg/kg and 1.0 mg/kg, 0.25 mg/kg and 0.5 mg/kg, 0.50 mg/kg and 150 mg/kg, 0.50 mg/kg and 100 mg/kg, 0.50 mg/kg and 75 mg/kg, 0.50 mg/kg and 60 mg/kg, 0.50 mg/kg and 50 mg/kg, 0.50 mg/kg and 25 mg/kg, 0.50 mg/kg and 10 mg/kg, 0.50 mg/kg and 7.5 mg/kg, 0.50 mg/kg and 5.0 mg/kg, 0.50 mg/kg and 2.5 mg/kg, 0.50 mg/kg and 1.0 mg/kg, 1.0 mg/kg and 150 mg/kg, 1.0 mg/kg and 100 mg/kg, 1.0 mg/kg and 75 mg/kg, 1.0 mg/kg and 60 mg/kg, 1.0 mg/kg and 50 mg/kg, 1.0 mg/kg and 25 mg/kg, 1.0 mg/kg and 10 mg/kg, 1.0 mg/kg and 7.5 mg/kg, 1.0 mg/kg and 5.0 mg/kg, 1.0 mg/kg and 2.5 mg/kg, 2.5 mg/kg and 150 mg/kg, 2.5 mg/kg and 100 mg/kg, 2.5 mg/kg and 75 mg/kg, 2.5 mg/kg and 60 mg/kg, 2.5 mg/kg and 50 mg/kg, 2.5 mg/kg and 25 mg/kg, 2.5 mg/kg and 10 mg/kg, 2.5 mg/kg and 7.5 mg/kg, 2.5 mg/kg and 5.0 mg/kg, 5.0 mg/kg and 150 mg/kg, 5.0 mg/kg and 100 mg/kg, 5.0 mg/kg and 75 mg/kg, 5.0 mg/kg and 60 mg/kg, 5.0 mg/kg and 50 mg/kg, 5.0 mg/kg and 25 mg/kg, 5.0 mg/kg and 10 mg/kg, 5.0 mg/kg and 7.5 mg/kg, 7.5 mg/kg and 150 mg/kg, 7.5 mg/kg and 100 mg/kg, 7.5 mg/kg and 75 mg/kg, 7.5 mg/kg and 60 mg/kg, 7.5 mg/kg and 50 mg/kg, 7.5 mg/kg and 25 mg/kg, 7.5 mg/kg and 10 mg/kg, 10 mg/kg and 150 mg/kg, 10 mg/kg and 100 mg/kg, 10 mg/kg and 75 mg/kg, 10 mg/kg and 60 mg/kg, 10 mg/kg and 50 mg/kg, 10 mg/kg and 25 mg/kg, 25 mg/kg and 150 mg/kg, 25 mg/kg and 100 mg/kg, 25 mg/kg and 75 mg/kg, 25 mg/kg and 60 mg/kg, 25 mg/kg and 50 mg/kg, 50 mg/kg and 150 mg/kg, 50 mg/kg and 100 mg/kg, 50 mg/kg and 75 mg/kg, 50 mg/kg and 60 mg/kg, 60 mg/kg and 150 mg/kg, 60 mg/kg and 100 mg/kg, 60 mg/kg and 75 mg/kg, 75 mg/kg and 150 mg/kg, 75 mg/kg and 100 mg/kg, and 100 mg/kg and 150 mg/kg. In some embodiments, the therapeutically effective dose of the conjugate is no more than 0.25 mg/kg, 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 15 mg/kg, 20 mg/kg, 25 mg/kg, 30 mg/kg, 40 mg/kg, 50 mg/kg, 60 mg/kg, 70 mg/kg, 75 mg/kg, 80 mg/kg, 90 mg/kg, 100 mg/kg, 125 mg/kg or 150 mg/kg.

In some embodiments, the therapeutically effective amount is at least or at least about 0.01 mg, 0.1 mg, 0.5 mg, 1 mg, 5 mg, 10 mg, 50 mg, 100 mg, 200 mg, 500 mg, 600 mg, 700 mg, 800 mg, 900 mg, 1000 mg, 2000 mg, 3000 mg or more.

In some embodiments, the methods include administering to a subject having a disease or condition a therapeutically effective amount of a phthalocyanine dye-targeting molecule conjugate, e.g., IR700-antibody conjugate. In some embodiments, the phthalocyanine dye-targeting molecule conjugate is targeted to a cell present in the microenvironment of a tumor, lesion or hyperplasia. In some embodiments, a therapeutically effective dose of the conjugate is administered intravenously. In some embodiments, a therapeutically effective dose of the conjugate is administered intratumorally.

In some embodiments, the dose of the conjugate is at least 10 μg/kg, such as at least 100 μg/kg, at least 500 μg/kg, or at least 500 μg/kg, for example 10 μg/kg to 1000 μg/kg, such as a dose of about 100 μg/kg, about 250 μg/kg, about 500 μg/kg, about 750 μg/kg, or about 1000 μg/kg, for example when administered intratumorally or intraperitoneally (IP). In some embodiments, the dose is at least 1 μg/ml, such as at least 500 μg/ml, such as between 20 μg/ml to 100 μg/ml, such as about 10 μg/ml, about 20 μg/ml, about 30 μg/ml, about 40 μg/ml, about 50 g/ml, about 60 μg/ml, about 70 μg/ml, about 80 μg/ml, about 90 μg/ml or about 100 μg/ml, for example administered in topical solution.

In some embodiments, the therapeutically effective dose is a dose administered to a human. In some embodiments, the weight of an average human is 60 to 85 kg, such as about or approximately 75 kg.

In some embodiments, a therapeutically effective dose is one in which an administered conjugate containing a phthalocyanine dye conjugated to a targeting molecule (e.g., antibody or antigen-binding antibody fragment) achieves a systemic exposure that is no more than the therapeutically effective systemic exposure of the targeting molecule (e.g., antibody or antigen-binding antibody fragment) that is not so conjugated, such as occurs upon administration of a clinically acceptable dose of the drug targeting molecule drug alone.

The term "systemic exposure" refers to the actual body exposure of a drug targeting molecule in the plasma (blood or serum) after administration of the drug targeting molecule, and can be set forth as the area under the plasma drug concentration-time curve (AUC) as determined by pharmacokinetic analysis after administration of a dose of the drug targeting molecule. In some cases, the AUC is expressed in mg*h/L or in corresponding units thereof (e.g., μg*h/L). In some embodiments, the AUC is measured as an average AUC in a patient population, such as a sample patient population, e.g., the average AUC from one or more patient(s). In some embodiments, systemic exposure refers to the area under the curve (AUC) from 0 to infinity (inf or ∞) ($AUC_{0-\infty}$ or AUC[0-inf]), including all measured data and data extrapolated from measured pharmacokinetic (PK) parameters, such as an average AUC from a patient population, such as a sample patient population. In some embodiments, $AUC_{0-\infty}$ is predicted based on PK information for one month. In some embodiments, systemic exposure refers to the AUC from 0 to the last time-point that is experimentally measured ($AUC_{0-last}$). In some embodiments, the systemic exposure is the exposure (AUC) that occurs at the time of light irradiation or illumination, since the PIT depends on the dose or amount of the conjugate in the tumor at the time when the illumination or irradiation is carried out. In some embodiments, light irradiation or illumination is carried out within or about within or about 24 hours±3 hours, such as 24 hours±2 hours after administration of the conjugate. Thus, in some embodiments, systemic exposure refers to the area under the curve (AUC) from 0 to 24 hours ($AUC_{0-24}$ or AUC[0-24]). In some embodiments, systemic exposure refers to the average area under the curve (AUC) from 0 to 24 hours ($AUC_{0-24}$ or AUC[0-24]) from a patient population, such as a sample patient population.

In some embodiments, the therapeutically effective dose is one in which an administered conjugate containing a phthalocyanine dye conjugated to a targeting molecule (e.g., antibody or antigen-binding antibody fragment) achieves a systemic exposure as measured based on $AUC_{0-24}$ that is substantially lower than the $AUC_{0-\infty}$ of a clinically acceptable dose of the targeting molecule that is not so conjugated. In some cases, this is because a therapeutically effective systemic exposure of the conjugate achieved at the time of PIT (at the time of light irradiation or illumination) is the relevant period for the PIT activity as described above. In contrast, in some cases, for a therapeutically effective systemic exposure, such as to achieve pharmacological activity, for a targeting molecule that is not so conjugated (e.g. unconjugated cetuximab), the targeting molecule (e.g. antibody) must be present at a much higher exposure. For example, under the FDA guidelines for Erbitux (cetuximab), the antibody is administered at 400 mg/m$^2$ with weekly doses of 250 mg/m$^2$. In some cases, patients may require the continuous treatment of an unconjugated targeting molecule (e.g. antibody) for more than one month.

The term "therapeutically effective systemic exposure" refers to the systemic exposure achieved by a dose of a drug targeting molecule (e.g., antibody) for pharmacological activity that is deemed to be clinically acceptable and/or that achieves a therapeutic effect while having an acceptable safety profile. It is within the level of a skilled artisan to determine or identify a dose of a drug targeting molecule (e.g., antibody) that is clinically acceptable and/or that achieves a therapeutic effect having an acceptable safety profile. In some embodiments, a clinically acceptable dose of a drug targeting molecule is determined as the result of clinical trials in animals, and particularly humans, such as performed by the Food and Drug Administration (FDA) or other regulatory agencies (e.g. EMA, PDMA). In some embodiments, a therapeutically effective systemic exposure includes the systemic exposure resulting either from single dosage administration of a drug targeting molecule (e.g., antibody) or by repeated administration of a drug targeting molecule (e.g., agent) in a cycle of administration, such as daily, weekly, biweekly or monthly dosing.

Exemplary FDA approved clinically acceptable dosing schedules for exemplary antibody drugs are set forth in Table 1. In some embodiments, a therapeutically effective systemic exposure of a drug targeting molecule, including a drug targeting molecule that is not conjugated to a phthalocyanine dye, can be determined or is known from pharmacokinetic studies of a population of subjects at the clinically acceptable or approved dose administered as either a single administration of the initial dose or administered by repeated administrations in a dosage cycle (see e.g., Fracasso et al. (2007) Clin. Cancer. Res., 13:986 for observed systemic exposures (AUC) following single dosage administration of doses of cetuximab within the dosing range approved by the FDA).

TABLE 1

| FDA Approved Doses of Exemplary Drug Antibody Targeting molecules | | |
|---|---|---|
| Exemplary Antibody | Therapeutic Dose | Indication |
| Cetuximab (Erbitux ®) | 400 mg/m$^2$ (~10 mg/kg) followed by weekly dose of 250 mg/m$^2$ (~6.75 mg/kg) In combination with radiation therapy or platinum-based therapy with 5-FU | Head and Neck Cancer Colorectal Cancer |

TABLE 1-continued

FDA Approved Doses of Exemplary Drug Antibody Targeting molecules

| Exemplary Antibody | Therapeutic Dose | Indication |
| --- | --- | --- |
| Bevacizumab (Avastin ®) | 5 mg/kg (~185 mg/m$^2$) IV every 2 weeks with bolus-IFL | Metastatic colorectal cancer |
| | 10 mg/kg (~370 mg/m$^2$) IV every 2 weeks with FOLFOX4 | |
| | 5 mg/kg (~185 mg/m$^2$) IV every 2 weeks or 7.5 mg/kg IV every 3 weeks with fluoropyrimidine-irinotecan or fluoropyrimidine-oxaliplatin based chemotherapy | |
| | 15 mg/kg (~185 mg/m$^2$) IV every 3 weeks with carboplatin/paclitaxel | Non-squamous non-small cell lung cancer |
| | 10 mg/kg (~370 mg/m$^2$) IV every 2 weeks | Glioblastoma |
| | 10 mg/kg (~370 mg/m$^2$) IV every 2 weeks with interferon alfa | Metastatic renal cell carcinoma |
| Panitumumab (Vectibix ®) | 6 mg/kg (~220 mg/m$^2$) every 14 days | metastatic colorectal cancer |
| Retuximab (Rituxan ®) | 375 mg/m2 (~10 mg/kg) | Non-Hodgkin's Lymphoma (NHL) |
| | 375 mg/m2 (~10 mg/kg) in the first cycle and 500 mg/m2 ((~13 mg/kg) In cycles 2-6, in combination with FC, administered every 28 days | Chronic Lymphocytic Leukemia (CLL) |
| Alemtuzumab (Campath ®) | 30 mg/day three times per week for 12 weeks | B-cell chronic lymphocytic leukemia (B-CLL) |
| Novolumab (Opdivo Injection) | 3 mg/kg (~111 mg/m$^2$) intravenously every two weeks | metastatic non-small cell lung cancer (NSCLC) |
| pembrolizumab (KEYTRUDA) | 2 mg/kg (~74 mg/m$^2$) administered as an intravenous infusion over 30 minutes every 3 weeks | metastatic non-small cell lung cancer (NSCLC) | obtained from www.accessdata.fda.gov/scripts/cder/drugsatfda/index.cfm

In some embodiments, the therapeutically effective dose of the conjugate is one in which the administered conjugate containing a phthalocyanine dye (e.g., IR700) conjugated to a targeting molecule (e.g., antibody or antigen-binding antibody fragment) achieves an average systemic exposure (e.g., AUC) for a patient population, such as a sample patient population, that no more than 75%, no more than 70%, no more than 60%, no more than 50%, no more than 45%, no more than 40%, no more than 35%, no more than 25%, no more than 20% of the therapeutically average effective systemic exposure for a patient population, such as a sample patient population of the corresponding targeting molecule (e.g., antibody or antigen-binding antibody fragment) that is not so conjugated. Typically, the systemic exposure of the conjugate is sufficiently high to be capable of exhibiting phototoxicity by PIT.

In some embodiments, the conjugate is administered to achieve an average systemic exposure as measured by the area under the plasma conjugate concentration-time curve from time 0 to infinity (AUC[0-inf] or $AUC_{0-\infty}$) for patient population, such as a sample patient population, after administration of the conjugate is between or between about 250 µg/mL*h (used interchangeably with µg*h/mL) and 100,000 µg/mL*h, between or between about 500 g/mL*h and 50,000 µg/mL*h, between or about between 500 µg/mL*h and 25,000 µg/mL*h, between or between about 500 µg/mL*h and 18,000 µg/mL*h, between or between about 500 g/mL*h and 10,000 µg/mL*h, between or between about 500 µg/mL*h and 5,000 µg/mL*h or between or between about 500 µg/mL*h and 2,500 µg/mL*h. In some embodiments, the conjugate is administered to achieve a systemic exposure as measured by the average area under the plasma conjugate concentration-time curve from time 0 to infinity (AUC[0-inf] or $AUC_{0-\infty}$) for patient population, such as a sample patient population, after administration of the conjugate that is no more than 100,000 µg/mL*h, no more than 75,000 µg/mL*h, no more than 50,000 g/mL*h, no more than 40,000 µg/mL*h, no more than 30,000 µg/mL*h, no more than 20,000 g/mL*h, no more than 10,000 µg/mL*h, no more than 5,000 µg/mL*h, no more than 2,500 g/mL*h.

In some embodiments, the conjugate is administered to achieve an average systemic exposure as measured by the area under the plasma conjugate concentration-time curve from time 0 to 24 hours (AUC[0-24] or $AUC_{0-24}$) for patient population, such as a sample patient population, after administration of the conjugate that is between or between about 100 µg/mL*h and 25,000 µg/mL*h, between or between about 200 µg/mL*h and 10,000 µg/mL*h, between or between about 500 µg/mL*h and 5,000 µg/mL*h; or the average systemic exposure as measured by $AUC_{0-24}$ for patient population, such as a sample patient population, after administration of the conjugate is no more than 25,000 µg/mL*h, no more than 15,000 µg/mL*h, no more than 10,000 µg/mL*h, no more than 5,000 µg/mL*h, no more than 2,500 µg/mL*h, no more than 1,000 µg/mL*h, or no more than 500 µg/mL*h. In some embodiments, the plasma conjugate $AUC_{0-24}$ after administration of the conjugate is between or between about 500 µg/mL*h and 8,000 µg/mL*h, between or between about 500 µg/mL*h and 5,000 µg/mL*h, between or between about 500 µg/mL*h and 2,000 µg/mL*h or between or between about 1000 µg/mL*h and 4,000 µg/mL*h.

In some embodiments, the therapeutically effective dose of the phthalocyanine dye-targeting molecule conjugate (e.g., IR700-antibody conjugate) is less than the single administration therapeutically effective dose of the corresponding targeting molecule (e.g., antibody or antigen-binding antibody fragment) that is not so conjugated, such as is no more than 75%, no more than 70%, no more than 60%, no more than 50%, no more than 45%, no more than 40%, no more than 35%, no more than 25%, no more than 20% of the single administration therapeutically effective dose of the corresponding targeting molecule that is not so conjugated.

In some embodiments, the therapeutically effective dose of the phthalocyanine dye-targeting molecule conjugate (e.g., IR700-antibody conjugate) is less than the initial dose in a repeated dosage schedule of the therapeutically effective dose of the corresponding targeting molecule (e.g., antibody or antigen-binding antibody fragment) that is not so conjugated, such as is no more than 75%, no more than 70%, no more than 60%, no more than 50%, no more than 45%, no more than 40%, no more than 35%, no more than 25%, no more than 20% of the initial dose in a repeated dosage administration of the therapeutically effective dose of the corresponding targeting molecule that is not so conjugated.

In some embodiments, the therapeutically effective dose of the phthalocyanine dye-targeting molecule conjugate (e.g., IR700-antibody conjugate) is less than the average dose of a repeated dosage schedule of the therapeutically effective dose of the corresponding targeting molecule (e.g., antibody or antigen-binding antibody fragment) that is not so conjugated, such as is no more than 75%, no more than 70%, no more than 60%, no more than 50%, no more than 45%, no more than 40%, no more than 35%, no more than 25%, no more than 20% of the average dose in a repeated dosage schedule of the therapeutically effective dose of the corresponding targeting molecule that is not so conjugated.

In some embodiments, a therapeutically effective dose of the conjugate is less than 400 mg/m$^2$, less than 300 mg/m$^2$, less than 250 mg/m$^2$, less than 225 mg/m$^2$, less than 200 mg/m$^2$, less than 180 mg/m$^2$, less than 100 mg/m$^2$ or less than 50 mg/m$^2$. In some embodiments, a therapeutically effective dose of the conjugate is between or about between 50 mg/m$^2$ and 400 mg/m$^2$, 100 mg/m$^2$ and 300 mg/m$^2$, 100 mg/m$^2$ and 250 mg/m$^2$ or 100 mg/m$^2$ and 160 mg/m$^2$. In some embodiments, a therapeutically effective dose of the conjugate is between or between about 80 mg/m$^2$ and 240 mg/m$^2$, 80 mg/m$^2$ and 220 mg/m$^2$, 80 mg/m$^2$ and 200 mg/m$^2$, 80 mg/m$^2$ and 180 mg/m$^2$, 80 mg/m$^2$ and 160 mg/m$^2$, 80 mg/m$^2$ and 140 mg/m$^2$, 80 mg/m$^2$ and 120 mg/m$^2$, 80 mg/m$^2$ and 100 mg/m$^2$, 100 mg/m$^2$ and 240 mg/m$^2$, 100 mg/m$^2$ and 220 mg/m$^2$, 100 mg/m$^2$ and 200 mg/m$^2$, 100 mg/m$^2$ and 180 mg/m$^2$, 100 mg/m$^2$ and 160 mg/m$^2$, 100 mg/m$^2$ and 140 mg/m$^2$, 100 mg/m$^2$ and 120 mg/m$^2$, 120 mg/m$^2$ and 240 mg/m$^2$, 120 mg/m$^2$ and 220 mg/m$^2$, 120 mg/m$^2$ and 200 mg/m$^2$, 120 mg/m$^2$ and 180 mg/m$^2$, 120 mg/m$^2$ and 160 mg/m$^2$, 120 mg/m$^2$ and 140 mg/m$^2$, 140 mg/m$^2$ and 240 mg/m$^2$, 140 mg/m$^2$ and 220 mg/m$^2$, 140 mg/m$^2$ and 200 mg/m$^2$, 140 mg/m$^2$ and 180 mg/m$^2$, 140 mg/m$^2$ and 160 mg/m$^2$, 160 mg/m$^2$ and 240 mg/m$^2$, 160 mg/m$^2$ and 220 mg/m$^2$, 160 mg/m$^2$ and 200 mg/m$^2$, 160 mg/m$^2$ and 180 mg/m$^2$, 180 mg/m$^2$ and 240 mg/m$^2$, 180 mg/m$^2$ and 220 mg/m$^2$, 180 mg/m$^2$ and 200 mg/m$^2$, 200 mg/m$^2$ and 220 mg/m$^2$ or 200 mg/m$^2$ and 240 mg/m$^2$.

In some embodiments, a therapeutically effective dose of the conjugate is less than 12 mg/kg, less than 10 mg/kg, less than 8 mg/kg, less than 6 mg/kg, less than 4 mg/kg, less than 2 mg/kg or less than 1 mg/kg. In some embodiments, a therapeutically effective dose of the conjugate is between or between about 1 mg/kg and 12 mg/kg, 2 mg/kg and 10 mg/kg, 2 mg/kg and 6 mg/kg or 2 mg/kg and 4 mg/kg. In some embodiments, a therapeutically effective dose of the conjugate is between or between about 2.0 mg/kg and 6.5 mg/kg, 2.0 mg/kg and 6.0 mg/kg, 2.0 mg/kg and 5.0 mg/kg, 2.0 mg/kg and 4.0 mg/kg, 2.0 mg/kg and 3.0 mg/kg, 3.0 mg/kg and 6.5 mg/kg, 3.0 mg/kg and 6.0 mg/kg, 3.0 mg/kg and 5.0 mg·kg, 3.0 mg/kg and 4.0 mg/kg, 4.0 mg/kg and 6.5 mg/kg, 4.0 mg/kg and 6.0 mg/kg, 4.0 mg/kg and 5.0 mg/kg, 5.0 mg/kg and 6.5 mg/kg, 5.0 mg/kg and 6.0 mg/kg and 6.0 mg/kg and 6.5 mg/kg.

In some embodiments, the therapeutically effective amount is between about 75 mg and 500 mg, 75 mg and 400 mg, 75 mg and 400 mg, 75 mg and 300 mg, 75 mg and 200 mg, 75 mg and 150 mg, 150 mg and 500 mg, 150 mg and 400 mg, 150 mg and 300 mg, 150 mg and 200 mg, 200 mg and 500 mg, 200 mg and 400 mg, 200 mg and 300 mg, 300 mg and 500 mg, 300 mg and 400 mg or 400 mg and 500 mg.

In some embodiments, the conjugate is IR700-cetuximab. In some embodiments, the therapeutically effective amount of IR700-cetuximab conjugate is at least or about at least or is or is about 160 mg/m$^2$, 320 mg/m$^2$ or 640 mg/m$^2$. In some embodiments, the therapeutically effective amount of IR700-cetuximab conjugate is at least or about at least or is or is about 4.3 mg/kg, 8.6 mg/kg or 17 mg/kg.

In some embodiments, the therapeutically effective dose of the conjugate is for single dosage administration. In some embodiments, the therapeutically effective dose is administered as only a single injection or a single infusion in a dosage schedule or cycle, for example, is administered only one time in a dosage schedule or cycle. For example, in a dosing schedule or cycle, a subsequent dose of the conjugate is not administered. In some embodiments, the dosing schedule can be repeated. In some embodiments, the repeated dose, such as repeated single dose, is administered at a time in which the first dose has been cleared from the subject, which, in some cases, is a time at which there is no detectable systemic exposure of the conjugate. Thus, in some embodiments, the dosing of the conjugate is not administered to achieve a continuous systemic exposure of the conjugate, which is different than many existing therapies, including antibody therapies, in which repeating dosing in a dosing schedule or cycle is required to maintain continuous systemic exposure. In some embodiments, the dosing schedule or cycle is repeated once a week, every two weeks, once a month, twice a year, once a year or at a lesser frequency as needed.

In some embodiments, in any of the methods for treating provided herein, the dosing schedule is repeated, if residual lesion remains after a prior treatment with the conjugate. In some embodiments, the method additionally includes assessing the subject for the presence of a residual lesion and if residual lesion remains repeating the dosing schedule. In some embodiments, the dosing schedule is repeated if a residual lesion remains at a time that is more than or about or 1 week, 2 weeks, 3 weeks, 4 weeks, 2 months, 6 months or 1 year after initiation of the prior administration of the conjugate. In some embodiments, the dosing schedule is repeated if a residual lesion remains at or about 4 weeks after initiation of the prior administration of the conjugate.

In some embodiments, in a dosing schedule or cycle, a subsequent dose of the targeting molecule, e.g., therapeutic targeting molecules (e.g., therapeutic antibodies) that are not so conjugated to a photosensitizer (e.g., IR700), is not administered. For example, in some embodiments, a dose of the phthalocyanine dye-targeting molecule conjugate is not followed by a dose of the targeting molecule alone.

One skilled in the art will recognize that higher or lower dosages of the phthalocyanine dye-targeting molecule conjugate can also be used, for example depending on the particular agent. In some embodiments, dosages, such as daily dosages, are administered in one or more divided doses, such as 2, 3, or 4 doses, or in a single formulation. The phthalocyanine dye-targeting molecule conjugate can be administered alone, in the presence of a pharmaceutically acceptable carrier, or in the presence of other therapeutic agents, such as an immune-modulating agent, anti-cancer agent or other anti-neoplastic agents.

In some embodiments, the phthalocyanine dye-targeting molecule conjugate may be administered either systemically or locally to the organ or tissue to be treated. Exemplary routes of administration include, but are not limited to, topical, injection (such as subcutaneous, intramuscular, intradermal, intraperitoneal, intratumoral, and intravenous), oral, sublingual, rectal, transdermal, intranasal, vaginal and inhalation routes. In some embodiments, the phthalocyanine dye-targeting molecule conjugate is administered intravenously. In some embodiments, the phthalocyanine dye-targeting molecule conjugate is administered parenterally. In some embodiments, the phthalocyanine dye-targeting molecule conjugate is administered enterally. In some embodiments, the conjugate is administered by local injection. In some embodiments, the conjugate is administered as a topical application.

The compositions comprising the phthalocyanine dye-targeting molecule conjugate can be administered locally or systemically using any method known in the art, for example to subjects having a tumor, such as a cancer, or who has had a tumor previously removed, for example via surgery. Although specific examples are provided, one skilled in the art will appreciate that alternative methods of administration of the disclosed agents can be used. Such methods may include for example, the use of catheters or implantable pumps to provide continuous infusion over a period of several hours to several days into the subject in need of treatment.

In some embodiments, the phthalocyanine dye-targeting molecule conjugate is administered by parenteral means, including direct injection or infusion into a tumor, such as intratumorally. In some embodiments, the phthalocyanine dye-targeting molecule conjugate is administered to the tumor by applying the agent to the tumor, for example by bathing the tumor in a solution containing the agent, such as the phthalocyanine dye-targeting molecule conjugate, or by pouring the agent onto the tumor.

In addition, or alternatively, the disclosed compositions can be administered systemically, for example intravenously, intramuscularly, subcutaneously, intradermally, intraperitoneally, subcutaneously, or orally, to a subject having a tumor, such as cancer.

The dosages of the phthalocyanine dye-targeting molecule conjugate to be administered to a subject are not subject to absolute limits, but will depend on the nature of the composition and its active ingredients and its unwanted side effects, such as immune response against the agent, the subject being treated, and the type of condition being treated and the manner of administration. Generally, the dose will be a therapeutically effective amount, such as an amount sufficient to achieve a desired biological effect, for example an amount that is effective to decrease the size, such as volume and/or weight, of the tumor, or attenuate further growth of the tumor, or decrease undesired symptoms of the tumor.

In some embodiments, the compositions used for administration of the agent, such as the phthalocyanine dye-targeting molecule conjugate contain an effective amount of the agent along with conventional pharmaceutical carriers and excipients appropriate for the type of administration contemplated. For example, in some embodiments, parenteral formulations may contain a sterile aqueous solution or suspension of the conjugate. In some embodiments, compositions for enteral administration may contain an effective amount of the phthalocyanine dye-targeting molecule conjugate in aqueous solution or suspension that may optionally include buffers, surfactants, thixotropic agents, and flavoring agents.

C. Dosage Regime and Photoimmunotherapy

The PIT includes administration of a composition containing the phthalocyanine dye-targeting molecule conjugate (e.g., IR700-antibody conjugate) followed by irradiation. In some embodiments, the method includes irradiating the tumor.

In some embodiments, after the cells are contacted with the phthalocyanine dye-targeting molecule conjugate, the cells are irradiated. Methods of irradiation are known in the art. As only cells expressing the cell surface protein will typically be recognized by the targeting molecule, generally only those cells will have sufficient amounts of the conjugate bound to it. This may decrease the likelihood of undesired side effects, such as killing of normal cells, as the irradiation may only kill the cells to which the conjugate is bound, and generally not other cells.

In some embodiments, a cell is irradiated in vivo, for example irradiating a subject who has previously been administered the phthalocyanine dye-targeting molecule conjugate. In some embodiments, the subject is irradiated, for example a tumor in the subject can be irradiated.

In some embodiments, the irradiation is effected after administration of the phthalocyanine dye-targeting molecule conjugate. In some embodiments, the irradiation or illumination is carried out or effected between or between about 30 minutes and 96 hours after administering the phthalocyanine dye-targeting molecule conjugate (e.g., IR700-antibody conjugate), such as between 30 minutes and 48 hours, 30 minutes and 24 hours or 12 hours and 48 hours, such as generally at least 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours or more after administering the conjugate. For example, the irradiation can be performed within about 24 hours after administering the conjugate. In some embodiments, greater than 6 hours prior to irradiating or illuminating the tumor, the subject has been administered the conjugate comprising the targeting molecule, wherein the conjugate associates with the tumor. In some embodiments, the conjugate has been previously administered to the subject greater than or greater than about 12 hours, 24 hours, 26 hours, 48 hours, 72 hours or 96 hours prior to irradiating or illuminating the tumor.

In some embodiments, at the time of or after the irradiation, the subject can receive one or more other therapies (e.g., immune-modulating agent or anti-cancer agent) as described herein. In some cases, the one or more other therapies are thus also administered after administration of the phthalocyanine dye-targeting molecule conjugate (e.g., IR700-antibody conjugate). In some embodiments, the additional therapy is administered within or within about 0 to 24 hours of the irradiation, such as within or within about 5 minutes, 10 minutes, 30 minutes, 1 hour, 2 hours, 6 hours, 12 hours or 24 hours of the irradiation.

In some embodiments, prior to the irradiation, the subject can receive one or more other therapies as described herein. In some cases, the one or more other therapies can be administered prior to, during, or following administration of the phthalocyanine dye-targeting molecule conjugate (e.g., IR700-antibody conjugate), and generally prior to irradiation of the subject. In some embodiments, the additional therapeutic agent (e.g., immune-modulating agent or anti-cancer agent) can be administered during or simultaneously with administration of the phthalocyanine dye-targeting molecule conjugate. In some embodiments, the additional therapeutic agent (e.g., immune-modulating agent or anti-cancer agent) can be administered after or following administration of the phthalocyanine dye-targeting molecule conjugate. For example, in some embodiments, the conjugate is administered prior to the one or more other therapies and the conjugate and one or more other therapies are each administered prior to irradiating the tumor. In some embodiments, the conjugate is administered subsequent to the one or more other therapies and the conjugate and one or more other therapies are each administered prior to irradiating the tumor. In some embodiments, the irradiation is carried out after administration of the additional therapeutic (e.g., immune modulating agent or anti-cancer agent) and the phthalocyanine dye-targeting molecule conjugate.

In some embodiments, the additional therapeutic agent is an immune modulating agent and the immune modulating agent is administered 6 hours to 4 weeks prior to the irradiation, such as generally greater than or greater than about 12 hours, 24 hours, 36 hours, 72 hours, 96 hours, one week, two weeks, three weeks or four weeks prior to the irradiation. In some embodiments, the phthalocyanine dye-targeting molecule (e.g. IR700 antibody conjugate) is administered 6 hours to 96 hours prior to the irradiation, such as generally within or within about or about 6 hours, 12 hours, 24 hours, 36 hours, 72 hours or 96 hours prior to the irradiation.

In some embodiments, prior to the irradiation, the subject can receive an immune modulating agent, such as an immune checkpoint inhibitor. In some embodiments, the immune modulating agent is generally administered prior to irradiation of the subject. In some embodiments, the immune modulating agent is administered between or between about 12 hours and 2 months before effecting the irradiation, such as between 12 hours and 1 month, 12 hours and 3 weeks, 12 hours and 2 weeks, 12 hours and 1 week, and 1 week and 1 month, such as generally at least 12 hours, 24 hours, 48 hours, 96 hours, one week, two weeks, three weeks, or one month prior to irradiating the tumor. In some embodiments, the immune modulating agent can be administered prior to, subsequent to or simultaneously with the conjugate, so long as both the immune modulating agent and conjugate are administered prior to the irradiation. In some embodiments, the immune modulating agent can be administered prior to the administration of the phthalocyanine dye-targeting molecule conjugate (e.g., IR700-antibody conjugate). In some embodiments, the immune modulating agent can be administered during or simultaneously with administration of the phthalocyanine dye-targeting molecule conjugate. In some embodiments, the immune modulating agent can be administered subsequent to or following administration of the phthalocyanine dye-targeting molecule conjugate. For example, the immune modulating agent subsequent to the irradiation three times a week, two times a week, once every week, once every two weeks, once every three weeks or once a month.

For example, in some cases the conjugate is administered at least 12 hours, such as from or from about 12 hours to 48 hours, prior to irradiation and the immune modulating agent is administered at least 12 hours, such as from or from about 12 hours to about 1 month, prior to irradiation. In some embodiments, the conjugate is administered no more than or no more than about 36 hours, 24 hours, 18 hours or 12 hours prior to irradiation and the immune modulating agent is administered more than 12 hours prior to irradiation, such as generally more than 24 hours, 48 hours, 96 hours, one week, two weeks, three weeks or one month prior to irradiation.

In some embodiments, the immune modulating agent is itself a conjugate containing a phthalocyanine dye, such as a phthalocyanine dye linked to an antibody or antigen-binding fragment that is an immune modulating agent. In some embodiments, the immune modulating agent is an IR700-antibody conjugate that includes an immune modulating antibody (e.g. checkpoint inhibitor) that binds to a checkpoint protein on a tumor cell (e.g. PD-L1). In some embodiments, the immune modulating conjugate (e.g., IR700-antibody conjugate that is an immune modulating agent) is administered prior to administration of the phthalocyanine dye-targeting molecule conjugate, such as between 12 hours and 2 months, such as generally at least 12 hours, at least 24 hours, at least 48 hours, at least 96 hours, at least one week, at least two weeks, at least three weeks or at least one month prior to administration of the phthalocyanine dye-targeting molecule conjugate. In some embodiments, the immune modulating conjugate (e.g., IR700-antibody conjugate that is an immune modulating agent) is administered during or simultaneously with administration of the phthalocyanine dye-targeting molecule conjugate. In some embodiments, the immune modulating conjugate (e.g., IR700-antibody conjugate that is an immune modulating agent) is administered after administration of the phthalocyanine dye-targeting molecule conjugate, such as between 12 hours and 2 months, such as generally at least 12 hours, at least 24 hours, at least 48 hours, at least 96 hours, at least one week, at least two weeks, at least three weeks or at least one month after administration of the phthalocyanine dye-targeting molecule conjugate.

In some embodiments, the irradiation is carried out or effected after administration of the immune modulating conjugate (e.g., IR700-antibody conjugate that is an immune modulating agent) and the phthalocyanine dye-targeting molecule conjugate. In some embodiments, the irradiation is effected after administration of the phthalocyanine dye-targeting molecule conjugate.

In some embodiments, the method of combination therapy includes two irradiations or illuminations. In some embodiments, the method of combination therapy involves a first irradiation of the tumor after administering the immune modulating conjugate (e.g., IR700-antibody conjugate that is an immune modulating agent) and a second irradiation of the tumor after administering the phthalocyanine dye-targeting molecule conjugate. In some embodiments, each irradiation is performed within 6 to 48 hours after administering the respective conjugate, such as generally at least about 6 hours, 12 hours, 24 hours or 36 hours after administration of each conjugate.

In some embodiments, the method of combination therapy comprising the immune modulating conjugate (e.g., IR700-antibody conjugate that is an immune modulating agent) and the phthalocyanine dye-targeting molecule conjugate only includes a single irradiation. In some embodiments, the phthalocyanine dye-targeting molecule conjugate is administered at least 12 hours after administering the immune modulating conjugate (e.g., IR700-antibody conjugate that is an immune modulating agent) and within 6 to 48 hours prior to irradiating the tumor.

In some embodiments, the immune modulating conjugate (e.g., IR700-antibody conjugate that is an immune modulating agent) and the phthalocyanine dye-targeting molecule conjugate are administered by the same route of administration. In some embodiments, both the immune modulating conjugate (e.g., IR700-antibody conjugate that is an immune modulating agent) and the phthalocyanine dye-targeting molecule conjugate are administered systemically. In other embodiments, both of the conjugates are administered intravenously.

In some embodiments, prior to the irradiation, the subject can receive an anti-cancer agent. In some embodiments, the anti-cancer agent is generally administered prior to irradiation of the subject. In some embodiments, the irradiation is carried out or effected between or between about 5 minutes and 2 weeks after administering the anti-cancer agent, such as between 5 minutes and 1 week, 5 minutes and 3 days, 5 minutes and 48 hours, 5 minutes and 24 hours, 5 minutes and 12 hours, 5 minutes and 6 hours, and 5 minutes and 1 hour, such as generally at least about 15 minutes, 30 minutes, 1 hour, 2 hours, 3 hours, 4 hours, 5 hours, 6 hours, 12 hours, or 24 hours prior to irradiating the tumor. In some embodiments, the anti-cancer agent can be administered prior to, subsequent to or simultaneously with the conjugate, so long as both the anti-cancer agent and conjugate are administered prior to the irradiation. In some embodiments, the anti-cancer agent can be administered prior to the administration of the phthalocyanine dye-targeting molecule conjugate. In some embodiments, the anti-cancer agent can be administered during or simultaneously with administration of the phthalocyanine dye-targeting molecule conjugate. In some embodiments, the anti-cancer agent can be following administration of the phthalocyanine dye-targeting molecule conjugate.

For example, in some cases the conjugate is administered at least 12 hours, such as from or from about 12 hours to 48 hours, prior to irradiation and the anti-cancer agent is administered at least 5 minutes, such as from or from about 5 minutes to 24 hours, prior to irradiation. In some embodiments, the conjugate is administered no more than or no more than about 36 hours, 24 hours, 18 hours or 12 hours prior to irradiation and the anti-cancer agent is administered greater than 5 minutes prior to irradiation and generally no more than 30 minutes, 1 hour, 2 hours, 6 hours, 12 hours or 24 hours prior to irradiation.

In some embodiments, the cells, such as a tumor, are irradiated with a therapeutic dose of radiation at a wavelength within a range from or from about 400 nm to about 900 nm, such as from or from about 500 nm to about 900 nm, such as from or from about 600 nm to about 850 nm, such as from or from about 600 nm to about 740 nm, such as from about 660 nm to about 740 nm, from about 660 nm to about 710 nm, from about 660 nm to about 700 nm, from about 670 nm to about 690 nm, from about 680 nm to about 740 nm, or from about 690 nm to about 710 nm. In some embodiments, the cells, such as a tumor, are irradiated with a therapeutic dose of radiation at a wavelength of 600 nm to 850 nm, such as 660 nm to 740 nm. In some embodiments, the cells, such as a tumor, is irradiated at a wavelength of at least or about at least 600 nm, 620 nm, 640 nm, 660 nm, 680, nm, 700 nm, 720 nm or 740 nm, such as 690±50 nm, for example about 680 nm.

In some embodiments, the cells, such as a tumor, are irradiated at a dose of at least 1 J cm$^{-2}$, such as at least 10 J cm$^{-2}$, at least 30 J cm$^{-2}$, at least 50 J cm$^{-2}$, at least 100 J cm$^{-2}$, or at least 500 J cm$^{-2}$. In some embodiments, the dose of irradiation is from or from about 1 to about 1000 J cm$^{-2}$, from about 1 to about 500 J cm$^{-2}$, from about 5 to about 200 J cm$^{-2}$, from about 10 to about 100 J cm$^{-2}$, or from about 10 to about 50 J cm$^{-2}$. In some embodiments, the cells, such as a tumor, are irradiated at a dose of at least or at least about 2 J cm$^{-2}$, 5 J cm$^{-2}$, 10 J cm$^{-2}$, 25 J cm$^{-2}$, 50 J cm$^{-2}$, 75 J cm$^{-2}$, 100 J cm$^{-2}$, 150 J cm$^{-2}$, 200 J cm$^{-2}$, 300 J cm$^{-2}$, 400 J cm$^{-2}$, or 500 J cm$^{-2}$.

In some embodiments, the cells, such as a tumor, are irradiated or illuminated at a dose of at least 1 J/cm fiber length, such as at least 10 J/cm fiber length, at least 50 J/cm fiber length, at least 100 J/cm fiber length, at least 250 J/cm fiber length, or at least 500 J/cm fiber length. In some embodiments, the dose of irradiation is from or from about 1 to about 1000 J/cm fiber length, from about 1 to about 500 J/cm fiber length, from about 2 to about 500 J/cm fiber length, from about 50 to about 300 J/cm fiber length, from about 10 to about 100 J/cm fiber length, or from about 10 to about 50 J/cm fiber length. In some embodiments, the cells, such as a tumor, are irradiated at a dose of at least or at least about 2 J/cm fiber length, 5 J/cm fiber length, 10 J/cm fiber length, 25 J/cm fiber length, 50 J/cm fiber length, 75 J/cm fiber length, 100 J/cm fiber length, 150 J/cm fiber length, 200 J/cm fiber length, 250 J/cm fiber length, 300 J/cm fiber length, 400 J/cm fiber length or 500 J/cm fiber length.

In some embodiments, the dose of irradiation or illumination in a human subject is from or from about 1 to about 400 J cm$^{-2}$, from about 2 to about 400 J cm$^{-2}$, from about 1 to about 300 J cm$^{-2}$, from about 10 to about 100 J cm$^{-2}$ or from about 10 to about 50 J cm$^{-2}$, from about such as is at least or at least about or is or within or within about or is or is about 10 J cm$^{-2}$, at least 30 J cm$^{-2}$, at least 50 J cm$^{-2}$, at least 100 J cm$^{-2}$. In some embodiments, the dose of irradiation in a human subject is from or from about 1 to 300 J/cm fiber length, 10 to 100 J/cm fiber length or 10 to 50 J/cm fiber length, such as is at least or at least about or is or within or within about or is or is about 10 J/cm fiber length, at least 30 J/cm fiber length, at least 50 J/cm fiber length, at least 100 J/cm fiber length. In some cases, it is found that a dose of irradiation in a human subject to achieve PIT can be less than is necessary for PIT in a mouse. For example, in some cases, 50 J/cm$^2$ (50 J cm$^{-2}$) light dosimetry in an in vivo tumor mouse model is not effective for PIT, which is in contrast to what we can be observed in the clinic with human patients.

In some embodiments, the dose of irradiation following administration of the composition comprising the phthalocyanine dye-targeting molecule conjugate is at least 1 J cm$^{-2}$ or 1 J/cm of fiber length at a wavelength of 660-740 nm, for example, at least 10 J cm$^{-2}$ or 10 J/cm of fiber length at a wavelength of 660-740 nm, at least 50 J cm$^{-2}$ or 50 J/cm of fiber length at a wavelength of 660-740 nm, or at least 100 J cm$^{-2}$ or 100 J/cm of fiber length at a wavelength of 660-740 nm, for example 1.0 to 500 J cm$^{-2}$ or 1.0 to 500 J/cm of fiber length at a wavelength of 660-740 nm. In some embodiments, the wavelength is 660-710 nm. In some embodiments, the dose of irradiation following administration of the composition comprising the phthalocyanine dye-targeting molecule conjugate is at least 1.0 J cm$^{-2}$ or 1 J/cm of fiber length at a wavelength of 680 nm for example, at least 10 J cm$^{-2}$ or 10 J/cm of fiber length at a wavelength of 680 nm, at least 50 J cm$^{-2}$ or 50 J/cm of fiber length at a wavelength of 680 nm, or at least 100 J cm$^{-2}$ or 100 J/cm of fiber length at a wavelength of 680 nm, for example 1.0 to 500 J cm$^{-2}$ or 1.0 to 500 J/cm of fiber length at a wavelength of 680 nm. In some embodiments, multiple irradiations are performed, such as at least 2, at least 3, or at least 4 irradiations, such as 2, 3, 4, 5, 6, 7, 8, 9 or 10 separate administrations. Exemplary irradiation after administration of the conjugates or compositions provided herein include irradiating the tumor at a wavelength of 660 nm to 740 nm at a dose of at least 1 J cm$^{-2}$ or 1 J/cm of fiber length.

In some embodiments, a light or laser may be applied to the dye molecules, such as cells containing the conjugate, for from about 5 seconds to about 5 minutes. For example, in some embodiments, the light or laser is applied for or for about 5, 10, 15, 20, 25, 30, 35, 40, 45 50 or 55 seconds, or for within a range between any of two such values, to activate the dye molecules. In some embodiments, the light or laser is applied for or for about 1, 1.5, 2, 2.5, 3, 3.5, 4, 4.5 or 5 minutes, or more, or within a range between any two of such values. In some embodiments, the length of time a light or laser is applied can vary depending, for example, on the energy, such as wattage, of the light or laser. For example, lights or lasers with a lower wattage may be applied for a longer period of time in order to activate the dye molecule.

In some embodiments, a light or laser may be applied about 30 minutes to about 48 hours after administering the conjugate. For example, in some embodiments, the light or laser is applied at or at about 30, 35, 40, 45, 50 or 55 minutes after administering the conjugate, or within a range between any two of such values. In some embodiments, the light or laser is applied at or at about 1, 2, 3, 4, 5, 6, 7, 8, 9, 10, 11, 12, 13, 14, 15, 16, 17, 18, 19, 20, 21, 22, 23 or 24 hours after administering the conjugate, or is administered within a range between or between about any two of such values. In some embodiments, the light or laser is applied for between or between about 1 and 24 hours, such as between or between about 1 and 12 hours, 12 and 24 hours, 6 and 12 hours, or may be administered more than 24 following administration of the conjugate. In some embodiments, the light or laser is applied 36 or 48 hours after administering the conjugate.

In some embodiments, cells, or subjects, can be irradiated one or more times. Thus, irradiation can be completed in a single day, or may be done repeatedly on multiple days with the same or a different dosage, such as irradiation at least 2 different times, 3 different times, 4 different times 5 different times or 10 different times. In some embodiments, repeated irradiations may be done on the same day, on successive days, or every 1-3 days, every 3-7 days, every 1-2 weeks, every 2-4 weeks, every 1-2 months, or at even longer intervals.

In some embodiments, the dose or method of irradiation differs depending on the type or morphology of the tumor.

In some embodiments, the lesion is a tumor that is a superficial tumor. In some embodiments, the tumor is less than 10 mm thick. In some embodiments, irradiation is carried out using a microlens-tipped fiber for surface illumination. In some embodiments, the light irradiation dose is from or from about 5 J/cm$^2$ to about 200 J/cm$^2$.

In some embodiments, the provided methods include illuminating an superficial tumor in a subject with a microlens-tipped fiber for surface illumination with a light dose of from or from about 5 J/cm$^2$ to about 200 J/cm$^2$, wherein the tumor is associated with a phototoxic agent that includes a targeting molecule bound to a cell surface molecule of the tumor. In some embodiments, the light irradiation dose is or is about 50 J/cm$^2$.

In some embodiments, the lesion is a tumor that is an interstitial tumor. In some embodiments, the tumor is greater than 10 mm deep or is a subcutaneous tumor. In some embodiments, irradiation is carried out using cylindrical diffusing fibers that includes a diffuser length of 0.5 cm to 10 cm and spaced 1.8±0.2 cm apart. In some embodiments, the light irradiation dose is from or from about 20 J/cm fiber length to about 500 J/cm fiber length.

In some embodiments, the provided methods include illuminating an interstitial tumor in a subject with cylindrical diffusing fibers that includes a diffuser length of 0.5 cm to 10 cm and spaced 1.8±0.2 cm apart with a light dose of or about 100 J/cm fiber length or with a fluence rate of or about 400 mW/cm, wherein the tumor is associated with a phototoxic agent that includes a targeting molecule bound to a cell surface molecule of the tumor. In some embodiments, the tumor is greater than 10 mm deep or is a subcutaneous tumor. In some embodiments, the cylindrical diffusing fibers are placed in a catheter positioned in the tumor 1.8±0.2 cm apart. In some embodiments, the catheter is optically transparent.

In some embodiments, the provided methods include irradiation at one or more wavelengths. In some examples, after administering the conjugate, the lesion or tumor is irradiated at one or more wavelengths to induce phototoxic activity of the first dye of the conjugate and a fluorescent signal of the second dye of the conjugate. For example, in methods that employ a first and second dye conjugated to a targeting molecule that have different excitation wavelengths, two different wavelengths can be used for irradiation. In some embodiments, the provided methods include irradiating the lesion with a single wavelength. In some embodiments, the provided methods include irradiating the lesion at two different wavelengths, simultaneously or sequentially, wherein one wavelength induces the phototoxic activity and the other wavelength induces the fluorescent signal. For example, in some embodiments, the provided methods include irradiating the lesion at one or more wavelengths that is from or from about 400 to about 900 nm at a dose of at least 1 J cm$^{-2}$ or 1 J/cm of fiber length.

D. Additional Therapeutic Agents and Combination Therapy

In some embodiments, another therapeutic agent, such as an immune modulating agent or anti-cancer agent is administered in conjunction with a photoimmunotherapy agent, such as a phthalocyanine dye conjugate, for example an IR700-antibody conjugate. In some embodiments, the combination therapy can include administration of a phthalocyanine dye conjugate, for example an IR700-antibody conjugate, in combination with an anti-cancer agent or immune modulating agent.

In some embodiments, the other or additional agent or agents can be administered at a sufficient time prior to performing the irradiation so that a therapeutic effect on treating the tumor is increased. In some embodiments, prior to irradiation in the method of photoimmunotherapy, one or more other therapeutic agents, such as an immune modulating agent (e.g., immune checkpoint inhibitor) or anti-cancer agent (e.g., antimetabolite), are administered to the subject. In one embodiment, an immune modulating agent can be administered a sufficient time prior to the irradiation, such as generally at least 12 hours prior to the irradiation, to render the immune system responsive to tumor-associated agents released upon tumor cell lysis after photoimmunotherapy. In another embodiment, an anti-cancer agent can be administered a sufficient time prior to the irradiation, such as generally at least 5 minutes prior to the irradiation, to achieve systemic availability of the anti-cancer agent so that it can be immediately delivered into the tumor upon changes in vascular permeability after photoimmunotherapy.

The one or more other agents, such as an immune modulating agent or an anti-cancer agent, can be administered prior to, simultaneous with, subsequent to or intermittently with the phthalocyanine dye-targeting molecule conjugate. In some embodiments, the activation of the phthalocyanine dye photosensitizer of the conjugate by irradiation with light is not effected until a time after the administration of the other therapeutic agent, such as described herein. In some embodiments, the activation of the phthalocyanine dye photosensitizer of the conjugate by irradiation with light is carried out before the administration of the other therapeutic agent, such as described herein.

In some embodiments, the combined effect of the photoimmunotherapy in combination with the one or more other agents can be synergistic compared to treatments involving only photoimmunotherapy with the phthalocyanine dye-targeting molecule conjugate or monotherapy with the other therapeutic agent. In some embodiments, the methods provided herein result in an increase or an improvement in a desired anti-tumor therapeutic effect, such as an increased or an improvement in the reduction or inhibition of one or more symptoms associated with cancer, than photoimmunotherapy or monotherapy alone.

Treatments with a phthalocyanine dye-targeting molecule conjugate, and, optionally, an additional therapeutic immune modulating agent or anti-cancer agent, can each independently be completed in a single day, or may be done repeatedly on multiple days with the same or a different dosage. Repeated treatments may be done on the same day, on successive days, or every 1-3 days, every 3-7 days, every 1-2 weeks, every 2-4 weeks, every 1-2 months, or at even longer intervals.

In some embodiments, the combination therapy includes administering to a subject a therapeutically effective amount of the immune modulating agent, such as an immune checkpoint inhibitor. The immune modulating agent is administered in an amount that is from or from about 0.01 mg to 1000 mg, such as at a dose of at least 0.01 mg, 0.1 mg, 1 mg, 10 mg, 1000 mg, 2000 mg, 3000 mg or more. In an exemplary embodiment, an immune modulating agent such as an immune checkpoint inhibitor may be administered at about 0.3 mg/kg to 10 mg/kg, or the maximum tolerated dose, such as at least 0.5 mg/kg, or at least 1 mg/kg, or at least 2 mg/kg, or at least 3 mg/kg, or at least 5 mg/kg, or at least 8 mg/kg. In some cases, the dose can be administered as a single dose or in a plurality of doses. Alternatively, the immune modulating agent such as an immune checkpoint inhibitor may be administered by an escalating dosage regimen including administering a first dosage at about 3 mg/kg, a second dosage at about 5 mg/kg, and a third dosage at about 9 mg/kg. Alternatively, the escalating dosage regimen includes administering a first dosage of immune modulating agent at about 5 mg/kg and a second dosage at about 9 mg/kg. Another stepwise escalating dosage regimen may include administering a first dosage of immune modulating agent about 3 mg/kg, a second dosage of about 3 mg/kg, a third dosage of about 5 mg/kg, a fourth dosage of about 5 mg/kg, and a fifth dosage of about 9 mg/kg. In another aspect, a stepwise escalating dosage regimen may include administering a first dosage of 5 mg/kg, a second dosage of 5 mg/kg, and a third dosage of 9 mg/kg. In some embodiments, particular dosages can be administered twice weekly, once weekly, once every two weeks, once every three weeks or once a month or more. In some cases, the dosages can be administered over a course of a cycle that can be repeated, such as repeated for one month, two months, three months, six months, 1 year or more.

In some embodiments, the combination therapy includes administering to a subject a therapeutically effective amount of the anti-cancer agent, such as any described herein. In some embodiments, a therapeutically effective dose can be from or from about 0.01 mg to 1000 mg, such as a dose of at least 0.01 mg, 0.1 mg, 1 mg, 10 mg, 1000 mg, 2000 mg, 3000 mg or more. In some embodiments, a therapeutically effective dose of the anti-cancer agent is from or from about 0.01 mg/kg to about 50 mg/kg, such as about 0.1 mg/kg to about 20 mg/kg, about 0.1 to about 10 mg/kg, about 0.3 to about 10 mg/kg, about 0.5 mg/kg to about 5 mg/kg or about 0.5 mg/kg to about 1 mg/kg.

In some embodiments, the dose of the immune modulating agent (e.g. immune checkpoint inhibitor) or anti-cancer agent is continued or repeated in accord with its clinically dosing schedule after PIT treatment. Thus, in some embodiments, in a dose schedule or cycle of administration in accord with the provided methods, the phthalocyanine dye conjugate (e.g. IR700 antibody conjugate) can be administered only one time, such as in a single dose or infusion, for PIT, whereas the administration of the immune modulating agent is continued or repeated more than one time, such as three times a week, two times a week, once a week, once every two weeks, once every three weeks or once a month during a dosing schedule or cycle of administration. In some embodiments, the dosing schedule or cycle of administration is or is about 28 days or 4 weeks.

In some embodiments, the other or additional agent or agents administered, or the additional agent in a combination therapy, is an unconjugated targeting molecule. In some embodiments, the unconjugated targeting molecule is the same or substantially the same targeting molecule as the targeting molecule of the conjugate. For example, in some embodiments, prior to administration of the conjugate, the targeting molecule, e.g., an unconjugated antibody that targets a protein or antigen, is administered to the subject. In some embodiments, the targeting molecule is administered up to 96 hours prior to administration of the conjugate. In some embodiments, the targeting molecule is administered at a dose within a range from or from about 10 mg/m$^2$ to about 500 mg/m$^2$. For example, the targeting molecule is cetuximab, and cetuximab is administered to the subject up to 96 hours prior to administration of the conjugate.

1. Immune Modulating Agents

The present disclosure provides immune modulating agents that can be administered in combination with PIT methods employing phthalocyanine dye conjugates. Hence, the combination therapy provided herein, including combinations and methods of use thereof, include an immune modulating agent. In some aspects, an immune modulating agents, or immunomodulators, are substances that either, directly or indirectly, suppress or activate the body's immune response. For example, immune modulating agents that stimulate immune response to tumors and/or pathogens may be used in combination with photoimmunotherapy. In some embodiments, the immune modulating agent can include cell-based (e.g. combination treatment with immune cells such as dendritic cells or T cells) or non-cell based immune modulating agents.

Generally, cancerous cells contain tumor-specific antigens that should be recognized by the immune system. Typically, in an active immune system, immune cells, such as cytotoxic T cells, attack and eradicate these cancerous cells. Under normal physiological conditions, the T cell-mediated immune response is initiated by antigen recognition by the T cell receptor (TCR) and is regulated by a balance of co-stimulatory and inhibitory signals (e.g. immune checkpoint proteins). In particular, CD4+ and CD8+ T cells expressing a TCR can become activated upon recognition of antigenic peptides presented on antigen-presenting cells on major histocompatibility complex (MHC) class I or class II molecules, respectively. In some aspects, activated CD8+ cells, or cytotoxic T cells, can kill tumor cells expressing the antigen, which can be helped by the presence of CD4+ T cells. In some embodiments, the immune cell is an antigen presenting cell. In some embodiments, the immune cell is a dendritic cell.

In the case of tumors, however, the tumor microenvironment has mechanisms to suppress the immune system, thereby evading immune recognition and preventing or reducing killing of tumor cells. For example, in some cases, immune checkpoint proteins can be dysregulated in tumors, thereby resulting in a suppression of the immune response in the tumor microenvironment as a mechanism of evading the immune system. In some cases, other mechanisms can act to inhibit access of immune cells to tumor antigens, thereby also contributing to the tumors ability to evade the immune system. The combination therapies provided herein address both of these evasion mechanisms, in order to provide a more robust immune response against the tumor while also killing tumor cells by photolytic mechanisms.

In some embodiments of the combination therapy methods provided herein, an immune modulating agent is administered to a subject in order to inhibit immunosuppressive signaling or enhance immunostimulant signaling. For example, inhibitory checkpoint protein antagonists and/or agonists of co-stimulatory receptors can stimulate a host's endogenous anti-tumor immune response by amplifying antigen-specific T cell responses. In aspects of the provided methods, photoimmunotherapy also can be performed, which can result in the killing of tumor cells, thereby releasing tumor-antigens. By performing photoimmunotherapy in combination with administration of an immune-modulating agent, the subsequent release of PIT-induced antigens can provide a source of antigenic stimuli for the T cells whose response has been amplified or stimulated by the immune modulating agent. Thus, in some aspects, the enhanced immune response that is generated upon therapy with an immune modulating agent is primed and ready to respond to tumor antigens that are exposed upon lysis of cells after PIT. Thus, in some aspects, the combination therapies provided herein address the natural evasion mechanisms that can be present in a tumor microenvironment, in order to provide a more robust immune response against the tumor while also killing tumor cells by photolytic mechanisms.

Generally, in the provided methods, PIT-mediated cell killing by irradiation and activation of an administered phthalocyanine dye-conjugate is performed at a time after the immune response has been stimulated or enhanced following administration of an immune-modulating agent. In some embodiments, the immune-modulating agent is administered a sufficient time prior to irradiation of an administered phthalocyanine dye-conjugate so that amplification of the T cell response has occurred prior to PIT-induced cell lysis. Hence, generally, the immune-modulating agent is administered a sufficient time prior to irradiation to be therapeutically effective to amplify a T cell response, such as administered at least 12 hours, such as generally at least 24 hours, at least 48 hours, at least 96 hours, at least one week, at least two weeks, at least three weeks or at least one month prior to performing irradiation to induce PIT-mediated cell killing through activation of an administered phthalocyanine dye-conjugate (e.g., IR700-targeting molecule conjugate, such as an IR700-antibody dye conjugate).

In some embodiments, the conjugate is administered prior to, simultaneously or subsequently to administration of the immune-modulating agent. In some embodiments, the conjugate is administered after administering the immune modulating agent but prior to irradiating the tumor. In some embodiments, the conjugate is administered from or from about 12 hours to 48 hours prior to irradiating the tumor and the immune modulating agent is administered from or from about 12 hours to about 1 month prior to irradiating the tumor. In some embodiments, immune modulating agent is administered greater than or greater than about 30 minutes, 1 hour, 2 hours, 6 hours, 12 hours, 24 hours, 48 hours, 96 hours, one week, two weeks, three weeks or one month prior to irradiating the tumor.

In some embodiments, irradiation the tumor is carried out either i) after administration of the immune modulating agent and after administration of the conjugate or ii) only after administration of the conjugate.

Exemplary dosage regimes and schedules for administering an immune modulating agent, phthalocyanine dye-conjugate (e.g., IR700-targeting molecule conjugate, such as an IR700-antibody dye conjugate) and for performing irradiation are described elsewhere herein.

In some embodiments, the combination therapy methods can be performed with any immune modulating agent that can stimulate, amplify and/or otherwise enhance an anti-tumor immune response, such as by inhibiting immunosuppressive signaling or enhancing immunostimulant signaling. In some embodiments, the immune modulating agent is a peptide, protein or is a small molecule. In some embodiments, the protein can be a fusion protein or a recombinant protein. In some embodiments, the immune modulating agent binds to an immunologic target, such as a cell surface receptor expressed on immune cells, such a T cells, B cells or antigen-presenting cells. For example, in some embodiments, the immune modulating agent is an antibody or antigen-binding antibody fragment, a fusion protein, a small molecule or a polypeptide.

In some embodiments, the immune modulating agent inhibits an immune checkpoint pathway. The immune system has multiple inhibitory pathways that are involved in maintaining self-tolerance and for modulating immune responses. It is known that tumors can use certain immune-checkpoint pathways as a major mechanism of immune resistance, particularly against T cells that are specific for tumor antigens (Pardoll, 2012, Nature Reviews Cancer 12:252-264). Because many such immune checkpoints are initiated by ligand-receptor interactions, they can be readily blocked by antibodies against the ligands and/or their receptors.

Therefore, therapy with antagonistic molecules blocking an immune checkpoint pathway, such as small molecules, nucleic acid inhibitors (e.g., RNAi) or antibody molecules, are becoming promising avenues of immunotherapy for cancer and other diseases. In contrast to the majority of anti-cancer agents, checkpoint inhibitors do not necessarily target tumor cells directly, but rather target lymphocyte receptors or their ligands in order to enhance the endogenous antitumor activity of the immune system. (Pardoll, 2012, Nature Reviews Cancer 12:252-264).

As used herein, the term "immune checkpoint inhibitor" refers to molecules that totally or partially reduce, inhibit, interfere with or modulate one or more checkpoint proteins. Checkpoint proteins regulate T-cell activation or function. These proteins are responsible for co-stimulatory or inhibitory interactions of T-cell responses. Immune checkpoint proteins regulate and maintain self-tolerance and the duration and amplitude of physiological immune responses.

Immune checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptor ligands. Illustrative immune checkpoint molecules that may be targeted for blocking or inhibition include, but are not limited to, PD1 (CD279), PDL1 (CD274, B7-H1), PDL2 (CD273, B7-DC), CTLA-4, LAG3 (CD223), TIM3, 4-1BB (CD137), 4-1BBL (CD137L), GITR (TNFRSF18, AITR), CD40, Ox40 (CD134, TNFRSF4), CXCR2, tumor associated antigens (TAA), B7-H3, B7-H4, BTLA, HVEM, GAL9, B7H3, B7H4, VISTA, KIR, 2B4 (belongs to the CD2 family of molecules and is expressed on all NK, γδ, and memory CD8+ (αβ) T cells), CD160 (also referred to as BY55) and CGEN-15049. Immune checkpoint inhibitors include antibodies, or antigen binding fragments thereof, or other binding proteins, that bind to and block or inhibit the activity of one or more of PD1, PDL1, PDL2, CTLA-4, LAG3, TIM3, 4-1BB, 4-1BBL, GITR, CD40, Ox40, CXCR2, TAA, B7-H3, B7-H4, BTLA, HVEM, GAL9, B7H3, B7H4, VISTA, KIR, 2B4, CD160, and CGEN-15049. Illustrative immune checkpoint inhibitors include Tremelimumab (CTLA-4 blocking antibody), anti-OX40, PD-L1 monoclonal antibody (Anti-B7-H1; MED14736), MK-3475 (PD-1 blocker), nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor).

Programmed cell death 1 (PD1) is an immune checkpoint protein that is expressed in B cells, NK cells, and T cells (Shinohara et al., 1995, Genomics 23:704-6; Blank et al., 2007, Cancer Immunol Immunother 56:739-45; Finger et al., 1997, Gene 197:177-87; Pardoll, 2012, Nature Reviews Cancer 12:252-264). The major role of PD1 is to limit the activity of T cells in peripheral tissues during inflammation in response to infection, as well as to limit autoimmunity (Pardoll, 2012, Nature Reviews Cancer 12:252-264). PD1 expression is induced in activated T cells and binding of PD1 to one of its endogenous ligands acts to inhibit T-cell activation by inhibiting stimulatory kinases (Pardoll, 2012, Nature Reviews Cancer 12:252-264). PD1 also acts to inhibit the TCR "stop signal" (Pardoll, 2012, Nature Reviews Cancer 12:252-264). PD1 is highly expressed on Treg cells and may increase their proliferation in the presence of ligand (Pardoll, 2012, Nature Reviews Cancer 12:252-264). Anti-PD 1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85). Exemplary anti-PD1 antibodies include nivolumab (Opdivo by BMS), pembrolizumab (Keytruda by Merck), pidilizumab (CT-011 by Cure Tech), lambrolizumab (MK-3475 by Merck), and AMP-224 (Merck).

PD-L1 (also known as CD274 and B7-H1) and PD-L2 (also known as CD273 and B7-DC) are ligands for PD1, found on activated T cells, B cells, myeloid cells, macrophages, and some types of tumor cells. Anti-tumor therapies have focused on anti-PD-L1 antibodies. The complex of PD1 and PD-L1 inhibits proliferation of CD8+ T cells and reduces the immune response (Topalian et al., 2012, N Engl J Med 366:2443-54; Brahmer et al., 2012, N Eng J Med 366:2455-65). Anti-PD-L1 antibodies have been used for treatment of non-small cell lung cancer, melanoma, colorectal cancer, renal-cell cancer, pancreatic cancer, gastric cancer, ovarian cancer, breast cancer, and hematologic malignancies (Brahmer et al., N Eng J Med 366:2455-65; Ott et al., 2013, Clin Cancer Res 19:5300-9; Radvanyi et al., 2013, Clin Cancer Res 19:5541; Menzies & Long, 2013, Ther Adv Med Oncol 5:278-85; Berger et al., 2008, Clin Cancer Res 14:13044-51). Exemplary anti-PD-L1 antibodies include MDX-1105 (Medarex), MEDI4736 (Medimmune) MPDL3280A (Genentech), BMS-935559 (Bristol-Myers Squibb) and MSB0010718C.

Cytotoxic T-lymphocyte-associated antigen (CTLA-4), also known as CD152, is a co-inhibitory molecule that functions to regulate T-cell activation. CTLA-4 is a member of the immunoglobulin superfamily that is expressed exclusively on T-cells. CTLA-4 acts to inhibit T-cell activation and is reported to inhibit helper T-cell activity and enhance regulatory T-cell immunosuppressive activity (Pardoll, 2012, Nature Reviews Cancer 12:252-264). Although the precise mechanism of action of CTLA-4 remains under investigation, it has been suggested that it inhibits T cell activation by outcompeting CD28 in binding to CD80 and CD86, as well as actively delivering inhibitor signals to the T cell (Pardoll, 2012, Nature Reviews Cancer 12:252-264). Anti-CTLA-4 antibodies have been used in clinical trials for the treatment of melanoma, prostate cancer, small cell lung cancer, non-small cell lung cancer (Robert & Ghiringhelli, 2009, Oncologist 14:848-61; Ott et al., 2013, Clin Cancer Res 19:5300; Weber, 2007, Oncologist 12:864-72; Wada et al., 2013, J Transl Med 11:89). A significant feature of anti-CTLA-4 is the kinetics of anti-tumor effect, with a lag period of up to 6 months after initial treatment required for physiologic response (Pardoll, 2012, Nature Reviews Cancer 12:252-264). In some cases, tumors may actually increase in size after treatment initiation, before a reduction is seen (Pardoll, 2012, Nature Reviews Cancer 12:252-264). Exemplary anti-CTLA-4 antibodies include ipilimumab (Bristol-Myers Squibb) and tremelimumab (Pfizer). Ipilimumab has recently received FDA approval for treatment of metastatic melanoma (Wada et al., 2013, J Transl Med 11:89). In some embodiments, the immune modulating agent is not an anti-CTLA-4 antibody.

Lymphocyte activation gene-3 (LAG-3), also known as CD223, is another immune checkpoint protein. LAG-3 has been associated with the inhibition of lymphocyte activity and in some cases the induction of lymphocyte anergyh. LAG-3 is expressed on various cells in the immune system including B cells, NK cells, and dendritic cells. LAG-3 is a natural ligand for the MHC class II receptor, which is substantially expressed on melanoma-infiltrating T cells including those endowed with potent immune-suppressive activity. An exemplary anti-LAG-3 antibodies is BMS-986016. IMP321 is a soluble version of the immune checkpoint molecule LAG-3, which activates dendritic cells, increasing antigen presentation.

T-cell immunoglobulin domain and mucin domain-3 (TIM-3), initially identified on activated Th1 cells, has been shown to be a negative regulator of the immune response. Blockade of TIM-3 promotes T-cell mediated anti-tumor immunity and has anti-tumor activity in a range of mouse tumor models. Combinations of TIM-3 blockade with other immunotherapeutic agents such as TSR-042, anti-CD137 antibodies and others, can be additive or synergistic in increasing anti-tumor effects. TIM-3 expression has been associated with a number of different tumor types including melanoma, NSCLC and renal cancer, and additionally, expression of intratumoral TIM-3 has been shown to correlate with poor prognosis across a range of tumor types including NSCLC, cervical, and gastric cancers. Blockade of TIM-3 is also of interest in promoting increased immunity to a number of chronic viral diseases. TIM-3 has also been shown to interact with a number of ligands including galectin-9, phosphatidylserine and HMGB1, although which of these, if any, are relevant in regulation of anti-tumor responses is not clear at present.

4-1BB, also known as CD137, is transmembrane glycoprotein belonging to the TNFR superfamily. 4-1BB receptors are present on activated T cells and B cells and monocytes. An exemplary anti-4-1BB antibody is urelumab (BMS-663513), which has potential immunostimulatory and antineoplastic activities.

Glucocorticoid-induced TNFR family related gene (GITR) is also a member of the TNFR superfamily. GITR is upregulated on activated T cells, which enhances the immune system. An exemplary anti-GITR antibody is TRX518.

Cluster of differentiation 40 (CD40) is also a member of the TNFR superfamily. CD40 is a costimulatory protein found on antigen-presenting cells and mediates a broad variety of immune and inflammatory responses. CD40 is also expressed on some malignancies, where it promotes proliferation. Exemplary anti-CD40 antibodies are dacetuzumab (SGN-40), lucatumumab (Novartis, antagonist), SEA-CD40 (Seattle Genetics), and CP-870,893.

Tumor necrosis factor receptor superfamily, member 4 (TNFRSF4), also known as OX40 and CD134, is another member of the TNFR superfamily. OX40 is not constitutively expressed on resting naïve T cells and acts as a secondary co-stimulatory immune checkpoint molecule. Exemplary anti-OX40 antibodies are MEDI6469 and MOXR0916 (RG7888, Genentech).

In some embodiments, the immune modulating agent is an antibody or antigen-binding antibody fragment thereof. Exemplary of such antibodies include, but are not limited to, Daclizumab (Zenapax), Bevacizumab (Avastin®), Basiliximab, Ipilimumab, Nivolumab, pembrolizumab, MPDL3280A, Pidilizumab (CT-011), MK-3475, BMS-936559, MPDL3280A (Atezolizumab), tremelimumab, IMP321, BMS-986016, LAG525, urelumab, PF-05082566, TRX518, MK-4166, dacetuzumab (SGN-40), lucatumumab (HCD122), SEA-CD40, CP-870, CP-893, MEDI6469, MEDI6383, MOXR0916, AMP-224, MSB0010718C (Avelumab), MEDI4736, PDR001, rHIgM12B7, Ulocuplumab, BKT140, Varlilumab (CDX-1127), ARGX-110, MGA271, lirilumab (BMS-986015, IPH2101), IPH2201, ARGX-115, Emactuzumab, CC-90002 and MNRP1685A or an antibody-binding fragment thereof.

CXCR2 is a chemokine receptor that is expressed on myeloid-derived supressor cells (MDSCs). CXCR2s contribute to tumor immune escape. It has been shown that anti-CXCR2 monoclonal antibody therapy, enhanced an anti-PD1 antibody-induced anti-tumor immune response and anti-tumor efficacy.

In some embodiments, the immune-modulating agent is cytokine. In some embodiments, the immune modulating agent is a cytokine or is an agent that induces increased expression of a cytokine in the tumor microenvironment. By "cytokine" is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, L-6, L-7, L-8, L-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines. For example, the immune modulating agent is a cytokine and the cytokine is IL-4, TNF-α, GM-CSF or IL-2.

In some embodiments, the immune modulating agent is selected from among GM-CSF, CpG-ODN (CpG oligodeoxynucleotides), lipopolysaccharide (LPS), monophosphoryl lipid A (MPL), alum, recombinant *Leishmania* polyprotein, imiquimod, MF59, poly I:C, poly A:U, type 1 IFN, Pam3Cys, Pam2Cys, complete freund's adjuvant (CFA), alpha-galactosylceramide, RC-529, MDF2β, Loxoribine, anti-CD40 agonist, SIRPa antagonist, AS04, AS03, Flagellin, Resiquimod, DAP (diaminopimelic acid), MDP (muramyl dipeptide) and CAF01 (cationic adjuvant formulation-01). In some embodiments, the immune modulating agent is a Toll-like receptor (TLR) agonist, an adjuvant or a cytokine. In some embodiments, the immune modulating agent is a TLR agonist and the TLR agonist is TLR agonist is a TLR4 agonist, a TLR7 agonist, a TLR8 agonist, or a TLR9 agonist. In some embodiments, the TLR agonist is selected from among triacylated lipoprotein, diacylated lipopeptide, lipoteichoic acid, peptidoglycan, zymosan, Pam3CSK4, dsRNA, polyI:C, Poly G10, Poly G3, CpG, 3M003, flagellin, lipopolysaccharide (LPS) *Leishmania* homolog of eukaryotic ribosomal elongation and initiation factor 4a (LeIF), MEDI9197, SD-101, and imidazoquinoline TLR agonists.

In some embodiments, the immune modulating agent can contain one or more interleukins or other cytokines. For example, the interleukin can include leukocyte interleukin injection (Multikine), which is a combination of natural cytokines.

In some embodiments, the immune modulating agent is a Toll-like receptor (TLR) agonist. In some embodiments, such agonists can include a TLR4 agonist, a TLR8 agonist, or a TLR9 agonist. Such an agonist may be selected from peptidoglycan, polyI:C, CpG, 3M003, flagellin, and *Leishmania* homolog of eukaryotic ribosomal elongation and initiation factor 4a (LeIF).

In some embodiments, the immune modulating agent can be one that enhances the immunogenicity of tumor cells such as patupilone (epothilone B), epidermal-growth factor receptor (EGFR)-targeting monoclonal antibody 7A7.27, histone deacetylase inhibitors (e.g., vorinostat, romidepsin, panobinostat, belinostat, and entinostat), the n3-polyunsaturated fatty acid docosahexaenoic acid, proteasome inhibitors (e.g., bortezomib), shikonin (the major constituent of the root of *Lithospermum erythrorhizon*) and oncolytic viruses, such as TVec (talimogene laherparepvec). In some embodiments, the immune modulating agent activates immunogenic cell death of the cancer or tumor, such as antrhacyclins (doxorubicin, mitoxantron), BK channel agonists, bortezomib, botrtezomib plus mitocycin C plus hTert-Ad, Cardiac glycosides plus non-ICD inducers, cyclophosphamide, GADD34/PP1 inhibitors plus mitomycin, LV-tSMAC, and oxaliplatin. In some embodiments, the immune modulating agent can be an epigenetic therapy, such as DNA methyltransferase inhibitors (e.g., Decitabine, 5-aza-2'-deoxycytidine).

For example, in some embodiments, the immune modulating agent can be a DNA methyltransferase inhibitor, which can regulate expression of tumor associated antigens (TAA). TAAs are antigenic substances produced in tumor cells which triggers an immune response. TAAs are often down-regulated by DNA methylation in tumors to escape the immune system. Reversal of DNA methylation restores TAA expression, increasing the immunogencity of tumor cells. For example, demethylating agents such as decitabine (5-aza-2'-deoxycytidine) can upregulate expression of TAAs in tumor cells and increase immune recognition of the cancerous cells. Photoimmunotherapy would further expose TAAs to the immune system by disrupting cells.

In some embodiments, the immune modulating agent itself can be an antibody conjugate containing a phthalocyanine dye linked to an antibody or antigen-binding antibody fragment that is an immune modulating agent, such as an immune checkpoint inhibitor. In some embodiments, the immune modulating agent is one that targets or binds to an immunosuppressive molecule, such as an immune checkpoint molecule, on the surface of tumor cells. For example, PD-L1 is an immunosuppressive molecule that is constitutively expressed or induced on many tumor cells, and can prevent T cell activation through interactions with its receptor PD-1 expressed on immune cells. In some aspects, a phthalocyanine-dye conjugate containing an immune modulating agent that binds to an immunosuppressive molecule on a tumor cells (e.g., PD-L1) can be administered both to enhance an immune response and also to specifically kill cancer cells that express the immunosuppressive molecule, thereby reversing immune suppression in the tumor microenvironment. In particular, irradiation of tumor cells cells to which the conjugate binds can result in its activation to mediate PIT-induced cell killing of the PD-L1 cancer cells, which also would act to specifically eliminate the cancer cells in the tumor that control T-cell suppression in the tumor microenvironment.

Hence, provided herein is a conjugate containing a phthalocyanine dye (e.g., IR700) linked to an immune modulating agent that binds to an immunosuppressive molecule expressed on tumor cells. For example, in some embodiments, the immunosuppressive molecule expressed on tumor cells can be an immune checkpoint molecule. In some embodiments, the immune checkpoint molecule expressed on tumor cells is PD-L1. In some embodiments, the immune modulating agent that is part of the conjugate is an immune checkpoint inhibitor, such as an antibody or antigen-binding antibody fragment that binds to PD-L1. For example, provided herein is a conjugate containing a phthalocyanine dye (e.g., IR700) linked to an antibody or antigen-binding antibody fragment that binds to PD-L1. Exemplary immune checkpoint inhibitors, including antibodies or antigen-binding antibody fragments, against PD-L1 are described above, and any can be included in the provided conjugates. Exemplary anti-PD-L1 antibodies include, but are not limited to, BMS-935559, MEDI4736, MPDL3280A and MSB0010718C, or an antigen-binding antibody fragment thereof. Exemplary conjugate molecules provided herein include, for example, IR700-BMS-935559, IR700-MEDI4736, IR700-MPDL3280A and IR700-MSB0010718C. In some embodiments, such conjugates can be used in methods of photoimmunotherapy, for example, by irradiation with light at a wavelength sufficient to activate the dye. Such conjugates can be used in monotherapy-based photoimmunotherapy or can be used in combination therapy methods with other phthalocyanine dye conjugates.

For example, in some embodiments, combination therapy methods are provided in which a first conjugate containing a phthalocyanine dye (e.g., IR700) linked to an immune modulating agent that binds to an immunosuppressive molecule expressed on cells of a tumor (e.g., an anti-PD-L1 antibody, such as an IR700-anti-PD-L1 conjugate) is administered to a subject, and then a second conjugate containing a phthalocyanine dye linked to a targeting molecule is administered to the subject. Generally, the second conjugate can include any targeting molecule that is able to bind to a cell surface protein on a cell in a tumor, such as a cell present in a tumor microenvironment, such as any described above. In some embodiments, the first conjugate and the second conjugate bind to different proteins expressed on a cell in a tumor. In some embodiments, the second conjugate can include a phthalocyanine dye (e.g., IR700) linked to an antibody or antigen-binding antibody fragment that binds to a cell surface protein expressed on a cell in a tumor. Exemplary antibody or antigen-binding antibody fragments of the second conjugate can include, but are not limited to, bevacizumab, cetuximab, panitumumab, zalutumumab, nimotuzumab, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), and Basiliximab, nivolumab, pembrolizumab, pidilizumab, MK-3475, BMS-936559, MPDL3280A, ipilimumab, tremelimumab, IMP321, BMS-986016, LAG525, urelumab, PF-05082566, TRX518, MK-4166, dacetuzumab, lucatumumab, SEA-CD40, CP-870, CP-893, MEDI6469, MEDI6383, MEDI4736, MOXR0916, AMP-224, PDR001, MSB0010718C, rHIgM12B7, Ulocuplumab, BKT140, Varlilumab (CDX-1127), ARGX-110, MGA271, lirilumab (BMS-986015, IPH2101), IPH2201, AGX-115, Emactuzumab, CC-90002 and MNRP1685A or is an antibody-binding fragment thereof.

In some embodiments, for example, if the treatment of the tumor with the conjugate followed by light irradiation increases the presence of immunosuppressive cells in the tumor or increases the expression of immunosuppressive markers at the tumor, a therapeutically effective amount of an immune modulating agent capable of reducing the amount or activity of immunosuppressive cells in the tumor or capable of blocking the activity of the immunosuppressive marker or reducing the activity of a tumor promoting cell in the tumor or capable of blocking the activity of the tumor promoting marker can be administered. For example, in some embodiments, a conjugate with a first dye that is a phthalocyanine dye is administered, in combination with an immune modulating agent includes a conjugate that includes a second phthalocyanine dye conjugated to an immune modulating agent capable of binding to the immunosuppressive cell or a tumor promoting cell, and modulating the activity of such cell. In some embodiments, the first and second phthalocyanine dye is the same or different.

Thus, in some embodiments, the immune modulating agent is itself a conjugate containing a phthalocyanine dye, such as a phthalocyanine dye linked to an antibody or antigen-binding antibody fragment that is an immune modulating agent. In some embodiments, the immune modulating agent is an IR700-antibody conjugate that includes an immune modulating antibody (e.g., checkpoint inhibitor) that binds to a checkpoint protein on a tumor cell (e.g., PD-L1). In some embodiments, the immune modulating conjugate (e.g., IR700-antibody conjugate that is an immune modulating agent) is administered prior to administration of the phthalocyanine dye-targeting molecule conjugate, such as between 12 hours and 2 months, such as generally at least 12 hours, at least 24 hours, at least 48 hours, at least 96 hours, at least one week, at least two weeks, at least three weeks or at least one month prior to administration of the phthalocyanine dye-targeting molecule conjugate. In some embodiments, the immune modulating conjugate (e.g., IR700-antibody conjugate that is an immune modulating agent) is administered during or simultaneously with administration of the phthalocyanine dye-targeting molecule conjugate. In some embodiments, the immune modulating conjugate (e.g., IR700-antibody conjugate that is an immune modulating agent) is administered after administration of the phthalocyanine dye-targeting molecule conjugate, such as between 12 hours and 2 months, such as generally at least 12 hours, at least 24 hours, at least 48 hours, at least 96 hours, at least one week, at least two weeks, at least three weeks or at least one month after administration of the phthalocyanine dye-targeting molecule conjugate, or the irradiation after administration of the phthalocyanine dye-targeting molecule conjugate.

In such aspects, the combination therapy methods generally include one or more irradiations with light at a wavelength sufficient to activate the dye of the first and/or second conjugate.

In some embodiments, at least two irradiations are performed, where at least a first irradiation is provided to activate the first conjugate and a second irradiation is provided to activate the second conjugate. In some embodiments, a first irradiation with light is provided to the tumor after administration of the first conjugate. For example, from or from about 12 hours to 48 hours, such as about or approximately within 24 hours, after administering the first conjugate, the tumor can be treated with light to kill cancer cells that express the immunosuppressive molecule, such as to kill tumor cells that express PD-L1. In some embodiments, the killing of such cells may permit re-activation of or amplification of T cell responses at the tumor. In some embodiments, subsequent to photoimmunotherapy of the first conjugate by administration and irradiation, the second phthalocyanine dye conjugate can be administered to the subject, followed by a second irradiation with light from or from about 12 hours to 48 hours, such as about or approximately within 24 hours, after administering the second conjugate. In some embodiments, the second irradiation achieves activation of the second conjugate, which can result in selective cell killing of tumor cells that express the tumor-targeted molecule recognized by the second conjugate, thereby releasing tumor antigens to induce a strong immunogenic response as the T cell in the tumor are no longer suppressed by the immunosuppressive molecule (e.g., PD-L1). In some embodiments, the first irradiation is performed prior to administration of the second conjugate, such as at least or about at least 1 minute, 5 minutes, 10 minutes, 30 minutes, 1 hour, 2 hours, 3 hours, 6 hours, 12 hours or 24 hours prior to administration of the second conjugate.

In some embodiments, a single irradiation can performed to effect activation of both the first conjugate and the second conjugate in order cause PIT-induced cell killing of tumor cells expressing the immunosuppressive molecule (e.g., PD-L1) recognized by the first conjugate and tumor cells expressing the tumor-targeted molecule recognized by the second conjugate. Hence, in such aspects, the one light irradiation of the tumor may induce both effects to selectively kill specific tumor cells, thereby releasing tumor antigens, as well as inducing a strong immunogenic response due to the killing of the immunosuppressive tumor cells, such as the tumor cells expressing PD-L1. In some embodiments, prior to the irradiation, the first conjugate can be administered prior, simultaneously, subsequently or intermittently from administration of the second conjugate. In some embodiments, the first conjugate is administered prior to the second conjugate, such as at least 5 minutes prior, and generally at least 12 hours or at least 24 hours prior. In some embodiments, the first and second conjugates are administered simultaneously. In some embodiments, the first and second conjugates are formulated separately. In some embodiments, the first and second conjugates are formulated together in the same composition.

2. Anti-Cancer Agents

Also provided herein are anti-cancer agents that can be administered in combination with photoimmunotherapy employing phthalocyanine dye-targeting molecule conjugates. Hence, the combination therapy provided herein, including combinations and methods of use thereof, include an anti-cancer agent, which can include any agent whose use can reduce, arrest or prevent cancer in a subject. Optionally, an additional anti-cancer agent can be used in combination therapy with photoimmunotherapy using phthalocyanine dye-targeting molecule conjugates together with an immune modulating agent, for example to treat various cancers.

As described herein, PIT-induced cell killing of tumor cells by administration of one or more phthalocyanine dye conjugates to a subject having a tumor in combination with irradiation can lead to increases in tumor permeability, such as increases in vascular permeability around the tumor space. It is believed herein that the increase in permeability can result in rapid leakage of systemically available molecules into the tumor space, thereby maximizing exposure of the tumor to such molecules. Thus, in some embodiments, in the combination therapy methods provided herein, an anti-cancer agent is administered to a subject a sufficient time prior to irradiation of an administered phthalocyanine dye-targeting molecule conjugate to render the anti-cancer agent systemically available, such as generally at least 5 minutes prior to irradiation, for example at least 10 minutes, 15 minutes, 30 minutes, 1 hour, 2 hours, 3 hours, 4 hours, 5 hours, 6 hours, 12 hours or 24 hours prior to irradiation. In such embodiments, following irradiation and PIT-induced killing of tumor cells, the systemically available anti-cancer agent can be immediately taken up into the tumor space where the agent can provide a therapeutic effect. Thus, in contrast to methods in which the anti-cancer agent is administered after irradiation, and hence after PIT-induced cell killing, in the instant methods there is no lag time in achieving a therapeutic effect because the anti-cancer agent is available for direct and immediate uptake into the tumor space. This can maximize therapeutic responses to the anti-cancer agent.

It is within the level of a skilled artisan to determine the appropriate timing of administration of a particular anti-cancer agent prior to performing irradiation to ensure sufficient systemic availability of the anti-cancer agent. In many cases, the pharmacokinetics of particular anti-cancer agents are well known in the art. In some cases, pharmacokinetics can be assessed by measuring such parameters as the maximum (peak) plasma concentration ($C_{max}$), the peak time (i.e. when maximum plasma concentration occurs; $T_{max}$), the minimum plasma concentration (i.e. the minimum plasma concentration between doses of agent; $C_{min}$), the elimination half-life ($T_{1/2}$) and area under the curve (i.e. the area under the curve generated by plotting time versus plasma concentration of the agent; AUC), following administration. The concentration of a particular agent in the plasma following subcutaneous administration can be measured using any method known in the art suitable for assessing concentrations of agents in samples of blood. For example, an immunoassay, such as an ELISA, or chromatography/mass spectrometry-based assays can be used.

In some embodiments, the anti-cancer agent that is used in the combination therapy provided herein can refer to any agents, or compounds, used in anti-cancer treatment. These include any agents, when used alone or in combination with other compounds, that can alleviate, reduce, ameliorate, prevent, or place or maintain in a state of remission of clinical symptoms or diagnostic markers associated with tumors and cancer, and can be used in combinations and compositions provided herein. In some embodiments, the anti-cancer agent is one whose therapeutic effect is generally associated with penetration or delivery of the anti-cancer agent into the tumor microenvironment or tumor space. In some embodiments, the anti-cancer agent is an alkylating agent, a platinum drug, an antimetabolite, an anti-tumor antibiotic, a topoisomerase inhibitor, a mitotic inhibitor, a corticosteroid, a proteasome inhibitor, a kinase inhibitor, a histone-deacetylase inhibitor or an antibody or antigen-binding antibody fragment thereof. In some embodiments, the anti-cancer agent is a peptide, protein or small molecule drug.

In some embodiments, the anti-cancer agent is 5-Fluorouracil/leukovorin, oxaliplatin, irinotecan, regorafenib, zivafibercept, capecitabine, cisplatin, paclitaxel, toptecan, carboplatin, gemcitabine, docetaxel, 5-FU, ifosfamide, mitomycin, pemetrexed, vinorelbine, carmustine wager, temozolomide, methotrexate, capacitabine, lapatinib, etoposide, dabrafenib, vemurafenib, liposomal cytarabine, cytarabine, interferon alpha, erlotinib, vincristine, cyclophosphamide, lomusine, procarbazine, sunitinib, somastostatin, doxorubicin, pegylated liposomal encapsulated doxorubicin, epirubicin, eribulin, albumin-bound paclitaxel, ixabepilone, cotrimoxazole, taxane, vinblastine, temsirolimus, temozolomide, bendamustine, oral etoposide, everolimus, octreotide, lanredtide, dacarbazine, mesna, pazopanib, eribulin, imatinib, regorafenib, sorafenib, nilotinib, dasantinib, celecoxib, tamoxifen, toremifene, dactinomycin, sirolimus, crizotinib, certinib, enzalutamide, abiraterone acetate, mitoxantrone, cabazitaxel, fluoropyrimidine, oxaliplatin, leucovorin, afatinib, ceritinib, gefitinib, cabozantinib, oxoliplatin or auroropyrimidine.

In some embodiments, the anti-cancer agent is an antibody or antigen-binding antibody fragment. In some embodiments, the anti-cancer agent can be any one or more of bevacizumab, cetuximab, panitumumab, ramucirumab, ipilimumab, rituximab, trastuzumab, ado-trastuzumab emtansine, pertuzumab, nivolumab, lapatinib, dabrafenib, vemurafenib, erlotinib, sunitinib, pazopanib, imatinib, regorafenib, sorafenib, nilotinib, dasantinib, celecoxib, crizotinib, certinib, afatinib, axitinib, bevacizumab, bosutinib, cabozantinib, afatinib, gefitinib, temsirolimus, everolimus, sirolimus, ibrutinib, imatinib, lenvatinib, olaparib, palbociclib, ruxolitinib, trametinib, vandetanib or vismodegib, or an antigen-binding antibody fragment thereof.

In some embodiments, the anti-cancer agent is an alkylating agent. Alkylating agents are compounds that directly damage DNA by forming covalent bonds with nucleic acids and inhibiting DNA synthesis. Exemplary alkylating agents include, but are not limited to, mechlorethamine, cyclophosphamide, ifosamide, melphalan, chlorambucil, busulfan, and thiotepa as well as nitrosurea alkylating agents such as carmustine and lomustine.

In some embodiments, the anti-cancer agent is a platinum drug. Platinum drugs bind to and cause crosslinking of DNA, which ultimately triggers apoptosis. Exemplary platinum drugs include, but are not limited to, cisplatin, carboplatin, oxaliplatin, satraplatin, picoplatin, nedaplatin, triplatin, and lipoplatin.

In some embodiments, the anti-cancer agent is an antimetabolite. Antimetabolites interfere with DNA and RNA growth by substituting for the normal building blocks of RNA and DNA. These agents damage cells during the S phase, when the cell's chromosomes are being copied. In some cases, antimetabolites can be used to treat leukemias, cancers of the breast, ovary, and the intestinal tract, as well as other types of cancer. Exemplary antimetabolites include, but are not limited to, 5-fluorouracil (5-FU), 6-mercaptopurine (6-MP), capecitabine (Xeloda®), cytarabine (Ara-C®), floxuridine, fludarabine, gemcitabine (Gemzar®), hydroxyurea, methotrexate, and pemetrexed (Alimta®).

In some embodiments, the anti-cancer agent is an anti-tumor antibiotic. Anti-tumor antibiotics work by altering the DNA inside cancer cells to keep them from growing and multiplying. Anthracyclines are anti-tumor antibiotics that interfere with enzymes involved in DNA replication. These drugs generally work in all phases of the cell cycle. They can be widely used for a variety of cancers. Exemplary anthracyclines include, but are not limited to, daunorubicin, doxorubicin, epirubicin, and idarubicin. Other anti-tumor antibiotics include actinomycin-D, bleomycin, mitomycin-C, and mitoxantrone.

In some embodiments, the anti-cancer agent is a topoisomerase inhibitor. These drugs interfere with enzymes called topoisomerases, which help separate the strands of DNA so they can be copied during the S phase. Topoisomerase inhibitors can be used to treat certain leukemias, as well as lung, ovarian, gastrointestinal, and other cancers. Exemplary toposiomerase inhibitors include, but are not limited to, doxorubicin, topotecan, irinotecan (CPT-11), etoposide (VP-16), teniposide, and mitoxantrone.

In some embodiments, the anti-cancer agent is a mitotic inhibitor. Mitotic inhibitors are often plant alkaloids and other compounds derived from natural plant products. They work by stopping mitosis in the M phase of the cell cycle but, in some cases, can damage cells in all phases by keeping enzymes from making proteins needed for cell reproduction. Exemplary mitotic inhibitors include, but are not limited to, paclitaxel (Taxol®), docetaxel (Taxotere®), ixabepilone (Ixempra®), vinblastine (Velban®), vincristine (Oncovin®), vinorelbine (Navelbine®), and estramustine (Emcyt®).

In some embodiments, the anti-cancer agent is a corticosteroid. Corticosteroids, often simply called steroids, are natural hormones and hormone-like drugs that are useful in the treatment of many types of cancer. Corticosteroids can also be used before chemotherapy to help prevent allergic reactions as well as during and after chemotherapy to help prevent nausea and vomiting. Exemplary corticosteroids include, but are not limited to, prednisone, methylprednisolone (Solumedrol®), and dexamethasone (Decadron®).

In some embodiments, the anti-cancer agent is another type of chemotherapy drug, such as a proteosome inhibitor, a kinase inhibitor, or a histone-deacetylase inhibitor. In other embodiments, the anti-cancer agent is a biologic such as an antibody used in cancer therapy.

In some embodiments, the anti-cancer agent targets tumors associated with various cancers. The cancer can be any cancer located in the body of a subject, such as, but not limited to, cancers located at the head and neck, breast, liver, colon, ovary, prostate, pancreas, brain, cervix, bone, skin, eye, bladder, stomach, esophagus, peritoneum, or lung. For example, the anti-cancer agent can be used for the treatment of colon cancer, cervical cancer, cancer of the central nervous system, breast cancer, bladder cancer, anal carcinoma, head and neck cancer, ovarian cancer, endometrial cancer, small cell lung cancer, non-small cell lung carcinoma, neuroendocrine cancer, soft tissue carcinoma, penile cancer, prostate cancer, pancreatic cancer, gastric cancer, gall bladder cancer or espohageal cancer. In some cases, the cancer can be a cancer of the blood.

E. Exemplary Features

In some embodiments, a desired response of treatment according to the provided methods is to reduce or inhibit one or more symptoms associated with a tumor or a cancer. In some embodiments, the one or more symptoms do not have to be completely eliminated for the composition to be effective.

For example, administration of a composition containing the phthalocyanine dye-targeting molecule conjugate followed by irradiation can decrease the size of a tumor, such as the volume or weight of a tumor, or metastasis of a tumor, for example by at least 20%, at least 305, at least 40%, at least 50%, at least 60%, at least 70%, at least 80%, at least 90%, at least 95%, at least 98%, or at least 100%, as compared to the tumor size, volume, weight, or metastasis in the absence of the conjugate. In some embodiments, the difference in tumor size, volume, weight or metastasis is evident after at least 7 days, at least 10 days, at least 14 days, at least 30 days, at least 60 days, at least 90 days, or at least 120 days after the treatment(s). In some embodiments, tumor size and volume can be monitored by radiography, ultrasound imaging, necropsy, by use of calipers, by microCT or by $^{18}$F-FDG-PET. Tumor size also can be assessed visually. In particular examples, tumor size (diameter) can be measured directly using calipers.

In some embodiments, combining the phthalocyanine dye-targeting molecule conjugates and PIT (e.g. antibody-IR700 molecules/PIT) with the additional therapy, such as an immune modulating agent or anti-cancer agent, in accord with the methods herein can result in a tumor size, volume, weight or metastasis that is less than the tumor size, volume, weight or metastasis would be if it were treated with either the phthalocyanine dye-targeting molecule conjugate/PIT alone or the additional therapy alone, that is, there is a synergistic effect. For example, the combination therapy provided herein can decrease the size of a tumor, such as the volume or weight of a tumor, or metastasis of a tumor, for example by at least 1.2-fold, 1.5-fold, 2-fold, 3-fold, 4-fold, 5-fold, 6-fold, 7-fold, 8-fold, 9-fold, 10-fold or more as compared to the tumor size, volume, weight, or metastasis achieved in therapy methods involving only photoimmunotherapy with a composition containing the phthalocyanine dye-targeting molecule conjugate followed by irradiation or in therapy methods involving monotherapy with the immune modulating agent or anti-cancer agent alone.

In some embodiments, a desired response of treatment according to the provided methods is to kill a population of cells by a desired amount, for example by killing at least 20%, at least 50%, at least 60%, at least 70%, at least 80%, at least 90%, at least 95%, at least 98%, or at least 100% of the cells, as compared to cell killing in the absence of the conjugate and irradiation. In some embodiments, the difference in tumor cell killing is evident after at least 1 hour, at least 2 hours, at least 6 hours, at least 12 hours, at least 1 day, at least 2 days, at least 3 days, at least 4 days, at least 5 days, at least 6 days, at least 7 days, at least 10 days, at least 14 days or at least 30 days, after the treatment(s). In some embodiments, cell killing activity can be assessed by a variety of techniques known in the art including, but not limited to, cytotoxicity/cell viability assays that can be employed to measure cell necrosis and/or apoptosis, such as from a biopsy sample, following treatment(s), such as MTT (3-(4,5-dimethylthiazol-2-yl)-2,5-diphenyltetrazolium bromide) assays and other related tetrazolium salt based assays (e.g., XTT, MTS or WST), ATP assays, apoptosis assays (e.g., using labeled annexin V), such as TUNEL staining of infected cells, DNA fragmentation assays, DNA laddering assays, and cytochrome C release assays. In some cases, imaging methods can be used, such as positron emission tomography (PET), including FDG-PET, single photon emission CT (SPECT), diffusion weighted imaging (DWI), dynamic susceptibility-weighted contrast-enhanced (DSC) MR imaging or dynamic contrast-enhanced (DCE) MR imaging, CT perfusion methods, magnetic resonance spectroscopy (MRS) Such assays and methods are well known to one of skill in the art.

In some embodiments, the combination therapy provided herein can increase the killing of tumor cells, for example, by at least by at least 1.2-fold, 1.5-fold, 2-fold, 3-fold, 4-fold, 5-fold, 6-fold, 7-fold, 8-fold, 9-fold, 10-fold or more as compared to cell killing in therapy methods involving only photoimmunotherapy with a composition containing the phthalocyanine dye-targeting molecule conjugate followed by irradiation or in therapy methods involving monotherapy with the immune modulating agent or anti-cancer agent alone.

In some embodiments, a desired response is to increase the survival time of a patient with a tumor, or who has had a tumor recently removed, by a desired amount, for example to increase survival by at least 20%, at least 50%, at least 60%, at least 70%, at least 80%, at least 90%, at least 95%, at least 98%, or at least 100%, as compared to the survival time in the absence of the conjugate and irradiation. In some embodiments, increased survival is evident by an increase in one or more survival indicators from among duration of median progression-free survival, duration of response, median overall survival or other survival-related clinical endpoint. In some embodiments, the difference in survival is evident after at least 7 days, at least 10 days, at least 14 days, at least 30 days, at least 60 days, at least 90 days, at least 120 days, at least 6 months, at least 12 months, at least 24 months, or at least 5 years or more after the treatment(s). In some embodiments, antibody-IR700 molecules/PIT alone in accord with the methods herein, increases the duration of median progression-free survival, duration of response, median overall survival or other survival-related clinical endpoint by at least 3 months, at least 4 months, at least 5 months, at least 6 months, at least 7 months, at least 8 months, at least 9 months, at least 10 months, at least 11 months, at least 12 months, at least 18 months, at least 24 months, or at least 5 years or or more compared to if a subject were treated with the corresponding targeting molecule that was not so conjugated. In some embodiments, antibody-IR700 molecules/PIT in combination the additional therapy, such as an immune modulating agent or anti-cancer agent, in accord with the methods herein, increases the duration of median progression-free survival, duration of response, median overall survival or other survival-related clinical endpoint by at least 3 months, at least 4 months, at least 5 months, at least 6 months, at least 7 months, at least 8 months, at least 9 months, at least 10 months, at least 11 months, at least 12 months, at least 18 months, at least 24 months, or at least 5 years or or more compared to if the subject were treated with the phthalocyanine dye-targeting molecule conjugate/PIT alone or the additional therapy alone.

In some embodiments, the combination therapy provided herein can increase the survival time of a treated subject, for example, by at least 1.2-fold, 1.5-fold, 2-fold, 3-fold, 4-fold, 5-fold, 6-fold, 7-fold, 8-fold, 9-fold, 10-fold or more as compared to the survival time in a subject receiving a therapy involving only photoimmunotherapy with a composition containing the phthalocyanine dye-targeting molecule conjugate followed by irradiation or in therapy methods involving monotherapy with the immune modulating agent or anti-cancer agent alone. In some embodiments, combining the antibody-IR700 molecules/PIT with the additional therapy, such as an immune modulating agent or anti-cancer agent, in accord with the methods herein, increases the duration of median progression-free survival, duration of response, median overall survival or other survival-related clinical endpoint by at least 3 months, at least 4 months, at least 5 months, at least 6 months, at least 7 months, at least 8 months, at least 9 months, at least 10 months, at least 11 months, at least 12 months, at least 18 months, at least 24 months, or at least 5 years or or more compared to if it were treated with either the phthalocyanine dye-targeting molecule conjugate/PIT alone or the additional therapy alone.

In one aspect, the response to treatment is characterized utilizing Response Evaluation Criteria in Solid Tumors (RECIST) criteria, which is the recommended guideline for assessment of tumor response by the National Cancer Institute (see Therasse et al., J. Natl. Cancer Inst. 92:205-216, 2000). In some embodiments, patients can be assessed for response to the therapy using RECIST criteria as outlined in the revised version 1.1 guidelines (RECIST 1.1, see Eisenhauer et al. (2009) European Journal of Cancer, 45:228-247). The criteria for objective status are required for protocols to assess solid tumor response. Representative criteria include the following: (1) Complete Response (CR), defined as complete disappearance of all measurable disease; no new lesions; no disease related symptoms; no evidence of non-measurable disease; (2) Partial Response (PR) defined as 30% decrease in the sum of the longest diameter of target lesions (e.g., tumor); (3) Progressive Disease (PD), defined as 20% increase in the sum of the longest diameter of target lesions or appearance of any new lesion; (4) Stable or No Response, defined as not qualifying for CR, PR, or PD. (See Therasse et al., supra.) In some embodiments, the objective response rate (ORR) can be determined, which is the percentage of subjects in which a CR or PR response is observed. ORR is commonly used to measure tumor response to treatment in oncology clinical trials.

In some embodiments, administration of the phthalocyanine dye-targeting molecule conjugate in accord with the provided methods, either as a monotherapy or in a combination therapy, achieves a reduction in the size or volume of the tumor by at least 30%, at least 40%, at least 50%, at least 60%, at least 70%, at least 80% at least 90% or more within two weeks or one month of the irradiation compared to the size or volume of the tumor prior to the administration and irradiation.

In some embodiments, in a population of treated subjects, administration of the phthalocyanine dye-targeting molecule conjugate in accord with the provided methods, either as a monotherapy or as a combination therapy, effects an improvement of a disorder- or cancer-related parameter compared to a similarly situated population of subjects treated with the targeting molecule (e.g., antibody or antigen-binding antibody fragment) that is not conjugated, wherein the parameter is selected from one or more of: a) objective response rate (ORR); b) progression free survival (PFS); c) overall survival (OS); d) reduction in toxicity; e) tumor response; of f) quality of life. In some embodiments, the parameter is improved by at least 10%, at least 20%, at least 30%, at least 40%, at least 50%, at least 60%, at least 70%, at least 80%, at least 90%, at least 100% or more.

In some embodiments, in a population of treated subjects, administration of the phthalocyanine dye-targeting molecule conjugate in accord with the provided methods, either as a monotherapy or in a combination therapy, results in a PR in at least 50%, 60%, 70%, 80%, 90%, 95% or 100% of the treated subjects. In some embodiments, in a population of treated subjects, administration of the phthalocyanine dye-targeting molecule conjugate in accord with the provided methods results in a CR in at least 10%, 20%, 30%, 40%, 50%, 60%, 70%, 80%, 90%, 95% or 100% of the treated subjects.

In some embodiments, in a population of treated subjects, administration of the phthalocyanine dye-targeting molecule conjugate in accord with the provided methods, either as a monotherapy or in a combination therapy, results in an ORR that is greater than about 13%, for example greater than about 15%, greater than about 20%, greater than about 30%, greater than about 40%, greater than about 50%, greater than about 60%, greater than about 70%, greater than about 80%, greater than about 95%, or greater than about 99%.

In some embodiments, the combination therapy provided herein, such as therapies that employing an immune modulating agent, can be used to stimulate an immune response in a cancer patient. Typically, immune responses may be detected by any of a variety of well-known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); an increase in cytotoxic T-cells, activated macrophages or natural killer cells; or any other criterion by which the presence of an immune response may be detected.

Procedures for performing these and similar assays are widely known and may be found, for example in Lefkovits (Immunology Methods Manual: The Comprehensive Sourcebook of Techniques, 1998; see also Current Protocols in Immunology; see also, e.g., Weir, Handbook of Experimental Immunology, 1986 Blackwell Scientific, Boston, Mass.; Mishell and Shigii (eds.) Selected Methods in Cellular Immunology, 1979 Freeman Publishing, San Francisco, Calif.; Green and Reed, 1998 Science 281:1309 and references cited therein.).

Detection of the proliferation of tumor-reactive T cells may be accomplished by a variety of known techniques. For example, T cell proliferation can be detected by measuring the rate of DNA synthesis, and tumor specificity can be determined by controlling the stimuli (such as, for example, a specific desired tumor- or a control antigen-pulsed antigen presenting cells) to which candidate tumor-reactive T cells are exposed. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyltetrazolium Alternatively, synthesis of lymphokines (such as interferon-gamma) can be measured or the relative number of T cells that can respond to a particular antigen may be quantified.

Detection of antibody production (e.g., tumor specific antibody production) may be achieved, for example, by assaying a sample (e.g., an immunoglobulin containing sample such as serum, plasma or blood) from a host treated with a composition according to the present invention using in vitro methodologies such as radioimmunoassay (RIA), enzyme linked immunosorbent assays (ELISA), equilibrium dialysis or solid phase immunoblotting including Western blotting. In preferred embodiments ELISA assays may further include tumor antigen-capture immobilization of a target tumor antigen with a solid phase monoclonal antibody specific for the antigen, for example, to enhance the sensitivity of the assay. Elaboration of soluble mediators (e.g., cytokines, chemokines, lymphokines, prostaglandins, etc.) may also be readily determined by enzyme-linked immunosorbent assay (ELISA), for example, using methods, apparatus and reagents that are readily available from commercial sources (e.g., Sigma, St. Louis, Mo.; see also R & D Systems 2006 Catalog, R & D Systems, Minneapolis, Minn.).

Any number of other immunological parameters may be monitored using routine assays that are well known in the art. These may include, for example, antibody dependent cell-mediated cytotoxicity (ADCC) assays, secondary in vitro antibody responses, flow immunocytofluorimetric analysis of various peripheral blood or lymphoid mononuclear cell subpopulations using well established marker antigen systems, immunohistochemistry or other relevant assays. These and other assays may be found, for example, in Rose et al. (Eds.), Manual of Clinical Laboratory Immunology, 5th Ed., 1997 American Society of Microbiology, Washington, D.C.

IV. Imaging

In some embodiments, administration of the conjugate to the subject also can facilitate imaging of the subject for fluorescence signal. In some embodiments, the conjugates can be used as in vitro or in vivo optical imaging agents of cells, tissues or organs in various biomedical applications. In some embodiments, the phthalocyanine dye-targeting molecule conjugates can be used as in vivo optical imaging agents of tumors, tissues, and organs in a subject. In some embodiments, the phthalocyanine dye-targeting molecule conjugates are used for the detection of tumors and other abnormalities. For example, the existence of cancer cells or cancer tissues can be verified by administering the phthalocyanine dye-targeting molecule conjugate to the subject for detection and imaging of the tumor.

In some embodiments, the detection or evaluation of a fluorescence signal can be used to monitor uploading of the conjugate at the lesion (e.g., tumor) prior to PIT. In some embodiments, the detection or evaluation of a fluorescence signal can be used to monitor the location of the lesion (e.g., tumor) by illuminating the area around or near the lesion to which the conjugate is selectively localized upon administration. In some embodiments, the detection or evaluation of a fluorescence signal can be used to visualize any residual cancer cells that may be present in a surgical setting, for example, after tumor resection, which, in some cases, can be used to facilitate targeting of such cells by PIT.

In some embodiments, the fluorescence signal of the phthalocyanine dye used for PIT (e.g., IR700) can be directly monitored.

In some embodiments, the phthalocyanine dye-targeting molecule conjugate may contain an additional dye as described above, which, in some cases, has an emission and excitation wavelength that is different than the phthalocyanine dye (e.g., IR700). In some embodiments, the phthalocyanine dye-targeting molecule conjugates of Formula I or Formula II are used for imaging of a subject. In some embodiments, the phthalocyanine dye-targeting molecule conjugates are administered to a subject, and irradiation or illumination is performed to identify, detect, locate, and/or follow the movement of the conjugate in the subject. In some embodiments, imaging of the subject is performed by illuminating at a wavelength capable of being absorbed by the second or addition dye of the conjugate but not by the phthalocyanine dye.

In some embodiments, light at a wavelength corresponding to that which is absorbed by the dye is exposed to the conjugate. In some embodiments, the targeted area to which the phthalocyanine dye-targeting molecule conjugates bind is exposed to light of the wavelength of electromagnetic radiation absorbed by the dye, such as the phthalocyanine dye (e.g., IR700) or the additional or second dye. In some embodiments, the conjugates, when exposed to light of an appropriate wavelength, absorb the light, causing substances to be produced that illuminate the target cells or tissue within the subject to which the conjugate is bound. In some embodiments, illumination is performed to identify, detect, locate, and/or characterize a cancer cell or tumor in the subject.

In some embodiments, the conjugate is exposed to light using a device selected from among a hand-held ultraviolet lamp, a mercury lamp, a xenon lamp, a laser, a laser diode or an LED imaging device. In some embodiments, the LED imaging device contains a near-infrared (NIR) LED.

In some embodiments, irradiation is carried out using a microlens-tipped fiber for surface illumination. In some embodiments, irradiation is carried out using cylindrical diffusing fibers. In some embodiments, the cylindrical diffusing fibers have a diffuser length of 0.5 cm to 10 cm and are spaced 1.8±0.2 cm apart. In some embodiments, the cylindrical diffusing fibers are placed in a catheter positioned in the tumor 1.8±0.2 cm apart. In some embodiments, the catheter is optically transparent.

In some embodiments, the phthalocyanine dye-targeting molecule conjugates of Formula I or Formula II are used for fluorescence imaging in surgery. In some embodiments, the phthalocyanine dye-targeting molecule conjugates are used to image the targeted area (e.g., tumor) prior to surgery to provide information about tumor location. In some embodiments, the phthalocyanine dye-targeting molecule conjugates are used to image the targeted area at and around the tumor so that the margins of the tumor can be visualized with fluorescence and residual cancer cells in the margins can be eradicated with PIT. In some embodiments, presurgery imaging methods include but are not limited to magnetic resonance imaging (MRI) and computerized tomography (CT).

In some embodiments, the conjugates can be used to directly stain or label a sample so that the sample can be identified or quantified. For instance, the conjugate can be added as part of an assay for a biological target analyte, or as a detectable tracer element in a biological or non-biological fluid. Typically, the sample is obtained directly from a liquid source or as a wash from a solid material or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, and the like. In some embodiments, imaging of the cells or tissues is performed by irradiating or illuminating at a wavelength capable of being absorbed by one or more of the dyes of the conjugate. In some embodiments, in vitro imaging methods include but are not limited to phase contrast microscopy, fluorescent microscopy, multiphoton microscopy, confocal laser scanning microscopy, confocal Raman microscopy, magnetic resonance microscopy, optical coherence tomography, and electron microscopy.

V. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a "conjugate" refers to a polypeptide linked directly or indirectly to one or more other polypeptides or chemical moieties. Such conjugates include fusion proteins, those produced by chemical conjugates and those produced by any other methods. For example, a conjugate can refer to a phthalocyanine dye, such as an IR700 molecule, linked directly or indirectly to one or more other polypeptides or chemical moieties, such as to a targeting molecule that binds to or targets to a cell surface protein.

As used herein, a composition refers to any mixture of two or more products, substances, or compounds, including cells. It may be a solution, a suspension, liquid, powder, a paste, aqueous, non-aqueous or any combination thereof.

As used herein, a "pharmaceutical composition" or "pharmaceutical formulation" refers to a preparation which is in such form as to permit the biological activity of an active ingredient contained therein to be effective, and which contains no additional components which are unacceptably toxic to a subject to which the formulation would be administered.

As used herein, a "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, a combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, a derivative refers to a form of a drug that has undergone change or modification from a reference drug or agent, but still retains activity (e.g., exhibits increased or decreased activity) compared to the reference drug or agent. Typically a derivative form of a compound means that a side chain of the compound has been modified or changed.

As used herein, an analogue or analog of a drug or agent is a drug or agent that is related to a reference drug, but whose chemical and biological activities can be different. Typically, analogues exhibit similar activities to a reference drug or agent, but the activity can be increased or decreased or otherwise improved. Typically, an analogue form of a compound or drug means that the backbone core of the structure is modified or changed compared to a reference drug.

As used herein, a kit is a packaged combination that optionally includes other elements, such as additional reagents and instructions for use of the combination or elements thereof.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, an "article of manufacture" is a product that is made and, in some cases, that can be sold. In some embodiments, the term can refer to compositions contained in articles of packaging, such as in a container.

As used herein, "combination therapy" refers to a treatment in which a subject is given two or more therapeutic agents, such as at least two or at least three therapeutic agents, for treating a single disease. In some embodiments, each therapy can result in an independent pharmaceutical effect, and together can result in an additive or synergistic pharmaceutical effect.

As used herein, "disease or disorder" refers to a pathological condition in an organism resulting from cause or condition including, but not limited to, infections, acquired conditions, genetic conditions, and characterized by identifiable symptoms.

As used herein, "treating" a subject with a disease or condition means that the subject's symptoms are partially or totally alleviated, or remain static following treatment. Hence treating encompasses prophylaxis, therapy and/or cure. Prophylaxis refers to prevention of a potential disease and/or a prevention of worsening of symptoms or progression of a disease.

As used herein, "treatment" means any manner in which the symptoms of a condition, disorder or disease or other indication, are ameliorated or otherwise beneficially altered.

As used herein, "therapeutic effect" means an effect resulting from treatment of a subject that alters, typically improves or ameliorates the symptoms of a disease or condition or that cures a disease or condition.

As used herein, a "therapeutically effective amount" or a "therapeutically effective dose" refers to the quantity of an agent, compound, material, or composition containing a compound that is at least sufficient to produce a therapeutic effect. Hence, it is the quantity necessary for preventing, curing, ameliorating, arresting or partially arresting a symptom of a disease or disorder.

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, the term "subject" refers to an animal, including a mammal, such as a human being.

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

VI. Exemplary Embodiments

Among the provided embodiments are:

1. A method of treating a disease or condition in a subject, comprising:

a) administering to a subject having a disease or condition a conjugate comprising a phthalocyanine dye linked to a targeting molecule that binds to a protein on the surface of a cell present in the microenvironment of a lesion associated with the disease or condition, wherein the conjugate is administered to effect a systemic exposure that is no more than 75% of the therapeutically effective systemic exposure of the antibody or antigen-binding antibody fragment that is not so conjugated for treating the same disease or condition; and b) after administering the conjugate, irradiating the lesion at a wavelength of 500 nm to 900 nm at a dose of at least 1 J $cm^{-2}$ or 1 J/cm of fiber length, thereby treating the disease in the subject.

2. The method of embodiment 1, wherein the wavelength is 600 nm to 850 nm.

3. The method of embodiment 1 or embodiment 2, wherein the wavelength is 660 nm to 740 nm.

4. The method of any of embodiments 1-3, wherein the conjugate is administered in a dosing schedule in which:

the administration of the conjugate is performed only one time as a single injection or infusion; or the dosing schedule does not comprise a subsequent dose of the conjugate; or the dosing schedule does not comprise a subsequent dose of the macromolecule that is not so conjugated.

5. The method of any of embodiments 1-4, wherein the conjugate is administered systemically.

6. The method of any of embodiments 1-5, wherein the conjugate is administered intravenously.

7. The method of any of embodiments 1-6, wherein the conjugate is administered to effect a systemic exposure (AUC) that is no more than 60%, no more than 50%, no more than 40% or no more than 30% of the therapeutically effective systemic exposure of the antibody or antigen-binding antibody fragment that is not so conjugated for treating the same disease or condition.

8. The method of any of embodiments 1-7, wherein the disease or condition is a tumor, whereby the antibody or an antigen-binding antibody fragment binds to a molecule on the surface of a cell present in the tumor microenvironment and the tumor is irradiated.

9. The method of any of embodiments 1-8, wherein:

the systemic exposure as measured by the average area under the plasma conjugate concentration-time curve from time 0 to infinity (AUC[0-inf]) for a patient population after administration of the conjugate is between or between about 250 μg/mL*h and 100,000 g/mL*h, between or between about 500 μg/mL*h and 50,000 μg/mL*h, between or between about 500 μg/mL*h and 18,000 μg/mL*h; between or between about 500 μg/mL*h and 10,000 g/mL*h; or the systemic exposure as measured by the average area under the plasma conjugate concentration-time curve from time 0 to infinity (AUC[0-inf]) for a patient population after administration of the conjugate is no more than 100,000 μg/mL*h, no more than 75,000 g/mL*h, no more than 50,000 μg/mL*h, no more than 40,000 μg/mL*h, no more than 30,000 g/mL*h, no more than 20,000 μg/mL*h, no more than 10,000 μg/mL*h, no more than 5,000 g/mL*h, no more than 2,500 μg/mL*h.

10. The method of any of embodiments 1-9, wherein:

the systemic exposure as measured by the average area under the plasma conjugate concentration-time curve from time 0 to 24 hours (AUC[0-24]) for a patient population after administration of the conjugate is between or between about 100 μg/mL*h and 25,000 μg/mL*h, between or between about 200 μg/mL*h and 10,000 μg/mL*h, between or between about 500 g/mL*h and 5,000 μg/mL*h; or the systemic exposure as measured by the average area under the plasma conjugate concentration-time curve from time 0 to 24 hours (AUC[0-24]) for a patient population after administration of the conjugate is no more than 25,000 μg/mL*h, no more than 15,000 μg/mL*h, no more than 10,000 μg/mL*h, no more than 5,000 μg/mL*h, no more than 2,500 μg/mL*h, no more than 1,000 μg/mL*h, or no more than 500 μg/mL*h.

11. The method of any of embodiments 1-10, wherein the conjugate is administered in a dosage range that is at least about 10 mg/m$^2$ (body surface area of the subject), at least about 50 mg/m$^2$ or at least about 75 mg/m$^2$ and is no more than 5000 mg/m$^2$, no more than 2000 mg/m$^2$, no more than 1000 mg/m$^2$, no more than 500 mg/m$^2$, no more than 250 mg/m$^2$ or no more than 200 mg/m$^2$.

12. The method of any of embodiments 1-11, wherein the conjugate is administered at a dosage that is between or between about 100 mg/m$^2$ and 1500 mg/m$^2$ or 150 mg/m$^2$ and 750 mg/m$^2$.

13. The method of any of embodiments 1-12, wherein the conjugate is administered at a dosage that is or is about 160 mg/m$^2$, 320 mg/m$^2$, 640 mg/m$^2$ or 1280 mg/m$^2$.

14. The method of any of embodiments 1-13, wherein the targeting molecule is an antibody or an antigen-binding antibody fragment.

15. The method of embodiment 14, wherein the antibody is an antigen-binding antibody fragment that is a Fab, single $V_H$ domain, a single chain variable fragment (scFv), a multivalent scFv, a bispecific scFv or an scFv-CH3 dimer.

16. The method of any of embodiments 1-15, wherein the irradiation is carried out between or between about 30 minutes and 96 hours after administering the conjugate.

17. The method of any of embodiments 1-16, wherein the lesion is irradiated at a wavelength of 690±50 nm or at a wavelength of or about 690±20 nm.

18. The method of any of embodiments 1-17, wherein the lesion is irradiated at a dose of from or from about 2 J cm$^{-2}$ to about 400 J cm$^{-2}$ or from or from about 2 J/cm fiber length to about 500 J/cm fiber length.

19. The method of any of embodiments 1-18, wherein:

the lesion is irradiated at a dose of at least or at least about 2 J cm$^{-2}$, 5 J cm$^{-2}$, 10 J cm$^{-2}$, 25 J cm$^{-2}$, 50 J cm$^{-2}$, 75 J cm$^{-2}$, 100 J cm$^{-2}$, 150 J cm$^{-2}$, 200 J cm$^{-2}$, 300 J cm$^{-2}$, 400 J cm$^{-2}$, or 500 J cm$^{-2}$; or the lesion is irradiated at a dose of at least or at least about 2 J/cm fiber length, 5 J/cm fiber length, 10 J/cm fiber length, 25 J/cm fiber length, 50 J/cm fiber length, 75 J/cm fiber length, 100 J/cm fiber length, 150 J/cm fiber length, 200 J/cm fiber length, 250 J/cm fiber length, 300 J/cm fiber length, 400 J/cm fiber length or 500 J/cm fiber length.

20. The method of any of embodiments 1-19, wherein the phthalocyanine dye has a maximum absorption wavelength from or from about 600 nm to about 850 nm.

21. The method of any of embodiments 1-20, wherein the phthalocyanine dye is linked directly or indirectly to the targeting molecule.

22. The method of any of embodiments 1-21, wherein the phthalocyanine dye comprises the formula:

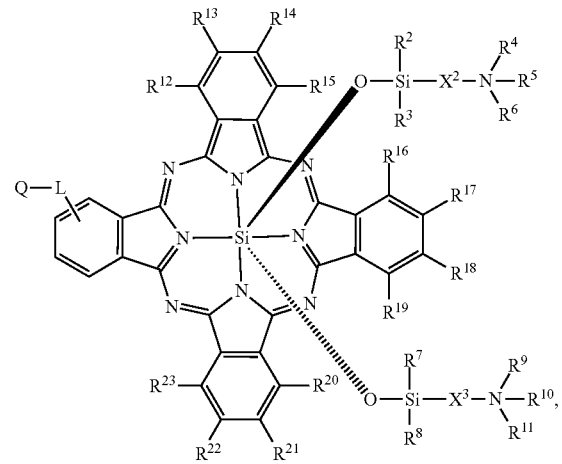

wherein:

L is a linker;

Q is a reactive group for attachment of the dye to the targeting molecule;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from hydrogen, halogen, optionally substituted alkylthio, optionally substituted alkylamino and optionally substituted alkoxy; and $X^2$ and $X^3$ are each independently $C_1$-$C_{10}$ alkylene, optionally interrupted by a heteroatom.

23. The method of any of embodiments 1-22, wherein the phthalocyanine dye comprises the formula:

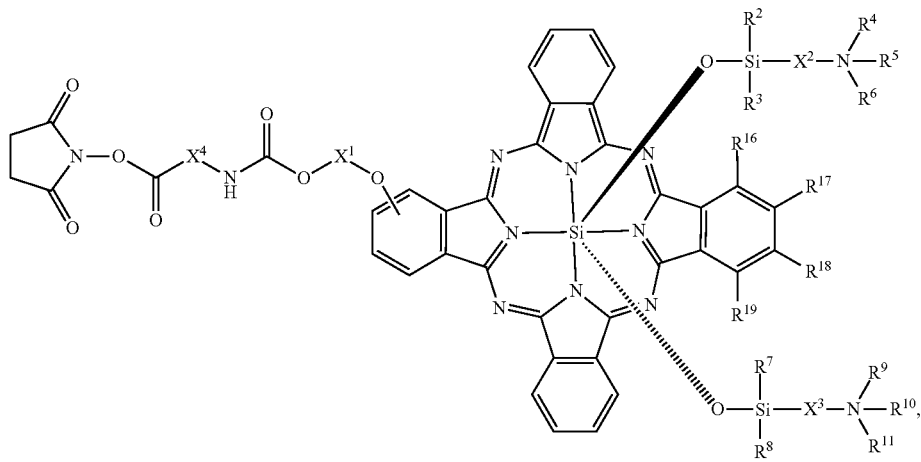

wherein:

$X^1$ and $X^4$ are each independently a $C_1$-$C_{10}$ alkylene optionally interrupted by a heteroatom;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; and $R^{16}$, $R^{17}$, $R^{18}$ and $R^{19}$ are each independently selected from hydrogen, halogen, optionally substituted alkylthio, optionally substituted alkylamino and optionally substituted alkoxy.

24. The method of any of embodiments 1-23, wherein the phthalocyanine dye comprises IRDye 700DX (IR700).

25. The method of any of embodiments 1-24, wherein the cell surface protein is selected from among ACTHR, endothelial cell Anxa-1, aminopetidase N, anti-IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CD133, CD7, CD15, CD34, CD44, CD206, CD271, CEA (CarcinoEmbryonic Antigen), CGRP, chemokine receptors, cell-surface annexin-1, cell-surface plectin-1, Cripto-1, CRLR, CXCR2, CXCR4, DCC, DLL3, E2 glycoprotein, EGFR, EGFRvIII, EMR1, Endosialin, EP2, EP4, EpCAM, EphA2, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like) like), G-protein coupled receptors of the Family C (Metabotropic Glutamate Receptor-like), GD2, GP100, GP120, Glypican-3, hemagglutinin, Heparin sulfates, HER1, HER2, HER3, HER4, HMFG, HPV 16/18 and E6/E7 antigens, hTERT, IL11-R, IL-13R, ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/HABP1), p75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family (e.g., P2X1-5), mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP (e.g., TRPV1-6, TRPA1, TRPC1-7, TRPM1-8, TRPP1-5, TRPML1-3), TSH receptor, VEGF receptors (VEGFR1 or Flt-1, VEGFR2 or FLK-1/KDR, and VEGF-3 or FLT-4), voltage-gated ion channels, VPAC1, VPAC2, Wilms tumor 1, Y1, Y2, Y4, and Y5.

26. The method of any of embodiments 1-25, wherein the cell surface protein is selected from among HER1/EGFR, HER2/ERBB2, CD20, CD25 (IL-2Rα receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), integrin αVβ3, integrin α5131, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, and SK-1 antigen.

27. The method of any of embodiments 1-26, wherein the cell surface protein is selected from among CD25, PD-1 (CD279), PD-L1 (CD274, B7-H1), PD-L2 (CD273, B7-DC), CTLA-4, LAG3 (CD223), TIM3 (HAVCR2), 4-1BB (CD137, TNFRSF9), CXCR2, CXCR4 (CD184), CD27, CEACAM1, Galectin 9, BTLA, CD160, VISTA (PD1 homologue), B7-H4 (VCTN1), CD80 (B7-1), CD86 (B7-2), CD28, HHLA2 (B7-H7), CD28H, CD155, CD226, TIGIT, CD96, Galectin 3, CD40, CD40L, CD70, LIGHT (TNFSF14), HVEM (TNFRSF14), B7-H3 (CD276), Ox40L (TNFSF4), CD137L (TNFSF9, GITRL), B7RP1, ICOS (CD278), ICOSL, KIR, GAL9, NKG2A (CD94), GARP, TL1A, TNFRSF25, TMIGD2, BTNL2, Butyrophilin family, CD48, CD244, Siglec family, CD30, CSF1R, MICA (MHC class I polypeptide-related sequence A), MICB (MHC class I polypeptide-related sequence B), NKG2D, KIR family (Killer-cell immunoglobulin-like receptor, LILR family (Leukocyte immunoglobulin-like receptors, CD85, ILTs, LIRs), SIRPA (Signal regulatory protein alpha), CD47 (IAP), Neuropilin 1 (NRP-1), a VEGFR, and VEGF.

28. The method of any of embodiments 1-27, wherein the antibody or an antigen-binding antibody fragment is selected from among cetuximab, panitumumab, zalutumumab, nimotuzumab, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Basiliximab, nivolumab, pembrolizumab, pidilizumab, MK-3475, BMS-936559, MPDL3280A, ipilimumab, tremelimumab, IMP321, BMS-986016, LAG525, urelumab, PF-05082566, TRX518, MK-4166, dacetuzumab, lucatumumab, SEA-CD40, CP-870, CP-893, MED16469, MEDI6383, MEDI4736, MOXR0916, AMP-224, PDR001, MSB0010718C, rHIgM12B7, Ulocuplumab, BKT140, Varlilumab (CDX-1127), ARGX-110, MGA271, lirilumab (BMS-986015, IPH2101), IPH2201, AGX-115, Emactuzumab, CC-90002 and MNRP1685A or is an antigen-binding antibody fragment thereof.

29. The method of any of embodiments 1-28, wherein the conjugate is selected from among cetuximab-IR700, panitumumab-IR700, zalutumumab-IR700, nimotuzumab-IR700, Tositumomab-IR700, Rituximab-IR700, Ibritumomab tiuxetan-IR700, Daclizumab-IR700, Gemtuzumab-IR700, Alemtuzumab-IR700, CEA-scan Fab fragment-IR700, OC125-IR700, ab75705-IR700, B72.3-IR700, Bevacizumab-IR700, Basiliximab-IR700, nivolumab-IR700, pembrolizumab-IR700, pidilizumab-IR700, MK-3475-IR700, BMS-936559-IR700, MPDL3280A-IR700, ipilimumab-IR700, tremelimumab-IR700, IMP321-IR700, BMS-986016-IR700, LAG525-IR700, urelumab-IR700, PF-05082566-IR700, TRX518-IR700, MK-4166-IR700, dacetuzumab-IR700, lucatumumab-IR700, SEA-CD40-IR700, CP-870-IR700, CP-893-IR700, MED16469-IR700, MEDI6383-IR700, MEDI4736-IR700, MOXR0916-IR700, AMP-224-IR700, PDR001-IR700, MSB0010718C-IR700, rHIgM12B7-IR700, Ulocuplumab-IR700, BKT140-IR700, Varlilumab-IR700, ARGX-110-IR700, MGA271-IR700, lirilumab-IR700, IPH2201-IR700, AGX-115-IR700, Emactuzumab-IR700, CC-90002-IR700 and MNRP1685A-IR700.

30. The method of embodiment 29, wherein the targeting molecule is an antibody that is cetuximab or is an antigen-binding antibody fragment thereof or the conjugate is cetuximab-IR700.

31. The method of embodiment 30, wherein the average area under the plasma conjugate concentration-time curve from time 0 to infinity (AUC[0-inf]) for a patient population after administration of the conjugate is between or between about 500 µg/mL*h and 18,000 g/mL*h, between or between about 500 µg/mL*h and 10,000 µg/mL*h, between or between about 500 µg/mL*h and 5,000 µg/mL*h, or between or between about 500 µg/mL*h and 2,500 g/mL*h.

32. The method of embodiment 30, wherein the average area under the plasma conjugate concentration-time curve from time 0 to 24 hours (AUC[0-24]) for a patient population after administration of the conjugate is between or between about 500 µg/mL*h and 8,000 µg/mL*h, between or between about 500 µg/mL*h and 5,000 µg/mL*h, between or between about 500 µg/mL*h and 2,000 µg/mL*h or between or between about 1000 µg/mL*h and 4,000 µg/mL*h.

33. The method of any of embodiments 30-32, wherein:
the conjugate is administered in a dosage range that between or between about 75 mg/m$^2$ (body surface area of the subject) and 1500 mg/m$^2$, between or between about 75 mg/m$^2$ and 1000 mg/m$^2$, between or between about 75 mg/m$^2$ and 500 mg/m$^2$ or between or between about 75 mg/m$^2$ and 225 mg/m$^2$; or
is at least about or is about 160 mg/m$^2$, 320 mg/m$^2$, 640 mg/m$^2$ or 1280 mg/m$^2$.

34. A method of treating a disease lesion in a subject, comprising:
a) intravenously administering to a subject having a lesion associated with a disease or condition a cetuximab-IR700 conjugate, wherein the conjugate is administered in an amount that is or is about 640 mg/m$^2$; and
b) after administering the conjugate, irradiating the lesion at a wavelength of 690±20 nm at a dose of at least or about at least or about 50 J cm$^{-2}$ or 100 J/cm of fiber length, thereby treating the disease or condition in the subject.

35. The method of embodiment 34, wherein the conjugate is administered in a dosing schedule in which:
the administration of the conjugate is performed only one time as a single injection or infusion; or
the dosing schedule does not comprise a subsequent dose of the conjugate; or
the dosing schedule does not comprise a subsequent dose of the macromolecule that is not so conjugated.

36. The method of any of embodiments 1-35, wherein the irradiation is carried out 24 hours±3 hours after administering the conjugate.

37. The method of any of embodiments 34-36, wherein the lesion is a tumor and the disease or condition is a tumor or a cancer.

38. The method of any of embodiments 1-37, wherein the lesion is a tumor that is a superficial tumor.

39. The method of embodiment 38, wherein the tumor is less than 10 mm thick.

40. The method of embodiment 38 or embodiment 39, wherein irradiation is carried out using a microlens-tipped fiber for surface illumination.

41. The method of any of embodiments 1-40, wherein the light irradiation dose is from or from about 5 J/cm$^2$ to about 200 J/cm$^2$.

42. A method for treating a superficial tumor with photoimmunotherapy, comprising illuminating an superficial tumor in a subject with a microlens-tipped fiber for surface illumination with a light dose of from or from about 5 J/cm$^2$ to about 200 J/cm$^2$, wherein the tumor is associated with a phototoxic agent comprising a targeting molecule bound to a cell surface molecule of the tumor.

43. The method embodiment 41 or embodiment 42, wherein the light irradiation dose is or is about 50 J/cm$^2$.

44. The method of any of embodiments 1-40, wherein the lesion is a tumor that is an interstitial tumor.

45. The method of embodiment 44, wherein the tumor is greater than 10 mm deep or is a subcutaneous tumor.

46. The method of embodiment 44 or embodiment 45, wherein irradiation is carried out using cylindrical diffusing fibers comprising a diffuser length of 0.5 cm to 10 cm and spaced 1.8±0.2 cm apart.

47. The method of any of embodiments 1-37 and 44-46, wherein the light irradiation dose is from or from about 20 J/cm fiber length to about 500 J/cm fiber length.

48. A method for treating an interstitial tumor with photoimmunotherapy, comprising illuminating an interstitial tumor in a subject with cylindrical diffusing fibers comprising a diffuser length of 0.5 cm to 10 cm and spaced 1.8±0.2 cm apart with a light dose of or about 100 J/cm fiber length or with a fluence rate of or about 400 mW/cm, wherein the tumor is associated with a phototoxic agent comprising a targeting molecule bound to a cell surface molecule of the tumor.

49. The method of embodiment 47 or embodiment 48, wherein the light irradiation dose is from or from about 50 J/cm fiber length to about 300 J/cm fiber length.

50. The method of any of embodiments 47-49, wherein the light irradiation dose is or is about 100 J/cm fiber length.

51. The method of any of embodiments 48-50, wherein the tumor is greater than 10 mm deep or is a subcutaneous tumor.

52. The method of any of embodiments 47-51, wherein the cylindrical diffusing fibers are placed in a catheter positioned in the tumor 1.8±0.2 cm apart.

53. The method of embodiment 52, wherein the catheter is optically transparent.

54. The method of any of embodiments 42, 43 and 48-53, wherein greater than 6 hours prior to illuminating the tumor, the subject has been administered the phototoxic agent comprising the targeting molecule, wherein the phototoxic agent associates with the tumor.

55. The method of embodiment 54, wherein the phototoxic agent has been previously administered to the subject greater than or greater than about 12 hours, 24 hours, 26 hours, 48 hours, 72 hours or 96 hours prior to illuminating the tumor.

56. The method of any of embodiments 42, 43 and 48-55, wherein the phototoxic agent is a phthalocyanine dye-targeting molecule conjugate.

57. The method of embodiment 56, wherein the phthalocyanine dye is IR700.

58. The method of any of embodiments 1-41, 44-47, 49, 50 and 52-54, wherein the dosing schedule is repeated, whereby steps (a) and (b) are repeated.

59. The method of embodiment 58, wherein the dosing schedule is repeated if residual lesion remains after a prior treatment with the conjugate.

60. The method of embodiment 58 or embodiment 59, comprising assessing the subject for the presence of a residual lesion and if residual lesion remains repeating the dosing schedule.

61, The method of any of embodiments 58-60, wherein the dosing schedule is repeated if a residual lesion remains at a time that is more than or about or 1 week, 2 weeks, 3 weeks, 4 weeks, 2 months, 6 months or 1 year after initiation of the prior administration of the conjugate.

62. The method of any of embodiments 58-61, wherein the dosing schedule is repeated if a residual lesion remains at or about 4 weeks after initiation of the prior administration of the conjugate.

63. The method of any of embodiments 1-62, wherein the conjugate comprises 1 to 100, 1 to 10 or 2 to 5 phthalocyanine dye molecules per macromolecule.

64. The method of any of embodiments 1-63, wherein the method does not comprise administration of an additional therapeutic agent or anti-cancer treatment.

65. The method of any of embodiments 1-63, wherein the method comprises administration of an additional therapeutic agent or anti-cancer treatment.

66. The method of embodiment 65, wherein the anti-cancer treatment comprises radiation therapy.

67. The method of embodiment 66, wherein the additional therapeutic agent is an anti-cancer agent or an immune modulating agent, with immune modulating agent optionally is a cell-based (e.g. combination treatment with immune cells such as dendritic cells) or non-cell based immune modulating agents.

68. The method of embodiment 67, wherein the additional therapeutic agent is an immune modulating agent that is an immune checkpoint inhibitor.

69. The method of embodiment 68, wherein the immune checkpoint inhibitor specifically binds a molecule selected from among CD25, PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28 and VISTA.

70. The method of embodiment 68 or embodiment 69, wherein the immune checkpoint inhibitor is and antibody or antigen-binding fragment, a small molecule or a polypeptide.

71. The method of any of embodiments 68-70, wherein the immune checkpoint inhibitor is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MEDI4736, MOXR0916, AMP-224, and MSB001078C, or is an antigen-binding fragment thereof.

72. The method of any of embodiments 67-71, wherein the additional therapeutic agent is administered prior to irradiating the lesion or tumor.

73. The method of embodiment 72, wherein the additional therapeutic agent is administered greater than or greater than about 30 minutes, 1 hour, 2 hours, 6 hours, 12 hours, 24 hours, 48 hours, 96 hours, one week, two weeks, three weeks or one month prior to irradiating the tumor.

74. The method of any of embodiments 67-73, comprising continued administration of the additional therapeutic agent subsequent to the irradiation three times a week, two times a week, once every week, once every two weeks, once every three weeks or once a month.

75. A method of treating a tumor in a subject comprising:
a) administering to a subject an immune modulating agent;
b) administering to the subject a therapeutically effective amount of a conjugate comprising a phthalocyanine dye linked to a targeting molecule capable of binding to a molecule on the surface of a cell present in the microenvironment of a tumor; and
c) greater than 12 hours after administering the immune modulating agent, irradiating the tumor at a wavelength that renders the conjugate cytotoxic, thereby treating the tumor.

76. The method of embodiment 75, wherein the immune modulating agent is administered greater than or greater than about 24 hours, 48 hours, 96 hours, one week, two weeks, three weeks or one month prior to irradiating the tumor.

77. The method of embodiment 75 or embodiment 76, wherein the conjugate binds to a protein on the surface of a cell present in the microenvironment of the tumor.

78. The method of any of embodiments 75-77, wherein step c) of irradiating the tumor is carried out either i) after administration of the immune modulating agent and after administration of the conjugate or ii) only after administration of the conjugate.

79. The method of any of embodiments 67-78, wherein the conjugate is administered prior to, simultaneously or subsequently to administration of the immune-modulating agent.

80. The method of any of embodiments 67-79, wherein the conjugate is administered after administering the immune modulating agent but prior to irradiating the tumor.

81. The method of any of embodiments 67-80, wherein the conjugate is administered from or from about 12 hours to 48 hours prior to irradiating the tumor and the immune modulating agent is administered from or from about 12 hours to about 1 month prior to irradiating the tumor.

82. The method of any of embodiments 75-81, wherein the immune modulating agent is an immune checkpoint inhibitor.

83. The method of embodiment 82, wherein the immune checkpoint inhibitor specifically binds a molecule selected from among CD25, PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28 and VISTA.

84. The method of embodiment 82 or embodiment 83, wherein the immune checkpoint inhibitor is and antibody or antigen-binding fragment, a small molecule or a polypeptide.

85. The method of any of embodiments 82-84, wherein the immune checkpoint inhibitor is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MEDI4736, MOXR0916, AMP-224, and MSB001078C, or is an antigen-binding fragment thereof of any of the foregoing.

86. The method of any of embodiments 75-81, wherein the immune modulating agent that is a demethylating agent that upregulates expression of a tumor associated antigen (TAA) or is a cytokine.

87. The method of any of embodiments 75-86, comprising continued administration of the immune modulating agent subsequent to the irradiation three times a week, two times a week, once every week, once every two weeks, once every three weeks or once a month.

88. A method of treating a tumor in a subject comprising:
a) administering to a subject an immune modulating agent that enhances the expression of a molecule on the surface of a cell present in the microenvironment of the tumor;
b) administering to the subject a therapeutically effective amount of a conjugate comprising a phthalocyanine dye linked to a targeting molecule that is capable of binding to the cell surface molecule; and
c) greater than 5 minutes after administering the conjugate, irradiating the tumor at a wavelength that renders the conjugate cytotoxic, thereby treating the tumor.

89. The method of embodiment 88, wherein the immune modulating agent is a cytokine or is an agent that induces increased expression of a cytokine in the tumor microenvironment.

90. The method of embodiment 88 or embodiment 89, wherein the cytokine is interferon gamma.

91. The method of any of embodiments 88-90, wherein the molecule on the surface of the cells is selected from CD25, PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28 and VISTA.

92. The method of any of embodiments 88-91, wherein the molecule on the surface of the cell is PD-L1.

93. The method of any of embodiments 88-92, wherein the targeting molecule is an immune checkpoint inhibitor.

94. The method of any of embodiments 88-93, wherein the targeting molecule is an antibody or antibody fragment, a small molecule or a polypeptide.

95. The method of any of embodiments 88-94, wherein the targeting molecule is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MED14736, MOXR0916, AMP-224, and MSB001078C, or is an antigen-binding fragment thereof of any of the foregoing.

96. A method of treating a tumor in a subject comprising:
a) administering to a subject a conjugate comprising a phthalocyanine dye linked to a targeting molecule capable of binding a cell surface molecule on a cell in the microenvironment of the tumor;
b) greater than 5 minutes after administering the conjugate, irradiating the tumor at a wavelength that renders the conjugate cytotoxic, wherein the treatment of the tumor with the conjugate followed by light irradiation increases the presence of immunosuppressive cells in the tumor or increases the expression of immunosuppressive markers at the tumor; and
c) administering to the subject a therapeutically effective amount of an immune modulating agent capable of reducing the amount or activity of immunosuppressive cells in the tumor or capable of blocking the activity of the immunosuppressive marker.

97. The method of embodiment 96, wherein the phthalocyanine dye is a first dye and the immune modulating agent comprises a conjugate comprising a second phthalocyanine dye conjugated to an immune modulating agent capable of binding to the immunosuppressive cell.

98. The method of embodiment 97, wherein the first and second phthalocyanine dye is the same or different.

99. The method of any of embodiments 96-98, wherein the immune modulating agent is an immune checkpoint inhibitor.

100. The method of any of embodiments 96-99, wherein the immune modulating agent specifically binds a molecule selected from among CD25, PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28 and VISTA.

101. The method of any of embodiments 96-100, wherein the immune modulating agent is an antibody or antibody fragment, a small molecule or a polypeptide.

102. The method of any of embodiments 96-101, wherein the immune modulating agent is not an anti-CTLA4 antibody.

103. The method of any of embodiments 96-102, wherein the immune modulating agent is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MED14736, MOXR0916, AMP-224, and MSB001078C, or is an antigen-binding fragment thereof of any of the foregoing.

104. A method of treating a tumor in a subject comprising:
a) administering to a subject a conjugate comprising a phthalocyanine dye linked to a targeting macromolecule capable of binding to a molecule on the surface of a cell present in the microenvironment of the tumor;
b) greater than 5 minutes after administering the conjugate, irradiating the tumor at a wavelength that renders the conjugate cytotoxic, wherein the treatment of the tumor with the conjugate followed by light irradiation primes activation of immune cells; and c) administering to the subject a therapeutically effective amount of an immune modulating agent capable of increasing the activity of the immune cell.

105. The method of embodiment 104, wherein the immune cell is an antigen presenting cell.

106. The method of embodiment 105, wherein the immune cell is a dendritic cell.

107. The method of any of embodiments 104-106, wherein the immune modulating agent is selected from among GM-CSF, CpG-ODN (CpG oligodeoxynucleotides), lipopolysaccharide (LPS), monophosphoryl lipid A (MPL), alum, recombinant *Leishmania* polyprotein, imiquimod, MF59, poly I:C, poly A:U, type 1 IFN, Pam3Cys, Pam2Cys, complete freund's adjuvant (CFA), alpha-galactosylceramide, RC-529, MDF2β, Loxoribine, anti-CD40 agonist, SIRPa antagonist, AS04, AS03, Flagellin, Resiquimod, DAP (diaminopimelic acid), MDP (muramyl dipeptide) CAF01 (cationic adjuvant formulation-01), antrhacyclins (doxorubicin, mitoxantron), BK channel agonists, bortezomib, botrtezomib plus mitocycin C plus hTert-Ad, Cardiac glycosides plus non-Immunogenic cell death inducers, cyclophosphamide, GADD34/PP1 inhibitors plus mitomycin, LV-tS-MAC, and oxaliplatin.

108. The method of any of embodiments 104-107, wherein the immune modulating agent is a Toll-like receptor (TLR) agonist, an adjuvant or a cytokine.

109. The method of embodiment 108, wherein the immune modulating agent is a TLR agonist and the TLR agonist is TLR agonist is a TLR4 agonist, a TLR7 agonist, a TLR8 agonist, or a TLR9 agonist.

110. The method of embodiment 108 or embodiment 109, wherein the TLR agonist is selected from among triacylated lipoprotein, diacylated lipopeptide, lipoteichoic acid, peptidoglycan, zymosan, Pam3CSK4, dsRNA, polyI:C, Poly G10, Poly G3, CpG, 3M003, flagellin, lipopolysaccharide (LPS) *Leishmania* homolog of eukaryotic ribosomal elongation and initiation factor 4a (LeIF), MEDI9197, SD-101, and imidazoquinoline TLR agonists.

111. The method of any of embodiments 104-107, wherein the immune modulating agent is a cytokine and the cytokine is IL-4, TNF-α, GM-CSF or IL-2.

112. The method of any of embodiments 96-111, wherein the immune modulating agent is administered prior to, simultaneously with or after the irradiation.

113. The method of embodiment 112, wherein the immune modulating agent is administered no more than 5 minutes, 30 minutes, 60 minutes, 2 hours, 6 hours, 12 hours or 24 hours after the irradiation.

114. The method of any of embodiments 75-113, wherein the targeting molecule binds to molecule or protein directly or indirectly.

115. The method of embodiment 114, wherein the targeting molecule is a second binding molecule that binds to a first binding molecule, said first binding molecule being capable of binding to the molecule or protein.

116. The method of embodiment 114 or embodiment 115, wherein the targeting molecule is a secondary antibody.

117. The method of any of embodiments 75-116, wherein the phthalocyanine dye has a maximum absorption wavelength from or from about 600 nm to about 850 nm.

118. The method of any of embodiments 75-117, wherein the phthalocyanine dye is covalently or non-covalently linked to the targeting molecule.

119. The method of any of embodiments 75-118, wherein the phthalocyanine dye comprises a linker comprising a reactive group for attachment of the dye to the targeting molecule.

120. The method of embodiment 119, wherein the phthalocyanine dye comprises the formula:

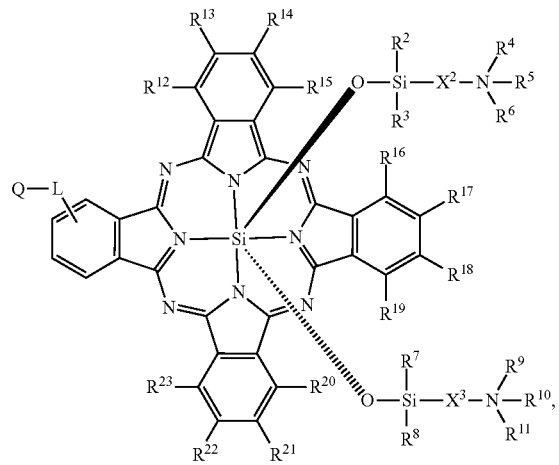

wherein:

L is a linker;

Q is a reactive group for attachment of the dye to the targeting molecule;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from hydrogen, halogen, optionally substituted alkylthio, optionally substituted alkylamino and optionally substituted alkoxy; and $X^2$ and $X^3$ are each independently $C_1$-$C_{10}$ alkylene, optionally interrupted by a heteroatom.

121. The method of embodiment 119 or embodiment 120, wherein the phthalocyanine dye comprises the formula:

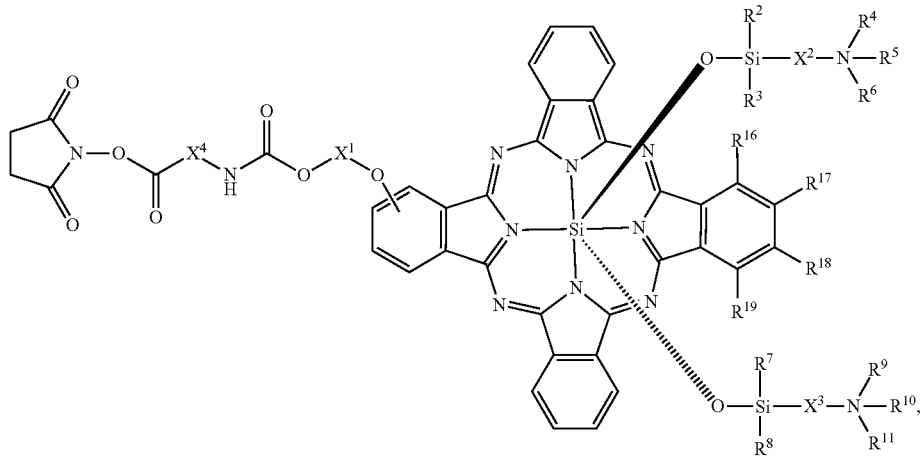

wherein:

$X^1$ and $X^4$ are each independently a $C_1$-$C_{10}$ alkylene optionally interrupted by a heteroatom;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; and $R^{16}$, $R^{17}$, $R^{18}$ and $R^{19}$ are each independently selected from hydrogen, halogen, optionally substituted alkylthio, optionally substituted alkylamino and optionally substituted alkoxy.

122. The method of any of embodiments 75-121, wherein the phthalocyanine dye comprises IRDye 700DX (IR700).

123. The method of any of embodiments 75-122, wherein the conjugate is administered at a dose from or from about 50 mg/m² to about 5000 mg/m², from about 250 mg/m² to about 2500 mg/m², from about 750 mg/m² to about 1250 mg/m² or from about 100 mg/m² to about 1000 mg/m².

124. The method of any of embodiments 8-33 and 37-123, wherein the tumor is a cancer.

125. The method of embodiment 124, wherein the cancer is a cancer located at the head and neck, breast, liver, colon, ovary, prostate, pancreas, brain, cervix, bone, skin, eye, bladder, stomach, esophagus, peritoneum, or lung.

126. The method of any of embodiments 8-33 and 37-125, wherein the tumor is a sarcoma or carcinoma.

127. The method of embodiment 126, wherein the tumor is a carcinoma that is a squamous cell carcinoma, basal cell carcinoma or adenocarcinoma.

128. The method of embodiment 127, wherein the tumor is a carcinoma that is a carcinoma of the bladder, pancreas, colon, ovary, lung, breast, stomach, prostate, cervix, esophagus or head and neck.

129. The method of any of embodiments 75-128, wherein the tumor is irradiated at a wavelength of 600 nm to 850 nm at a dose of at least 1 J cm$^{-2}$ or at least 1 J/cm fiber length.

130. The method of any of embodiments 75-129, wherein the tumor is irradiated at a wavelength of 690 nm±50 nm or at a wavelength of or about 690±20 nm.

131. The method of any of embodiments 1-130, wherein the method reduces the size or volume of the tumor by at least 30%, at least 40%, at least 50%, at least 60%, at least 70%, at least 80% at least 90% or more within one month of the irradiation compared to the size or volume of the tumor prior to the administration and irradiation.

132. The method of any of embodiments 1-131, which, in a population of treated subjects, effects an improvement of a disorder- or cancer-related parameter compared to a similarly situated population of subjects treated with the antibody or antigen-binding antibody fragment that is not conjugated, wherein the parameter is selected from one or more of: a) objective response rate (ORR); b) progression free survival (PFS); c) overall survival (OS); d) reduction in toxicity; e) tumor response; of f) quality of life.

133. The method of embodiment 132, wherein the parameter is improved by at least 10%, at least 20%, at least 30%, at least 40%, at least 50%, at least 60%, at least 70%, at least 80%, at least 90%, at least 100% or more.

134. The method of any of embodiments 1-133, which, in a population of treated subjects, effects an objective response rate (ORR) of at least 15%, at least 25%, at least 50%, at least 55%, at least 60%, at least 65%, at least 70%, at least 75%, at least 80%, at least 85%, at least 90%, at least 95% or more.

135. The method of any of embodiments 1-133, wherein the phthalocyanine dye is a first dye and the conjugate further comprises a second fluorescent dye linked to the macromolecule that is different than the first dye.

136. The method of embodiment 135, wherein irradiating the lesion or tumor emits a fluorescence signal from the second fluorescent dye to effect detection of the presence of the conjugate at the lesion or tumor in the subject.

137. The method of embodiment 135 or embodiment 136, further comprising imaging the lesion or tumor in the subject by irradiating or illuminating the tumor at a wavelength capable of being absorbed by the second dye.

138. The method of any of embodiments 135-137, wherein the second fluorescent dye exhibits one or more spectral properties selected from among fluorescent quantum yield in water, extinction coefficient, Stokes shift, absorption and emission at long wavelength and photostability that is greater compared to the corresponding spectral property of the first dye.

139. The method of any of embodiments 135-138, wherein the first dye is IR700.

140. The method of any of embodiments 135-139, wherein the second dye is not IR700.

141. The method of any of embodiments 135-140, wherein the second dye is selected from among hydroxycoumarin, Cascade Blue, Dylight 405, Pacific Orange, Alexa Fluor 430, Fluorescein, Oregon Green, Alexa Fluor 488, BODIPY 493, 2.7-Diochlorofluorescien, ATTO 488, Chromeo 488, Dylight 488, HiLyte 488, Alexa Fluor 555, ATTO 550, BODIPY TMR-X, CF 555, Chromeo 546, Cy3, TMR, TRITC, Dy547, Dy548, Dy549, HiLyte 555, Dylight 550, BODIPY 564, Alexa Fluor 568, Alexa Fluor 594, Rhodamine, Texas Red, Alexa Fluor 610, Alexa Fluor 633, Dylight 633, Alexa Fluor 647, APC, ATTO 655, CF633, CF640R, Chromeo642, Cy5, Dylight 650, Alexa Fluor 680, IRDye 680, Alexa Fluor 700, Cy 5.5, ICG, Alexa Fluor 750, Dylight 755, IRDye 750, Cy7.5, Alexa Fluor 790, Dylight 800, IRDye 800, Qdot® 525, Qdot® 565, Qdot® 605, Qdot® 655, Qdot® 705 and Qdot® 800.

142. The method of any of embodiments 135-141, wherein the first dye is IR700 and the conjugate comprises 1 to 10 or 1 to 5 second dye molecules per macromolecule.

143. The method of any of embodiments 135-142, wherein the second dye exhibits a Stokes shift that is greater than 15 nm, greater than 20 nm, greater than 30 nm, greater than 40 nm, greater than 50 nm, greater than 60 nm, greater than 70 nm, greater than 80 nm, greater than 90 nm or greater than 100 nm.

144. The method of any of embodiments 135-143, wherein the second dye has a quantum yield in water that is greater than 10%, greater than 15%, greater than 20% or greater than 25%, greater than 30%, greater than 40%, greater than 50% or greater.

145. The method of any of embodiments 135-144, wherein the second dye has an absorption and emission wavelength in the spectrum between or between about 650 nm and 950 nm, between or between about 700 nm and 1000 nm, or between or between about 1000 nm and 1700 nm.

146. The method of any of embodiments 135-145, wherein the first dye and second dye do not exhibit an overlapping emission and absorption spectra.

147. The method of any of embodiments 135-1146, wherein the second dye is selected from among ICG, IRDye 680, Alexa Fluor 750, Dylight 755, IRDye 750, Cy7.5, Alexa Fluor 790, Dylight 800 and IRDye 800.

148. The method of any of embodiments 135-147, wherein the second dye is Alexa Fluor 488, IRDye 680, IRDye 800 or Dylight 755.

149. The method of any of embodiments 1-148, wherein the irradiating or illuminating is performed with a device selected from among a hand-held ultraviolet lamp, a mercury lamp, a xenon lamp, a laser, a laser diode or an LED imaging device.

150. The method of embodiment 149, wherein the imaging device comprises a near-infrared (NIR) diode.

151. A composition, comprising a conjugate comprising a phthalocyanine dye linked to an antibody or antigen-binding antibody fragment that binds to a molecule on the surface of a cell present in the microenvironment of a lesion, wherein the composition is formulated for single dosage administration of the conjugate in an amount that is between or between about 100 mg and 2000 mg.

152. The composition of embodiment 151, wherein the composition is formulated for single dosage administration of an amount between or between about 100 mg and 500 mg, between or between about 200 mg and 400 mg.

153. The composition of embodiment 151 or embodiment 152, wherein the composition is formulated for single dosage administration of an amount between or between about 500 mg and 1500 mg, 800 mg and 1200 mg, or 1000 mg and 1500 mg.

154. The composition of any of embodiments 151-153, wherein:
the volume of the composition is between or between about 10 mL and 1000 mL, or 50 mL and 500 mL; or
the volume of the composition is at least 10 mL, 20 mL, 30 mL, 40 mL, 50 mL, 75 mL, 100 mL, 150 mL, 200 mL, 250 mL, 300 mL, 400 mL, 500 mL or 1000 mL.

155. An article of manufacture, comprising:
a plurality of sealable containers, each individually comprising a fraction of a single administration dose of a composition comprising a conjugate comprising a phthalocyanine dye linked to an antibody or antigen-binding antibody fragment that binds to a molecule on the surface of a cell present in the microenvironment of a lesion, wherein the combined amount of the conjugate in the plurality of sealable containers is between or between about 100 mg and 1500 mg;
packaging material; and
a label or package insert comprising instructions for combining the contents of the plurality of vials to prepare a single dosage formulation of the composition.

156. The article of manufacture of embodiment 155, wherein the combined amount of the conjugate in the plurality of sealable containers is between or between about 100 mg and 1200 mg.

157. The article of manufacture of embodiment 155 or embodiment 156, wherein the combined amount of the conjugate in the plurality of sealable container is between or between about 100 mg and 500 mg, between or between about 200 mg and 400 mg, between or between about 500 mg and 1500 mg, between or between about 800 mg and 1200 mg or between or between about 1000 mg and 1500 mg.

158. The composition of any of embodiments 151-154 or the article of manufacture of any of embodiments 155-157, wherein the lesion is a tumor.

159. A conjugate, comprising a phthalocyanine dye linked to an antibody or antigen-binding fragment that is an immune modulating agent.

160. The conjugate of embodiment 159, wherein the immune modulating agent is an immune checkpoint inhibitor.

161. The conjugate of embodiment 159 or embodiment 160, wherein the immune modulating agent is an antibody or antigen binding fragment that binds to the surface of a tumor, tumor cell or cancer cell.

162. The conjugate of any of embodiments 159-161, wherein the immune modulating agent specifically binds a molecule selected from among CD25, PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28 and VISTA.

163. The conjugate of any of embodiments 159-162, wherein the immune modulating agent is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MED14736, MOXR0916, AMP-224, and MSB001078C, or is an antigen-binding fragment thereof of any of the foregoing.

164. The conjugate of any of embodiments 159-163, wherein the immune modulating agent is an antibody or antibody fragment that binds to PD-L1.

165. The conjugate of embodiment 164, wherein the immune modulating agent is an antibody selected from BMS-935559, MEDI4736, MPDL3280A and MSB0010718C, or an antigen-binding fragment thereof.

166. A conjugate, comprising a targeting molecule linked to at least a first and second fluorescent dye, wherein the first fluorescent dye is a phthalocyanine dye capable of exhibiting phototoxicity.

167. The conjugate of embodiment 166, comprising the formula:

$[D_1-(L_1)_n]_p-A-[(L_2)_n-D_2]_o$, wherein:

A is a targeting molecule that can bind to a molecule on the surface of a cell;

$L_1$ and $L_2$ are each an independently selected linker, which can be the same or different;

n and m are independently 1 or 2;

$D_1$ is a first dye that is the phthalocyanine dye capable of exhibiting phototoxicity;

$D_2$ is a second dye that is a fluorescent dye, wherein $D_2$ is different than $D_1$;

p is 1 to 10; and o is 1 to 10.

168. The conjugate of embodiment 166 or embodiment 167, wherein the targeting molecule is an antibody or an antigen-binding antibody fragment.

169. The conjugate of any of embodiments 166-168, wherein the cell surface molecule comprises an antigen, a polypeptide, a lipid, or a carbohydrate or a combination of these molecules.

170. The conjugate of any of embodiments 166-169, wherein the cell surface molecule is selected from among ACTHR, endothelial cell Anxa-1, aminopetidase N, anti-IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CD133, CD7, CD15, CD34, CD44, CD206, CD271, CEA (CarcinoEmbryonic Antigen), CGRP, chemokine receptors, cell-surface annexin-1, cell-surface plectin-1, Cripto-1, CRLR, CXCR2, CXCR4, DCC, DLL3, E2 glycoprotein, EGFR, EGFRvIII, EMR1, Endosialin, EP2, EP4, EpCAM, EphA2, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like) like), G-protein coupled receptors of the Family C (Metabotropic Glutamate Receptor-like), GD2, GP100, GP120, Glypican-3, hemagglutinin, Heparin sulfates, HER1, HER2, HER3, HER4, HMFG, HPV 16/18 and E6/E7 antigens, hTERT, IL11-R, IL-13R, ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/HABP1), p75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family (e.g., P2X1-5), mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP (e.g., TRPV1-6, TRPA1, TRPC1-7, TRPM1-8, TRPP1-5, TRPML1-3), TSH receptor, VEGF receptors (VEGFR1 or Flt-1, VEGFR2 or FLK-1/KDR, and VEGF-3 or FLT-4), voltage-gated ion channels, VPAC1, VPAC2, Wilms tumor 1, Y1, Y2, Y4, and Y5.

171. The conjugate of any of embodiments 166-170, wherein the cell surface molecule is selected from among HER1/EGFR, HER2/ERBB2, CD20, CD25 (IL-2Rα receptor), CD33, CD52, CD133, CD206, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, EphA2, Glypican-3, gpA33, mucins, CAIX, PSMA, folate-binding protein, gangliosides (such as GD2, GD3, GM1 and GM2), VEGF receptor (VEGFR), integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, and SK-1 antigen.

172. The conjugate of any of embodiments 166-171, wherein the cell surface molecule is selected from among CD25, PD-1 (CD279), PD-L1 (CD274, B7-H1), PD-L2 (CD273, B7-DC), CTLA-4, LAG3 (CD223), TIM3 (HAVCR2), 4-1BB (CD137, TNFRSF9), CXCR2, CXCR4 (CD184), CD27, CEACAM1, Galectin 9, BTLA, CD160, VISTA (PD1 homologue), B7-H4 (VCTN1), CD80 (B7-1), CD86 (B7-2), CD28, HHLA2 (B7-H7), CD28H, CD155, CD226, TIGIT, CD96, Galectin 3, CD40, CD40L, CD70, LIGHT (TNFSF14), HVEM (TNFRSF14), B7-H3 (CD276), Ox40L (TNFSF4), CD137L (TNFSF9, GITRL), B7RP1, ICOS (CD278), ICOSL, KIR, GAL9, NKG2A (CD94), GARP, TL1A, TNFRSF25, TMIGD2, BTNL2, Butyrophilin family, CD48, CD244, Siglec family, CD30, CSF1R, MICA (MHC class I polypeptide-related sequence A), MICB (MHC class I polypeptide-related sequence B), NKG2D, KIR family (Killer-cell immunoglobulin-like receptor, LILR family (Leukocyte immunoglobulin-like receptors, CD85, ILTs, LIRs), SIRPA (Signal regulatory protein alpha), CD47 (IAP), Neuropilin 1 (NRP-1), a VEGFR, and VEGF.

173. The conjugate of any of embodiments 166-172, wherein the macromolecule is an antibody or an antigen-binding antibody fragment that is selected from among cetuximab, panitumumab, zalutumumab, nimotuzumab, Tositumomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), Basiliximab, nivolumab, pembrolizumab, pidilizumab, MK-3475, BMS-936559, MPDL3280A, ipilimumab, tremelimumab, IMP321, BMS-986016, LAG525, urelumab, PF-05082566, TRX518, MK-4166, dacetuzumab, lucatumumab, SEA-CD40, CP-870, CP-893, MED16469, MEDI6383, MEDI4736, MOXR0916, AMP-224, PDR001, MSB0010718C, rHIgM12B7, Ulocuplumab, BKT140, Varlilumab (CDX-1127), ARGX-110, MGA271, lirilumab (BMS-986015, IPH2101), IPH2201, AGX-115, Emactuzumab, CC-90002 and MNRP1685A or is an antigen-binding antibody fragment thereof.

174. The conjugate of any of embodiments 166-173, wherein the targeting molecule is not or does not comprise a nanocarrier.

175. The conjugate of any of embodiments 166-174, wherein the targeting molecule is not or does not comprise a virus-like particle, a nanoparticle, a liposome, a quantum dot, or a combination thereof.

176. The conjugate of any of embodiments 166-175, wherein the first dye that is a phthalocyanine dye that has a maximum absorption wavelength from or from about 600 nm to about 850 nm.

177. The conjugate of any of embodiments 166-176, wherein the first dye that is a phthalocyanine dye comprises the formula:

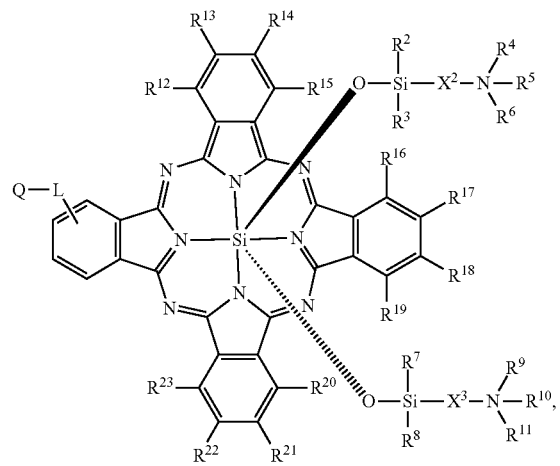

wherein:
L is a linker;
Q is a reactive group for attachment of the dye to the targeting molecule;
$R^2$, $R^3$, $R^7$, and $R^8$ are each independently selected from optionally substituted alkyl and optionally substituted aryl;
$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group;
$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from hydrogen, halogen, optionally substituted alkylthio, optionally substituted alkylamino and optionally substituted alkoxy; and
$X^2$ and $X^3$ are each independently $C_1$-$C_{10}$ alkylene, optionally interrupted by a heteroatom.

178. The conjugate of any of embodiments 166-177, wherein the first dye that is a phthalocyanine dye comprises the formula:

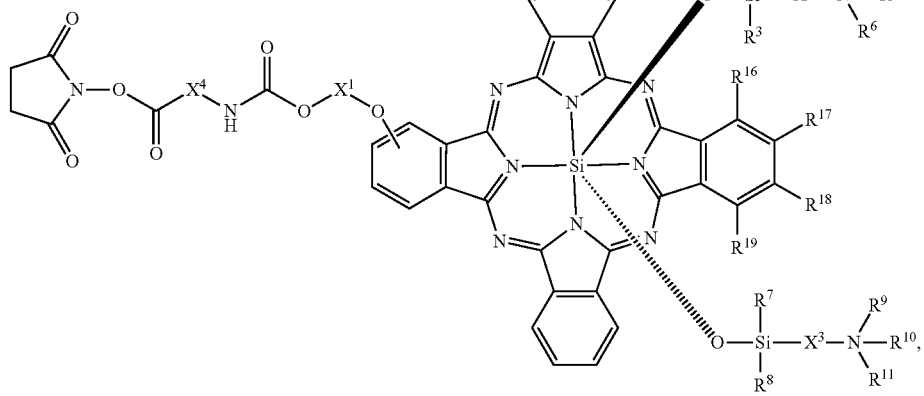

wherein:
$X^1$ and $X^4$ are each independently a $C_1$-$C_{10}$ alkylene optionally interrupted by a heteroatom;
$R^2$, $R^3$, $R^7$, and $R^8$ are each independently selected from optionally substituted alkyl and optionally substituted aryl;
$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; and
$R^{16}$, $R^{17}$, $R^{18}$ and $R^{19}$ are each independently selected from hydrogen, halogen, optionally substituted alkylthio, optionally substituted alkylamino and optionally substituted alkoxy.

179. The conjugate of any of embodiments 166-178, wherein the first dye that is a phthalocyanine dye comprises IRDye 700DX (IR700).

180. The conjugate of any of embodiments 166-179, wherein the second fluorescent dye exhibits one or more spectral properties selected from among fluorescent quantum yield in water, extinction coefficient, Stokes shift, absorption and emission at long wavelength and photostability that is greater compared to the corresponding spectral property of the first dye.

181. The conjugate of any of embodiments 166-180, wherein the second dye is not IR700.

182. The conjugate of any of embodiments 166-181, wherein the second dye is selected from among hydroxycoumarin, Cascade Blue, Dylight 405, Pacific Orange, Alexa Fluor 430, Fluorescein, Oregon Green, Alexa Fluor 488, BODIPY 493, 2.7-Diochlorofluorescien, ATTO 488, Chromeo 488, Dylight 488, HiLyte 488, Alexa Fluor 555, ATTO 550, BODIPY TMR-X, CF 555, Chromeo 546, Cy3, TMR, TRITC, Dy547, Dy548, Dy549, HiLyte 555, Dylight 550, BODIPY 564, Alexa Fluor 568, Alexa Fluor 594, Rhodamine, Texas Red, Alexa Fluor 610, Alexa Fluor 633, Dylight 633, Alexa Fluor 647, APC, ATTO 655, CF633, CF640R, Chromeo642, Cy5, Dylight 650, Alexa Fluor 680, IRDye 680, Alexa Fluor 700, Cy 5.5, ICG, Alexa Fluor 750, Dylight 755, IRDye 750, Cy7.5, Alexa Fluor 790, Dylight 800, IRDye 800, Qdot® 525, Qdot® 565, Qdot® 605, Qdot® 655, Qdot® 705 and Qdot® 800.

183. The conjugate of any of embodiments 166-182, wherein the first dye is IR700 and the conjugate comprises 1 to 10 or 1 to 5 second dye molecules per macromolecule.

184. The conjugate of any of embodiments 166-1838, wherein the second dye exhibits a Stokes shift that is greater than 15 nm, greater than 20 nm, greater than 30 nm, greater than 40 nm, greater than 50 nm, greater than 60 nm, greater than 70 nm, greater than 80 nm, greater than 90 nm or greater than 100 nm.

185. The conjugate of any of embodiments 166-184, wherein the second dye has a quantum yield in water that is greater than 10%, greater than 15%, greater than 20% or greater than 25%, greater than 30%, greater than 40%, greater than 50% or greater.

186. The conjugate of any of embodiments 166-185, wherein the second dye has an absorption and emission wavelength in the spectrum between or between about 650 nm and 950 nm, between or between about 700 nm and 1000 nm, between or between about 1000 nm and 1700 nm.

187. The conjugate of any of embodiments 166-186, wherein the first dye and second dye do not exhibit an overlapping emission and absorption spectra.

188. The conjugate of any of embodiments 166-187, wherein the second dye is selected from among ICG, IRDye 680, Alexa Fluor 750, Dylight 755, IRDye 750, Cy7.5, Alexa Fluor 790, Dylight 800 and IRDye 800.

189. The conjugate of any of embodiments 166-188, wherein the second dye is Alexa Fluor 488, IRDye 680, IRDye 800 or Dylight 755.

190. A composition, comprising the conjugate of any of embodiments 159-189.

191. The composition of embodiment 190, further comprising a pharmaceutically acceptable excipient.

192. A method of treating a disease or condition in a subject comprising:
a) administering to the subject a therapeutically effective amount of the conjugate of any of embodiments 159-165 or composition of embodiment 190 or embodiment 191, wherein the conjugate binds to a cell present in the microenvironment of a lesion associated with a disease or condition; and
b) after administering the conjugate, irradiating the lesion at one or more wavelengths to induce phototoxic activity of the conjugate, thereby treating the disease or condition.

193. A method of treating a disease or condition in a subject comprising:
a) administering to the subject a therapeutically effective amount of the conjugate of any of embodiments 166-189 or composition of embodiment 190 or embodiment 191, wherein the conjugate binds to a cell present in the microenvironment of a lesion associated with a disease or condition; and
b) after administering the conjugate, irradiating the lesion at one or more wavelengths to induce phototoxic activity of the first dye of the conjugate and a fluorescent signal of the second dye of the conjugate.

194. The method of embodiment 192 or embodiment 193, comprising irradiating the lesion at a wavelength that is from or from about 400 to about 900 nm at a dose of at least 1 J cm$^{-2}$ or 1 J/cm of fiber length.

195. The method of embodiment 193 or embodiment 194, comprising irradiating the lesion with a single wavelength.

196. The method of embodiment 193 or embodiment 195, comprising irradiating the lesion at two different wavelengths, simultaneously or sequentially, wherein one wavelength induces the phototoxic activity and the other wavelength induces the fluorescent signal.

197. The method of any of embodiments 192-196, wherein the disease or condition is a tumor.

198. The method of embodiment 197, comprising irradiating the tumor at a wavelength of 660 nm to 740 nm and at a dose of at least 1 J cm$^{-2}$, thereby treating the tumor in the subject.

199. The method of embodiment 197 or embodiment 198, wherein the tumor is a cancer.

200. The method of embodiment 199, wherein the cancer is a cancer located at the head and neck, breast, liver, colon, ovary, prostate, pancreas, brain, cervix, bone, skin, eye, bladder, stomach, esophagus, peritoneum, or lung.

201. The method of any of embodiments 197-200, wherein the tumor is a sarcoma or carcinoma.

202. The method of embodiment 201, wherein the tumor is a carcinoma that is a squamous cell carcinoma, basal cell carcinoma or adenocarcinoma.

203. The method of embodiment 202, wherein the tumor is a carcinoma that is a carcinoma of the bladder, pancreas, colon, ovary, lung, breast, stomach, prostate, cervix, esophagus or head and neck.

204. The method of any of embodiments 1-150 and 192-203, wherein prior to administration of the conjugate the targeting molecule is administered to the subject.

205. The method of any of embodiments 1-150 and 192-204, wherein the targeting molecule is administered up to 96 hours prior to administration of the conjugate.

206. The method of embodiment 204 or embodiment 205, wherein the targeting molecule is administered at a dose within a range from or from about 10 mg/m$^2$ to about 500 mg/m$^2$.

207. The method of any of embodiments 1-150 and 192-206, wherein the targeting molecule is an antibody or antigen binding fragment.

208. The method of embodiment 207, wherein the antibody is cetuximab.

209. A method of treating a tumor in a subject comprising:
a) administering to a subject a first agent that is an immune modulating agent;
b) administering to the subject a therapeutically effective amount of a conjugate comprising a phthalocyanine dye linked to a tumor-targeting macromolecule, wherein the conjugate binds to a tumor; and
c) greater than 12 hours after administering the first agent, irradiating the tumor at a wavelength that renders the conjugate cytotoxic, thereby treating the tumor.

210. The method of embodiment 209, wherein the conjugate binds to a cell surface molecule of a tumor.

211. The method of embodiment 209 or embodiment 210, wherein the conjugate binds to a cell surface molecule of a tumor cell.

212. The method of any of embodiments 209-211, wherein the first agent is administered at least or at least about 24 hours, 48 hours, 96 hours, one week, two weeks, three weeks or one month prior to irradiating the tumor.

213. The method of any of embodiments 209-212, wherein the first agent is an immune modulating agent that is a demethylating agent that upregulates expression of a tumor associated antigen (TAA) or is a cytokine.

214. The method of any of embodiments 209-213, wherein:
the immune modulating agent is a cytokine that is leukocyte interleukin injection (Multikine); or
the immune modulating agent is a demethylating agent that is 5-aza-2'-deoxycytidine.

215. The method of any of embodiments 209-212, wherein the first agent is an immune modulating agent that is an immune checkpoint inhibitor.

216. The method of embodiment 215, wherein the immune checkpoint inhibitor specifically binds a molecule selected from among PD-1, PD-L1, PD-L2, CTLA-4, LAG-3, TIM-3, 4-1BB, GITR, CD40, CD40L, OX40, OX40L, CXCR2, B7-H3, B7-H4, BTLA, HVEM, CD28 and VISTA.

217. The method of any of embodiments 209-216, wherein the immune modulating agent is a small molecule or a polypeptide.

218. The method of any of embodiments 209-216, wherein the immune modulating agent is an antibody or an antigen-binding fragment thereof.

219. The method of embodiment 218, wherein the antibody is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MEDI4736, MOXR0916, AMP-224, and MSB001078C, or is an antigen-binding fragment thereof.

220. The method of any of embodiments 209-216, wherein the first agent is an antibody conjugate comprising a phthalocyanine dye linked to an antibody or antigen-binding fragment that is an immune modulating agent.

221. The method of embodiment 220, wherein the immune modulating agent is an immune checkpoint inhibitor.

222. The method of embodiment 2218, embodiment 220 or embodiment 221, wherein the immune modulating agent is an antibody or antibody fragment that binds to the surface of a cancer cell.

223. The method of embodiment 222, wherein the immune modulating agent is an antibody or antibody fragment that binds to PD-L1.

224. The method of embodiment 223, wherein the immune modulating agent is an antibody selected from BMS-935559, MEDI4736, MPDL3280A and MSB0010718C, or an antigen-binding fragment thereof.

225. The method of any of embodiments 220-224, wherein step c) of irradiating the tumor is effected either i) after administration of the first agent and after administration of the conjugate or ii) only after administration of the conjugate.

226. The method of any of embodiments 220-225, wherein phalocyanine dye of the first agent and conjugate are the same or different.

227. A method of treating a tumor in a subject comprising:
a) administering to a subject a first agent that is an anti-cancer agent;
b) administering to the subject a therapeutically effective amount of a conjugate comprising a phthalocyanine dye linked to a tumor-targeting macromolecule, wherein the conjugate is binds to a tumor; and
c) greater than 5 minutes after administering the first agent, irradiating the tumor at a wavelength that renders the conjugate cytotoxic, thereby treating the tumor.

228. The method of embodiment 227, wherein the conjugate binds to a cell surface molecule of a tumor.

229. The method of embodiment 227 or embodiment 228, wherein the conjugate binds to a cell surface molecule of a tumor cell.

230. The method of any of embodiments 227-229, wherein the first agent is administered at least or at least about 15 minutes, 30 minutes, 1 hour, 2 hours, 3 hours, 4 hours, 5 hours, 6 hours, 12 hours or 24 hours prior to irradiating the tumor.

231. The method of any of embodiments 227-230, wherein the anti-cancer agent is selected from among an alkylating agent, a platinum drug, an antimetabolite, an anti-tumor antibiotic, a topoisomerase inhibitor, a mitotic inhibitor, a corticosteroid, a proteasome inhibitor, a kinase inhibitor, a histone-deacetylase inhibitor and an antibody.

232. The method of any of embodiments 227-231, wherein the anti-cancer agent is selected from among 5-Fluorouracil/leukovorin, oxaliplatin, irinotecan, ziv-afibercept, capecitabine, cisplatin, paclitaxel, toptecan, carboplatin, gemcitabine, docetaxel, 5-FU, ifosfamide, mitomycin, pemetrexed, vinorelbine, carmustine wager, temozolomide, methotrexate, capacitabine, etoposide, liposomal cytarabine, cytarabine, interferon alpha, vincristine, cyclophosphamide, lomusine, procarbazine, somastostatin, doxorubicin, pegylated liposomal encapsulated doxorubicin, epirubicin, eribulin, albumin-bound paclitaxel, ixabepilone, cotrimoxazole, taxane, vinblastine, temozolomide, bendamustine, oral etoposide, octreotide, lanredtide, dacarbazine, mesna, eribulin, tamoxifen, toremifene, dactinomycin, enzalutamide, abiraterone acetate, mitoxantrone, cabazitaxel, fluoropyrimidine, oxaliplatin, leucovorin, oxoliplatin and auroropyrimidine.

233. The method of any of embodiments 227-231, wherein the anti-cancer agent is selected from bevacizumab, cetuximab, panitumumab, ramucirumab, ipilimumab, rituximab, trastuzumab, ado-trastuzumab emtansine, pertuzumab, nivolumab, lapatinib, dabrafenib, vemurafenib, erlotinib, sunitinib, pazopanib, imatinib, regorafenib, sorafenib, nilotinib, dasantinib, celecoxib, crizotinib, certinib, afatinib, axitinib, bevacizumab, bosutinib, cabozantinib, afatinib, gefitinib, temsirolimus, everolimus, sirolimus, ibrutinib, imatinib, lenvatinib, olaparib, palbociclib, ruxolitinib, trametinib, vandetanib and vismodegib.

234. The method of any of embodiments 20209-233, wherein the conjugate is administered at a dose from or from about 50 mg/m$^2$ to 5000 mg/m$^2$, 250 mg/m$^2$ to 2500 mg/m$^2$, 750 mg/m$^2$ to 1250 mg/m$^2$ or 100 mg/m$^2$ to 1000 mg/m$^2$.

235. The method of any of embodiments 209-234, wherein the conjugate is administered at a dose of at least 0.01 mg, 0.1 mg, 1 mg, 10 mg, 100 mg, 1000 mg, 2000 mg, or 3000 mg.

236. The method of any of embodiments 209-235, wherein the first agent is administered in a dosage range that is from or from about 0.01 mg per kg body weight (mg/kg BW) to about 50 mg/kg BW, about 0.1 mg/kg to about 20 mg/kg BW, about 0.1 to about 10 mg/kg BW, about 0.3 to about 10 mg/kg, about 0.5 mg/kg to 5 mg/kg or 0.5 mg/kg to 1 mg/kg.

237. The method of any of embodiments 209-236, wherein the conjugate is administered prior to, simultaneously or subsequently to administration of the first agent.

238. The method of any of embodiments 209-237, wherein the conjugate and the first agent are administered prior to irradiating the tumor.

239. The method of any of embodiments 209-226 and embodiment 238, wherein the first agent is an immune modulating agent and the conjugate is administered from or from about 12 hours to 48 hours prior to irradiating the tumor and the immune modulating agent is administered from or from about 12 hours to 1 month prior to irradiating the tumor.

240. The method of any of embodiments 227-239, wherein the first agent is an anti-cancer agent and the conjugate is administered from or from about 12 hours to 48 hours prior to irradiating the tumor and the anti-cancer agent is administered from or from about 5 minutes to 24 hours prior to irradiating the tumor.

241. The method of any of embodiments 209-240, wherein the first agent and the conjugate are administered by the same route of administration.

242. The method of any of embodiments 209-241, wherein the first agent and the conjugate are administered systemically.

243. The method of any of embodiments 209-242, wherein the first agent and the conjugate are administered intravenously.

244. A method of treating a tumor in a subject comprising:
  a) administering to a subject a first conjugate comprising a phthalocyanine dye linked to an antibody or antigen-binding fragment that is an immune modulating agent;
  b) administering to the subject a therapeutically effective amount of a second conjugate comprising a phthalocyanine dye linked to a tumor-targeting macromolecule, wherein the conjugate binds to a tumor; and
  c) irradiating the tumor either i) after administration of the first conjugate and after administration of the second conjugate or ii) only after administration of the second conjugate, wherein irradiation is at a wavelength that renders the first and second conjugate cytotoxic, thereby treating the tumor.

245. The method of embodiment 244, wherein the second conjugate binds to a cell surface molecule of a tumor.

246. The method of embodiment 244 or 245, wherein the second conjugate binds to a cell surface molecule of a tumor cell.

247. The method of any of embodiments 244-246, wherein the immune modulating agent is an immune checkpoint inhibitor.

248. The method of any of embodiments 244-246, wherein the immune modulating agent is an antibody or antigen binding fragment that binds to the surface of a cancer cell.

249. The method of any of embodiments 244-248, wherein the immune modulating agent is an antibody or antibody fragment that binds to PD-L1.

250. The method of embodiment 249, wherein the immune modulating agent is an antibody selected from BMS-935559, MEDI4736, MPDL3280A and MSB0010718C, or an antigen-binding fragment thereof.

251. The method of any of embodiments 244-250, wherein phalocyanine dye of the first conjugate and the second conjugate are the same or different.

252. The method of any of embodiments 244-251, wherein the first conjugate is administered prior to administration of the second conjugate.

253. The method of embodiment 252, wherein the first conjugate is administered at least 12 hours, at least 24 hours, at least 48 hours, at least 96 hours, at least one week, at least two weeks, at least three weeks or at least one month prior to administration of the second conjugate.

254. The method of any of embodiments 244-253, wherein the method comprises a first irradiation of the tumor after administering the first conjugate and a second irradiation of the tumor after administering the second conjugate, wherein each irradiation is performed within 6 to 48 hours after administering the respective conjugate.

255. The method of any of embodiments 244-253, wherein:
  the method comprises only a single irradiation after administering the second conjugate; and
  the second conjugate is administered within 6 to 48 hours prior to irradiating the tumor and at least 12 hours after administering the first conjugate.

256. The method of any of embodiments 244-255, wherein the first conjugate and the second conjugate are administered by the same route of administration.

257. The method of any of embodiments 244-256, wherein the first conjugate and the second conjugate are administered systemically.

258. The method of any of embodiments 244-257, wherein the first conjugate and the second conjugate are administered intravenously.

259. The method of any of embodiments 209-258, wherein the phthalocyanine dye has a maximum absorption wavelength from or from about 600 nm to 850 nm.

260. The method of any of embodiments 209-259, wherein the phthalocyanine dye comprises a linker comprising a reactive group for attachment of the dye to the tumor-targeting macromolecule.

261. The method of embodiment 260, wherein the phthalocyanine dye comprises the formula:

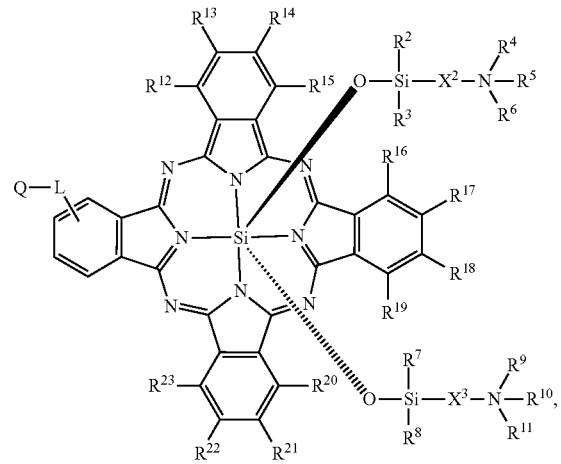

wherein:
  L is a linker;
  Q is a reactive group for attachment of the dye to the tumor-targeting macromolecule;
  $R^2$, $R^3$, $R^7$, and $R^8$ are each independently selected from optionally substituted alkyl and optionally substituted aryl;
  $R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group;

$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from hydrogen, halogen, optionally substituted alkylthio, optionally substituted alkylamino and optionally substituted alkoxy; and $X^2$ and $X^3$ are each independently $C_1$-$C_{10}$ alkylene, optionally interrupted by a heteroatom.

262. The method of embodiment 260 or embodiment 261, wherein the phthalocyanine dye comprises the formula:

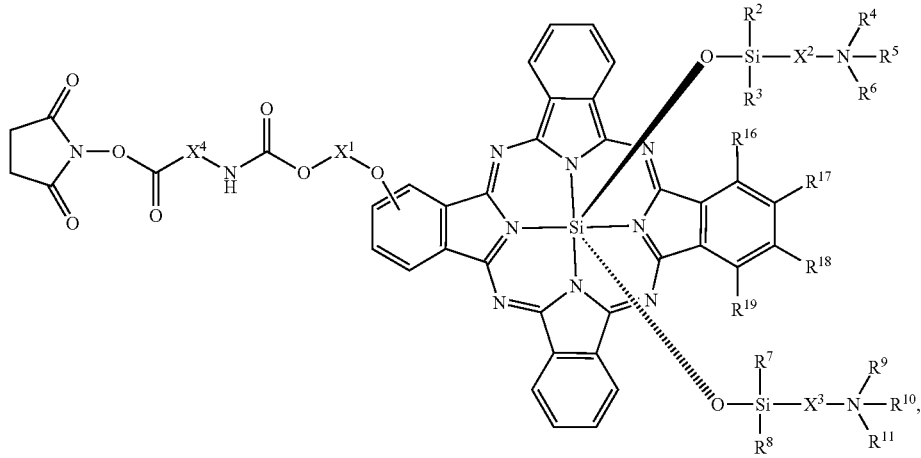

wherein:

$X^1$ and $X^4$ are each independently a $C_1$-$C_{10}$ alkylene optionally interrupted by a heteroatom;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; and $R^{16}$, $R^{17}$, $R^{18}$ and $R^{19}$ are each independently selected from hydrogen, halogen, optionally substituted alkylthio, optionally substituted alkylamino and optionally substituted alkoxy.

263. The method of any of embodiments 209-262, wherein the phthalocyanine dye comprises IRDye 700DX (IR700).

264. The method of any of embodiments 220-226, wherein phalocyanine dye of the first agent and the conjugate are the same and each is IR700.

265. The method of any of embodiments 244-258, wherein phalocyanine dye of the first conjugate and the second conjugate are the same and each is IR700.

266. The method of any of embodiments 209-265, wherein the tumor-targeting macromolecule comprises a molecule or biomolecule selected from a protein, a glycoprotein, an antibody, an antibody fragment, an antigen, an antigen binding fragment, a peptide, a polypeptide, a small molecule, a polymeric synthetic molecule, a polymeric nanoparticle, a liposome, an enzyme substrate, a hormone, a neurotransmitter, a cell metabolite, a viral particle, a viral capsid, a viral nanoparticle, a bacterial particle, a marker, a cell, a hapten, an avidin, a streptavidin, biotin, a carbohydrate, an oligosaccharide, a polysaccharide, a nucleic acid, a deoxy nucleic acid, a fragment of DNA, a fragment of RNA, nucleotide triphosphates, acyclo terminator triphosphates, and PNA.

267. The method of embodiment 266, wherein the tumor targeting macromolecule binds to a cell surface molecule expressed in tumors or cancer cells.

268. The method of embodiment 267, wherein cell surface molecule comprises an antigen, a polypeptide, a lipid, or a carbohydrate or a combination of these molecules.

269. The method of embodiment 267 or embodiment 268, wherein the cell surface molecule is selected from among ACTHR, endothelial cell Anxa-1, aminopetidase N, anti-IL-6R, alpha-4-integrin, alpha-5-beta-3 integrin, alpha-5-beta-5 integrin, alpha-fetoprotein (AFP), ANPA, ANPB, APA, APN, APP, 1AR, 2AR, AT1, B1, B2, BAGE1, BAGE2, B-cell receptor BB1, BB2, BB4, calcitonin receptor, cancer antigen 125 (CA 125), CCK1, CCK2, CD5, CD10, CD11a, CD13, CD14, CD19, CD20, CD22, CD25, CD30, CD33, CD38, CD45, CD52, CD56, CD68, CD90, CEA (CarcinoEmbryonic Antigen), CGRP, chemokine receptors, cell-surface annexin-1, cell-surface plectin-1, Cripto-1, CRLR, CXCR2, CXCR4, DCC, E2 glycoprotein, EGFR, EGFRvIII, EMR1, Endosialin, EP2, EP4, ET receptors, Fibronectin, Fibronectin ED-B, FGFR, frizzled receptors, GAGE1, GAGE2, GAGE3, GAGE4, GAGE5, GAGE6, GLP-1 receptor, G-protein coupled receptors of the Family A (Rhodopsin-like), G-protein coupled receptors of the Family B (Secretin receptor-like) like), G-protein coupled receptors of the Family C (Metabotropic Glutamate Receptor-like), GD2, GP100, GP120, hemagglutinin, Heparin sulfates, HER1, HER2, HER3, HER4, HMFG, HPV 16/18 and E6/E7 antigens, hTERT, IL11-R, IL-13R, ITGAM, Kalikrien-9, Lewis Y, LH receptor, LHRH-R, LPA1, MAC-1, MAGE 1, MAGE 2, MAGE 3, MAGE 4, MART1, MC1R, Mesothelin, MUC1, MUC16, Neu (cell-surface Nucleolin), Neprilysin, Neuropilin-1, Neuropilin-2, NG2, NK1, NK2, NK3, NMB-R, Notch-1, NY-ESO-1, OT-R, mutant p53, p97 melanoma antigen, NTR2, NTR3, p32 (p32/gC1q-R/HABP1), p75, PAC1, PAR1, Patched (PTCH), PDGFR, PDFG receptors, PDT, Protease-cleaved collagen IV, proteinase 3, prohibitin, protein tyrosine kinase 7, PSA, PSMA, purinergic P2X family (e.g., P2X1-5), mutant Ras, RAMP1, RAMP2, RAMP3 patched, RET receptor, plexins, smoothened, sst1, sst2A, sst2B, sst3, sst4, sst5, substance P, TEMs, T-cell CD3 Receptor, TAG72, TGFBR1, TGFBR2, Tie-1, Tie-2, Trk-A, Trk-B, Trk-C, TR1, TRPA, TRPC, TRPV, TRPM, TRPML, TRPP (e.g., TRPV1-6, TRPA1, TRPC1-7, TRPM1-8, TRPP1-5, TRPML1-3), TSH receptor, VEGF receptors (VEGFR1 or Flt-1, VEGFR2 or FLK-1/KDR, and VEGF-3 or FLT-4), voltage-gated ion channels, VPAC1, VPAC2, Wilms tumor 1, Y1, Y2, Y4, and Y5.

270. The method of any of embodiments 267-269 wherein the cell surface molecule is selected from among HER1/EGFR, HER2/ERBB2, CD20, CD25 (IL-2Rα receptor), CD33, CD52, CEA, CEACAM1, CEACAM3, CEACAM5, CEACAM6, cancer antigen 125 (CA125), alpha-fetoprotein (AFP), Lewis Y, TAG72, Caprin-1, mesothelin, PDGF receptor, PD-1, PD-L1, CTLA-4, IL-2 receptor, vascular endothelial growth factor (VEGF), CD30, EpCAM, gpA33, mucins, CAIX, PSMA, folate-binding protein, gangliosides (such as GD2, GD3, and GM2), VEGF receptor (VEGFR), integrin αVβ3, integrin α5β1, ERBB3, MET, IGF1R, EPHA3, TRAILR1, TRAILR2, RANKL, FAP, tenascin, AFP, BCR complex, CD3, CD18, CD44, CTLA-4, gp72, HLA-DR 10 β, HLA-DR antigen, IgE, MUC-1, nuC242, PEM antigen, metalloproteinases, Ephrin receptor, Ephrin ligands, HGF receptor, CXCR4, CXCR4, Bombesin receptor, and SK-1 antigen.

271. The method of any of embodiments 209-270, wherein the tumor-targeting macromolecule is an antibody or an antibody fragment.

272. The method of embodiment 271, wherein the antibody is selected from cetuximab, panitumumab, zalutumumab, nimotuzumab, Tositomomab (Bexxar®), Rituximab (Rituxan, Mabthera), Ibritumomab tiuxetan (Zevalin), Daclizumab (Zenapax), Gemtuzumab (Mylotarg), Alemtuzumab, CEA-scan Fab fragment, OC125 monoclonal antibody, ab75705, B72.3, Bevacizumab (Avastin®), and Basiliximab, nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MEDI6469, MEDI4736, MOXR0916, AMP-224, and MSB001078C, or is an antibody-binding fragment thereof.

273. The method of embodiment 272, wherein the antibody is selected from cetuximab, panitumumab and trastuzumab.

274. The method of any of embodiments 209-273, wherein the conjugate is selected from cetuximab-IR700, panitumumab-IR700 and trastuzumab-IR700.

275. The method of any of embodiments 209-274, wherein the tumor-targeting macromolecule is a tissue-specific homing peptide.

276. The method of embodiment 275, wherein the homing polypeptide comprises the sequence of amino acids set forth in any of SEQ ID NOS: 1-52.

277. The method of any of embodiments 209-276, wherein the tumor-targeting macromolecule is an RGD polypeptide, an iRGD polypeptide, a Lyp-1 polypeptide, a cripto-1 binding polypeptide, a somatostatin receptor binding polypeptide, a prohibitin binding polypeptide, a NGR polypeptide, or an iNGR polypeptide.

278. The method of any of embodiments 209-277, wherein the tumor-targeting macromolecule is selected from among adrenocorticotropic hormone (ACTH), angiotensin II, atrial natriuretic factor (ANF), bombesin, bradykinin, brain derived neurotropihic factor (BDNF), bone morphogenetic protein 2 (BMP-2), bone morphogenetic protein 6 (BMP-6), bone morphogenetic protein 7 (BMP-7), calcitonin, cardiotrophin 1 (BMP-2), CD22, CD40, cholecystokinin (CCK), ciliary neurotrophic factor (CNTF), CCL1-CCL28, CXCL1-CXCL17, XCL1, XCL2, CX3CL1, cripto 1 binding peptide, vascular endothelial cell growth factor (VEGF), epidermal growth factor (EGF), endothelin 1, endothelin 1/3, FAS-ligand, fibroblast growth factor 1 (FGF-1), fibroblast growth factor 2 (FGF-2), fibroblast growth factor 4 (FGF-4), fibroblast growth factor 5 (FGF-5), fibroblast growth factor 6 (FGF-6), fibroblast growth factor 1 (FGF-7), fibroblast growth factor 1 (FGF-10), Flt-3, gastrin, gastrin releasing peptide (GRP), granulocyte colony-stimulating factor (G-CSF), granulocyte macrophage stimulating factor (GM-CSF), glucagon like peptide (GLP-1), hepatocyte growth factor (HGF), interferon alpha (IFN-α), interferon beta (IFN-b), interferon gamma (IFNg), insulin-like growth factor 1 (IGF-1), insulin-like growth factor 2 (IGF-2), interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 15 (IL-15), interleukin 17 (IL-17), interleukin 19 (IL-19), luteinizing hormone (LH), luteinizing-releasing hormone (LHRH), macrophage colony-stimulating factor (M-CSF), monocyte chemotactic protein 1 (MCP-1), macrophage inflammatory protein 3a (MIP-3a), macrophage inflammatory protein 3b (MIP-3b), nerve growth factor (NGF), neuromedin B, neurotrophin 3 (NT-3), neurotrophin 4 (NT-4), neurotensin, neuropeptide Y, oxytocin, pituitary adenylate cyclase activating peptide (PACAP), platelet derived growth factor AA (PDGF-AA), platelet derived growth factor AB (PDGF-AB), platelet derived growth factor BB (PDGF-BB), platelet derived growth factor CC (PDGF-CC), platelet derived growth factor DD (PDGF-DD), netrin-1 (NTN1), netrin-2 (NTN2), netrin-4 (NTN4), netrin-G1 (NTNG1) and netrin-G2 (NTNG2), ephrin A1 (EFNA1), ephrin A2 (EFNA2), ephrin A3 (EFNA3), ephrin A4 (EFNA4), ephrin A5 (EFNA5), semaphorin 3A (SEMA3A), semaphorin 3B (SEMA3B), semaphorin 3C (SEMA3C), semaphorin 3D (SEMA3D), semaphorin 3F (SEMA3F), semaphorin 3G (SEMA3G), semaphorin 4A (SEMA4A), semaphorin 4B (SEMA4B), semaphorin 4C (SEMA4C), semaphorin 4D (SEMA4D), semaphorin 4F (SEMA4F), semaphorin 4G (SEMA4G), semaphorin 5A (SEMASA), semaphorin 5B (SEMA5B), semaphorin 6A (SEMA6A), semaphorin 6B (SEMA6B), semaphorin 6D (SEMA6D), semaphorin 7A (SEMA7A), SLIT1, SLIT2, SLIT3, SLIT and NTRK-like family, member 1 (SLITRK1), SLIT and NTRK-like family, member 2 (SLITRK2), SLIT and NTRK-like family, member 3 (SLITRK3), SLIT and NTRK-like family, member 4 (SLITRK4), SLIT and NTRK-like family, member 5 (SLITRK5), SLIT and NTRK-like family, member 6 (SLITRK6), prostaglandin E2 (PGE2), RANTES, Somatostatin-14, Somatostatin-28, stem cell factor (SCF), stromal cell derived factor 1 (SDF-1), substance P, thyroid stimulating hormone (TSH), transforming growth factor alpha (TGF-α), transforming growth factor beta (TGF-b), tumor necrosis factor alpha (TNF-α), thrombin, vasoactive intestinal peptide (VIP), Wnt1, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, Wnt10a, Wnt10b, Wnt11, Wnt14, Wnt15, or Wnt16, Sonic hedgehog, Desert hedgehog, and Indian hedgehog.

279. The method of any of embodiments 209-278, wherein the conjugate comprises from or from about 1 to 1000 phthalocyanine dye molecules per macromolecule.

280. The method of any of embodiments 209-279, wherein the conjugate comprises 1 to 100, 1 to 10 or 2 to 5 phthalocyanine dye molecules per macromolecule.

281. The method of any of embodiments 209-279, wherein the macromolecule is a nanoparticle and the conjugate comprises 100 to 1000 phthalocyanine dye molecules per macromolecule.

282. The method of any of embodiments 209-281, wherein the tumor is a cancer.

283. The method of any of embodiments 209-282, wherein the cancer is a cancer located at the head and neck, breast, liver, colon, ovary, prostate, pancreas, brain, cervix, bone, skin, eye, bladder, stomach, esophagus, peritoneum, or lung.

284. The method of any of embodiments 209-282, wherein the cancer is a cancer of the blood.

285. The method of any of embodiments 209-284, wherein the tumor is irradiated at a wavelength of 600 to 850 nm at a dose of at least 1 J cm$^{-2}$.

286. The method of any of embodiments 209-285, wherein the tumor is irradiated at a wavelength of 690 nm±50 nm.

287. The method of any of embodiments 209-286, wherein the tumor is irradiated at a wavelength of or about 690±20 nm.

288. A conjugate, comprising a phthalocyanine dye linked to an antibody or antigen-binding fragment that is an immune modulating agent.

289. The conjugate of embodiment 288, wherein the immune modulating agent is an immune checkpoint inhibitor.

290. The conjugate of embodiment 288 or embodiment 289, wherein the immune modulating agent is an antibody or antigen binding fragment that binds to the surface of a tumor, tumor cell or cancer cell.

291. The conjugate of any of embodiments 288-290, wherein the immune modulating agent is an antibody or antibody fragment that binds to PD-L1.

292. The conjugate of embodiment 291, wherein the immune modulating agent is an antibody selected from BMS-935559, MEDI4736, MPDL3280A and MSB0010718C, or an antigen-binding fragment thereof.

293. A composition, comprising the conjugate of any of embodiments 288-292.

294. A pharmaceutical composition, comprising the conjugate of any of embodiments 288-293 and a pharmaceutically acceptable carrier.

295. A combination, comprising:
a first composition comprising an immune modulating agent, with the proviso that the immune modulating agent is not 5-aza-2'-deoxycytidine or an anti-CTLA4 antibody; and
a second composition comprising a conjugate comprising a phthalocyanine dye linked to a tumor-targeting macro molecule, wherein the conjugate binds to a tumor.

296. The combination of embodiment 295, wherein the conjugate binds to a cell surface molecule of a tumor.

297. The combination of embodiment 295 or embodiment 296, wherein the conjugate binds to a cell surface molecule of a tumor cell.

298. The combination of any of embodiments 295-297, wherein the immune modulating agent is an immune checkpoint inhibitor.

299. The combination of embodiment 298, wherein the immune checkpoint inhibitor specifically binds a molecule selected from among PD-1, PD-L1, PD-L2, LAG-3, TIM-3, 4-1BB, GITR, CD40, CD40L, OX40, OX40L, CXCR2, B7-H3, B7-H4, BTLA, HVEM, CD28 and VISTA.

300. The combination of any of embodiments 295-299, wherein the immune modulating agent is a small molecule or a polypeptide.

301. The combination of any of embodiments 295-300, wherein the immune modulating agent is an antibody or an antigen-binding fragment thereof.

302. The combination of embodiment 296, wherein the antibody is selected from among nivolumab, pembrolizumab, pidilizumab, MK-3475, BMS-936559, MPDL3280A, ipilimumab, tremelimumab, IMP31, BMS-986016, urelumab, TRX518, dacetuzumab, lucatumumab, SEQ-CD40, CP-870, CP-893, MED16469, MEDI4736, MOXR0916, AMP-224, and MSB001078C, or is an antigen-binding fragment thereof.

303. The conjugate of any of embodiments 288-292 or combination of any of embodiments 295-302, wherein the phthalocyanine dye comprises the formula:

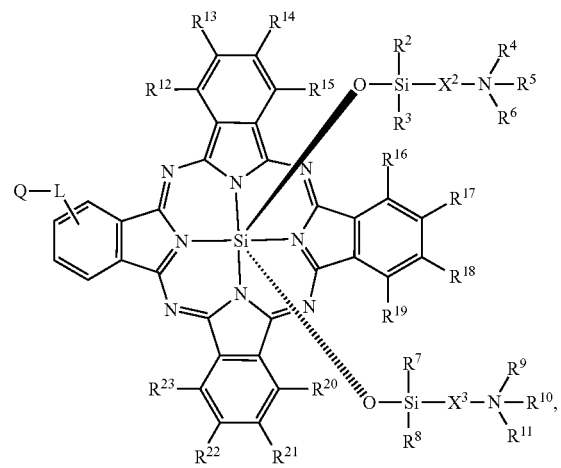

wherein:
L is a linker;
Q is a reactive group for attachment of the dye to the targeting molecule;
$R^2$, $R^3$, $R^7$, and $R^8$ are each independently selected from optionally substituted alkyl and optionally substituted aryl;
$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group;
$R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are each independently selected from hydrogen, halogen, optionally substituted alkylthio, optionally substituted alkylamino and optionally substituted alkoxy; and
$X^2$ and $X^3$ are each independently $C_1$-$C_{10}$ alkylene, optionally interrupted by a heteroatom.

304. The conjugate or combination of embodiment 288-292 or 295-303, wherein the phthalocyanine dye comprises the formula:

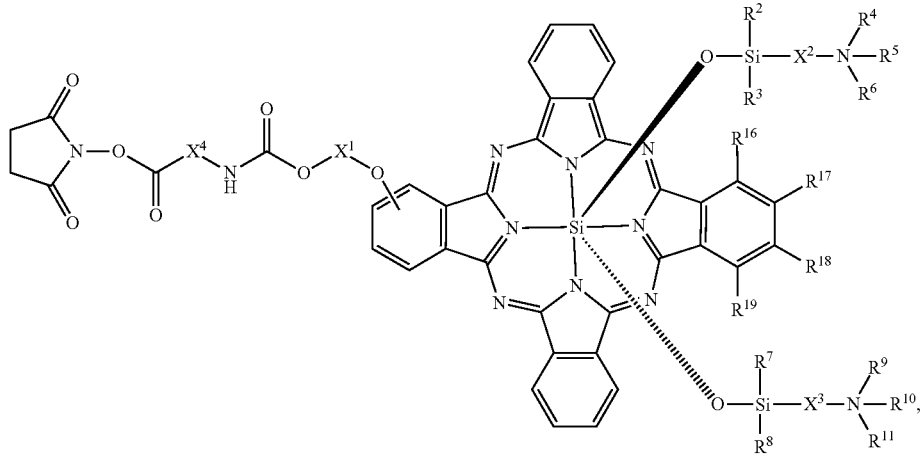

wherein:

$X^1$ and $X^4$ are each independently a $C_1$-$C_{10}$ alkylene optionally interrupted by a heteroatom;

$R^2$, $R^3$, $R^7$, and $R^8$ are each independently selected from optionally substituted alkyl and optionally substituted aryl;

$R^4$, $R^5$, $R^6$, $R^9$, $R^{10}$, and $R^{11}$ are each independently selected from hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; and $R^{16}$, $R^{17}$, $R^{18}$ and $R^{19}$ are each independently selected from hydrogen, halogen, optionally substituted alkylthio, optionally substituted alkylamino and optionally substituted alkoxy.

305. The conjugate or combination of any of embodiments 288-292 or 295-2304 wherein the phthalocyanine dye comprises IRDye 700DX (IR700).

306. A kit, comprising the conjugate, composition or combination of any of embodiments 288-305 and, optionally, instructions for use.

307. An article of manufacture, comprising the conjugate, composition or combination of any of embodiments 288-305.

308. The article of manufacture of embodiment 307 that is a container.

309. The article of manufacture of embodiment 308, wherein the container protects from transmission of light having a wavelength from or from about 500 to 725 or 650 to 725.

3010. The article of manufacture of embodiment 309, wherein the percentage of light transmission through the container is less than 50%, less than 40%, less than 30%, less than 20%, less than 10% or less than 5%.

311. The article of manufacture of any of embodiments 308-310, wherein the container is green, amber, translucent, opaque, or is wrapped in an opaque foil.

312. A method of treating a tumor in a subject comprising:
a) administering to a subject a conjugate of any of embodiments 288-292, composition of embodiment 293 or embodiment 294 or combination of any of embodiments 295-302; and
c) irradiating the tumor at a wavelength that renders the conjugate cytotoxic, thereby treating the tumor 313. The method of embodiment 312, wherein the tumor is a cancer.

314. The method of embodiment 312 or embodiment 313, wherein the cancer is a cancer located at the head and neck, breast, liver, colon, ovary, prostate, pancreas, brain, cervix, bone, skin, eye, bladder, stomach, esophagus, peritoneum, or lung.

315. The method of any of embodiments 312-314, wherein the cancer is a cancer of the blood.

316. The method of any of embodiments 312-315, wherein the tumor is irradiated at a wavelength of 600 to 850 nm at a dose of at least 1 J cm$^{-2}$.

317. The method of any of embodiments 312-316, wherein the tumor is irradiated at a wavelength of 690 nm±50 nm.

318. The method of any of embodiments 312-317, wherein the tumor is irradiated at a wavelength of or about 690±20 nm.

VII. Examples

The following examples are included for illustrative purposes only and are not intended to limit the scope of the invention.

Example 1: Generation of Cetuximab-IRDye 700DX Conjugate

This example describes a method for preparing a conjugate containing IRDye 700DX (IR700) linked to cetuximab to produce cetuximab-IRDye 700DX (cetuximab-IR700). The provided methods are exemplary and similar methods may be employed to conjugate another targeting molecule to IRDye 700Dx. The methods were performed to limit exposure of the dye and conjugate to light due to the photosensitivity of the dye, which included the use of low levels of green light having a wavelength from 425 to 575 nm and an intensity of less than 200 Lux in the manufacturing facility.

A. Preparation of Buffers

Buffers were prepared using Highly Purified Water (HPW) or Water for Injection (WFI) and were filtered through a 0.22 μm filter prior to storage at ambient temperature. Tables 2-4 show in-process controls and tests for prepared buffers: conjugation buffer (100 mM sodium phosphate, pH 8.65), quenching buffer (1.0 M glycine, pH 9) and final phosphate buffered saline (PBS) formulation buffer: (5.60 mM Na$_2$HPO$_4$, 1.058 KH$_2$PO$_4$, 154 mM NaCl, pH 7.1), respectively.

TABLE 2

Preparation of Conjugation Buffer
(100 mM sodium phosphate, pH 8.65)

| In-process Controls and Tests | Specification or Range |
|---|---|
| Mixing time | ≥30 min |
| pH | 8.5-8.8 |
| Conductivity | 11.7-14.1 mS/cm |
| Filter integrity testing | Pass |
| Endotoxin | ≤1.5 EU/mL |

TABLE 3

Preparation of Quenching Buffer (1.0M glycine, pH 9)

| In-process Controls and Tests | Specification or Range |
|---|---|
| Mixing time | ≥30 min |
| pH | 8.9-9.1 |
| Conductivity | 5-11 mS/cm |
| Filter integrity testing | Pass |
| Endotoxin | ≤1.5 EU/mL |

TABLE 4

Buffer release test for 1x PBS

| Tests | Specification or Range |
|---|---|
| Appearance | Clear solution |
| pH | 7.0-7.2 |
| Osmolality | 280-330 mOsm/kg |
| Sterility | No growth |
| Cytotoxicity | Non-toxic |

B. Preparation of Dye and Cetuximab

1. Cetuximab Preparation

Prior to conjugation, Cetuximab vials (Myoderm USA, Norristown, Pa.) were sprayed with sterile isopropyl alcohol and placed in a Laminar Flow Hood. A total of 423 vials were used to prepare drug substance. The vials were de-crimped using an electronic decrimper, the stoppers were removed with autoclaved forceps, and the contents were poured into sterile 2 L PETG bottles. The bottles were capped when filled. The Cetuximab was then filtered through a 0.22 µm filter and pooled into a 50 L HyQtainer. Pooled, filtered Cetuximab was stored at 2-8° C.

A concentration and buffer exchange step was then performed by ultrafiltration/diafiltration (UF/DF). Cleaning of the UF/DF device was performed prior to use. The storage solution was drained and the membrane flushed with at least 20 L of HPW. The unit was flushed with 0.1 M NaOH for 30-40 min and then flushed with HPW. The pH of the rinsate was confirmed. The system was equilibrated with 100 mM sodium phosphate, pH 8.65 buffer. Permeate and retentate effluent pH and conductivity were confirmed prior to use. Endotoxin testing was also performed; the system was used within 48 hours of endotoxin testing.

Prior to UF/DF operations, the pooled, filtered Cetuximab was warmed by placing it in an incubator at 25° C. for 120-150 min. The material was first concentrated to a target of 5 mg/mL and then diafiltered into 100 mM sodium phosphate, pH 8.65 buffer. Diafiltration was performed until the permeate pH and conductivity targets were met. The system was flushed with buffer and the flush was added to the diafiltered retentate. UF/DF system pressures were monitored and recorded during the operation as described in Table 5.

The diafiltered Cetuximab product concentration was determined and then diluted to a target concentration of 2 mg/mL (1.8-2.4 mg/mL) using 100 mM sodium phosphate, pH 8.65 buffer. The product was aseptically filtered through a 0.22 µm filter and split into two autoclaved product-dedicated 40 L carboys containing stir bars and forward-processed directly into the conjugation operation. The weight of Cetuximab in each carboy was determined.

TABLE 5

In-process controls and tests for Cetuximab processing

| In-process Controls and Tests | Specification or Range |
|---|---|
| Cetuximab pooling | |
| Filter integrity test (0.22 µm) (after pooling) | Pass |
| Protein concentration after pooling | Report results |
| TFF Unit Preparation | |
| TFF parts 1.0M NaOH contact time | ≥60 min |
| pH of TFF rinsed parts | <7 |
| TOC of UF/DF rinsed parts | <1000 ppb |
| HPW volume rinse with membrane | >20 L |
| UF/DF Integrity testing prior to use | Air displacement <90 mL/min |
| 0.1M NaOH flush time | 30-40 min |
| UF/DF permeate and retentate pH after HPW rinsing | <7 |
| TFF Equilibration | |
| UF/DF permeate and retentate effluent pH | 8.5-8.8 |
| UF/DF permeate and retentate effluent conductivity | 11.7-14.1 mS/cm |
| UF/DF permeate and retentate effluent endotoxin | ≤0.134 EU/mL |
| Cetuximab Diafiltration | |
| Pooled, filtered Cetuximab incubation temperature | 25° C. |
| Pooled, filtered Cetuximab incubation time | 120-150 min |
| Feed inlet pressure during concentration | <25 psi |
| Retentate outlet pressure during concentration | 10-12 psi |

TABLE 5-continued

In-process controls and tests for Cetuximab processing

| In-process Controls and Tests | Specification or Range |
|---|---|
| Retentate pressure during diafiltration | 10-12 psi |
| UF/DF system pressure during diafiltration | <32 psi |
| UF/DF permeate pH after diafiltration | 8.5-8.8 |
| UF/DF permeate conductivity after diafiltration | 11.7-14.1 mS/cm |
| Cetuximab concentration ($A_{280}$) after diafiltration | 4.5 mg/mL |
| Cetuximab concentration ($A_{280}$) after dilution | 1.8-2.4 mg/mL |

2. Dye Preparation

Prior to conjugation, IRDye 700DX NHS Ester (dye; Cat. No. 929-70011; Li-COR, Lincoln, Nebr.) was prepared by dissolving it to a concentration of 10 mg/mL in anhydrous DMSO. The steps were performed under green light (e.g., wavelength from 425 to 575 nm and an intensity of less than 200 Lux) to protect the dye from the wavelengths of light that are strongly absorbed by the dye.

C. Conjugation

The conjugation and quenching steps were performed in the 2×40 L carboys (wrapped in aluminum foil for light protection) containing diafiltered Cetuximab. The steps were performed at room temperature under green light (e.g., wavelength from 425 to 575 nm and an intensity of less than 200 Lux) to protect the conjugate from photo-degradation.

For the conjugation reaction, the appropriate amount of IRDye 700DX NHS ester in DMSO was calculated (based on the weight of Cetuximab in each carboy, typically from 80-120 g) to achieve a final molar ratio of 4:1 (IRDye 700DX NHS ester: Cetuximab). Process development studies have determined that this ratio, in conjugation with the targeted conjugation incubation time, should incorporate 2-3 dye residues per Cetuximab molecule. The calculated amount of the IRDye 700DX NHS ester was added to the carboys containing Cetuximab and mixed on a stir plate for 10-15 min. The conjugation reaction then proceeded for 120 min by placing the carboys in a 25° C. incubator.

The conjugation reaction was quenched by the addition of 1 M glycine to a final concentration of 4.2 mM and mixing for 10-12 min. The carboys were incubated for an additional 20-25 min in the 25° C. incubator. Table 6 displays in-process controls and tests for the conjugation and quenching steps.

TABLE 6

In-process controls and tests for conjugation and quenching steps

| In-process Controls and Tests | Specification or Range |
|---|---|
| Conjugation step mixing time | 10-15 min |
| Conjugation step incubation time | 120 (115-125) min |
| Conjugation step incubation temperature | 25 (23-27)° C. |
| Quenching step mixing time | 10-12 min |
| Quenching step incubation time | 20-25 min |
| Quenching step incubation temperature | 25 (23-27)° C. |

A final UF/DF step was performed to exchange the conjugated product into the final PBS formulation buffer. Cleaning of the UF/DF system was performed prior to use. The unit was cleaned and parts were soaked in 1.0 M NaOH and then rinsed with HPW. The system was equilibrated with PBS, pH 7.1 until the permeate was within specifications. Permeate and retentate were tested for endotoxin.

The quenched conjugate was transferred to the UF/DF system and was first concentrated to 8-10 L followed by diafiltration with 8-12 diavolumes of PBS in order to exchange the product into the final formulation buffer. The pH and conductivity were confirmed. The system was flushed with buffer and the flush was added to the final product. The protein concentration was determined and if needed, further dilution with PBS was performed to reach a final target product concentration of 2.0 mg/mL (1.8-2.1 mg/mL).

A final filtration through a 0.22 m filter was performed and the Cetuximab-IRDye 700DX conjugate was stored in the dark at 2-8° C. in a 50 L HyQtainer covered with aluminum foil to protect the contents from light. The steps were performed at room temperature under green light to protect the Cetuximab-IRDye 700DX conjugate. Table 7 displays in-process controls and tests for the final UF/DF, filtration, and storage. In some cases, dilution was required.

TABLE 7

In-process controls and tests for final UF/DF, filtration, and storage

| In-process Controls and Tests | Specification or Range |
|---|---|
| TFF Unit Preparation | |
| 0.1M NaOH flush time | 30-40 min |
| HPW rinse volume | ≥20 L |
| TFF Equilibration | |
| pH of permeate after equilibration | 7.0-7.2 |
| UF/DF permeate and retentate effluent endotoxin | ≤0.134 EU/mL |
| Cetuximab-IRDye 700DX Conjugate Diafiltration | |
| pH of permeate after diafiltration | 7.0-7.2 |
| Conductivity of permeate after diafiltration | 11-16 mS/cm |
| Target conjugate protein concentration after (SEC-HPLC) diafiltration | 1.8-2.1 mg/mL |
| Filter integrity test | Pass |

After preparing the conjugated material, the sample was submitted for SEC-HPLC to determine concentration, dye to antibody ratio (DAR), identity and purity. Other tests for appearance, pH, bioburden, and endotoxin level also were performed. Table 8 shows the results of these tests for an exemplary batch product with reference to general acceptance criterion for the drug substance.

TABLE 8

Drug Substance Specifications

| Test | Acceptance Criterion | Result | Pass/Fail |
|---|---|---|---|
| Appearance | Green to blue liquid May contain visible particulates | Conforms | Pass |
| Bioburden | <1 CFU/mL | 0 CFU/mL | Pass |
| Endotoxin (LAL) | ≤0.067 EU/mg | <0.06 EU/mg | Pass |
| pH | 7.1 ± 0.5 | 7.1 | Pass |
| Concentration by SEC-HPLC | 1.8 to 2.1 mg/mL | 2.0 mg/mL | Pass |
| DARby SEC-HPLC (A690/A280 with dye correction) | 1.5 to 4.0 | 2.9 | Pass |
| Identity by SEC-HPLC (A690) | Relative retention time of monomer peak: 0.90 to 1.10 of Reference Standard monomer peak | Relative retention time of monomer peak: 0.99 of Reference Standard monomer peak | Pass |
| Purity by SEC-HPLC (A690) | Monomer ≥ 92.0% HMW ≤ 5.0% LMW ≤ 5.0% Free Dye: ≤ 3% | Monomer 100.0% HMW 0.0% LMW 0.0% Free Dye: 0% | Pass |

Example 2: Pharmacokinetics and Therapeutic Efficacy of Cetuximab-IRDye 700DX Conjugate This Example describes the interim results of a clinical study (Phases 1 and 2) assessing safety and efficacy in head and neck cancer patients treated with a single or multiple administration of cetuximab-IRDye 700DX conjugate followed, by irradiation to induce photoimmunotherapy (PIT). Pharmacokinetic parameters and tumor response in human patients after single dose administration of cetuximab-IRDye 700DX conjugate were determined to evaluate safety and efficacy of the therapy.

1. Methods

Nine (9) patients with squamous carcinoma of head and neck entered a dose escalation clinical trial. The patients were divided into three (3) dose cohorts, as listed in Table 8A below. Each cohort included three (3) patients. All patients enrolled in the trial had recurrent progressive cancers that had failed multiple rounds of commercially available treatments, some of which had failed previous treatment with the antibody Cetuximab. The study included both patients with HPV positive and negative tumors, and patients with P16 positive and negative tumors.

To ensure a safe initial dose based on ICH guidance for first in human administration of experimental therapeutics, a starting dose of 4.3 mg/kg (160 mg/m$^2$) was used in the dose escalation study. The starting dose was below the threshold of 6-fold below the Highest Non-Severely Toxic Dose (HNSTD).

TABLE 8A

Dose Cohorts for Phase I Clinical Study of Cetuximab-IRDye 700DX

| Cohort | No. of Patients | Human Clinical Dose (mg/kg) | Human Clinical Dose (mg/m$^2$) |
|---|---|---|---|
| 1 | 3 | 4.0 | 160 |
| 2 | 3 | 8.0 | 320 |
| 3 | 3 | 16.0 | 640 |

Intravenous (IV) bags containing the conjugate were prepared from vials containing 50 mL of a 2 mg/mL solution of cetuximab-IRDye 700DX conjugate produced as described in Example 1. As described in Example 1, the vials were packaged in a single carton and then in an opaque pouch prior to use. The handling of cetuximab-IRDye 700DX conjugate and its administration by infusion were performed in a darkened room with less than 400 lux of fluorescent light. No tungsten lighting was ever used during the preparation of the of the infusion bags. Any windows in the room were covered with shades so that the cetuximab-IRDye 700DX conjugate was never directly or indirectly exposed to sunlight.

In a biosafety cabinet or hood with the light switched-off so that the conjugate was exposed to an intensity of light of no more than 200 lux (equivalent to 60 Watt light bulb or 15 Watt fluorescent room light), each vial was removed from the opaque couch and then from the carton. The packaging of each vial containing the conjugate was opened and the contents of that vial were placed into a sterile IV bag until the desired dose of conjugate for infusion was achieved. Each vial was opened separately and placed into the IV bag so as to reduce the exposure of the drug product to ambient room light. The process was performed in less than 15 min. The IV bag was covered at all times by an opaque sleeve to protect the conjugate from light exposure. After preparation, the IV bag was stored at 2-8° C. for up to 1 hour.

Prior to conjugate administration, the subjects were pre-treated with 100 mg of Erbitux® (non-conjugated cetuximab) administered by IV infusion over 30 minutes as a screening step for evaluating possible infusion reactions. During the infusion, the subject was evaluated for possible infusion reactions to Erbitux® of Grade 3 or greater, which did not occur in any of the treated patients. After the 100 mg Erbitux® infusion, but just prior to cetuximab-IRDye 700DX conjugate infusion, the subjects were pre-treated with 50 mg of anti-histaminic Benadryl (Diphenhydramine) and 10 mg of the steroid Decadron (Dexamethasone) by IV administration to limit the risk of hypersensitivity to cetuximab-IRDye 700DX conjugate infusion.

The patients were intravenously administered with a single dose of the cetuximab-IRDye 700DX conjugate at the clinical doses set forth above in Table 8A. The conjugate was administered via IV infusion over 2 hours on Day 1. The intravenous (IV) infusion bag was covered during the administration by an opaque sleeve to protect the conjugate from light exposure. Any light exposure was limited to less than 5 minutes. If the flow of the cetuximab-IRDye 700DX conjugate during the infusion from the IV infusion bag was stopped for more than 5 minutes, the tubing and filter were protected from light exposure using an opaque cover, such as aluminum foil.

To induce photoimmunotherapy (PIT), one light application with a light having a wavelength of 690 nm was performed at 24 hours±3 hours (Day 2) post conjugate administration. 690 nm light was administered to the tumor via 400 micron glass fiber microlens forward firing fibers for surface illumination of tumors that were less than 10 mm thick, or via cylindrical diffuser fibers placed into the tumor for tumors that were greater than 10 mm thick or for subcutaneous tumors. Light treatment was fixed at a low fluence of 50 J/cm$^2$ for superficial illumination or 100 J/cm fiber length for interstitial illumination (at a fluence rate of 150 mW/cm$^2$ for superficial illumination and 400 mW/cm fiber length for interstitial illumination).

For microlens surface light treatment, normal tissue located 0.5-1.0 cm around the periphery of the tumor was also included in the light treatment field to reach microscopic infiltrating disease at the margin of the tumor. All other normal tissue were covered with surgical towels, moist surgical sponges or cottonoids to prevent reflected 690 nm light from potentially activating the cetuximab-IRDye 700DX conjugate in normal cutaneous tissues, to reduce the risk of edema, ulceration or necrosis of normal tissue. In the oral cavity, pharynx and larynx, all tissues not to be treated were covered with moist surgical sponges or cottonoids to prevent reflected light from activating cetuximab-IRDye 700DX conjugate that may be present in the mucosa. If the larynx was treated, the entire laryngeal airway was protected from light exposure using moist surgical sponges. The microlens fiber was connected to the laser console according to the manufacturer's instructions. Lighting in the treatment room or operating room were standard overhead room lighting, with no high intensity surgical lights turned on in the room. At all times, Class IV Medical Laser precautions were observed.

For cylindrical diffuser implantation directly into tumors, Best transparent 17 Fr brachytherapy catheters were placed into the tumor 1.8+/−0.2 cm apart to uniformly illuminate the entire tumor volume plus at least 0.5 cm margin of normal tissue around the tumor. Standard techniques were used to place brachytherapy catheters, including ultrasound (US) or computerized tomography (CT) guidance based on interventional radiologic methods. In some instances, a brachytherapy grid was employed to place the fibers 1.8 cm apart and parallel to each other in the treatment field. Positioning of the catheters was confirmed by lateral X-ray, US or CT. The cylindrical diffuser fibers were then connected to the 690 nm laser console, according to the manufacturer's instructions. After ensuring proper light output of each cylindrical diffuser, the cylindrical diffuser fibers of previously determined length (1.0, 2.0, 3.0 or 4.0 cm length) depending on tumor diameter, were placed down the catheter up to its tip and secured in place to the catheter externally with surgical tape. Lighting in the treatment room or operating room were standard overhead room lighting, with no high intensity surgical lights turned on in the room. At all times, Class IV Medical Laser precautions were observed.

None of the patients showed adverse effects to the infusion and did not report any pain. No skin photosensitivity to ambient light was detected.

2. Response and Pharmacokinetics

Patients with head and neck cancer patients treated with a single administration of cetuximab-IRDye 700DX conjugate followed by irradiation to induce photoimmunotherapy (PIT) were assessed for tumor response. The tumor response was evaluated according to the RECIST (Response Evaluation Criteria In Solid Tumors) criteria as outlined in the revised version 1.1 guidelines (RECIST 1.1, see Eisenhauer et al. (2009) European Journal of Cancer, 45:228-247). A response was determined to be a "complete response" (CR) if there was a disappearance of all target lesions, and any pathological lymph nodes (whether target or non-target) were reduced in short axis to <10 mm. A response was determined to be a "partial response" (PR) if there was at least a 30% decrease in the sum of diameter of target lesions (e.g., at least 30% reduction in tumor growth), taking as reference the baseline sum diameters of the target lesions prior to the treatment. The "objective response rate" (ORR) is the percentage of subjects in which a CR or PR response was observed.

The tumor response was observed as early as four days with evidence of tumor necrosis. All patients in all three cohorts showed a partial or complete response to the PIT treatment.

To examine exposure of cetuximab in the blood from the lower administered single dose of cetuximab-IRDye 700Dx conjugate, blood samples from each patient were collected and subjected to pharmacokinetic analyses. The exposure of Cetuximab-IRDye 700DX in the human subjects was determined by bioanalytical studies using Good Laboratory Practice validated methods that specifically detect Cetuximab-IRDye 700DX in human serum. Serum concentration versus time was analyzed by a non-compartment model with linear elimination. The area under the curve (AUC) at 24 hours ($AUC_{0-24}$) described the total amount of drug exposure in human blood from the infusion to the time of pharmacological activity at 24 h post drug infusion that is when the drug is activated at the tumor to induce cancer killing in a localized fashion.

A summary of the pharmacokinetic variables for the cetuximab-IRDye 700DX conjugate in Cohort 1 (4 mg/kg; 160 mg/m$^2$ dose), Cohort 2 (8 mg/kg; 320 mg/m$^2$ dose) and Cohort 3 (16 mg/kg; 640 mg/m$^2$ dose) is presented in Table 9. The mean $AUC_{0-24}$ is the relevant exposure for cetuximab-IR700, as the pharmacological activity is activated only through light irradiation, which occurs at 24 hours post cetuximab-IR700 dosing.

TABLE 9

Pharmacokinetic data for dose escalation of Cetuximab-IRDye 700DX conjugate

| Dosing (mg/kg) | Dosing (mg/m$^2$) | Cetuximab-IR700 Mean $AUC_{0-24}$ (hr*µg/mL) |
|---|---|---|
| 4.0 mg/kg | 160 mg/m$^2$ | 770 +/− 47.5 |
| 8.0 mg/kg | 320 mg/m$^2$ | 1700 +/− 166 |
| 16.0 mg/kg | 640 mg/m$^2$ | 3,690 +/− 1,060 |

Table 9A summarizes the exposure of Erbitux® based on single doses as reported in Fracasso et al. (2007) Clin Cancer Res, 13(3), 986-993 (see Table 3 therein). The FDA-approved dosing regimen for Erbitux® in the treatment of head and neck cancer is an initial infusion of 400 mg/m$^2$ followed by weekly 250 mg/m$^2$ infusions. Based on the reported exposures in Fracasso et al., the exposure for a 1-month treatment based on the FDA-approved dosing regimen for head and neck cancer was extrapolated and is also listed in Table 9A.

TABLE 9A

Exposure of Erbitux ® based on single doses and FDA-approved dosing regimen (see Fracasso et al. (2007) Clin Cancer Res, 13(3), 986-993, Table 3)

| Dosing | Erbitux Mean $AUC_{0\text{-}inf}$ |
|---|---|
| 50 mg/m² | 858 +/− 271 |
| 100 mg/m² | 3,038 +/− 655 |
| 250 mg/m² | 11,812 +/− 3,656 |
| 400 mg/m² | 24,620 +/− 9,555 |
| 500 mg/m² | 24,740 +/− 8,259 |
| 400 mg/m² + 3 × 250 mg/m² (1 month treatment) | 60,056 (predicted) |

As shown in Table 9A, the $AUC_{0\text{-}\infty}$ value for Erbitux® at the 400 mg/m² and the 250 mg/m² doses are reported to be approximately 24,620 μg/mL*h and 11,812 μg/mL*h, respectively, and are predicted to be approximately 60,056 μg/mL*h following infusion according to the FDA-approved dosage regimen. In contrast, the exposure of cetuximab-IRDye 700DX following administration in accord with the above dosage regimen described in this Example is much lower. The results show that the mean $AUC_{0\text{-}24}$, even at the highest dose used in the current study (640 mg/m²), was approximately 15% of the AUC for 400 mg/m² Erbitux® (3,690 vs. 24,740 μg/mL*h, respectively). Thus, these results demonstrate that the single dose of cetuximab-IRDye 700Dx conjugate resulted in exposure of cetuximab that was far lower than the reported exposure observed to a single dose at the therapeutic higher doses of Erbitux®.

Further, the single dose of cetuximab-IRDye 700DX conjugate administered in this study was far lower than the dose of cetuximab that has been approved by the FDA for treatment of head and neck cancer. For example, the approved dose of Erbitux® to treat head and neck cancer is an initial dose of 400 mg/m² followed by weekly administration of 250 mg/m², and the mean $AUC_{0\text{-}24}$, even at the highest dose used in the current study (640 mg/m²), was approximately 6% of the extrapolated AUC the 1-month treatment with Erbitux® according to the FDA-approved dosage regimen (3,690 vs. 60,056 μg/mL*h, respectively).

The results showed that even at this reduced exposure, cetuximab-IRDye 700DX conjugate elicited a rapid and effective tumor response upon light activation at 24 h post infusion, in all patients in the study. Thus, despite the lower exposure, the results demonstrated that a single dose treatment with cetuximab-IRDye 700DX conjugate followed by irradiation resulted in a rapid and robust tumor response.

3. Trial of Photoimmunotherapy (PIT) with Repeated Cetuximab-IRDye 700DX Administration A treatment regimen is tested to determine the safety and efficacy of repeated treatment with administration of cetuximab-IRDye 700DX conjugate followed by photoimmunotherapy (PIT). Up to twenty (20) adult male and female patients that have confirmed recurrent squamous carcinoma of head and neck that cannot be satisfactorily treated with surgery, radiation or platinum chemotherapy are included in the study. Patients included have received prior systemic platinum-based chemotherapy unless contraindicated, have a life expectancy of greater than 6 months, and have an Eastern Cooperative Oncology Group (ECOG) performance score of 0 to 2.

Selected patients are administered with a single dose of 640 mg/m² cetuximab-IRDye 700DX conjugate via IV infusion over 2 hours on Day 1 of the beginning of treatment. To induce photoimmunotherapy (PIT), one light application with a light having a wavelength of 690 nm was performed at 24 hours±3 hours (Day 2) post conjugate administration, at a fluence of 50 J/cm² for superficial illumination or 100 J/cm fiber length for interstitial illumination. Follow-up observations are made at 1 week, 2 weeks, and 1 month after the initial treatment (Treatment 1). For long-term follow-up, observations are made every 3 months for 2 years following Treatment 1. Patients with remaining residual tumor four (4) weeks after Treatment 1 receive Treatment 2, with same dose and PIT regimen. Patients with remaining residual tumor four (4) weeks after Treatment 2 receive a further Treatment 3, maintaining the same dose and PIT regimen. Patients with remaining residual tumor four (4) weeks after Treatment 3 receive a further Treatment 4, maintaining the same dose and PIT regimen, for up to a total of four (4) treatments.

Primary endpoint for the study is safety associated with up to four (4) repeated treatments. Secondary endpoints include evaluation of pharmacokinetic parameters of the cetuximab-IRDye 700DX conjugate, tumor response evaluation using RECIST 1.1 Criteria at 1 month after last treatment via computerized tomography (CT) and/or positron emission tomography (PET) scan, evaluation of long-term outcomes for overall survival (OS) and progression-free survival (PFS), and assessment of development of anti-drug antibodies and neutralizing antibodies.

Example 3: Comparison of Conjugate Concentration to Alter Activity of Cell Surface Protein Versus to Mediate Cell Killing by Photoimmunotherapy in In Vitro Assays In vitro assays were employed to compare the effect of an IRDye 700DX-antibody conjugate upon binding to its cell surface protein antigen in functional assays for protein activity and in photoimmunotherapy (PIT) assays. The assays were performed using the exemplary cetuximab-IRDye 700Dx conjugate, which specifically binds to the cell surface protein epidermal growth factor receptor (EGFR) via the anti-EGFR antibody cetuximab. Similar in vitro assays are within the level of a skilled artisan to perform to assess other IRDye 700DX-targeting molecule conjugates, e.g., IRDye 700DX-antibody conjugates, using cell lines that express the protein to which the targeting molecule (e.g., antibody) binds and/or assays that assess a functional activity induced upon such binding.

A. In Vitro Phosphorylation Assay to Assess Functional Activity Upon Binding EGFR To assess the effects of cetuximab-IRDye 700Dx conjugate on regulating functional activity of EGFR, a phosphorylation assay was performed. EGF is a natural ligand for EGFR that induces phosphorylation of EGFR upon binding. A431 cells (ATCC CRL 1555) were plated in wells of a 96-well plate and then were pre-incubated for 5 minutes with increasing amounts of cetuximab or cetuximab-IRDye 700DX conjugate. Cells were then stimulated with 100 ng/mL EGF ligand for 10 min to induce phosphorylation of EGFR. The cells were fixed in the assay plate with formaldehyde and incubated with an anti-phospho-EGFR-specific antibody. After washing, phosphorylation of EGFR was measured by colorimetric quantification following addition of an anti-phospho-EFGR antibody conjugated to HRP in an ELISA assay. Stop solution was added and the optical density (OD) of the wells was measured in a microplate reader set to 450 nm. As a positive control, cells were stimulated with EGF in the absence of any added cetuximab or cetuximab-IRDye 700DX conjugate (designated "NT"), and the phosphorylation (as indicated by the OD) induced in the positive control was set at 100%. The relative percent (%) phosphorylation of EGFR was determined as a percent of the phosphorylation of the positive control.

As shown in FIG. 1, cetuximab and cetuximab-IRDye 700DX conjugate both prevented EGF-induced phosphorylation with equal potency. The inhibitory effect of cetuximab and cetuximab-IRDye 700DX was dose-dependent, with an $IC_{50}$ of 694 and 570 ng/mL, respectively. Thus, the results of the In-Cell ELISA assay showed that, like cetuximab, the cetuximab-IRDye 700DX conjugate also is able to bind to EGFR at or near the EGF binding site to prevent the stimulation and phosphorylation of EGFR by EGF. Since antibody binding is rapid and nearly irreversible, it is likely that the potency curve for prevention of phosphorylation closely reflects receptor occupancy by the antibody.

B. In Vitro Photoimmunotherapy (PIT) Assays

As a comparison to EGFR-induced phosphorylation, in vitro PIT experiments were performed for the cetuximab-IRDye 700DX conjugate. A431 cells were incubated with increasing concentrations of cetuximab-IRDye 700DX conjugate for 2 hours at 37° C. Then, 8 J/cm$^2$ of 690 nm light was applied to induce PIT. To monitor the progression of cell death after light treatment, the conjugate containing medium was replaced by fresh medium containing CellTox Green (Promega), a dye that reports cell death based on compromised cell membrane integrity. Time dependent increase in cell death was observed over 24 hours. As a control, cell death also was assessed in cells in which cetuximab-IRDye 700DX conjugate was not added (designated "NT").

Figure 2:
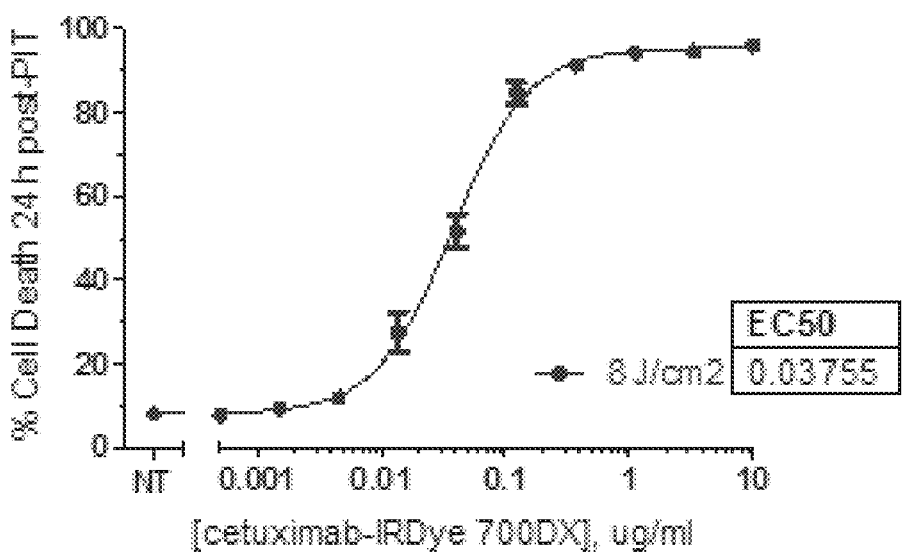
FIG. 2 shows the dose response curve for photoimmunotherapy (PIT) with the cetuximab-IRDye 700DX conjugate using 8 J/cm$^2$ of 690 nm light on A431 cells.

As shown in FIG. 2, the extent of cell death was dose-dependent. The half maximal cell death ($EC_{50}$) resulting from PIT with the cetuximab-IRDye 700DX conjugate was 37.6 ng/mL. Thus, this result showed that the concentration of cetuximab-IRDye 700DX conjugate required to induce half maximal cell death by PIT was more than 15 times lower than the concentration required to block half the phosphorylation in the ELISA experiment described above (570 ng/mL). Additionally, the cetuximab-IRDye 700DX conjugate concentration that led to 90% cell death (257 ng/mL) resulted only in about 25% reduction of phosphorylation.

Figure 3:
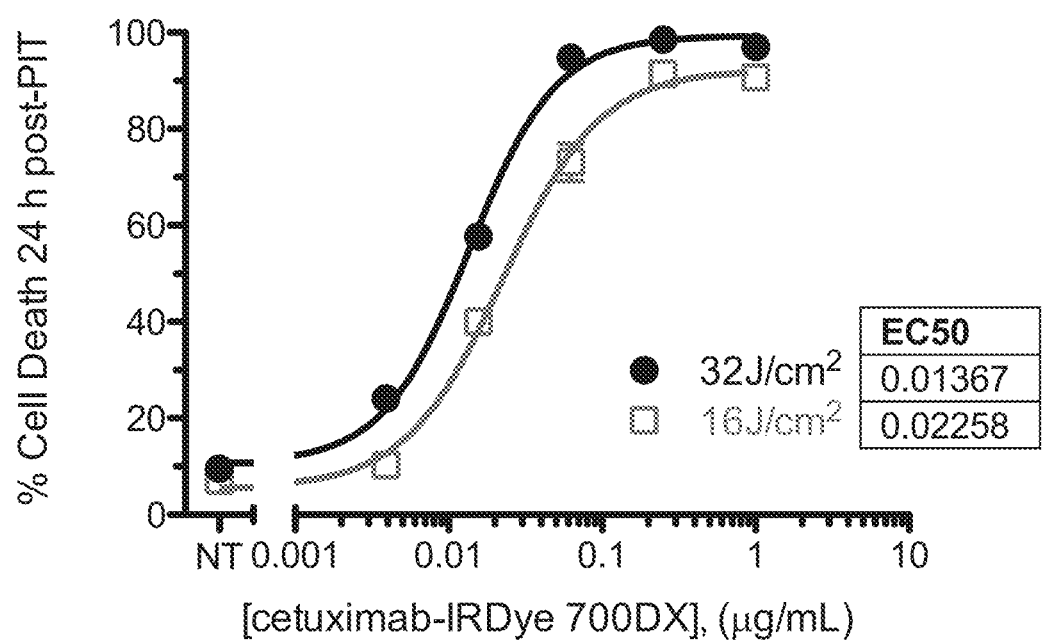
FIG. 3 shows the comparison of dose response curves for the photoimmunotherapy (PIT) with the cetuximab-IRDye 700DX conjugate using 16 J/cm$^2$ versus 32 J/cm$^2$ of 690 nm light on BxPC3 cells.

Similar experiments were performed with BxPC3 cells, in which PIT induced by increasing titrating doses of the cetuximab-IRDye 700DX conjugate was compared at two higher light doses (16 J/cm$^2$ and 32 J/cm$^2$). As shown in FIG. 3, the results also showed the potency of the cetuximab-IRDye 700DX conjugate for inducing PIT even at very low concentrations. In particular, the results showed that the $EC_{50}$ resulting from PIT with the cetuximab-IRDye 700DX conjugate was even lower, which likely is due to the higher light doses that were applied. For example, increasing the light dose from 16 J/cm$^2$ to 32 J/cm$^2$ resulted in a decrease in the half maximal cell death ($EC_{50}$) from 22.6 to 13.7 ng/mL. Thus, the results showed that higher light doses may require even lower concentrations of cetuximab-IRDye 700DX conjugate (that means lower receptor occupancy) for the same extent of cell killing.

Example 4: Synthesis and Evaluation of a Panitumunab-IRDye 700DX-Alexa-488 Dual Label Conjugate A dual-label conjugate was prepared in which the exemplary antibody panitumunab was conjugated both to IRDye 700DX and Alexa Fluor 488.

A. Materials

The water-soluble, silicon-phthalocyanine derivative, IRDye 700DX NHS ester (IR-700; $C_{74}H_{96}N_{12}Na_4O_{27}S_6Si_3$, molecular weight of 1954.22), was obtained from LI-COR Bioscience (Lincoln, Nebr.). Alexa Fluor 488 carboxylic acid, succinnimidyl ester Alexa Fluor 488-NHS was obtained from Life Technologies (Carlsbad, Calif.). Panitumumab, a fully humanized IgG2 mAb directed against the human epidermal growth factor receptor 1 (HER1), was purchased from Amgen (Thousand Oaks, Calif.). All other chemicals used were of reagent grade.

B. Synthesis of Panitumunab-IRDye 700DX-Alexa-488 (Pan-IRDye 700DX-Alexa-488)

Panitumumab (2 mg, 13.6 nmol) in 0.1 mol/L Na$_2$HPO$_4$ (pH 8.5) was incubated with 7 μL of a 5 mM DMSO solution of Alexa Fluor 488-NHS (35 nmol) for 45 minutes in the dark at room temperature, whereupon IR-700DX (66.8 μg, 35.0 nmol, 5 mmol/L in DMSO) was added. After an additional incubation time of 45 min at room temperature, 15 μL of 100 mM Tris base was added to stop the conjugation reactions. Extraneous dye and other small molecule impurities were removed by filtration and excessive buffer exchange (30 reaction volumes of HyCLone PBS pH=7.1 using Amicon® Ultra 15 Centrifugal Filter Units (Merck Millipore Ltd, Billerica, Mass.)).

C. Characterization of Conjugate

The conjugate was evaluated by size exclusion chromatography (SEC) on a TSKgel G2000 SWxl, 7.6×300 mm SEC column (TOSOH Biosciences, King of Prussia, Pa.) using an Agilent 1100 HPLC system equipped with an Agilent G1315A diode array detector (DAD) monitoring the wavelengths of 280, 488 and 690 nm, along with an Agilent G1321A fluorescence (FLS) detector monitoring at the excitation wavelength at 488 nm and emission wavelength at 505 nm.

Figure 4:
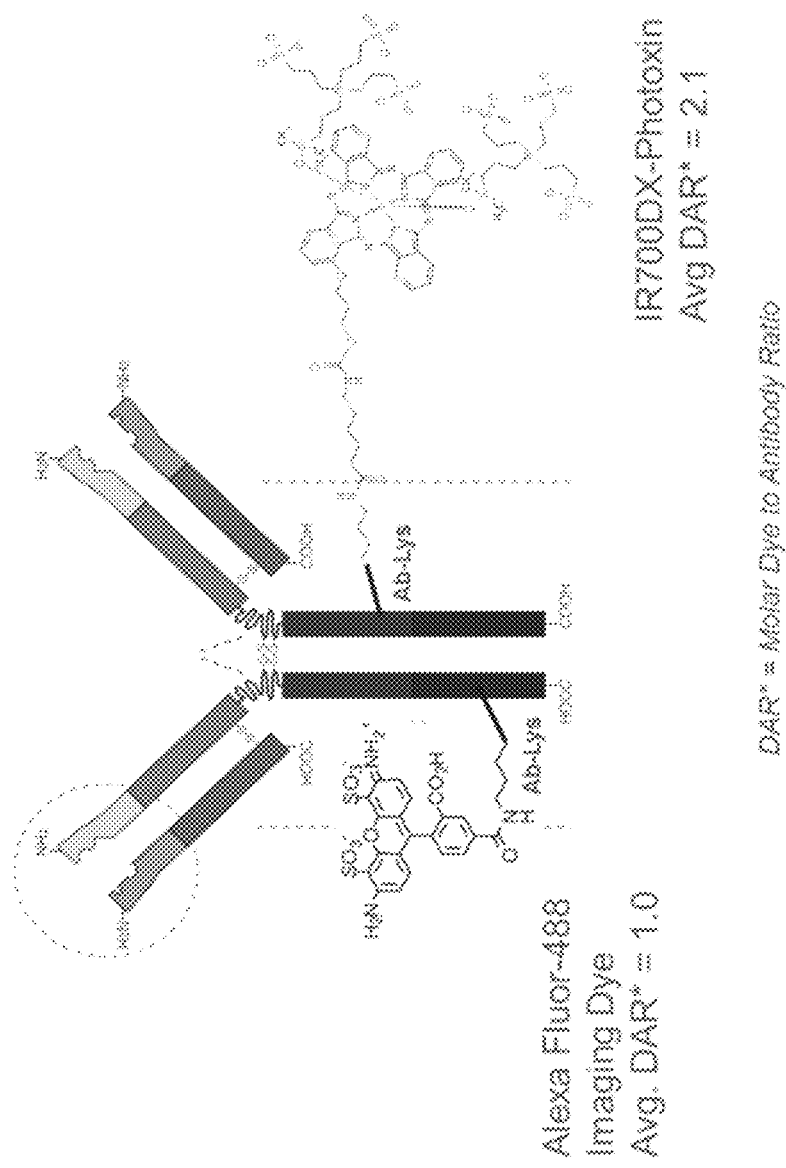
FIG. 4 shows the schematic structure for the dual-labeled panitumumab-IR700DX-Alexa-488 conjugate.

The antibody concentration and average dye to antibody ratio (DAR) for both dyes were determined using 280, 488 and 690 nm absorbance unit integration area for the antibody monomer peak after the appropriate extinction coefficient value correction factors were applied as needed for each respective dye. The DAR for the Alexa-488 and IRDye 700DX dyes were calculated to be 1.0 and 2.1, respectively. The schematic structure for the panitumumab-IRDye 700DXDX-Alexa-488 conjugate is shown in FIG. 4.

The fluorescence results showed a strong Agilent HPLC signal, which was observed at 505 nm using an excitation wavelength of 488 nm for the Alexa Flour-488 conjugated antibody at the appropriate retention time for an IgG1 150,000 dalton protein. In addition, a characteristic visible green fluorescence was observed by eye from the Pan-IRDye 700DX-Alexa-488 labeled conjugate using both ambient and 365 nm excitation light (hand-held lamp).

D. Photoimmunotherapy (PIT) Using IRDye 700DX-Conjugated Antibodies

To evaluate whether photoimmunotherapy with IRDye 700DX-conjugated antibody was impacted by the presence of an additional dye conjugated to the same antibody, the PIT activity of the panitumunab-IRDye 700DX-Alexa-488 dual label conjugate (Pan-IRDye 700DX-Alexa-488) was compared to an anti-human EGFR antibody drug panitumumab conjugated only with IRDye 700DX (Pan-IRDye 700DX).

The two conjugates were tested for efficiency in killing cells in an in vitro PIT assay using the pancreatic cancer line BxPC3. BxPC3 were seeded into 96-well white-wall plates (4,000 cells/well) the day before the experiment. Antibody conjugates were added to cells at a concentration of 10 μg/mL and were incubated for 2 hours at 37° C. Light of 690 nm was applied by a diode at a constant power output of 50 mW/cm$^2$. The illumination time was modulated to achieve the fluences 4 J/cm², 8 J/cm² or 16 J/cm². As a control, a group of cells was not irradiated with light (0 J/cm²). To monitor the progression of cell death after light treatment, the conjugate containing medium was replaced by fresh medium containing CellTox Green (Promega), a dye that reports cell death based on compromised cell membrane integrity. Time dependent increase in cell death was observed over 24 hours.

Figure 5A:
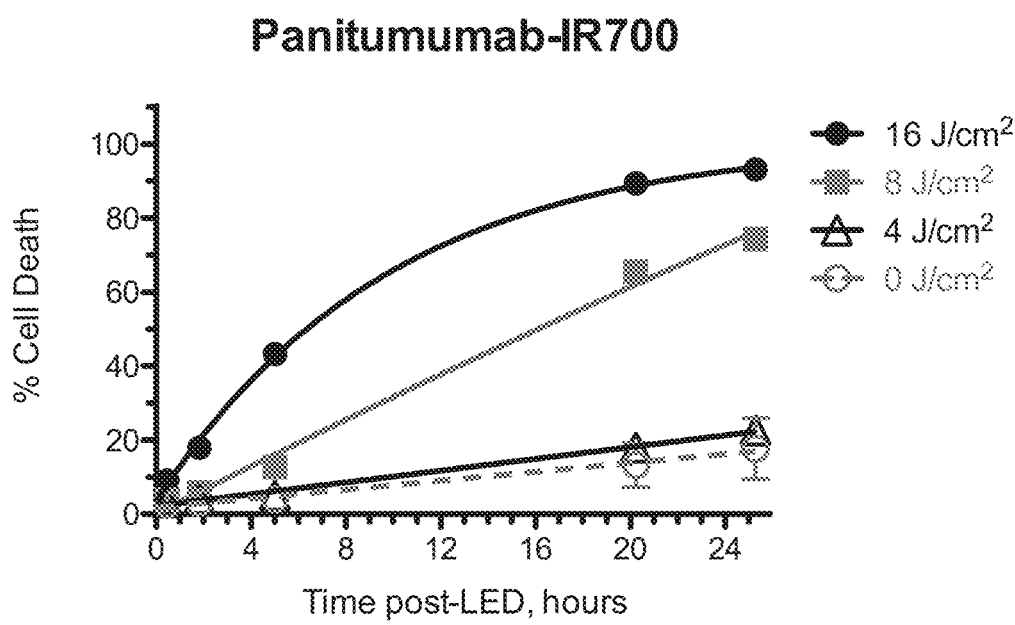
FIGS. 5A and 5B show the progression of cell death after photoimmunotherapy (PIT) induced by different conjugates at various light dosages (0-16 J/cm$^2$) on BxPC3 pancreatic cancer cells.
Figure 5B:
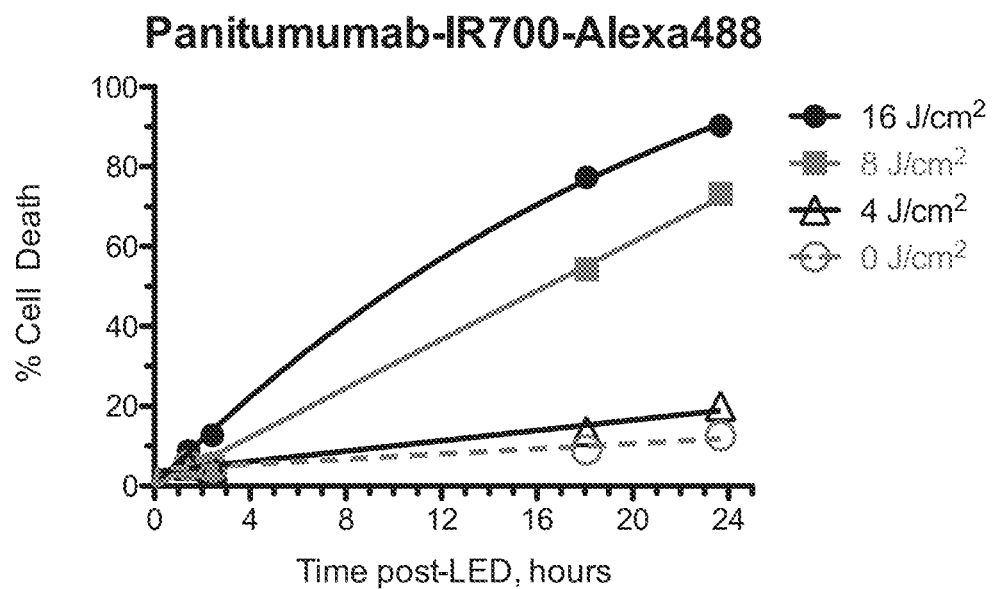

As shown in FIG. 5A (Pan-IRDye 700DX) or FIG. 5B (Pan-IRDye 700DX-Alexa-488), both conjugates led to near complete cell killing with 16 J/cm² of light at 690 nm. Moreover, the sensitivity of the two conjugates to light to induce killing was almost identical. A light dose of 8 J/cm² at 690 nm resulted in 74% and 73% killing by single (Pan-IRDye 700DX) and dual-labeled (Pan-IRDye 700DX-Alexa-488) panitumumab, respectively, and a light dose of 4 J/cm² at 690 nm was only marginally effective for both conjugates. Thus, the results showed that the presence of the dye Alexa488 did not interfere with the abilities of a panitumumab-IRDye 700DX conjugate to induce 690 nm light-dependent cell killing.

Example 5: Assessment of Cell Killing Activity and Composition of Various Antibody:IR700 DX Conjugates Studies were performed to assess whether antibody-IRDye 700DX conjugates pre-exposed to different wavelengths of light differentially affect soluble aggregate formation. Two different antibodies-mouse anti-human anti-PD-L1 (Catalog No: 329728, Biolegend, San Diego, Calif.) and anti-EGFR (cetuximab; Myoderm USA, Norristown, Pa.)—were labeled with IRDye 700DX and were evaluated to assess if pre-exposure to different wavelengths of light affected soluble aggregate formation.

A. Antibody Conjugation

Both antibodies were conjugated with IRDye 700DX using the same approach. For all conjugates described below, the general protocol used to conjugate the antibodies was similar to that of larger scale conjugation with cetuximab-IRDye 700DX described in Example 1. Modifications to the protocol were made for smaller scale reaction volumes that used 3 mg or less of protein.

The antibody solution (either anti-PD-L1 antibody or anti-EGFR antibody) was first exchanged with phosphate buffer saline pH 7 using a 30,000 Dalton molecular weight cutoff centrifugal filter, then the antibody solution pH was adjusted to a pH of 8.5 with addition of phosphate buffer at pH=9. Frozen solid aliquots of IRDye 700DX NHS Ester (Catalog No. 929-70011; Li-COR, Lincoln, Nebr.) were thawed at room temperature, then dissolved with DMSO to achieve a 10 mg/mL concentration. In a dark environment, the solubilized IR700 NHS Ester was then added to the antibody solution at a 4 (IR700 NHS Ester) to 1 (antibody) molar ratio. The conjugation reaction proceeded at 25° C. for 2 hours protected from light. Glycine (pH 8.2) was added to a final concentration of 10 mM for 15 minutes to quench the reaction. The antibody conjugate solution was then exchanged with a 30,000 Dalton molecular weight cutoff centrifugal filter with 24 mL of PBS pH 7 to remove free dye, glycine, and glycine-IR700, and to adjust the pH of the solution back to pH 7. The antibody conjugates were analyzed with size exclusion chromatography to evaluate antibody-IR700 concentration, monomer purity, % soluble aggregate, and dye to antibody ratio (DAR).

B. Effects of Light Pre-Exposure on Composition of IRDye 700DX Conjugate

The antibody-IRDye 700DX conjugate was tested for formation of soluble aggregates under four different conditions with at least 30 µL of conjugate at an antibody conjugate concentration of 850 µg/mL. The four treatment conditions were as follows: (1) antibody-IRDye 700DX conjugate stored at 4° C. protected from light ("4° C." control); (2) antibody-IRDye 700DX conjugate placed in a clear glass HPLC tube under a halogen lamp (Catalog No: PL-800, Dolan-Jenner, Boxborough, Mass.) at 2500 lux for 24 hrs ("white light"); (3) antibody-IRDye 700DX conjugate placed in a clear glass HPLC tube wrapped in aluminum foil to protect from light exposure under halogen lamp at 2500 lux for 24 hrs ("no light", used to control for thermal heating effects on the formation of aggregates); and (4) antibody-IRDye 700DX conjugate placed in a clear glass HPLC tube and exposed to green LED lamp (Catalog No: Green-ECS GP19 EcoSmart) at 2500 lux for 24 hrs ("green light"). After 24 hours under each treatment condition, monomer purity and soluble aggregate formation was assessed by size exclusion chromatography.

The results for the anti-PD-L1-IRDye 700DX conjugate are shown in Table 10. As shown, anti-PD-L1-IRDye 700DX conjugate (DAR~3) that was stored at 4° C. exhibited low soluble aggregate formation (<1.5%) and high monomer purity (>96%) as measured by 280 nm absorbance and 690 nm absorbance. Exposure of the anti-PD-L1-IRDye 700DX conjugate to 2500 lux of white light from a halogen lamp resulted in a significant increase in soluble aggregate formation (~30%) and concomitant decrease in monomer purity (~65%) as measured by 280 nm absorbance and 690 nm absorbance. Anti-PD-L1 IRDye 700DX exposed to the thermal heating effects of 2500 lux white light from a halogen lamp, but protected from light illumination using aluminum foil, did not induce any increase in soluble aggregate formation when compared to that of the 4° C. control sample. Anti-PD-L1 IRDye 700DX conjugate exposed to light from a green LED lamp resulted in a very minor increase in soluble aggregate formation (~5%), which was a significantly lower amount of soluble aggregate formation than that of anti-PD-L1 IRDye 700DX exposed to white light.

TABLE 10

Anti-PD-L1 IRDye 700DX aggregate formation with different types of light exposures.

| Treatment | Aggregate Retention time [min] | Monomer Retention time [min] | % Aggregate (Aggregate/Total) | % monomer (Monomer/Total) |
|---|---|---|---|---|
| 1) Anti-PD-L1-IRDye 700DX: 4° C. | 7.2 | 8.3 | 1.2% (280 nm) 1.1% (690 nm) | 96.7% (280 nm) 98.4% (690 nm) |
| 2) Anti-PD-L1-IRDye 700DX: 2500 Lux white light, 24 hours | 6.8 | 7.6 | 30.9% (280 nm) 29.5% (690 nm) | 65.0% (280 nm) 64.7% (690 nm) |

TABLE 10-continued

Anti-PD-L1 IRDye 700DX aggregate formation with different types of light exposures.

| Treatment | Aggregate Retention time [min] | Monomer Retention time [min] | % Aggregate (Aggregate/Total) | % monomer (Monomer/Total) |
|---|---|---|---|---|
| 3) Anti-PD-L1-IRDye 700DX: No light, 24 hours | 7.2 | 8.3 | 1.1% (280 nm)<br>1.1% (690 nm) | 98.9% (280 nm)<br>98.2% (690 nm) |
| 4) Anti-PD-L1-IRDye 700DX: 2500 Lux green light, 24 hours | 7.2 | 8.3 | 5.4% (280 nm)<br>5.1% (690 nm) | 94.6% (280 nm)<br>94.4% (690 nm) |

The results for the cetuximab-IRDye 700DX conjugate are shown in Table 11. Cetuximab-IRDye 700DX conjugates (DAR~3) that were stored at 4° C. did not have any detectable soluble aggregate formation (~0%) and high monomer purity (~100%) as measured at 280 nm absorbance and 690 nm absorbance. Exposure of the cetuximab-IRDye 700DX conjugate to white light of 2500 lux from a halogen lamp resulted in a significant increase in soluble aggregate formation (~40%) and concomitant decrease in monomer purity (~55%) as measured by 280 nm absorbance and 690 nm absorbance. Cetuximab-IRDye 700DX exposed to the thermal heating effects of 2500 lux white light from a halogen lamp, but protected from light illumination using aluminum foil, did not induce any increase in soluble aggregate formation when compared to that of the 4° C. control sample. Cetuximab-IRDye 700DX conjugate exposure to light from a green LED lamp resulted in a minor increase in soluble aggregate formation (~4%), which was significantly lower amount of soluble aggregate formation than that of cetuximab-IRDye 700DX exposed to white light.

minutes; sample was exposed to 500 lux of green LED lighting (Catalog No: Green-ECS GP19 EcoSmart) at 25° C. for different durations of light exposure at 24 hours, 12 hours, 6 hours, 3 hours, 1.5 hours, and 45 minutes; sample was exposed to no light at 25° C.; and sample was exposed to no light at 4° C. The duration of the light exposure for 24 hours, 12 hours, 6 hours, 3 hours, 1.5 hours, 45 minutes corresponds to 12,000 lux-hours, 6,000 lux-hours, 3,000 lux-hours, 1,500 lux-hours, 750 lux-hours, or 375 lux-hours, respectively. For each condition, 30 µL of conjugate was placed in a clear HPLC vial per sample at an antibody conjugate concentration of 2 mg/mL and the sample was exposed to each light condition.

The composition of cetuximab-IRDye 700DX conjugate following white light or green light exposure for different durations of time was assessed by monitoring formation of soluble aggregates and PIT killing activity.

1. Aggregate Formation

Cetuximab-IRDye 700DX was analyzed with HPLC size exclusion chromatography to evaluate the monomer purity and soluble aggregate formation. The percent soluble aggre-

TABLE 11

Cetuximab-IRDye 700DX aggregate formation with different types of light exposures.

| Sample | Aggregate Retention time [min] | Monomer Retention time [min] | % Aggregate (Aggregate/Total) | % monomer (Monomer/Total) |
|---|---|---|---|---|
| 1) cetuximab-IRDye 700DX: 4° C. | ND | 8.2 | 0% (280 nm)<br>0.2% (690 nm) | 100% (280 nm)<br>99.3% (690 nm) |
| 2) cetuximab-IRDye 700DX: 2500 Lux white light, 24 hours | 7.1 | 7.9 | 40.5% (280 nm)<br>41.8% (690 nm) | 55.3% (280 nm)<br>53.8% (690 nm) |
| 3) cetuximab-IRDye 700DX: No light, 24 hours | 7.3 | 8.2 | 0.3% (280 nm)<br>0.2% (690 nm) | 99.6% (280 nm)<br>99.6% (690 nm) |
| 4) cetuximab-IRDye 700DX: 2500 Lux green light, 24 hours | 7.3 | 8.2 | 3.9% (280 nm)<br>3.5% (690 nm) | 96.1% (280 nm)<br>96.0% (690 nm) |

Example 6: Duration of Pre-Exposure of White Fluorescent Vs. Green LED Lighting and their Effect on Cetuximab-IRDye 700DX Soluble Aggregate Formation and PIT Potency The following studies were performed to assess whether cetuximab-IRDye 700DX conjugates pre-exposed to different wavelengths of light and for different durations of exposure differentially affect soluble aggregate formation and pharmacological activity.

Cetuximab-IRDye 700DX was conjugated as described in Example 1. The following 14 different conditions were assessed: sample was exposed to 500 lux white fluorescent lighting at 25° C. for different durations of light exposure at 24 hours, 12 hours, 6 hours, 3 hours, 1.5 hours, and 45 gate formation was measured as a function of cetuximab-IRDye 700DX lux-hours exposure to white light, green light, or no light.

Figure 6A:
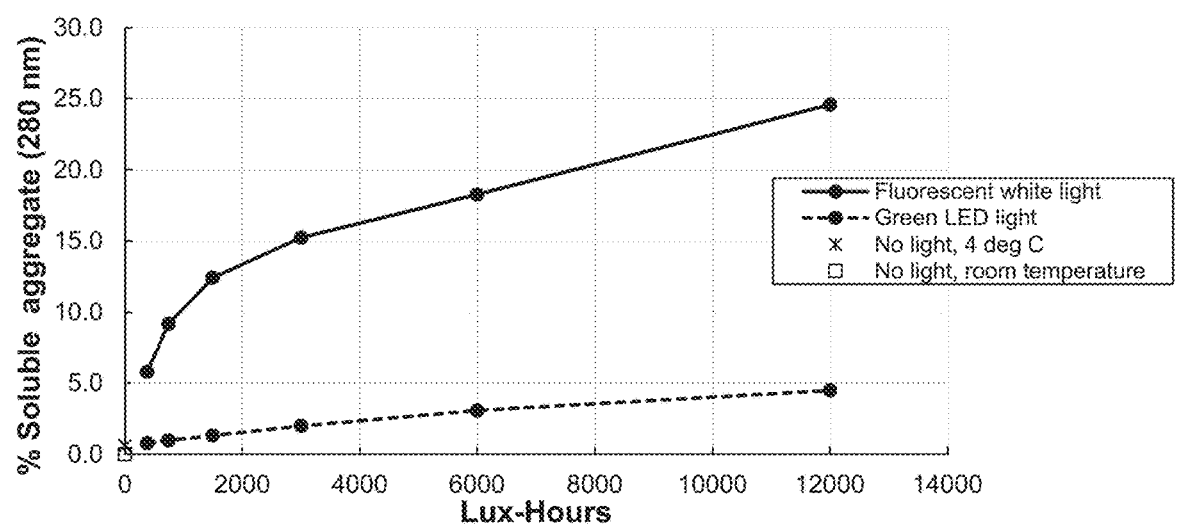
FIG. 6A shows the duration of exposure of Cetuximab-IRDye 700DX to 500 Lux white fluorescent light or green LED light and its effect on soluble aggregate formation.

As shown in FIG. 6A, the duration of exposure of cetuximab-IRDye 700DX to 500 Lux white fluorescent light had a direct effect on the formation of soluble aggregates. Cetuximab-IRDye 700DX exposure to white fluorescent light resulted in a rapid increase in soluble aggregate formation with the presence of greater than 5.0% soluble aggregate formation observed even after only 375 lux-hours (45 minutes at 500 lux) of exposure to white light, which increased further with the increased duration of exposure to white fluorescent lighting. Cetuximab-IRDye 700DX green light exposure also slightly increased soluble aggregate formation albeit at a rate much slower than that of white light; the percentage of aggregates formed even after exposure to 12,000 lux-hours (24 hours at 500 lux) of green light was no more than 5.0%. The results showed that there was a greater cetuximab-IRDye 700DX soluble aggregate formation with an increase in time of exposure to white light than that of green light. Less than 1% soluble aggregate formation was observed in samples either incubated at 4° C. or 25° C. when protected from any light exposure.

2. PIT Killing

To evaluate PIT killing activity by the cetuximab-IRDye 700DX pre-exposed to the various light conditions, BxPC3 cells (#CRL-1687, ATCC, Manassas Va.) were incubated for one hour at 4° C. with or without 1 µg/mL cetuximab-IRDye 700DX in RPMI-1640 media supplemented with 10% FBS and 1% Penicillin/Streptomycin (complete culture media), and then washed one time with complete culture media to remove unbound cetuximab-IRDye 700DX. The cells were then illuminated with a 690 nm laser at a light dose of 32 J/cm$^2$ or protected from light (0 J/cm$^2$).

The effect of different treatment regimens on cell death was measured using the fluorescent stain, CellTox Green (Cat No: G8731, Promega, Madison, Wis.). CellTox Green is a non-permeable fluorescent dye that exhibits increased fluorescence upon binding to DNA. Therefore, only cells that have compromised plasma membranes exhibit strong CellTox Green staining. After the light treatment, all cells were incubated with 1× CellTox Green reagent diluted in RPMI-1640 supplemented with 10% fetal bovine serum and 1% Penicillin/Streptomycin (complete culture media). Wells that did not include any cells were also incubated with 1× CellTox Green reagent diluted in complete culture media to serve as background subtraction wells during fluorescent signal detection. The CellTox Green fluorescence signal was measured at 24 hours after light treatment using a fluorescence plate reader. The cells were then lysed with detergent, incubated at 37° C. for 30 minutes, and the CellTox Green fluorescence signal was measured again post lysis. The percent dead cells was calculated by taking the ratio between background (lx CellTox Green in complete culture media without cells) subtracted CellTox Green signal per well prior to and post lysis and multiplying the ratio by 100.

Figure 6B:
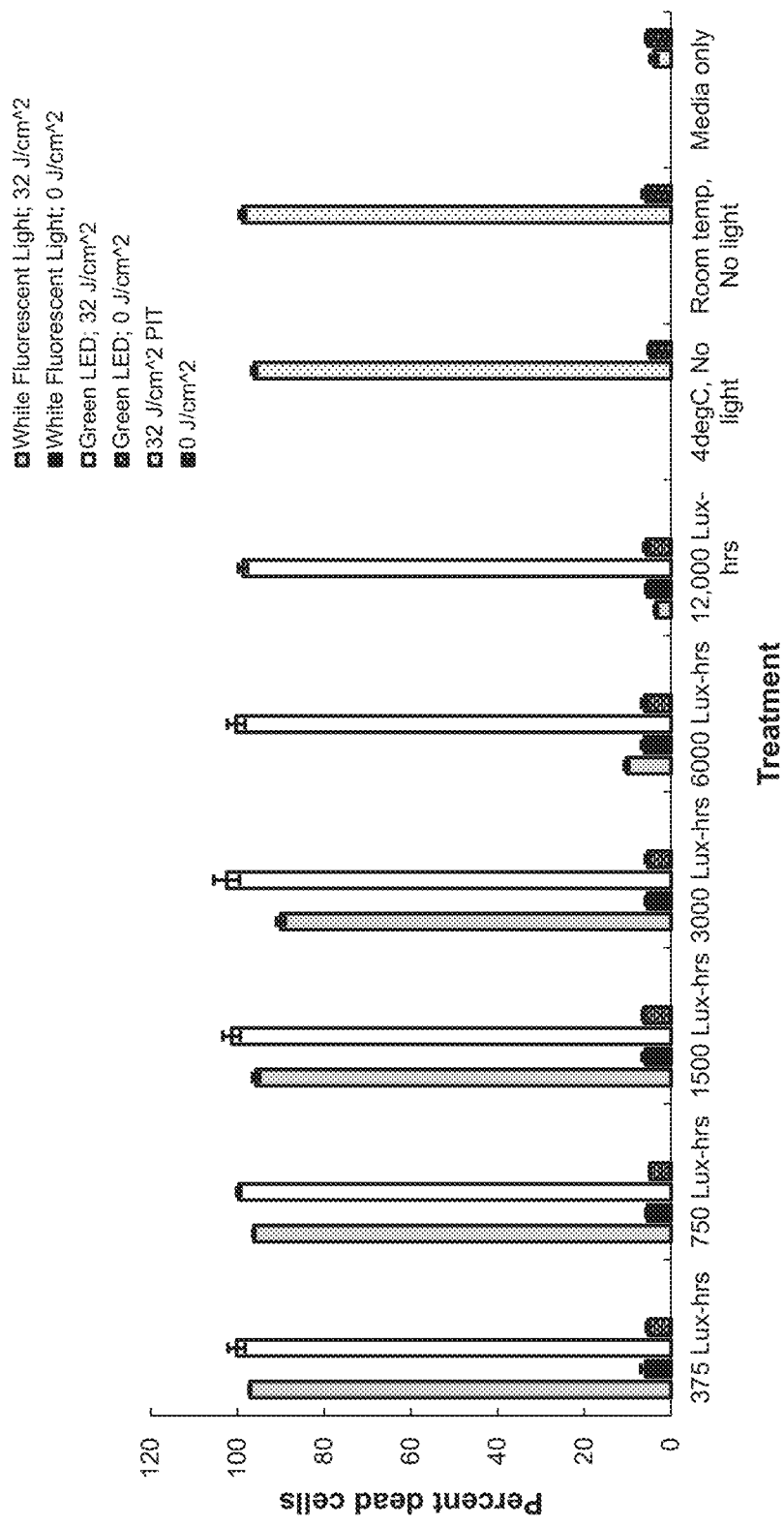
FIG. 6B shows the effect of pre-exposure of Cetuximab-IRDye 700DX to white fluorescent light or green LED light on BxPC3 PIT activity.

As shown in FIG. 6B, no effect on cell death was observed for all samples exposed to 0 J/cm$^2$ during the PIT treatment, indicating that, despite the increase in soluble aggregates after pre-exposure to white light, the soluble aggregates were not cytotoxic in that absence of light irradiation. In contrast, cell killing was observed for samples that were subsequently irradiated with a 690 nm laser at a light dose 32 J/cm$^2$, although the extent of cell killing was substantially reduced by the cetuximab-IRDye 700DX exposed to increased durations of white light. As shown, cetuximab-IRDye 700DX pre-exposed to 3,000 Lux-Hours (500 lux for 6 hours) or more of white fluorescent light exhibited less than 90% or less effect on PIT activity. However, cetuximab-IRDye 700DX exposed to all lux-hour doses of green light evaluated did not result in an effect in PIT potency, indicating that pre-exposure to green light did not substantially impact light-activated killing activity.

Figure 6C:
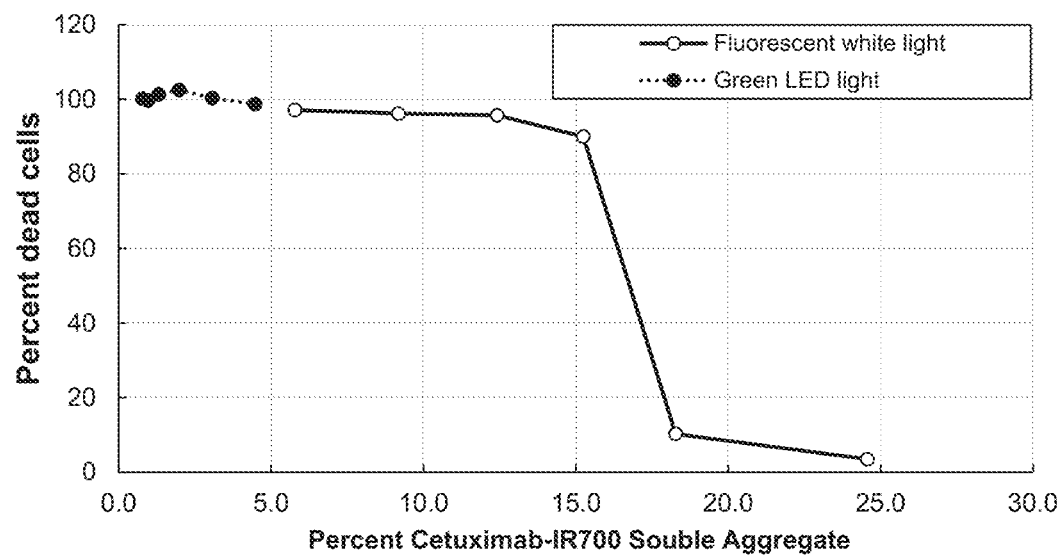
FIG. 6C shows the effect of percent Cetuximab-IRDye 700DX soluble aggregate formation on PIT activity.

The effect of aggregate formation on PIT activity is shown in FIG. 6C. As shown, the PIT potency (percent dead cells) for all cetuximab-IR700 treatment regimens for evaluating white light and green light exposure were plotted as a function of the measured percent soluble aggregate for each respective sample. The results showed that greater than 15% soluble aggregate formation of cetuximab-IRDye 700DX results in a significant decrease in PIT potency.

Example 7: Effect of Indirect Conjugation with Phthalocyanine Dye on PIT Killing and Specificity of PIT The following studies were performed to assess whether antibodies that bind directly to cell surface molecules require direct conjugation with a phthalocyanine photosensitizer, such as IRDye 700DX, to mediate PIT killing activity.

A. IR700 Conjugation of Secondary Antibody Against Cell Targeting Antibody

Instead of directly conjugating a targeting antibody targeted against a cell surface molecule (e.g. on a cancer cell) with IR700, a secondary anti-human IgG antibody that bound the targeting antibody was conjugated with IR700. Specifically, AffiniPure Donkey Anti-Human IgG, Fcγ Fragment Specific (DxHu) antibody (Catalog number: 709-005-098, Jackson ImmunoResearch Laboratories, West Grove, Pa.) was labeled with IRDye 700DX to evaluate whether non-covalent labeling of primary antibodies with secondary antibody-IRDye 700DX could be used in PIT-mediated killing. The protocol used for conjugating the DxHu antibody with IRDye 700DX was substantially the same as the protocol for antibody conjugation used in Example 5.

PIT killing of BxPC3 cells was evaluated similar to the method described in Example 6, except the cells were first incubated for one hour at 4° C. with or without anti-EGFR antibody, cetuximab (Myoderm USA, Norristown, Pa.) in RPMI-1640 media supplemented with 10% FBS and 1% Penicillin/Streptomycin (complete culture media). The cells were then washed one time with complete culture media, incubated for 30 minutes at 4° C. with or without IRDye 700DX conjugated (DxHu IRDye 700DX) secondary antibody diluted with complete culture media, and then washed one time with complete culture media. As a control, BxPC3 cells were incubated with cetuximab-IRDye 700DX in which the cetuximab was directly conjugated to IRDye 700DX. To induce cell killing, the cells were then illuminated with a 690 nm laser at a light dose of 16 J/cm$^2$ or protected from light ("no light"). Cell death was evaluated as described in Example 6 using CellTox Green.

Figure 7:
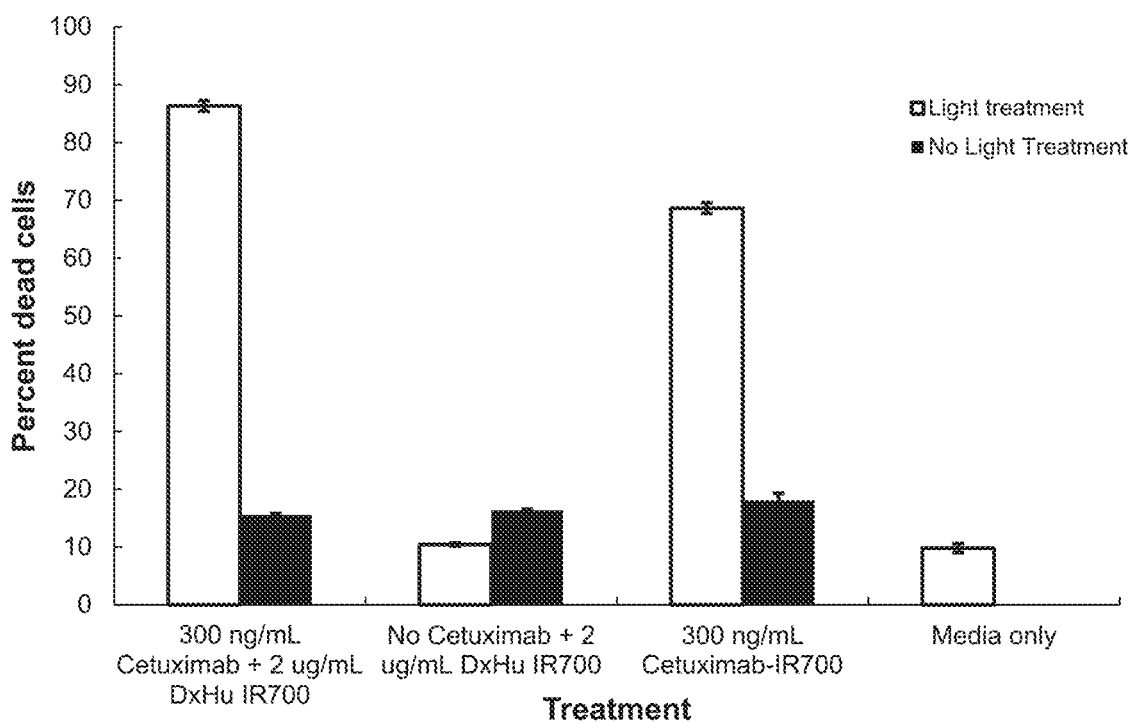
FIG. 7 shows the PIT killing activity with sequential staining using Cetuximab and donkey anti-human-IRDye 700DX (DxHu IR700) secondary antibody.

As shown in FIG. 7, BxPC3 cells that were sequentially labeled with cetuximab and donkey anti-human IRDye 700DX secondary antibody and treated with light exhibited ~90% cell death. The same treatment with the primary and secondary antibody did not result in cell death when cells were not exposed to the 690 nm light treatment. Light illumination of cells treated only with the secondary antibody did not lead to cell death because the DxHu IRDye 700DX secondary antibody does not bind directly to cells in the absence of pre-incubation with a human-derived primary antibody targeting a cell surface antigen. The extent of cell killing induced by sequential exposure to the antibodies was even slightly greater than in BxPC3 cells incubated with cetuximab that had been directly labeled with IRDye 700DX. Light treatment of BxPC3 cells treated only with media alone with no incubation with either cetuximab or DxHu IRDye 700DX resulted in a basal cell death level of ~10%, which was similar to the background cell death in cells that were not irradiated with light (no light treatment). Thus, the results showed that antibodies that bind directly to cancer cells do not require direct conjugation of a phthalocyanine photosensitizer such as IRDye 700DX to mediate PIT killing activity. Indirect labeling of anti-cancer antibodies mediated by a secondary antibody conjugated IRDye 700DX can also induce effective PIT killing activity.

B. IR700 Conjugation of Monomeric Streptavidin Against a Biotinylated Cell Targeting Antibody In another study, the PIT killing activity of cells sequentially incubated with a biotinylated anti-EGFR antibody (biotinylated cetuximab) and monomeric streptavidin-conjugated IRDye 700DX was examined. Furthermore, the effect of pre-exposure of the monomeric streptavidin-IR700 to white light on the PIT killing activity was also examined.

1. Conjugations a. Conjugation of Biotin to Cetuximab

To conjugate the anti-EGFR antibody cetuximab to biotin, a 5 mL volume of anti-EGFR antibody (cetuximab; Myoderm USA, Norristown, Pa.) supplied at a concentration of 2 mg/mL in PBS pH 7.2 was concentrated to a volume of 2 mL (5 mg/mL) using a 30,000 Dalton molecular weight cutoff centrifugal filter (Cat No: UFC903024, Merck-Millipore, Cork, IRL.) The solution was diluted to 5 mL with 100 mM $Na_2HPO_4$ (pH 8.9) to final volume of 5 mL and pH of ~8.5.

EZ-Link Sulfo-NHS-LC-Biotin (sulfocussinimidyl-6-[biotin-amido]hexanoate) was used to label the antibody according to the manufacturer's instructions (Cat. No. 21327, ThermoScientific, Rockford, Ill.). Specifically, a 2 mg sample of Sulfo-NHS-Biotin ($SO_3$-biotin-NHS ester, Cat #: 1854200, Thermo Scientific) was thawed at room temperature, then dissolved with deionized (DI) water to achieve a 10 mg/mL concentration. A volume of 130 µL of the solubilized $SO_3$-biotin-NHS ester was added to the cetuximab antibody solution at a 20 ($SO_3$—Biotin-NHS Ester) to 1 (cetuximab antibody) molar ratio. The conjugation reaction proceeded at 25° C. for 2 hours protected from light where upon, excess glycine was added to quench the reaction for 15 minutes. The cetuximab-biotin conjugate solution was then exchanged with ten times the equivalent conjugation volume with PBS pH 7.2 using a 30,000 Dalton molecular weight cutoff centrifugal filter to remove free dye, glycine, and glycine-IRDye 700DX, and to adjust the pH back to pH 7.2.

The cetuximab-biotin conjugate was analyzed with size exclusion chromatography (SE-HPLC) to evaluate monomeric cetuximab-biotin purity, % soluble aggregate and reaction product residual impurity levels. The average molar Biotin to Antibody Ratio (BAR) for the conjugate was determined using the Pierce Colorimetric Biotin Quantification Assay (Cat No: 128005, Thermo Scientific, Rockford, Ill.) according to supplier instructions. The results are shown in Table 12.

TABLE 12

Cetuximab-Biotin Analysis Results

| Biotin to Antibody Ratio (BAR) | | 7.2 |
|---|---|---|
| SE-HPLC Purity | A210 | 99.1% monomer, 0.3% HMW, 0.6 LMW |
| | A280 | 100% | b. Conjugation of Monomeric Streptavidin to IR700

The general protocol used to conjugate engineered monomeric streptavidin 2 (mSA2) (Catalog No: EBU001/2, Kerafast, Boston, Mass.) with IR700 was substantially the same as the protocol for antibody conjugation described in Example 5, except that prior to conjugation, the mSA2 solution was first exchanged with phosphate buffer saline pH 7 using a 3,000 Dalton molecular weight cutoff centrifugal filter. For the conjugation, the solubilized IR700 NHS Ester was then added to the mSA2 solution at a 2 (IR700 NHS Ester) to 1 (monomeric streptavidin) molar ratio. After the conjugation reaction performed substantially as described in Example 5, the monomeric streptavidin conjugate solution was then exchanged with 24 mL of PBS pH 7 using a 10,000 Dalton molecular weight cutoff centrifugal filter to remove free dye, glycine, and glycine-IR700, and to adjust the pH back to pH 7.

2. PIT Killing

Biotinylated cetuximab was pre-incubated with monomeric streptavidin-IRDye 700DX at a 20 (monomeric streptavidin IRDye 700DX) to 1 (1 µg/mL biotinylated cetuximab) molar ratio for 1 hour at room temperature. BxPC3 cells were incubated with RPMI media supplemented with 10% FBS and 1% Penicillin/Streptomycin (complete culture media) containing 1 µg/mL of biotinylated cetuximab pre-complexed with monomeric streptavidin-IRDye 700DX or complete culture media only for one hour at 37° C. The cells were then washed one time with complete culture media. The cells were either protected from light (light dose 0 $J/cm^2$) or were illuminated with a 690 nm laser with different light dosimetries (2 $J/cm^2$, 8 $J/cm^2$, 32 $J/cm^2$ or 64 $J/cm^2$). Cell death was evaluated as described in Example 6 using CellTox Green.

Figure 8A:
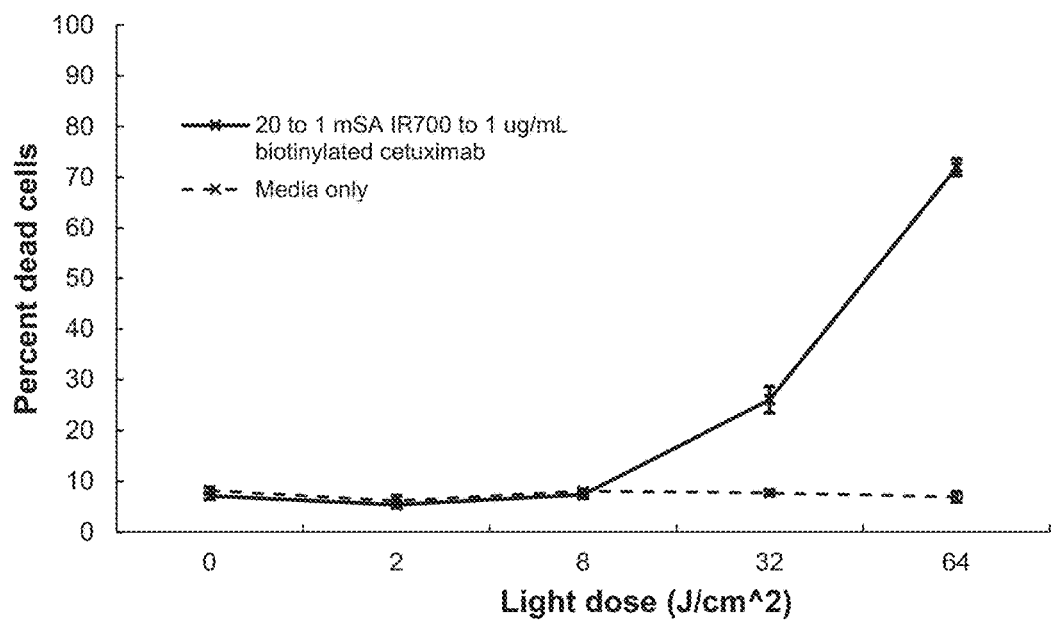
FIG. 8A shows the light-dependent killing of BxPC3 cells with biotinylated cetuximab pre-complexed with monomeric streptavidin-IRDye 700DX (mSA IR700).

As shown in FIG. 8A, the light-dependent PIT killing activity of BxPC3 cells with biotinylated cetuximab pre-complexed with monomeric streptavidin-IRDye 700DX (mSA IRDye 700DX) was light dose dependent. No light-dependent killing activity was observed with cells incubated with complete culture media alone.

To confirm specificity of the effect, the effect of biotinylated cetuximab pre-complexed with monomeric streptavidin-IRDye 700DX was evaluated in the presence of either unconjugated cetuximab or unconjugated monomeric streptavidin to assess if the effect could be competed. In one condition, BxPC3 cells were first pre-incubated with 100 µg/mL unconjugated cetuximab or complete culture media alone for one hour at 37° C. The cells were then washed one time. The cells pre-incubated with unconjugated cetuximab were then incubated with complete culture media containing 1 µg/mL biotinylated cetuximab pre-complexed with 2 µg/mL monomeric streptavidin IRDye 700DX. In another condition, cells that had been pre-incubated with complete culture media alone (but not preincubated with unconjugated cetuximab) were incubated with 1 µg/mL biotinylated cetuximab that had been pre-complexed in the presence of 10-fold excess unconjugated monomeric streptavidin (complexing performed with 20 µg/mL unconjugated monmeric streptavidin and 2 µg/mL monomeric streptavidin IRDye 700DX). In addition, cells that had been preincubated with cell culture media (but not preincubated with unconjugated cetuximab) either incubated with 2 µg/mL monomeric streptavidin IRDye 700DX alone or complete culture media only for one hour at 37° C. The cells were then washed one time with complete culture media.

Figure 8B:
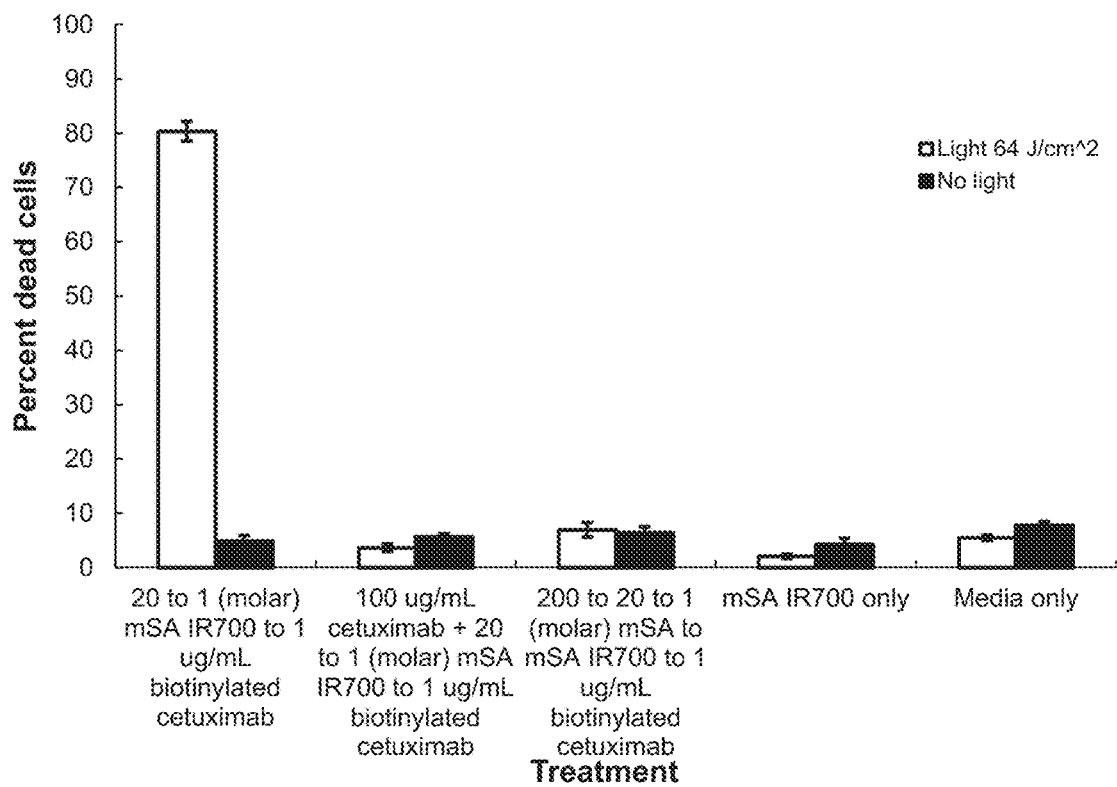
FIG. 8B shows the specificity of PIT with biotinylated cetuximab pre-complexed with monomeric streptavidin-IRDye 700DX (mSA IR700).

The results shown in FIG. 8B demonstrated the PIT-mediated killing with biotinylated cetuximab pre-complexed with monomeric streptavidin-IRDye 700DX (mSA IRDye 700DX) was specific to cells having bound cetuximab associated with IR700. No light-dependent PIT killing was observed when BxPC3 cells were pre-exposed to 100 µg/mL unconjugated cetuximab prior to incubation with biotinylated cetuximab pre-complexed with monomeric streptavidin-IRDye 700DX. The results also showed that the PIT killing was dependent on the association of the IR700 conjugated monomeric streptavidin and biotinylated antibody, since no light-dependent PIT killing of BxPC3 cells incubated with biotinylated cetuximab pre-complexed with 10× molar excess of unconjugated monomeric streptavidin over monomeric streptavidin-IRDye 700DX was observed. Further, the results demonstrated that no light-dependent PIT killing of BxPC3 cells was observed in cells incubated with monomeric streptavidin-IRDye 700DX alone in the absence of biotinylated cetuximab or BxPC3 cells incubated in culture media alone.

3. Effects of Light Pre-Exposure on Composition and Activity

The effect of indirect killing of cells using monomeric streptavidin-IRDye 700DX that had been exposed to different types of light was also evaluated. Thirty microliters of monomeric streptavidin-IRDye 700DX conjugate (DAR 1.35) was added per clear HPLC vial at a monomeric streptavidin conjugate concentration of 865 µg/mL. The following conditions were tested: (1) the monomeric streptavidin-IRDye 700DX conjugate was placed in a clear glass HPLC tube wrapped in aluminum foil to protect from light exposure under a halogen lamp at 2500 lux for 24 hrs ("no light"; to control for thermal heating effects); (2) the monomeric streptavidin-IRDye 700DX conjugate was placed in a clear glass HPLC tube under a halogen lamp at 2500 lux for 24 hrs ("white light"); (3) the monomeric streptavidin-IRDye 700DX conjugate was placed in a clear glass HPLC tube and exposed to green LED lamp at 2500 lux for 24 hrs ("green light").

Cell killing induced by the monomeric streptavidin-IRDye 700DX pre-exposed under the various conditions and that had been complexed with biotinylated cetuximab was assessed on BxPC3 cells as described above. Thus, all BxPC3 cell treatments were incubated with either complete culture media or complete culture media containing biotinylated cetuximab pre-complexed monomeric streptavidin-IRDye 700DX that had undergone pre-exposure to light of different wavelengths of light as described above.

Figure 8C:
FIG. 8C shows the effect of monomeric streptavidin-IRDye 700DX pre-exposure to white light on the PIT killing activity with biotinylated Cetuximab in BxPC3 cells.

As shown in FIG. 8C, the results revealed that monomeric streptavidin-IRDye 700DX pre-exposure to white light inhibits potential for PIT killing activity. The expected light-dependent killing of BxPC3 cells was observed when cells were incubated with biotinylated cetuximab pre-complexed with monomeric streptavidin-IRDye 700DX that had been protected from light exposure with aluminum foil. In contrast, no light-dependent PIT killing of BxPC3 cells was observed when cells were incubated with biotinylated cetuximab pre-complexed with monomeric streptavidin that had been exposed to white light from a halogen lamp at 2500 lux for 24 hours.

The results showed that the loss of PIT killing upon light exposure was reduced when BxPC3 cells were incubated with biotinylated cetuximab pre-complexed with monomeric streptavidin-IRDye 700DX that had been exposed to green light from a green LED lamp at 2500 lux for 24 hours, although in this experiment there was some decrease in PIT killing even when the IR700 conjugate was pre-exposed to green light. No light-dependent PIT killing of BxPC3 cells incubated with complete culture media alone.

Example 8: Effect of Anti-EpCAM Antibody-IR700 Conjugate on PIT Killing

A further additional study was performed to assess the effect on cell killing of an anti-mouse CD326 (EpCAM) (Catalog No: 118202, BioLegend, San Diego, Calif.) conjugated to a phthalocyanine photosensitizer such as IRDye 700DX. The antibody targets a further alternative cell surface molecule, EpCAM. To prepare the anti-EpCAM-IRDye 700DX, conjugation was performed as described in Example 5.

To evaluate PIT killing activity by the anti-EpCAM-IRDye 700DX conjugate, 4T1 cells were incubated with RPMI media supplemented with 10% FBS and 1% Penicillin/Streptomycin (complete culture media) containing increasing concentrations of anti-EpCAM-IRDye 700DX as indicated or complete culture media only for one hour at 37° C. The cells were then washed one time with complete culture media. The cells were then illuminated with a 690 nm laser at 0 or 32 J/cm$^2$ light dosimetries. Cell death was evaluated as described in Example 6 using CellTox Green.

Figure 9A:
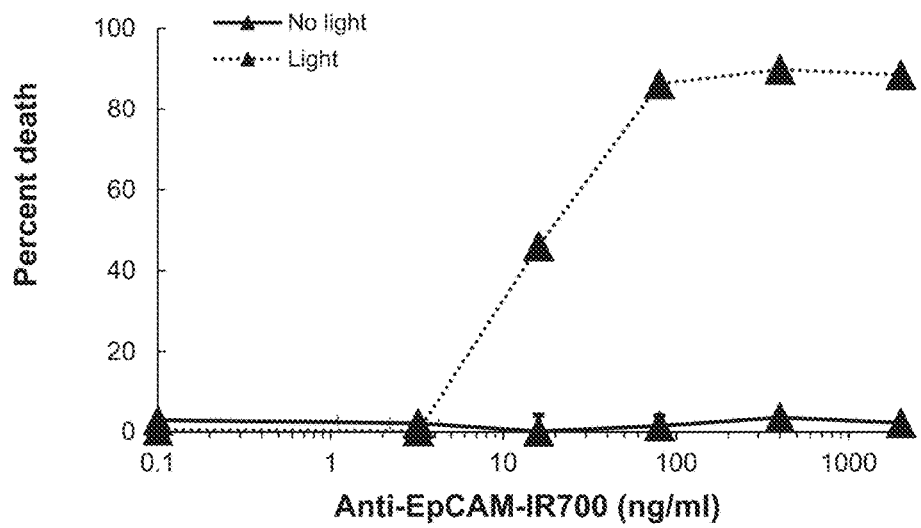
FIG. 9A shows the antibody dose-dependent killing of 4T1 cells with directly conjugated anti-EpCAM-IRDye 700DX.

As shown in FIG. 9A, the results showed that 4T1 cells incubated with anti-EpCAM-IRDye 700DX and illuminated at 32 J/cm$^2$ were killed in an antibody dose dependent manner. No significant cell death was observed at any antibody concentration without light illumination.

To confirm specificity of the cell killing, 4T1 cells were incubated with a molar excess unconjugated anti-EpCAM antibody to block binding of the anti-EpCAM-IRDye 700DX conjugate to the cell surface. Specifically, 10, 1, or 0.1 µg/mL unconjugated anti-EpCAM antibody or complete culture media alone for one hour at 37° C. Without washing the cells, anti-EpCAM-IRDye 700DX was added to 4T1 cells to achieve a final concentration of 0.1 µg/mL and incubated for one hour at 37° C. Cell killing was induced by illumination with a 690 nm laser at a 32 J/cm$^2$ light dose and cell killing determined using CellTox Green as described above.

Figure 9B:
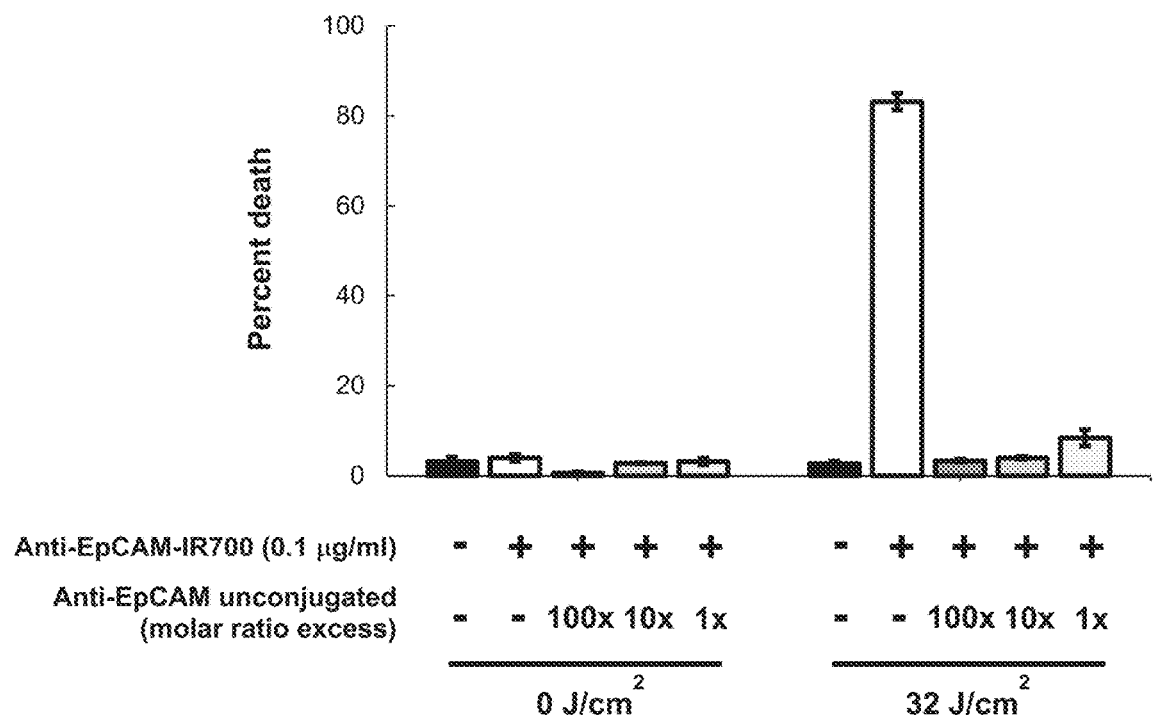
FIG. 9B shows the specificity of anti-EpCAM-IRDye 700DX PIT killing activity.

The results are shown in FIG. 9B, which shows the specificity of anti-EpCAM-IRDye 700DX PIT killing activity. The results showed that 4T1 cells that were pre-incubated with unconjugated anti-EpCAM antibody prior to incubation with anti-EpCAM-IRDye 700DX displayed significantly less cell death after exposure to 32 J/cm$^2$ laser illumination in comparison to the 4T1 cells that did not undergo the blocking step, demonstrating that cell binding of anti-EpCAM and conjugation with IRDye 700DX is necessary for photoimmunotherapy-based killing.

Example 9: PIT Killing of Fc Receptor-Expressing Target Cells with Cetuximab-IRDye 700DX The following studies were performed to assess whether antibody-IRDye 700DX drug conjugate can bind to Fc receptor (FcR) and whether activation with near infrared (~690 nm) light results in FcR+ cell killing. FcR are commonly found on wide variety of immune cells such as, monocytes, macrophages and myeloid derived suppressor cells (MDSCs). The role of these cells in solid tumors have been found to be detrimental and tumor promoting. Human monocytic cell line THP1 express surface Fc receptors and was used as the model cell system for this assay.

THP1 cells (ATCC, TIB-202) grown in complete RPMI 1640 medium were plated at 5000 cells in 100 µL total volume per well in a 96 well tissue culture plate for adherence overnight. The viability of the cells prior to plating was checked via trypan blue exclusion method and >95% cells were viable. The cells were divided into three groups (all in triplicate) as follows: (1) THP1 cells only (untreated); (2) THP1 cells treated with the drug cetuximab-IRDye 700DX at 500 ng/mL; and (3) THP1 cells first incubated with Fc receptor blocking solution (Catalog No: 564220, BD, Franklin Lakes, N.J.) at 1 µg/well for 20 min at room temperature followed by treatment with drug cetuximab-IRDye 700DX (500 ng/mL, 1 hr at 37° C. in incubator protected from light).

To induce killing, cells in each group were subjected to 690 nm laser light at a dose of 32 J/cm². The controls represented wells corresponding to the groups described above but not treated with light. Cell killing was assessed using CellTox Green as described substantially as described Example 6. CellTox Green dye (1×) was added to the wells and cells were incubated for 24 hours at 37° C. in an incubator. The dye was also added to couple of wells just containing 100 µL of the medium for background subtraction later. After the incubation, the tissue culture plate was immediately read on a plate reader. The cells were then subjected to lysis by adding 5 µL of diluted lysis solution (Promega, cat #G1821) including also the control wells containing just the media. The dilution was performed by adding culture medium to the lysis solution at 40% (lysis solution): 60% (culture medium) ratio. The plate was then read again to obtain values for 100% cell death. For each read, the two background wells were averaged and their values subtracted from all other wells. In order to calculate the % cell death for each well, the background subtracted value from the first read was divided by the value from the second read (after lysis), and multiplied by 100.

Figure 10:
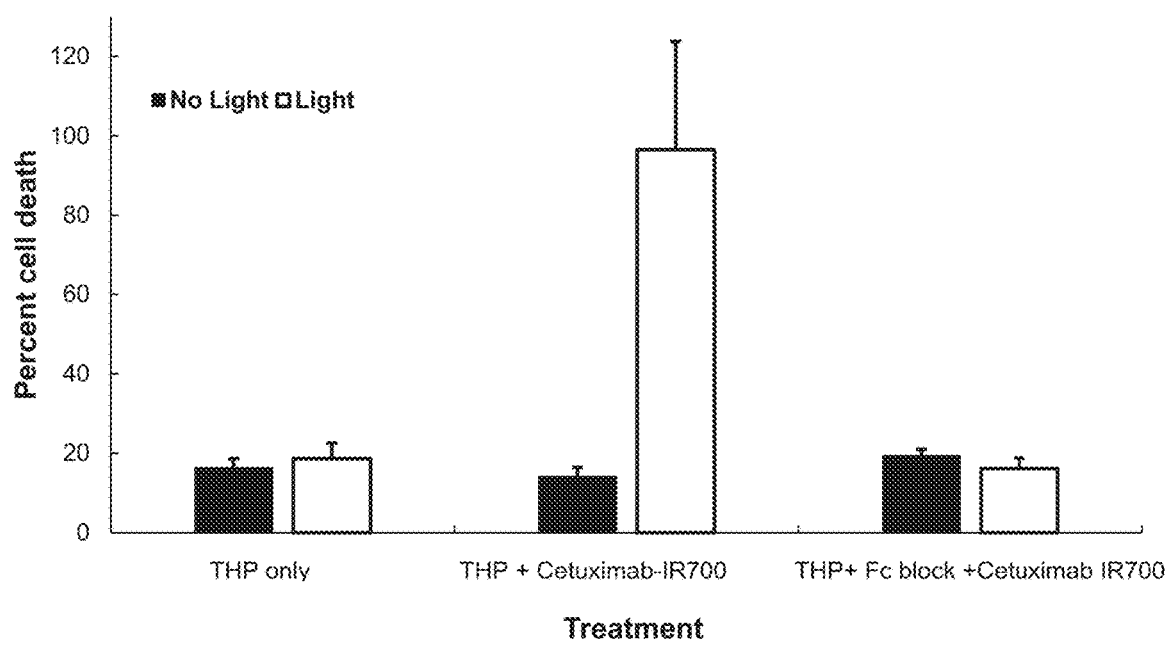
FIG. 10 shows the Fc receptor-specific killing of THP1 cells by Cetuximab-IRDye 700DX.

As shown in FIG. 10, the results showed the Fc receptor-specific killing of THP1 cells by cetuximab-IRDye 700DX. Maximum killing was observed in the group represented by drug treated THP1 cells subjected to 32 J/cm² light. The percent killing values are relative to the light and drug treated THP1 cells. Thus, the results showed that antibody-mediated killing can be mediated by specific binding to target molecules on the cell surface as well as, in some cases, binding of the antibody to the FcR.

Example 10: Assessment of Cell Killing Activity and Effect of White Light Exposure on Cell Killing Activity of Non-Antibody Molecule:IR700 DX Conjugates The following studies were performed to assess if non-antibody proteins, small proteins, and viruses can be conjugated with a phthalocyanine dye, such as IR700, to target cell killing. As shown below, the results showed that various other non-antibody molecules mediate cell killing that is dependent on activation with near infrared light (e.g. about 690 nm light), binding to cells, and/or affected by pre-exposure of the targeting molecule conjugate to white light.

A. Non-Antibody Protein:IR700 Conjugate

Human recombinant epidermal growth factor (EGF) (Catalog No: 01-401, EMD Millipore, Billerica, Mass.) was conjugated to IRDye 700DX and evaluated to assess its killing activity and if pre-exposure to different wavelengths of light affected soluble aggregate formation.

1. EGF Conjugation

The protocol used for labeling of the human recombinant EGF with IRDye 700DX was substantially the same as the protocol for antibody conjugation described in Example 5, except that the prior to conjugation, the EGF solution was first exchanged with phosphate buffer saline pH 7 using a 3,000 Dalton molecular weight cutoff centrifugal filter. For the conjugation, the solubilized IR700 NHS Ester was then added to the EGF solution at a 4 (IR700 NHS Ester) to 1 (EGF) molar ratio or at a molar ratio of 1.2 (IR700 NHS Ester) to 1 (EGF). After the conjugation reaction performed as described in part A, the EGF conjugate solution was then exchanged with six times the equivalent conjugation volume with PBS pH 7 using a 3,000 Dalton molecular weight cutoff centrifugal filter to remove free dye, glycine, and glycine-IR700, and to adjust the pH back to pH 7.

2. EGF-IR700 Light-Dependent Killing Activity

Photo-activated EGF-IR700 cell killing was assessed in A431 cells. A431 cells were seeded at 5000 cells per well in 96 well white clear bottom dishes one day prior to the experiment. The following day, the A431 cells were washed three times with EMEM supplemented with 1% Penicillin/Streptomycin (serum free media). The A431 cells were then washed one time with serum free media, then incubated with serum free media containing 1 µg/mL of EGF-IRDye 700DX for one hour at 4° C. or serum free media only. As a control to assess the specificity of the activity, in one condition A431 cells were pre-incubated with 100 µg/mL unconjugated cetuximab diluted in serum free media for one hour at 4° C. prior to incubation with 1 µg/mL of EGF-IRDye 700DX. Cetuximab is a competitive inhibitor of EGF binding to EGFR. The cells were then washed one time with serum free media.

To induce IR700-dependent killing, the cells were then illuminated with a 690 nm laser with 32 J/cm² of light or protected from light ("no light"). Cell death was evaluated as described in Example 6 using CellTox Green. The normalized percentage of dead cells was calculated by subtracting all wells by the percentage of dead cells from the no light serum free media only control, dividing by EGF-IRDye 700DX at 32 J/cm² minus the no light serum free media only control, and multiplied 100.

Figure 11A:
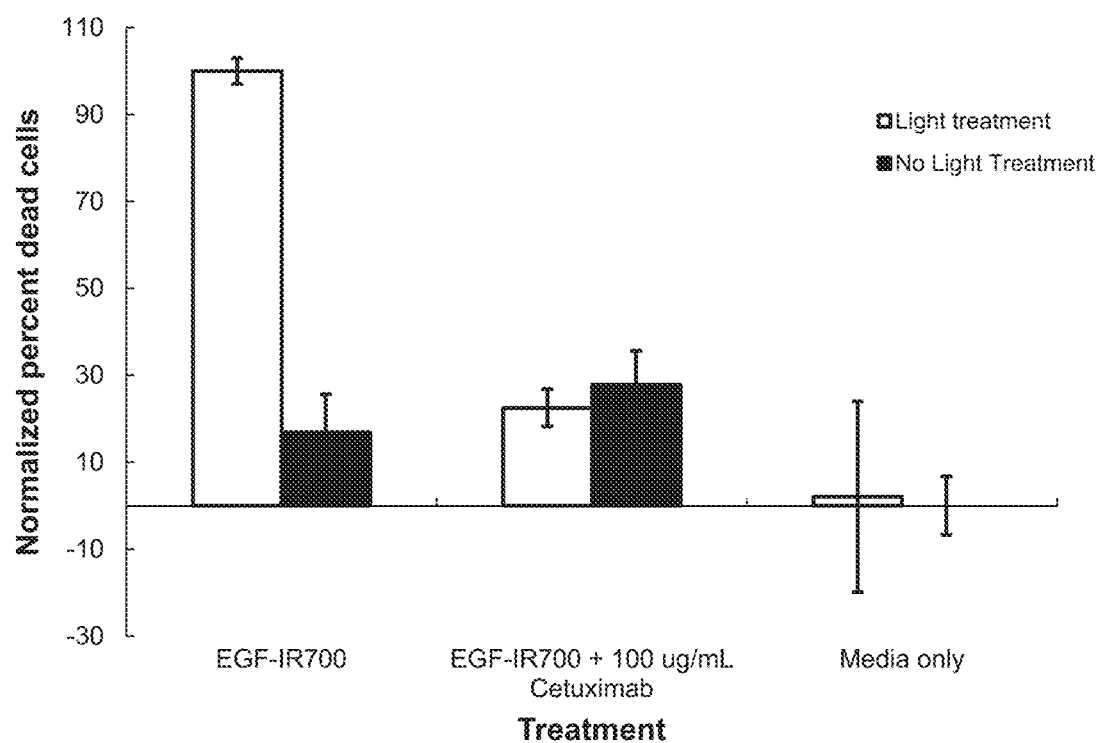
FIG. 11A shows the specificity of EGF-IRDye 700DX light-dependent killing in A431 cells.

As shown in FIG. 11A, the results showed that EGF-IRDye 700DX mediated cell killing is light-dependent killing with killing observed only when cells were treated with light to activate cell killing activity. Pre-exposure of A431 cells with 100 µg/mL unconjugated cetuximab prior to incubation with 1 µg/mL EGF-IRDye 700DX blocked light-dependent cell killing. A431 cells incubated with media alone did not exhibit any light-induced killing.

3. Effects of Light Pre-Exposure on Photo-Activated Activity

The effect of EGF-IRDye 700DX pre-exposure to white light versus green light on photo-activated cell killing was also evaluated in A431 cells. EGF-IRDye 700DX was pre-exposed to different types of light and the effect of light treatment on photo-activated killing activity was evaluated. Five microliters of EGF-IRDye 700DX conjugate (DAR 2) was added per clear HPLC vial at a EGF-IRDye 700DX concentration of 1.14 mg/mL. The following conditions were tested: (1) the antibody-IRDye 700DX conjugate stored at 4° C. protected from light ("4° C.", used as the control); (2) antibody-IRDye 700DX conjugate placed in a clear glass HPLC tube under a Halogen lamp at 2500 lux for 24 hrs ("white light"); (3) antibody-IRDye 700DX conjugate placed in a clear glass HPLC tube wrapped in aluminum foil to protect from light exposure under Halogen lamp at 2500 lux for 24 hrs ("no light"), used as a control for thermal heating effects on the formation of aggregates); and (4) antibody-IRDye 700DX conjugate placed in a clear glass HPLC tube and exposed to green LED lamp at 2500 lux for 24 hrs ("green light").

To assess cell killing activity, A431 cells were washed two times with serum free media, and incubated in serum free media alone for one hour at 4° C. The cells were then washed one time with serum free media and incubated with serum free media alone or serum free media containing 1 µg/mL of EGF-IRDye 700DX ("no light"), serum free media containing 1 µg/mL of EGF-IRDye 700DX pre-exposed to white light ("2500 Lux White light"), or serum free media containing 1 µg/mL EGF-IRDye 700DX pre-exposed to green light for one hour at 4° C. ("2500 Lux Green light"). The cells were then washed one time with serum free media.

To induce cell killing, the cells were either protected from light (light dose 0 J/cm$^2$) or were illuminated with a 690 nm laser with different light dosimetries (8 J/cm$^2$, 32 J/cm$^2$ or 64 J/cm$^2$).

Figure 11B:
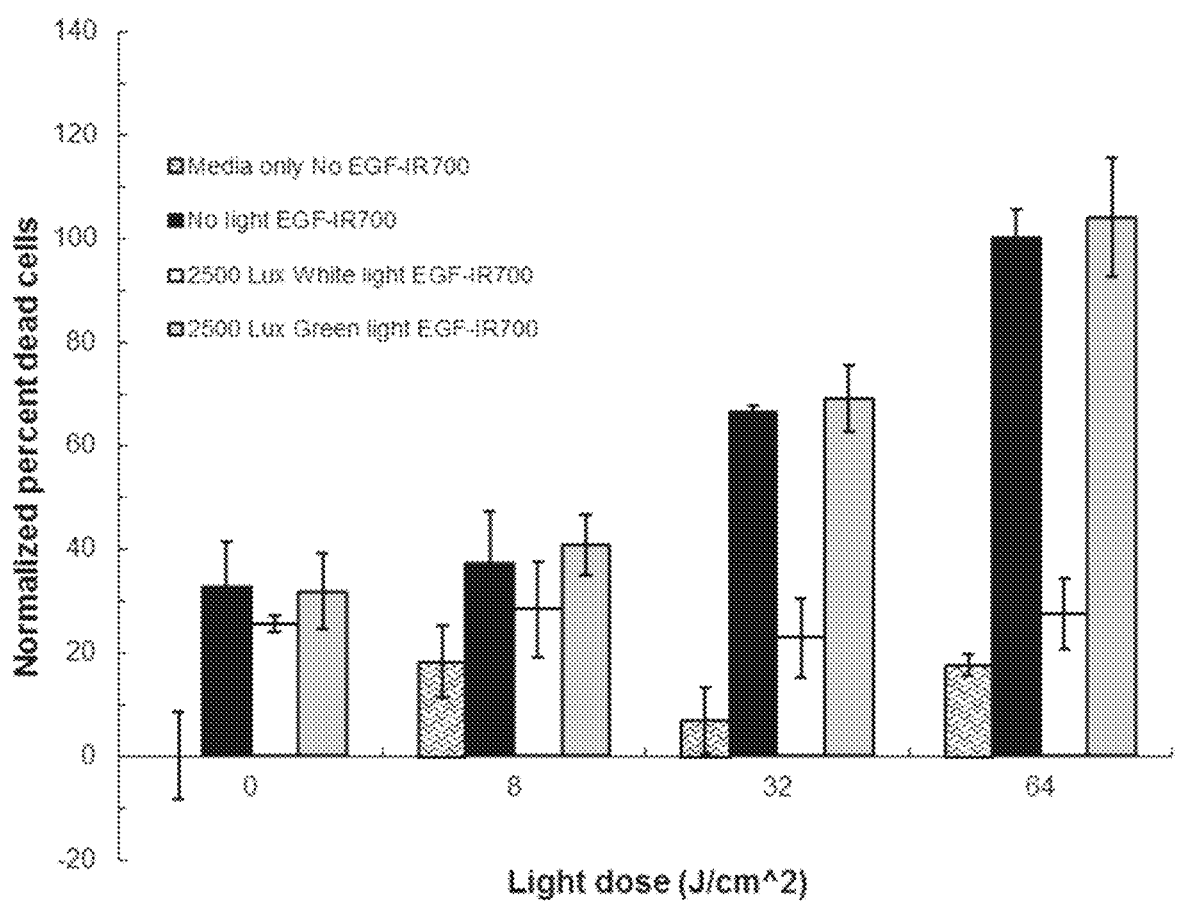
FIG. 11B shows the effect of EGF-IRDye 700DX pre-exposure to different types of light on light-dependent killing in A431 cells.

As shown in FIG. 11B, EGF-IRDye 700DX light-dependent killing activity was sensitive to pre-exposure to white light. A431 cells incubated with EGF-IRDye 700DX that had been protected from light exposure but not thermal heating under white light from a halogen lamp at 2500 lux for 24 hours exhibited light-dependent killing. A431 cells incubated with EGF-IRDye 700DX that had been exposed to white light from a halogen lamp at 2500 lux for 24 hours no longer exhibited light-dependent killing activity. A431 cells incubated with EGF-IRDye 700DX that had been exposed to green light from a green LED lamp at 2500 lux for 24 hours exhibited light-dependent killing activity comparable to that of the "no light" EGF-IRDye 700DX. A431 cells incubated with serum free media alone did not exhibit light-dependent killing activity.

B. Cholera Toxin B-IR700 Conjugate

To assess if cell killing can be mediated by a molecule that binds to non-protein molecules, Cholera Toxin B (Catalog No: C9903-2MG, Sigma Aldrich, St. Louis, Mo.) was conjugated to IRDye 700DX and evaluated to assess its killing activity upon pre-exposure to different wavelengths of light. Cholera toxin B binds specifically to glycolipid, GM1, which is a non-protein surface targeting molecule moiety.

1. Cholera Toxin B Conjugation

The protocol used for labeling of the Cholera Toxin B with IRDye 700DX was substantially the same as the protocol for antibody conjugation described in Example 5, except that the prior to conjugation, the Cholera Toxin B solution was first exchanged with phosphate buffer saline pH 7 using a 3,000 Dalton molecular weight cutoff centrifugal filter. For the conjugation, the solubilized IR700 NHS Ester was then added to the Cholera Toxin B solution at a 2 (IR700 NHS Ester) to 1 (Cholera Toxin B) molar ratio. After the conjugation reaction, which was performed substantially as described in Example 8, the Cholera Toxin B conjugate solution was then exchanged then exchanged with 24 mL of PBS pH 7 using a 10,000 Dalton molecular weight cutoff filter to remove free dye, glycine, and glycine-IR700, and to adjust the pH back to pH 7.

2. Cholera Toxin B-IR700 Killing Activity

Photo-activated cell killing using cholera toxin B-IR700 was assessed in BxPC3 cells. BxPC3 cells were washed three times with RPMI media supplemented with 1% Penicillin/Streptomycin (serum free media), then incubated with serum free media only or serum free media containing 2 µg/mL of cholera toxin B-IRDye 700DX (DAR ~2.9 per pentamer) for one hour at 4° C. The cells were then washed two times with serum free media.

To induce IR700-dependent killing, the cells were either protected from light (light dose 0 J/cm$^2$) or were illuminated with a 690 nm laser with different light dosimetries (2 J/cm$^2$, 8 J/cm$^2$ or 32 J/cm$^2$ or 96 J/cm$^2$). Cell death was evaluated as described in Example 6 using CellTox reagent. The normalized percentage of dead cells was calculated by subtracting all wells by the percentage of dead cells from the no light complete culture media only control, dividing by cholera toxin B-IRDye 700DX at 96 J/cm$^2$ minus no light complete culture media only control, and multiplied 100.

Figure 12A:
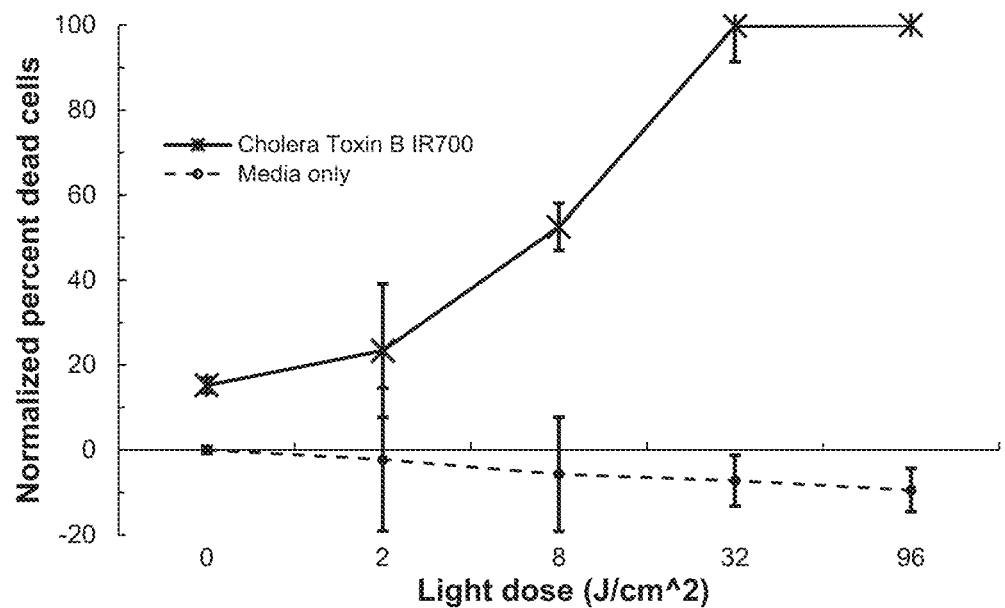
FIG. 12A shows the light-dependent killing of BxPC3 cells using Cholera Toxin B-IRDye 700DX.

As shown in FIG. 12A, the effect of light dose on light-dependent killing of BxPC3 cells was dose dependent, as evidenced by an increase in the normalized percent of dead BxPC3 cells that had been incubated with 2 µg/mL Cholera Toxin B-IRDye 700DX for 1 hour at 4° C. followed by irradiation in the presence of increasing light dose. No light dose dependent killing of BxPC3 cells treated only with complete culture media was observed.

To assess specificity of the photo-activated cell killing activity, BxPC3 cells were washed three times with serum free media, then incubated with complete culture media alone or complete culture media containing 100 µg/mL unconjugated cholera toxin B for one hour at 4° C. The cells were then washed one time with serum free media, and incubated for one hour at 4° C. with serum free media only, serum free media containing 2 µg/mL of cholera toxin B-IRDye 700DX, or 100 µg/mL unconjugated cholera toxin B with 2 µg/mL of cholera toxin B-IRDye 700DX. The cells were then washed two times with serum free media. To induce IR700-dependent killing, the cells were either protected from light (light dose 0 J/cm$^2$) or were illuminated with a 690 nm laser with at 96 J/cm$^2$ and cell death was evaluated as described above.

Figure 12B:
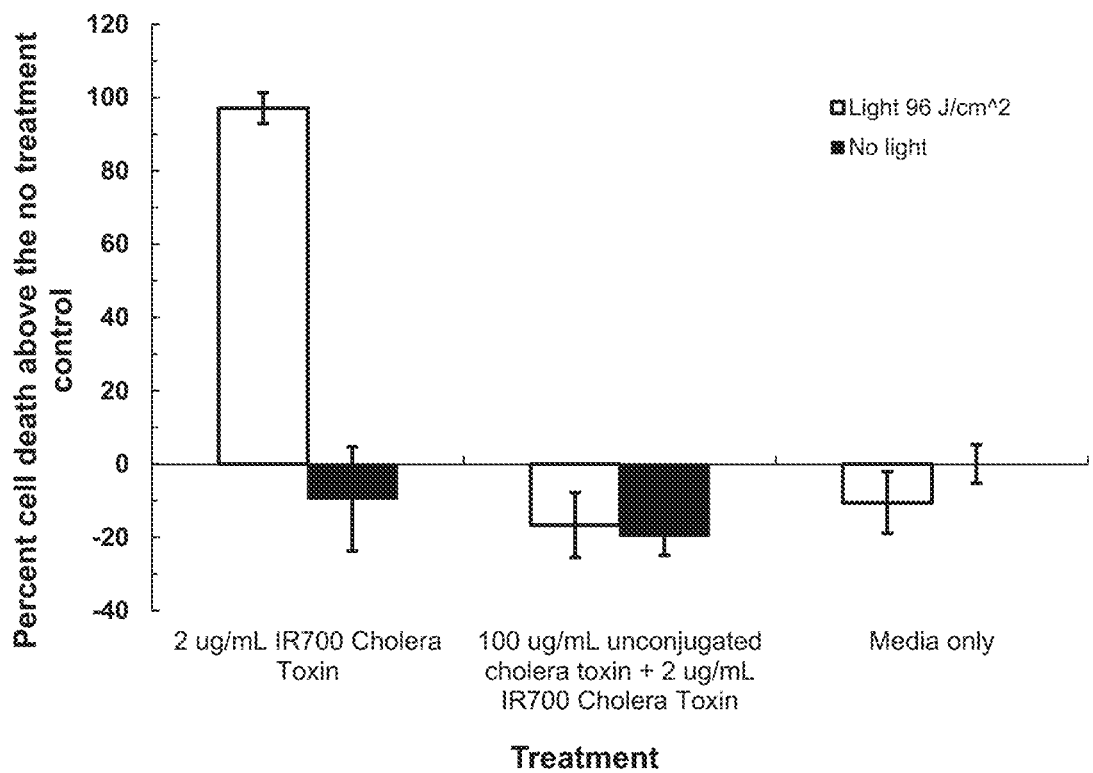
FIG. 12B shows the specificity of Cholera Toxin B-IRDye 700DX light-activated killing.

As shown in FIG. 12B, the results showed that pre-incubation of BxPC3 cells with 100× excess of the unconjugated cholera toxin B blocked Cholera Toxin B-IRDye 700DX light-dependent killing in BxPC3 cells, thereby indicating that the killing activity is dependent on binding of the Cholera toxin B to cells.

3. Effects of Light Pre-Exposure on Cell Killing Activity

The effect cholera Toxin B-IRDye 700DX pre-exposure to white versus green light on photo-activated killing activity was evaluated. Ten microliters of Cholera Toxin B-IRDye 700DX conjugate (DAR 2.9) was added per clear HPLC vial at a Cholera Toxin B-IRDye 700DX concentration of 1 mg/mL. The following conditions were tested: (1) Cholera Toxin B-IRDye 700DX conjugate placed in a clear glass HPLC tube wrapped in aluminum foil to protect from light exposure under Halogen lamp at 2500 lux for 24 hrs ("no light", used as a control for thermal heating effects on the formation of aggregates); (2) Cholera Toxin B-IRDye 700DX conjugate was placed in a clear glass HPLC tube under a Halogen lamp at 2500 lux for 24 hrs ("white light"); or (3) Cholera Toxin B-IRDye 700DX conjugate was placed in a clear glass HPLC tube and exposed to green LED lamp at 2500 lux for 24 hrs ("green light").

Cell killing induced by the cholera Toxin B-IRDye 700DX pre-exposed under the various conditions was assessed on BxPC3 cells as described above. Thus, all BxPC3 cell treatments were incubated with either serum free media alone or serum free media containing Cholera Toxin B-IRDye 700DX that had undergone pre-exposure to light of different wavelengths of light as described above.

Figure 12C:
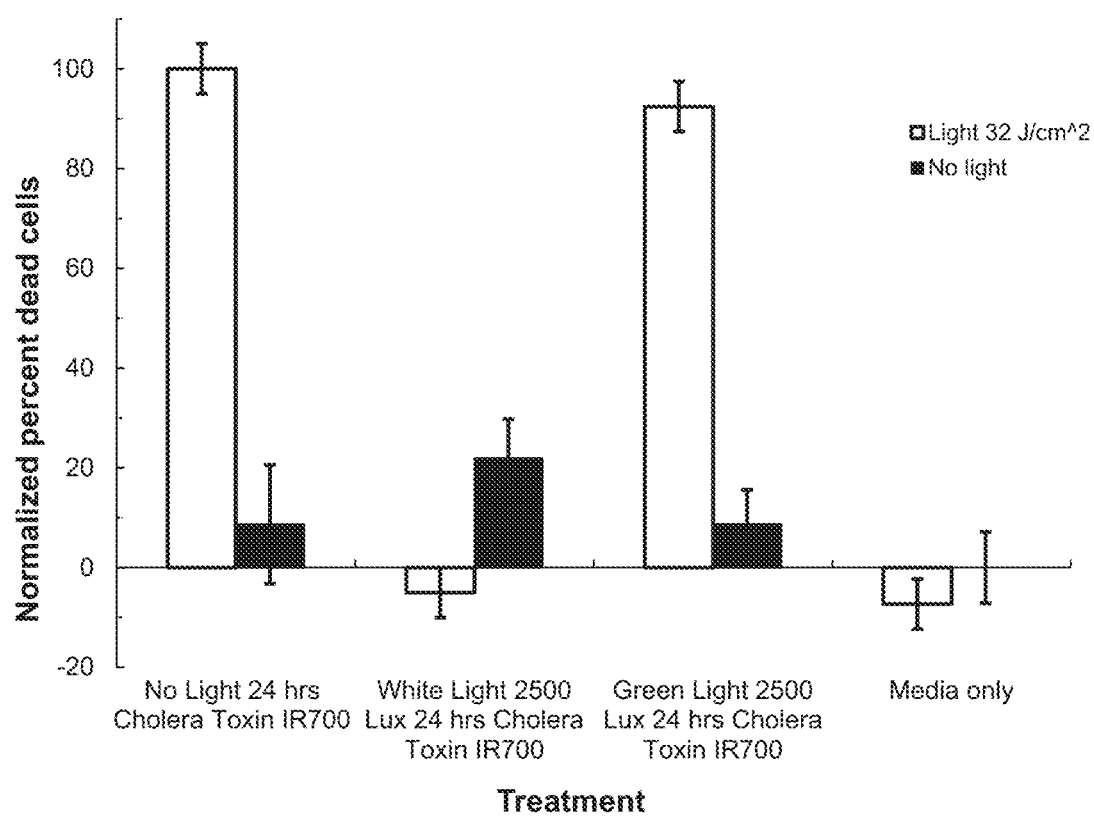
FIG. 12C shows the effect of pre-exposure of Cholera Toxin B-IRDye 700DX to different wavelengths of light on light-activated killing in BxPC3 cells.

As shown in FIG. 12C, light-dependent killing activity mediated by Cholera Toxin B-IRDye 700DX was sensitive to pre-exposure to white light. BxPC3 cells incubated with Cholera Toxin B-IRDye 700DX that had been protected from light exposure but not thermal heating under white light from a halogen lamp at 2500 lux for 24 hours exhibited light-dependent killing. BxPC3 cells incubated with Cholera Toxin B-IRDye 700DX that had been exposed to white light from a halogen lamp at 2500 lux for 24 hours no longer exhibited light-dependent killing activity. BxPC3 cells incubated with Cholera Toxin B-IRDye 700DX that had been exposed to green light from a green LED lamp at 2500 lux for 24 hours exhibited a slight decrease in light-dependent killing activity, but substantially less than that of the white light exposed Cholera Toxin B-IRDye 700DX treated cells.

BxPC3 cells incubated with serum free media alone did not exhibit light-dependent killing activity.

C. Influenza Virus-IR700

The following studies were performed to assess whether virus particles can be conjugated with phthalocyanine dyes such as IRDye 700DX for photo-activated cell killing. Effect of pre-exposure to white light on photo-activated virus-IR700 conjugate killing was also assessed.

1. Influenza Virus (X-31) Conjugation

Frozen solid aliquots of IRDye 700DX NHS Ester (Cat. No. 929-70011; Li-COR, Lincoln, Nebr.) were thawed at room temperature, then dissolved with DMSO to achieve a 10 mg/mL concentration. In a dark environment, 10 μg of IRDye 700DX NHS Ester was added to a 65,536 HA titer units of Influenza A X-31, A/Aichi/68 (H3N2) stock (Catalog No: 10100375, Charles River Laboratories, Wilmington, Mass.), and placed on the lowest setting possible on a table top vortexor for 2 hours at 25° C. A gravity flow column was used to separate the virus conjugate from the free dye by loading 100 μL of virus solution to a pre-phosphate buffer saline equilibrated Nap 5 gravity flow column (Catalog No: 17-0853-02, GE Healthcare Life Sciences, Pittsburgh, Pa.). After adding 650 μL of phosphate buffer saline, the flow through was discarded. An additional 400 μL phosphate buffer saline was loaded to the column and the flow through, which contained the conjugated virus, was collected. Prior to using the virus for experiments, the virus conjugate solution was filtered with a 0.2 μm pore size PVDF filter to remove any insoluble aggregates.

2. Influenza Virus (X-31)-IRDye 700DX Killing Activity

Vero cells were incubated with influenza virus (X-31)-IR700 to assess if cells associated with the influenza virus (X-31)-IR700 were susceptible to killing after light irradiation. Vero cells were washed four times with EMEM media supplemented with 1% Penicillin/Streptomycin (serum free media). Virus inoculation media was made by mixing 1200 μL serum free media with 400 μL of purified influenza virus (X-31)-IRDye 700DX flow through (prepared as described above), which was then filtered with a 0.2 μm pore size PVDF filter to remove any aggregates. 100 μL of virus inoculation media or 100 μL of serum free culture media was added to the cells, and incubated for 1 hr at 4° C. The cells then were washed once with 100 μL of serum free media.

Virus-associated cells or control Vero cells were then either protected from light (light dose 0 J/cm$^2$) or were illuminated with a 690 nm laser with different light dosimetries (2 J/cm$^2$, 8 J/cm$^2$, 32 J/cm$^2$ or 96 J/cm$^2$). Cell death was evaluated as described in Example 6 using CellTox Green.

Figure 13A:
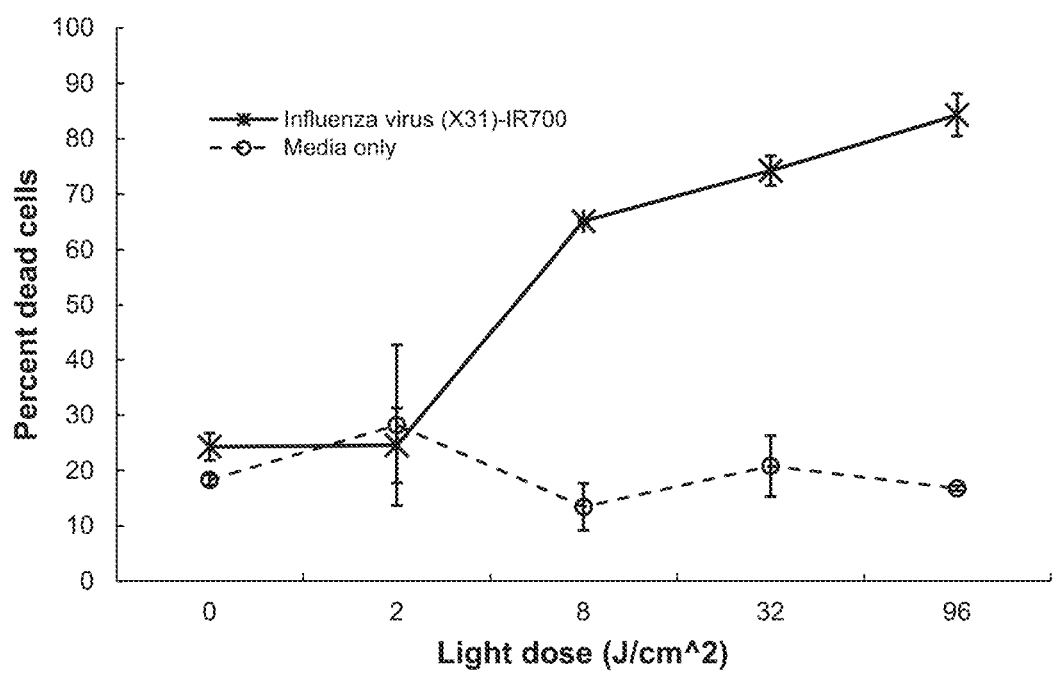
FIG. 13A shows the light-dependent killing of Vero cells with Influenza virus (X-31)-IRDye 700DX.

As shown in FIG. 13A, Vero cells that were inoculated with Influenza virus (X-31)-IRDye 700DX were killed in a light dose-dependent manner. Vero cells incubated in complete culture media without virus did not exhibit light dependent killing.

3. Effects of Light Pre-Exposure on Conjugate Activity

The influenza virus (X-31)-IRDye 700DX was tested for the effect of pre-exposure to light on photo-activated light-dependent killing activity under three different light-exposure conditions, including to the different wavelengths of white light vs. green light. Approximately 130 uL of influenza virus (X-31)-IRDye 700DX flow through was added per clear HPLC vial and tested after exposure to the following conditions: (1) influenza virus (X-31)-IRDye 700DX conjugate was placed in a clear glass HPLC tube wrapped in aluminum foil to protect from light exposure under a Halogen lamp (Catalog No: PL-800, Dolan-Jenner, Boxborough, Mass.) at 2500 lux for 18 hrs ("no light", to control for thermal heating effects); (2) the influenza virus (X-31)-IRDye 700DX conjugate was placed in a clear glass HPLC tube under a halogen lamp at 2500 lux for 18 hrs ("white light"); (3) influenza virus (X-31)-IRDye 700DX conjugate was placed in a clear glass HPLC tube and exposed to green LED lamp (Catalog No: Green-ECS GP19 EcoSmart) at 2500 lux for 18 hrs (("green light").

Cell killing induced by inoculation of Vero cells with influenza virus (X-31)-IRDye 700DX pre-exposed under the various conditions was assessed as described above after illumination with a 690 nm laser with a light dose of 96 J/cm$^2$. Thus, all Vero cell treatments were incubated with either serum free media alone or serum free media containing influenza virus (X-31)-IRDye 700DX that had undergone pre-exposure to light of different wavelengths of light.

Figure 13B:
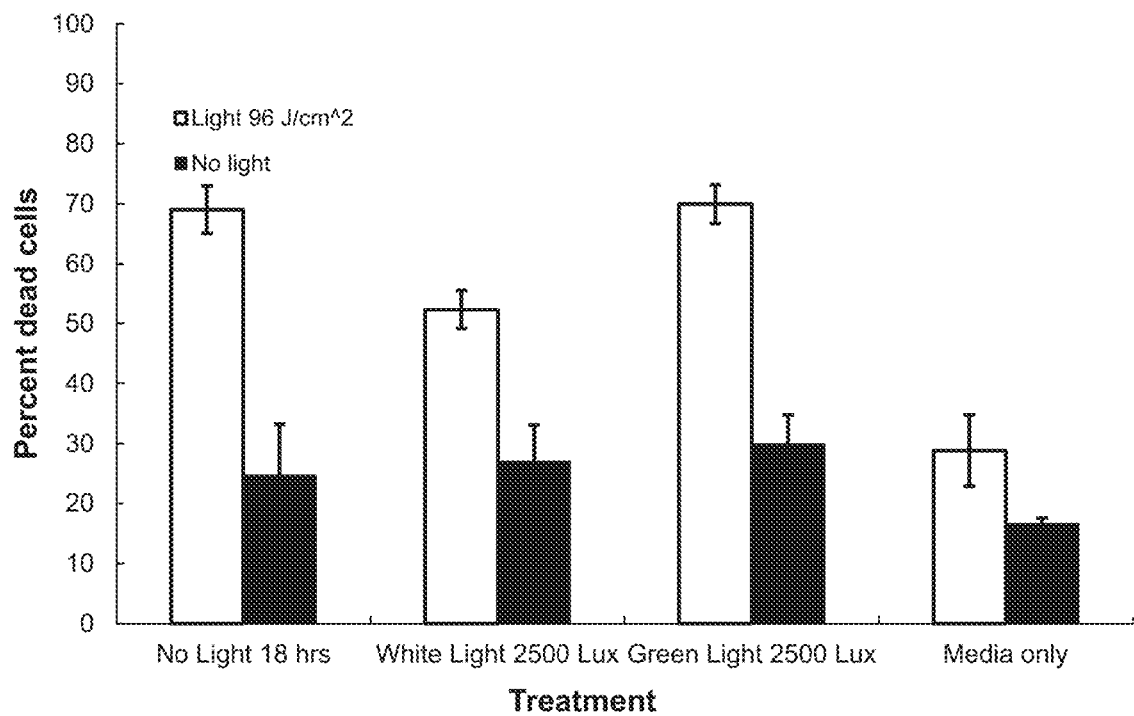
FIG. 13B shows the effect of pre-exposure of influenza virus (X-31)-IRDye 700DX to white light vs. green light on photo-activated cell killing.

As shown in FIG. 13B, light-dependent killing activity mediated by influenza virus (X-31)-IRDye 700DX is sensitive to pre-exposure to white light. Vero cells incubated with influenza virus (X-31)-IRDye 700DX that had been protected from light exposure with aluminum foil ("no light") exhibited light-dependent killing. However, the extent of cell killing was decreased in Vero cells incubated with influenza virus (X-31)-IRDye 700DX that had been exposed to white light from a halogen lamp at 2500 lux for 18 hours compared to cell treated with the "no light" influenza virus (X-31)-IRDye 700DX that had been protected from light. In contrast, incubation of Vero cells with influenza virus (X-31)-IRDye 700DX that had been exposed to green light from a green LED lamp at 2500 lux for 18 hours exhibited the same photo-activated killing activity as that of the "no light" influenza virus (X-31)-IRDye 700DX that had been protected from light. Vero cells incubated with serum free media alone did not exhibit light-dependent killing activity.

Example 11: Assessment of Cell Killing Activity of Additional Molecule:IR700 DX Conjugates Studies were performed to assess the cell killing activity of additional non-antibody IR700 conjugates that can bind to non-protein surface molecules. In an exemplary additional study, the effect of of *Sambucus Nigra* Lectin (SNA; also called Elderberry lectin, EBL) (Catalog No: L-1300, Vector Labs, Burlingame, Calif.) conjugated to IRDye 700DX was evaluated to assess its killing activity. SNA binds specifically to alpha(2,6)-linked sialic acids on glycoproteins on cells. The SNA-IR700 also was assessed for light-induced aggregation using size exclusion chromatography, but in this exemplary experiment there was no effect on the size exclusion chromatography of the SNA-IR700 conjugate exposed to white light versus green light.

1. Elderberry Lectin (SNA) Conjugation

The protocol used for labeling of the SNA with IRDye 700DX is substantially the same as the protocol for antibody conjugation described in Example 5.

2. SNA-IR700-Light-Dependent Killing Activity

To assess if SNA-IR700 was able to elicit cell killing after light irradiation, cell killing was assessed in BxPC3 cells. BxPC3 cells were dissociated from the cell culture plate and the cell culture media containing RPMI media supplemented with 10% Fetal Bovine Serum and 1% Penicillin/Streptomycin (complete culture media) was exchanged for RPMI media supplemented with 1% BSA and 1% Penicillin/Streptomycin (binding media). The BxPC3 cells were transferred to separate tubes containing binding media only or binding media containing 10 μg/mL SNA-IRDye 700DX at a dye antibody ratio (DAR) of ~2.5), and incubated for one hour at 4° C. The cells were then transferred to plates pre-coated with 200 μg/mL unconjugated SNA (1 hr coating treatment at 37° C., and washed 3 times with serum free media) to block non-specific binding of the SNA-IRDye 700DX to the plates.

To induce IR700-dependent killing, the cells were either protected from light (light dose 0 J/cm$^2$) or were illuminated with a 690 nm laser with different light dosimetries (8 J/cm$^2$, 32 J/cm$^2$ or 96 J/cm$^2$). Cell death was evaluated as described in Example 6 using CellTox Green.

Figure 14A:
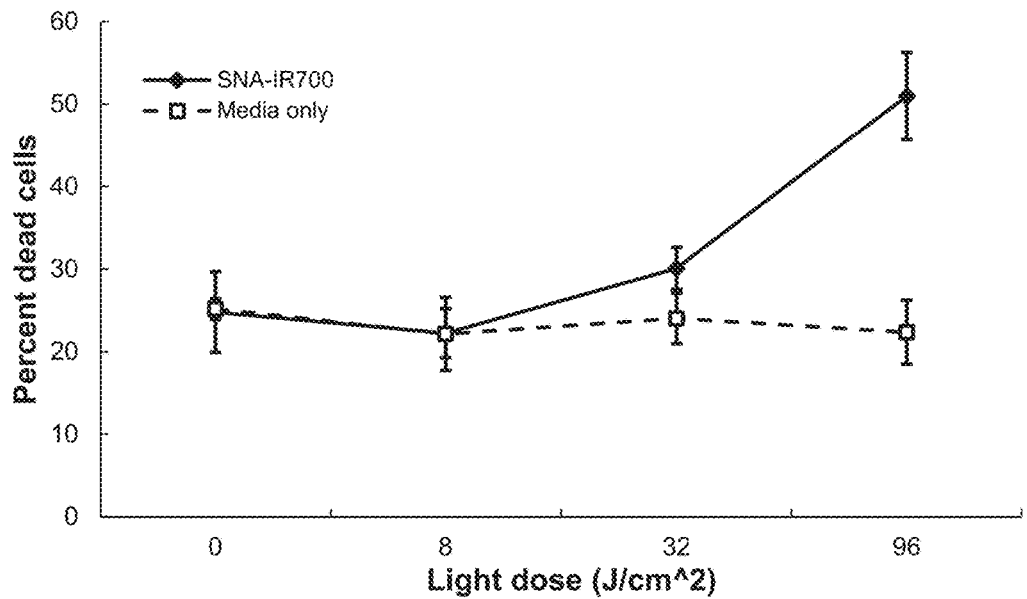
FIG. 14A shows the effect of light dose on SNA-IRDye 700DX killing activity in BxPC3 cells.

As shown in FIG. 14A, BxPC3 cells incubated with SNA-IRDye 700DX exhibited light dependent killing. BxPC3 cells treated with complete culture media in the absence of an IR700 conjugate did not exhibit light dependent killing.

To assess the specificity of the cell killing, BxPC3 cells were treated with sialidase A, which cleaves alpha(2,6)-linked sialic acids, the receptor for SNA. BxPC3 cells were dissociated from the tissue culture flask, and fixed with 10% formalin for 20 minutes. The cells were then washed 3 times with PBS, and treated with a 1× reaction buffer alone (diluted from a 5× Glyco Sialidase A-51 reaction buffer, catalog number GK80045, Prozyme), 1× reaction buffer containing 0.025 U sialidase A, or 1× reaction buffer containing 0.075 U sialidase A for 2 hours at 37° C. The cells were then washed three times with PBS, and then incubated with PBS alone or PBS containing 10 μg/mL SNA-IRDye 700DX for 1 hour at 4° C.

After the incubation, the cells were washed three times with PBS, stained with DAPI nuclear stain, and then plated onto 96 well dish and imaged on an epi-illumination fluorescent microscope. At least 10 regions were chosen and imaged to detect DAPI nuclear stain and SNA-IRDye 700DX fluorescent signal. To compare fluorescent intensity of the tested groups, background subtraction was performed by subtracting the minimum pixel intensity of a given image from all other pixels in the same image. The DAPI nuclear signal was thresholded and used as the representative area for each cell. The segmented DAPI image was then used to determine the area for each individual cell to be quantified for average fluorescence intensity in the channel used to image the SNA-IRDye 700DX. Because the SNA-IRDye 700DX staining is a membrane stain that is diffuse and because an epi-illumination microscope was used, the average fluorescent signal measured from the masked region as defined by the DAPI nuclear stain could be used as a representative average fluorescent intensity for SNA-IRDye 700DX staining per cell. The average fluorescence intensity was collect for hundreds of cells per treatment condition and plotted in a box and whisker plot.

Figure 14B:
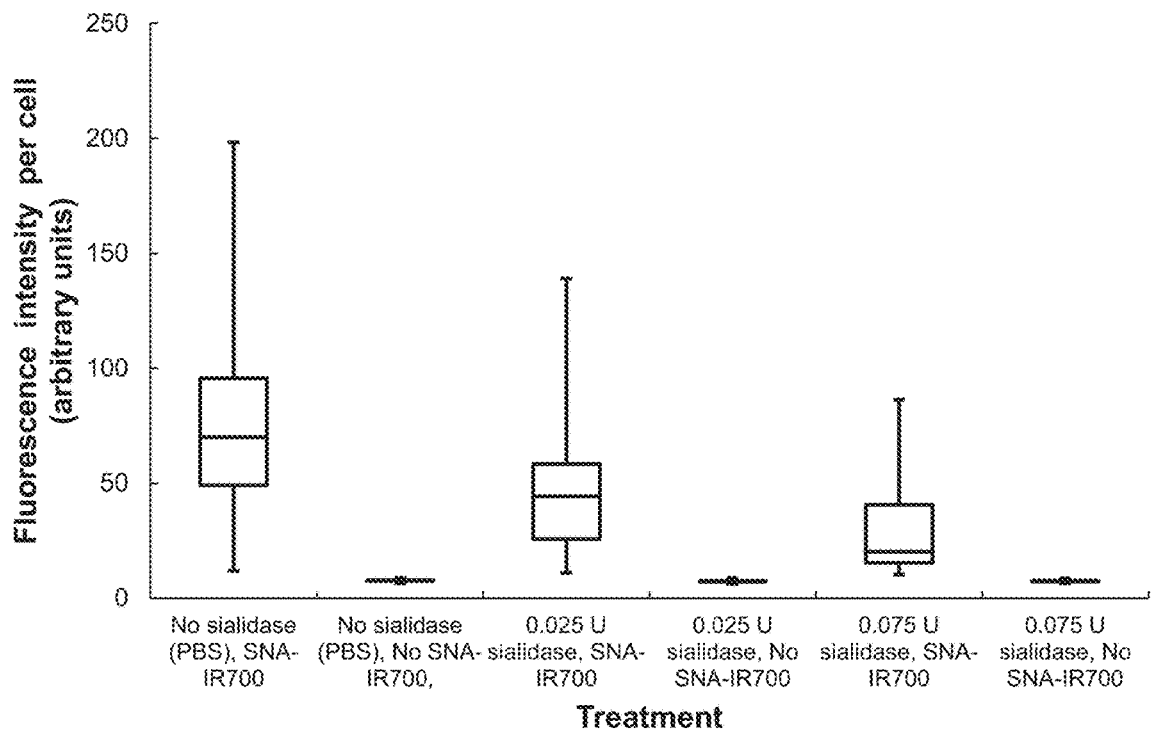
FIG. 14B shows the effect of sialidase treatment on the specificity of SNA-IRDye 700DX binding to cells.

The fluorescent intensity results of the tested groups after treatment of cells with sialidase A is shown in FIG. 14B. The results showed that a dose dependent increase in sialidase A treatment resulted in a concomitant decrease in SNA-IRDye 700DX staining in the sample. Dose dependent increase in sialidase A treatment did not result in any change in fluorescence from the channel used to detect the SNA-IRDye 700DX when BxPC3 cells were not stained with SNA-IRDye 700DX.

Example 12: IR700-Conjugate-Mediated PIT Killing of Bacterial Pathogens

The following studies were performed to assess whether antibodies directly conjugated to a phthalocyanine photosensitizer such as IRDye 700DX can kill bacterial cells by binding to proteins displayed on its cell surface. Protein A is a protein displayed on the cell surface of *Staphylococcus aureus* (*S. aureus*) that binds to the Fc region of antibodies.

Cetuximab-IR700, conjugated substantially as described in Example 1, was used in these studies. *S. aureus* was acquired from American Type Culture Collection (ATCC) ID 6538. *S. aureus* was grown on either Brain Heart Infusion (BHI) agar plates for colony selection and counting, or BHI broth (complete culture media) for population expansion.

To evaluate bacterial cell-induced PIT killing, *S. aureus* was incubated with 100 μg/mL of cetuximab-IRDye 700DX for one hour at room temperature. The cells were then illuminated with a 690 nm laser at 0 or 300 J/cm$^2$. The number of remaining viable bacterial cells was determined by counting colony forming units (CFU) on BHI agar plates under the following conditions. As a control, the number of viable bacterial cells also was assessed in cells treated with cetuximab-IRDye 700DX incubation alone but without laser illumination, laser illumination alone, or untreated. Percent of viable CFU was normalized to bacterial cells with no treatment.

Figure 15:
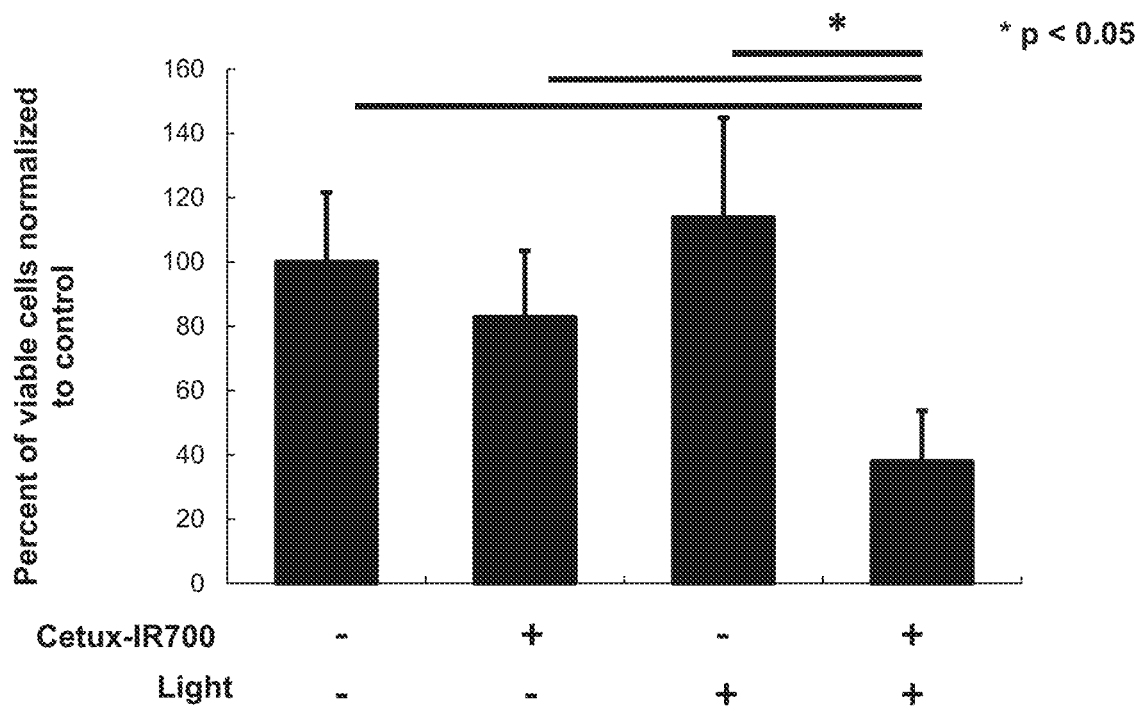
FIG. 15 shows the PIT killing of S. aureus by Cetuximab-IRDye 700DX in combination with laser illumination.

The results are shown in FIG. 15, which shows that PIT-mediated cell killing of *S. aureus* can occur in the presence of an antibody-IR700 conjugate that binds to Protein A. Only the bacterial cells that were incubated with cetuximab-IRDye 700DX with subsequent laser illumination had a statistically significant CFU reduction in comparison to the other three groups.

Example 13: IR700-Conjugate-Mediated PIT Killing of Virus Pathogens

The following studies were performed to assess whether virus infectivity can be inhibited by performing PIT on virus particles with phthalocyanine-labeled anti-virus antibodies. An exemplary study was performed using influenza virus as a specific example in which indirect PIT treatment was performed against influenza virus particles coated with mouse anti-influenza virus A (H3N2) and goat anti-mouse Fab-IRDye 700DX antibodies. Because indirect labeling of primary unconjugated antibodies with secondary antibody-IRDye 700DX conjugates can induce PIT killing similar to that of direct conjugated primary antibodies, the findings can be generalized to directly conjugated anti-virus-IRDye 700DX antibodies. Thus, these results demonstrate that PIT treatment can lead to inhibition of virus infection AffiniPure Fab Fragment Goat anti-mouse IgG1 specific (GtxMs Fab) antibody (Catalog number: 115-007-185, Jackson ImmunoResearch Laboratories, West Grove, Pa.) was conjugated to IR700 substantially as described in Example 5, except the GtxMs Fab antibody solution was first exchanged with phosphate buffer saline pH 7 using a 10,000 Dalton molecular weight cutoff centrifugal filter, then the antibody solution pH was adjusted to a pH of 8.5 with addition of phosphate buffer at pH=9. Frozen solid aliquots of IRDye 700DX NHS Ester (Cat. No. 929-70011; Li-COR, Lincoln, Nebr.) were thawed at room temperature, then dissolved with DMSO to achieve a 10 mg/mL concentration. In a dark environment, the solubilized IR700 NHS Ester was then added to the antibody solution at a 2 (IR700 NHS Ester) to 1 (antibody) molar ratio. The conjugation reaction proceeded at 25° C. for 2 hours protected from light. Glycine (pH 8.2) was added to a final concentration of 10 mM for 15 minutes to quench the reaction. The antibody conjugate solution was then exchanged with 24 mL of PBS pH 7 using a 10,000 Dalton molecular weight cutoff centrifugal filter to remove free dye, glycine, and glycine-IR700, and to adjust the pH back to pH 7.

For PIT, influenza A virus was indirectly associated with IR700 by mixing 1 µg of mouse Anti-Human Influenza A (H3N2) (F49) (Catalog No: M146, TaKaRa, Katsushika Tokyo, Japan) and 1 µg of GtxMs Fab-IRDye 700DX for 5 minutes at 25° C. in the dark, followed by a 30 minute incubation with 16,384 HA titer units of Influenza A X-31, A/Aichi/68 (H3N2) stock (Catalog No: 10100375, Charles River Laboratories, Wilmington, Mass.) for 30 minutes at 25° C. in the dark. Approximately 875 µL of EMEM supplemented with 1% Penicillin/Streptomycin (serum free media) was added, and the incubated virus was filtered with a 0.2 m pore size PVDF filter to remove any insoluble aggregates (virus inoculation media). The incubation was performed in duplicate. For one of the duplicate samples, the antibody-virus solution was exposed 144 J/cm$^2$ of 690 nm light, while the other sample was protected from light.

PIT-treated virus were evaluated for infectivity with Vero cells. Twenty four hours prior to labeling influenza virus (X-31) with the mouse-anti-influenza virus A (H3N2) and the GtxMs Fab-IRDye 700DX, 125,000 Vero cells were plated in a 6 well dish. The following day after seeding the cells and after labeling the influenza virus ($X^{31}$) with the mouse anti-influenza virus (H3N2) antibody with GtxMs Fab-IRDye 700DX, the cells were washed four times with serum free media. The cells were then incubated with 100 µL of light-treated virus inoculation media, no light treated virus inoculation media, or serum free media for 1 hour at 37° C. The media was then replaced with EMEM supplemented with 0.3% bovine serum albumin (BSA) and 1% Penicillin/Streptomycin. After 14 hours post virus inoculation, the cells were trypsinized, and resuspended in EMEM supplemented with 10% fetal bovine serum and 1% Penicillin/Streptomycin, and placed into Eppendorf tubes. Cells were then fixed with 10% formalin for 20 minutes, and subsequently washed 3 times with phosphate buffer saline (PBS, pH 7). For each wash step, cells were spun down at 1500 rpm for 3 minutes, supernatant was removed, and the cell pellet was resupended with 1 mL of PBS.

The cells were then incubated for 30 minutes at 25° C. with "block buffer" containing PBS supplemented with 3% Bovine Serum Albumin (IgG-Free, Protease-Free) (Catalog No: 001-000-162, Jackson ImmunoResearch Laboratories, Wilmington, Mass.) and 0.08% saponin. The cells were then incubated for 1 hour 10 minutes at 25° C. with 1:2000 mouse (IgG2a) Anti-Influenza A Virus Nucleoprotein antibody [AA5H] (Catalog no: ab20343, Abcam, Cambridge, United Kingdom) diluted in block buffer. The cells were subsequently washed 3 times with block buffer by spinning the cells down at 1500 rpm for 3 minutes, removing the supernatant, resuspending the cell pellet with 100 µL of block buffer, and incubating the cells for at least 5 minutes at 25° C. prior to the next wash. After washing out the primary antibody, the cells were incubated for 30 minutes at 25° C. with 1:250 AlexaFluor 488-conjugated AffiniPure Goat Anti-Mouse IgG FcGamma Subclass 2a specific (Catalog No: 115-545-206, Jackson ImmunoResearch Laboratories, Wilmington, Mass.) diluted in block buffer. The cells were then washed 3 times with 100 µL per wash of block buffer with at least 5 minutes per wash step, followed by 3 additional washes with PBS. The cells were then spotted on a 96 well plate, and imaged with a fluorescent microscope (Evos, Life Technologies). At least 12 random regions of interest were randomly chosen to obtain the brightfield image and corresponding fluorescent image taken with the GFP excitation and emission cube. The brightfield image was used to obtain the total number of cells, and the fluorescent image was used to detect the presence of nucleoprotein expression, a readout that the cell was infected with influenza virus infection.

Figure 16:
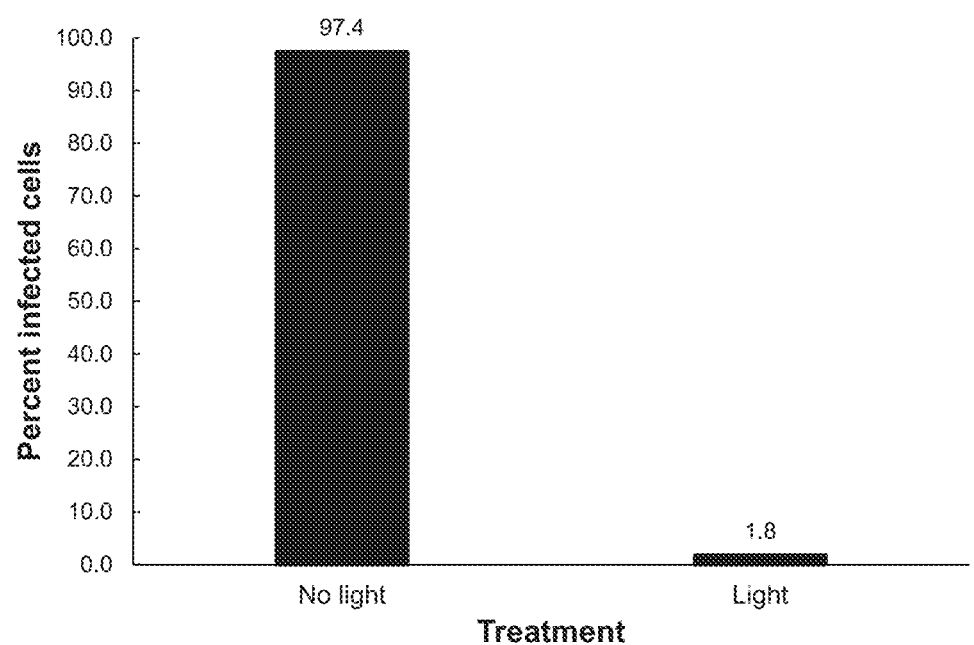
FIG. 16 shows the PIT of influenza virus particles using pre-complexed mouse anti-influenza virus (H3N2) with GtxMs Fab-IRDye 700DX.

The effect of influenza virus particles coated with anti-HA and goat anti-mouse IRDye 700DX (GtxMs Fab-IRDye 700DX) exposure to 690 nm light on virus infectivity was evaluated. The results in FIG. 16 show that PIT on influenza virus particles using pre-complexed mouse anti-influenza virus (H3N2) with GtxMs Fab-IRDye 700DX abrogates influenza virus infection. Vero cells incubated with virus coated with pre-complexed mouse anti-influenza virus (H3N2) and GtxMs Fab-IRDye 700DX that were not exposed to 690 nm light resulted in robust virus infection, with about 97.4% of the Vero cells staining for influenza virus nucleoprotein expression. In stark contrast, Vero cells incubated with PIT-treated virus coated with mouse anti-influenza virus (H3N2) and GtxMs Fab-IRDye 700DX exhibited a significant decrease in virus infection, with only 1.8% of the cells staining for influenza virus nucleoprotein expression.

Example 14: IR700-Conjugate-Mediated PIT Killing of Pathogen Infected Cells

The following studies were performed to assess whether virus-infected cells can be selectively treated with PIT with anti-virus antibodies labeled with phthalocyanine dyes (such as IRDye 700DX) either through direct conjugation or indirect labeling with secondary antibody conjugates. The exemplary data includes performing PIT on influenza virus-infected cells using indirect PIT with mouse anti-influenza virus (H3N2) antibodies and Goat anti-mouse-IRDye 700DX secondary antibodies.

In this study, conjugation of AffiniPure Fab Fragment Goat anti-mouse IgG1 specific (GtxMs Fab) antibody with IR700 was performed substantially as described in Example 5.

Vero cells were infected with Influenza virus prior to treating the virus or cells with PIT. Approximately 5,000 Vero cells were plated in a 96 well clear bottom, black plates. The following day after seeding the cells, the cells were washed four times with 100 µL of EMEM supplemented with 1% Penicillin/Streptomycin (serum free media), then incubated with serum free media containing 327.68 HA titer units of Influenza A X-31, A/Aichi/68 (H3N2) (Catalog No: 10100375, Charles River Laboratories, Wilmington, Mass.) per well. The cells were then incubated with the virus inoculation media or serum free media for 90 minutes at 37° C., after which the virus inoculation media was then replaced with EMEM supplemented with 0.3% bovine serum albumin (BSA) and 1% Penicillin/Streptomycin.

Virus infected cells were then labeled with IR700 14 hours post virus inoculation. Briefly, the cells were incubated for one hour at 4° C. with 1 µg/mL of of mouse Anti-Human Influenza A (H3N2) (F49) (Catalog No: M146, TaKaRa, Katsushika Tokyo, Japan) diluted with EMEM supplemented with 10% fetal bovine serum and 1% Penicillin/Streptomycin (complete culture media). The cells were then washed one time with complete culture media, and then incubated for one hour at 4° C. with 5 µg/mL of GtxMs-IRDye 700DX diluted in complete culture media. The cells were then washed once with 100 µL of complete culture media. To induce PIT, the cells were illuminated with a 690 nm laser at 64 J/cm$^2$ or protected from light ("no light").

Cell death was evaluated using CellTox Green reagent. After the light treatment, all cells were incubated with 1× CellTox Green reagent diluted in complete culture media for 15 minutes at 37° C., then imaged with a fluorescent microscope (Evos, Life Technologies). At least 5 random regions of interest per well for at least three different wells were randomly chosen to obtain the brightfield image, anti-influenza virus fluorescent image using a Cy5 excitation and emission cube, and CellTox Green fluorescent image using a GFP excitation and emission cube. Cells that were then scored for anti-influenza virus staining as an indication for the cell being virus infected. Of the virus infected cells, the cells were then scored for whether there was CellTox Green staining.

Figure 17:
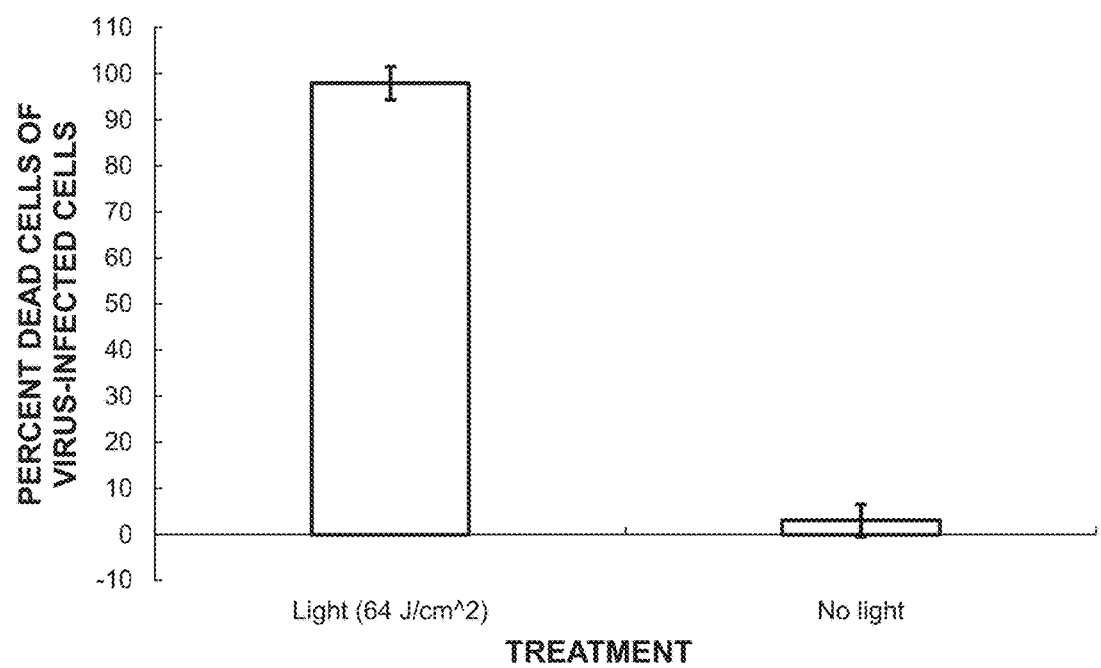
FIG. 17 shows the light-dependent killing of influenza virus infected cells with Mouse anti-influenza virus (H3N2) and Goat anti-Mouse IRDye 700DX (GtxMs-IR700).

As shown in FIG. 17, the results showed that PIT induced cell death was observed in influenza virus-infected Vero cells that had been sequentially labeled with mouse anti-influenza virus (H3N2) and goat anti-mouse IRDye 700DX (GtxMs-IRDye 700DX) followed by light irradiation. The extent of cell death that was observed was light-dependent, since only negligible cell death was observed in the absence of light treatment.

Example 15: IR700-Conjugate-Mediated PIT Killing of Neurons

The following study was performed to assess whether neurons can be killed by PIT using conjugates of IRDye 700DX. Dorsal Root Ganglion (DRG) neurons were subjected to PIT with the B subunit of Cholera Toxin conjugated with IRDye 700 DX. Irradiation with laser light of 690 nm resulted in complete cell death as measured in a luminescence based cell toxicity assay. Without light administration no significant cell death was observed. The findings demonstrate that PIT can be an effective treatment to kill neurons, and more broadly, to kill non-cancer cells, including primary cells.

Rat embryonic DRGs were obtained from Lonza (catalog number R-eDRG-515, Lonza Walkersville, Inc., Walkersville, Md.) in cryo-preserved format and stored in liquid Nitrogen until used. Black-wall 96-well plates were coated with 50 µL PBS per well containing 30 µg/mL poly-D-lysine (Sigma-Aldrich, catalog P0899, St. Louis, Mo.) and 2 µg/mL laminin (Sigma-Aldrich, L2020, St. Louis, Mo.) for 1 hour at room temperature, following stock solution preparation and procedures by Lonza. The coating solution was aspirated and the plates let dry for an hour (open lid in biosafety cabinet) and used immediately for cell seeding. The instructions provided by Lonza were strictly followed for thawing and plating the cells. The culture medium was PNBM supplemented at all times with 2 mM L-glutamine, 50 µg/mL Gentamicin, 37 ng/mL Amphotericin and 2% NSF-1, but the latter was added fresh each time before use. These components were part of a kit (catalog number CC-4461, Lonza, Basel, Switzerland). Additionally, nerve growth factor (NGF, catalog number N2513, Sigma, St. Louis, Mo.) was also added fresh at the time of use to 100 ng/mL. To plate cells, a 0.25 mL vial was thawed and dropwise diluted with 3.75 mL culture medium, and 200 µL suspension was seeded into wells. Cells were incubated for 4 hours at 37° C. and 5% CO2, and the medium was replaced with medium also containing the mitotic inhibitors 5-fluoro-2'-deoxyuridine (7.5 µg/mL final concentration, catalog number F-0503, Sigma, St. Louis, Mo.) and uridine (17.5 µg/mL final concentration, catalog number U-3003, Sigma, St. Louis, Mo.) that were added just before use. The medium was changed again every 3-4 days.

The conjugation of Cholera Toxin B with IR700 was performed as described in Example 10.B.

After culturing rat embryonic DRGs for for 11 days, 1 µg/mL stock solution of Cholera Toxin B-IR700 was diluted to 40 µg/mL with culture medium and 5 µL of the diluted conjugate was added directly to the wells of a 96-well plate containing DRG neurons in 200 µL medium, to achieve a final concentration of 5 µg/mL conjugate. Cells were incubated for 1 hour at 37° C. The culture medium was removed, the cells washed once with culture medium, and 100 µL fresh culture medium was added. The stained neurons were then illuminated with a 690 nm laser at a light dose of 64 J/cm$^2$ (150 mW/cm$^2$), or left protected from light as a control ("no light").

The effect of PIT on DRG neurons was measured with the luminescence based toxicity assay CytoTox Glo (catalog number G9291, Promega, Madison, Wis.). This assay is based on membrane integrity and employs a pro-substrate for luciferase that cannot penetrate intact cells. When cells die, damage in the plasma membrane allows enzymes to diffuse out of cells and activating the pro-substrate, now becoming a real substrate for luciferase, resulting in a luminescence signal. Plates were equilibrated to room temperature for 15 minutes, and 50 µL assay reagent was added. After incubating for 20 minutes at room temperature, luminescence was read on a multi-mode reader. To determine complete cell death, 50 µL digitonin solution was added to kill remaining viable cells, and after 20 minutes luminescence was read again. The background values from wells without cells were subtracted from each read, and percent cell death was calculated as the ratio between luminescence before and after lysis with digitonin, multiplied by 100.

Figure 18:
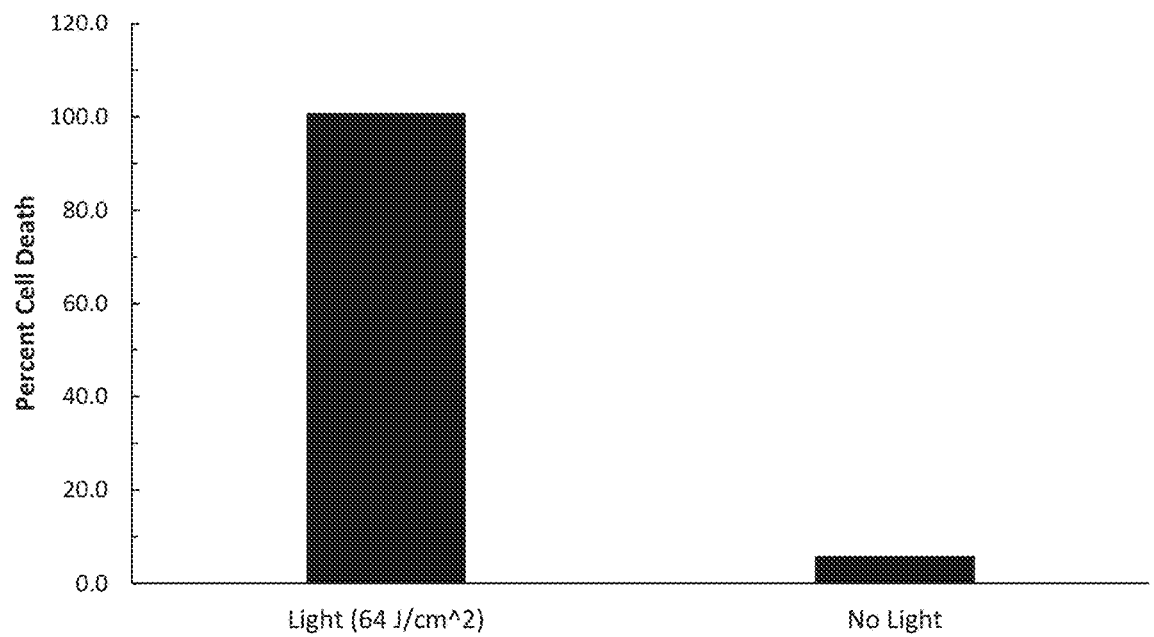
FIG. 18 shows the PIT killing of rat embryonic dorsal root ganglion (DRG) neurons using Cholera Toxin B-IRDye 700DX.

As shown in FIG. 18, PIT induced cell death in Rat Embryonic DRG Neurons. Irradiation with 690 nm laser light of 64 J/cm$^2$) lead to 100 percent cell death after 3 hours (left bar), whereas light protected cells ("No Light") remained unharmed (6% dead cells, right bar).

Example 16: Combination Treatment with Interferon Gamma and Anti-PD-L1-IR700 PIT The following studies were performed to assess whether PIT can be combined with immune modulatory agents-which can also affect cancer cells- to enhance PIT-killing activity.

A. Effect of Interferon Gamma on Cell Death

BxPC3 cells (#CRL-1687, ATCC, Manassas Va.) were seeded in 96 well black, clear-flat bottom dishes at 5000 cells per well, and placed in at 37° C., 5% CO$_2$ incubator. The following day, the cells were washed once with RPMI 1640 supplemented with 10% FBS and 1% Penicillin/Streptomyocin (complete culture media). The cells were then incubated for 18 hours with complete culture media containing different concentrations of recombinant human Interferon Gamma (IFNgamma) (carrier free) (Cat No: 570202, BioLegend, San Diego, Calif.) ranging from 0 ng/mL to 3.75 µg/mL.

After 18 hours, the media containing different concentrations of interferon gamma was replaced with complete culture media containing 1× CellTox Green (Cat No: G8731, Promega, Madison, Wis.). Wells that did not include any cells were also incubated with 1× CellTox Green reagent diluted in complete culture media to serve as background subtraction wells during fluorescent signal detection. The CellTox Green fluorescence signal was measured at 24.5 hours after light treatment using a fluorescence plate reader. The cells were then lysed with detergent, incubated at 37° C.

for 30 minutes, and the CellTox Green fluorescence signal was measured again post lysis. The percent dead cells was calculated by taking the ratio between background (1× CellTox Green in complete culture media without cells) subtracted CellTox Green signal per well prior to and post lysis and multiplying the ratio by 100.

Figure 19A:
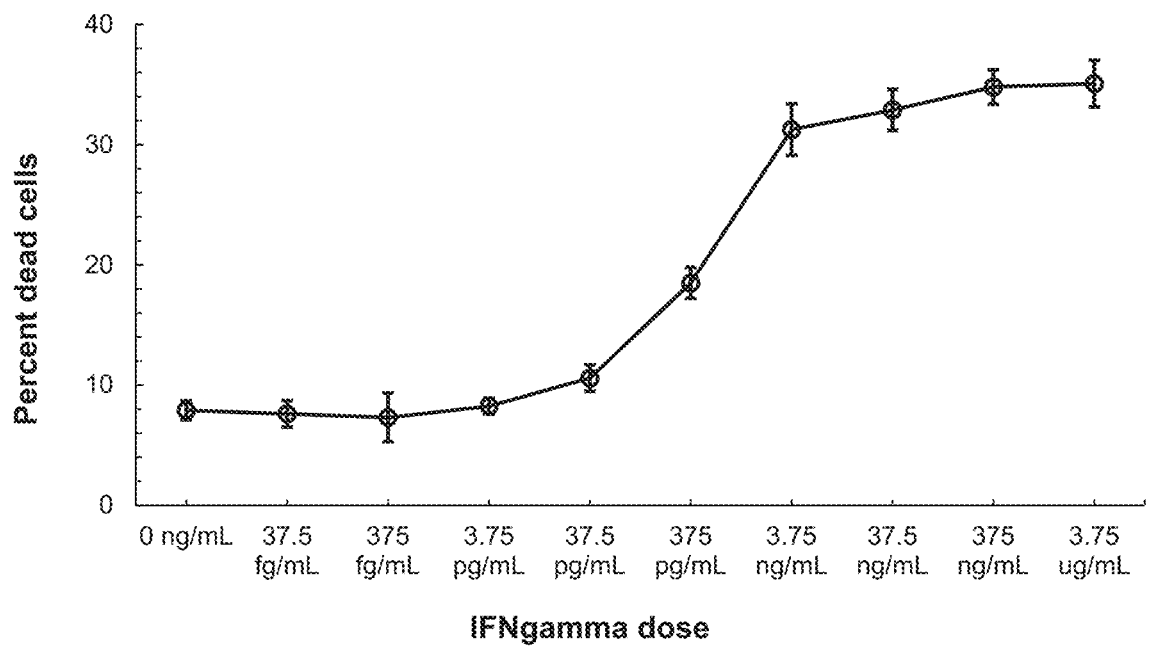
FIG. 19A shows the effect of IFNgamma treatment on the percent death of BxPC3 cells.

The results in FIG. 19A show the increasing IFNgamma concentration results in a dose-dependent increase in cell death of BxPC3 cells.

B. Effect of Interferon Gamma on PD-L1 Expression

BxPC3 cells were seeded in 12 well dishes at 145,000 cells per well, and placed at 37° C. in a 5% $CO_2$ incubator. The following day, the cells were washed once with RPMI 1640 supplemented with 10% FBS and 1% Penicillin/Streptomyocin (complete culture media). The cells were then incubated for 18 hours with complete culture media alone, complete culture media containing 375 pg/mL of recombinant human Interferon Gamma (carrier free) (Cat No: 570202, BioLegend, San Diego, Calif.), or complete culture media containing 37.5 ng/mL recombinant human Interferon Gamma (carrier free). After the 18 hour incubation with or without recombinant interferon gamma, the BxPC3 cells were washed one time with complete culture media.

The cells were then incubated for one hour at 37° C. with complete culture media alone or complete culture media containing 10 µg/mL anti-PD-L1-IRDye 700DX, which was prepared as described in Example 5.

After the one hour incubation, the cells were washed three times with phosphate buffer saline (pH 7) and incubated with enzyme free cell dissociation buffer (Catalog No: S-014-C, EMD Millipore, Billerica, Mass.) until cells were detached. After the cells detached, phosphate buffer saline containing 0.5% bovine serum albumin fraction V (Catalog No: 15260-037, ThermoFisher Scientific, Waltham, Mass.) was added to the cells, and the samples were immediately analyzed by flow cytometry for PD-L1 expression based on the fluorescent signal from the IR700 dye of the anti-PD-L1-IRDye 700DX. The fold increase in expression was calculated by first subtracting the fluorescent intensity from the anti-PD-L1-IRDye 700DX staining for each treatment from the unstained cells samples, then normalizing each treatment by subtracting the background fluorescent intensity as determined from the mean of the no interferon gamma treated, anti-PD-L1-IRDye 700DX stained samples.

Figure 19B:
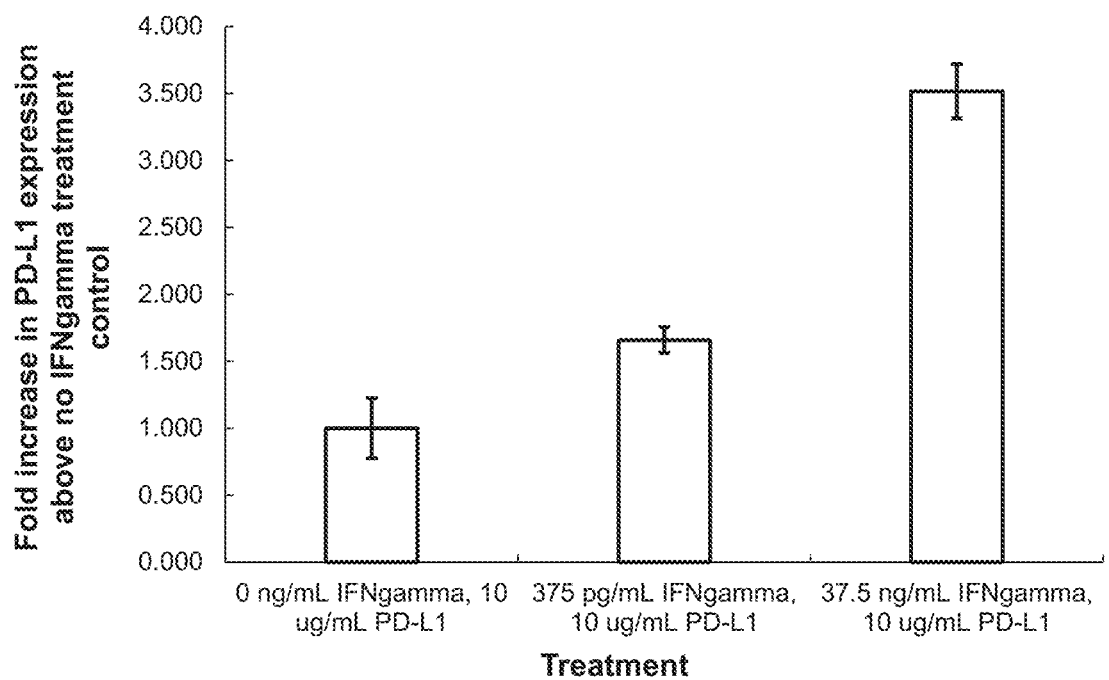
FIG. 19B shows the effect of IFNgamma treatment on PD-L1 expression in BxPC3 cells.

As shown in FIG. 19B, the results showed that increasing IFNgamma concentration resulted in a dose-dependent increase in PD-L1 expression in BxPC3 cells.

C. Combination of Interferon Gamma and Anti-PD-L1-IR700 Conjugate on PIT Cell Killing Studies were performed to assess if treatment of cells with interferon gamma to increase expression of PD-L1 can enhance anti-PD-L1-mediated PIT killing, BxPC3 cells were seeded in 96 well white, clear-flat bottom dishes at 5000 cells per well, and placed in a 37° C., 5% $CO_2$ incubator. The following day, the cells were washed once with RPMI 1640 supplemented with 10% FBS and 1% Penicillin/Streptomyocin (complete culture media). The cells were then incubated for 18 hours with complete culture media alone, complete culture media containing 375 pg/mL of recombinant human Interferon Gamma (carrier free) (Cat No: 570202, BioLegend, San Diego, Calif.), or complete culture media containing 37.5 ng/mL recombinant human Interferon Gamma (carrier free).

After the 18 hour incubation with or without recombinant interferon gamma, the BxPC3 cells were washed one time with complete culture media. The cells were then incubated for one hour at 37° C. with complete culture media alone or complete culture media containing 10 µg/mL anti-PD-L1-IRDye 700DX or 10 µg/mL anti-PD-L1-IRDye 700DX with 100 ug/mL unconjugated anti-PD-L1. After the one hour incubation, the cells were washed one time complete culture media.

The cells were then illuminated with a 690 nm laser with either 96 $J/cm^2$ of light with a 690 nm laser or were protected from light ("no light"). Cell death was assessed using CellTox Green reagent as described in Example 6.

Figure 19C:
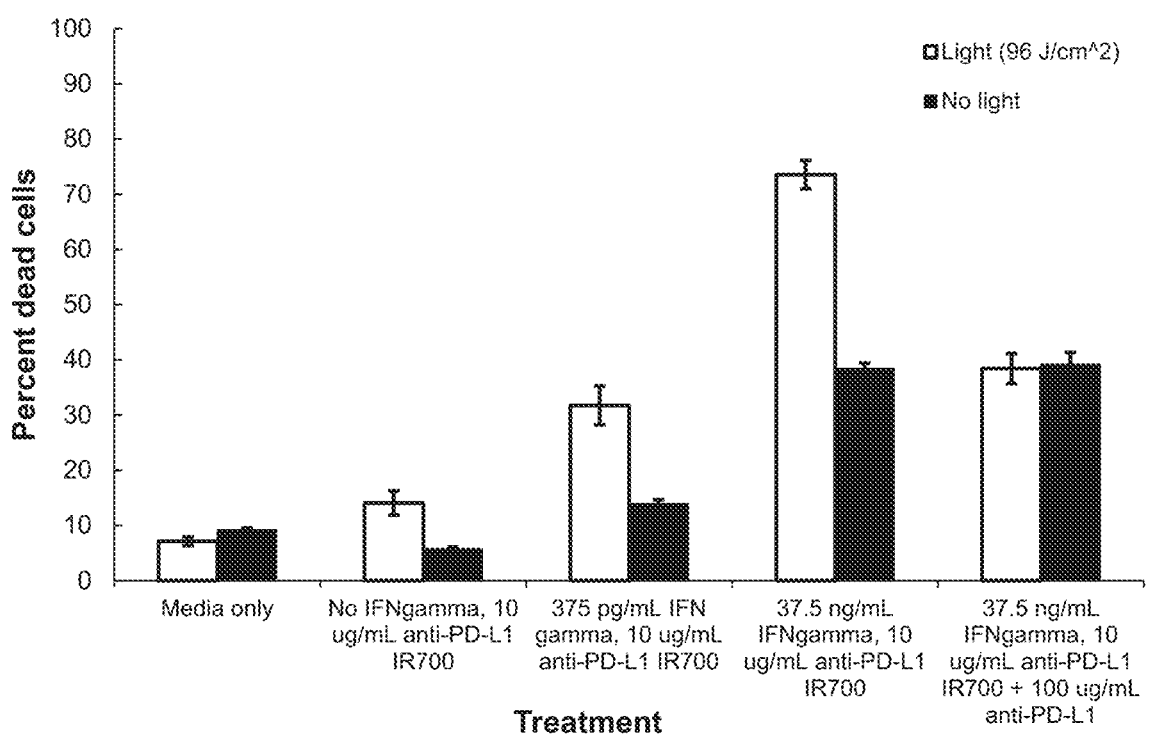
FIG. 19C shows the effect of IFNgamma treatment on anti-PD-L1 IRDye 700DX PIT killing activity in BxPC3 cells.

As shown in FIG. 19C, combination treatment with IFNgamma prior to treatment with the anti-PD-L1-IR700 conjugate enhanced the anti-PD-L1 photo-activated killing when compared to that of anti-PD-L1-IR700 PIT treatment alone. BxPC3 cells that were not treated with interferon gamma prior to anti-PD-L1-IR700 incubation exhibited a modest increase in cell death upon 690 nm light illumination when compared to that of the no light control. BxPC3 cells incubated with interferon gamma, followed by incubation with anti-PD-L1-IR700 conjugate exhibited an IFNgamma dose dependent increase in basal cell death in the no light treated cells, which is consistent with the effect of IFN-gamma to mediate cell death. BxPC3 cells incubated with IFNgamma, incubated with anti-PD-L1-IR700 conjugate, and illuminated with 690 nm light exhibited an IFNgamma dose dependent increase in cell death relative to the no light control for each respective treatment group. The results showed that anti-PD-L1-IR700 PIT killing activity was specific because out-competing anti-PD-L1-IR700 binding with 10× molar excess of unconjugated anti-PD-L1 abrogated the photo-activated killing of the anti-PD-L1-IR700 conjugate as demonstrated by the same percentage of cell death in the light and no light treatments.

The results demonstrated that combination treatment with interferon gamma, an anti-cancer agent and immune modulator, and anti-PD-L1-IR700 PIT exhibits enhanced anticancer activity that of anti-PD-L1-IR700 PIT treatment alone or interferon gamma treatment alone.

Example 17: Immunogenic Cell Death and Immune Activation by Antibody-IR700 Conjugate-Mediated PIT The following studies were performed to assess whether immune stimulatory changes occur in PIT-treated cells and whether PIT-treated cells have the potential to activate immune cells. To evaluate what immune stimulatory changes occur in PIT-treated cells, cancer cells treated with and without PIT were evaluated for expression of immunogenic cell death (ICD) markers. Immunogenic cell death is a specific type of cell death exhibited by necrotic cells, and is characterized by increased presentation and release of immune stimulatory markers. Cells exhibiting ICD display membrane changes such as elevated surface expression of heat shock protein 90, and secretion of soluble, intracellular markers known as danger associated molecular patterns (DAMPs), such as ATP and high-mobility group-box protein (HMGB1) (Kromer et al. (2013) Annual Review of Immunology, 31:51-72). As shown below, PIT-treated cancer cells exhibit increased HMGB1 secretion when compared to that of the non-PIT treated cells.

Because the PIT-treated cells exhibited elevated release of HMGB1, follow-up studies were performed to evaluate whether PIT-treated cells could activate immune cells. To determine whether the immune cells could be activated by PIT-treated tumor cells, the PIT and non-PIT treated cancer cells were co-cultured with monocyte derived immature dendritic cells (iDCs). The surface expression of DC maturation/activation markers CD80, CD86, CD40 and MHCII, which get upregulated upon inflammatory stimuli such as immunogenic cell death via PIT, were observed for any changes. Enhancement of co-stimulatory molecules CD80, CD86 and CD40 indicates augmentation in the ability of DCs to activate T cells and increased MHCII represents increased antigen presentation capabilities as DCs mature. Increased expression of both costimulatory molecules and MHCII was seen on iDCs exposed to tumor killed via PIT as compared to control (non-PIT treated tumor cells).

A similar tumor: APC co-culture was performed using another model system using THP1 cells, a human monocytic cell line that is widely used for in vitro based APC activation and functional assays. Upregulation of activation makers CD86 was seen on THP1 cells that are exposed to PIT killed tumor cells as opposed to THP1 cells which were co-cultured with non PIT treated tumor cells further confirming the immune-stimulatory potential of PIT.

Altogether, the data indicated that PIT-treated cells exhibit markers characteristic of ICD, and that the PIT-treated cells have the potential to activate immune cells. Therefore, combination treatment with PIT with an immune-modulating agent may further enhance the immune activating potential of PIT.

A. Estimation of the HMGB1 Levels from Tumor Cells Subjected to PIT Via Cetuximab-IR700

A431 and FaDu tumor cell lines were grown in complete RPMI 1640 and complete EMEM media, respectively. The cells were plated at 15,000 cells in 100 µL total volume per well in a 96 well tissue culture plate for adherence overnight. The viability of the cells prior to plating was checked via trypan blue exclusion method and >95% cells were viable.

The next day the cells were treated with cetuximab-IR700 (prepared as described in Example 1) at 500 ng/mL for 1 hr at 37° C. in the $CO_2$ incubator and then irradiated with 690 nm laser at a light fluence of 32 $J/cm^2$. The controls represented wells corresponding to the groups not treated with light.

After undergoing PIT, the media was removed from the treated cells followed by washing of the cells once with PBS. This was followed by addition of serum free version of the media and incubation for 1 hr at 37° C. in the $CO_2$ incubator. The supernatant was collected post incubation and stored at −20° C. until use.

The culture supernatants from various treated wells were subjected to HMGB1 ELISA (IBL International, cat #ST51011) as per manufacturer's instructions. Briefly, lyophilized HMGB1 control and standard were solvated with diluent buffer according to kit instructions. A calibration standard curve was prepared by diluting HMGB1 standard stock 1:4 in diluent buffer, then serial diluted 1:2 for a total of 6 points (80 ng/mL-2.5 ng/mL). 100 µL/well of diluent buffer was added to each used well of the ELISA plate provided in the kit. 10 µL/well of standard, control, or sample was added to each well, the plate was sealed, and incubated overnight at 37° C. After 20-24 hours unbound sample was washed away with provided wash buffer (diluted to 1× with distilled water). Lyophilized enzyme conjugate was solvated with enzyme conjugate diluent according to kit instructions and was added to washed plate at 100 µL/well. The plate was gently tapped to mix and was then sealed and incubated at room temperature for 2 hours. Excess enzyme conjugate was then washed off with 1× wash buffer and a 1:1 mix of colrea A and colrea B solutions added to plate at 100 µL/well and incubated for 30 min at room temperature. The reaction was then stopped by adding 100 µL/well of stop solution and gently tapping the plate to mix. The amount of yellow product was quantified by its absorption at 450 nm. The HMGB1 standard curve was graphed with 4 parameter logistics and the test sample data interpolated into the standard curve to determine HMGB1 concentration in each sample. The data was depicted as the fold increase over respective no light controls.

Figure 20A:
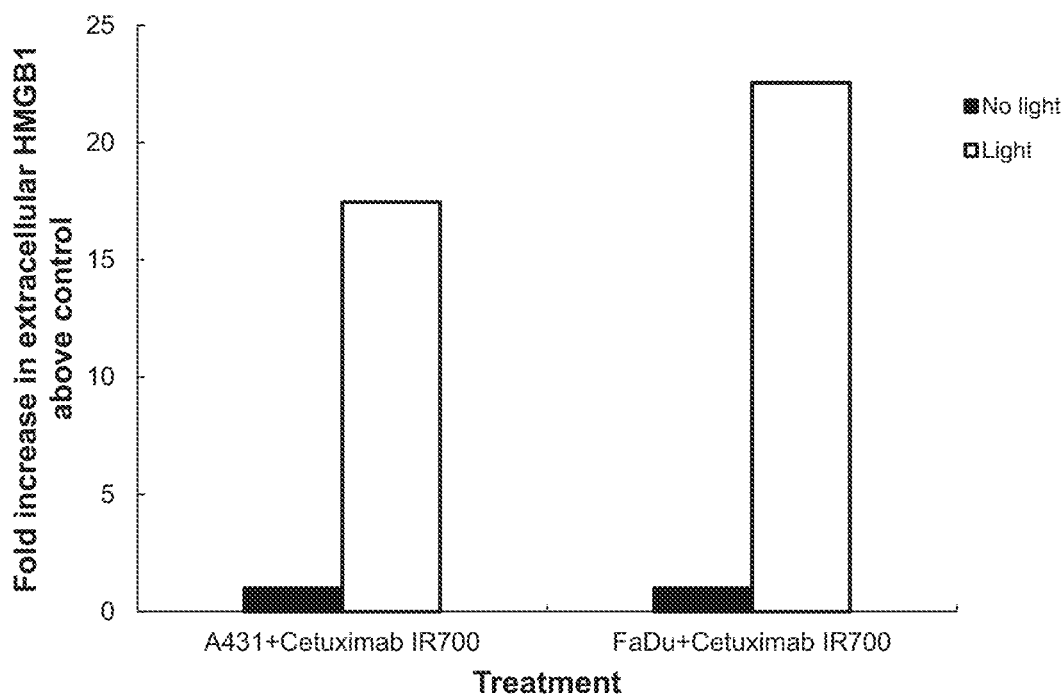
FIG. 20A shows the effect of PIT treatment in A431 and FaDu cells using Cetuximab-IRDye 700DX on the amount of HMGB1 detected in extracellular solution.

As shown in FIG. 20A, PIT via cetuximab-IR700 resulted in a robust HMGB1 secretion from the tumor cells. Both A431 and FaDu exhibited massive release of HMGB1 as compared to the no light controls.

B. Determination of the Upregulation of DC Maturation Markers CD80, CD86, CD40, and MHCII on DCs Co-Cultured with PIT-Treated Tumor Cells FaDu cells were grown in complete EMEM media. The cells were plated in 100 µL total volume per well in a 96 well tissue culture plate for adherence overnight. The viability of the cells prior to plating was checked via trypan blue exclusion method and >95% cells were viable.

The next day, the cells were treated with cetuximab-IRDye 700DX at 500 ng/mL for 1 hr at 37° C. in the $CO_2$ incubator and then were treated with light by subjecting the cells to 690 nm laser light fluence of 12 $J/cm^2$. The controls represented wells corresponding to the groups not treated with light (non-PIT treated tumor cells).

For co-culture, human iDCs (Astarte Biologics) from a healthy donor were directly added into the wells with PIT treated tumor cells and control wells (non-PIT treated tumor cells) at 1:1 ratio. The co-cultures were then incubated for 48 hours at 37° C. in the $CO_2$ incubator. The cells were then detached using a non-enzymatic detachment solution. The harvested cells from various treatment conditions were then incubated with live/dead discrimination dye Zombie Green (BioLegend, 1:500) for 20 min at room temperature followed by washing with stain buffer.

Cells were resuspended in stain buffer and human Fc blocking reagent (BD Biosciences) was then added and cells were incubated for 20 min at room temperature. Anti-human CD80 (BioLegend, clone 2D10), anti-human CD86 (BioLegend, clone IT2.2), anti-human CD40 (BioLegend, clone 5C3), anti-human CD11c (BD, clone B-ly6) and anti-human MHCII (BioLegend, clone L243) antibodies were then added (1:20), cells incubated for 30 min at room temperature. Respective isotype control staining was also performed to assess the background signal. This was followed by a wash and cells resuspended in stain buffer. Data was then acquired via flow cytometry (Attune® Acoustic Focusing Cytometer) under high sensitivity mode. Flow cytometry was performed using anti-human CD14 (clone 63D3, BioLegend, San Diego, Calif.) and anti-human CD86 (clone IT2.2, BioLegend, San Diego, Calif.) antibodies, wherein were added to cells at a 1:40 dilution, and then the cells were incubated for 30 min at room temperature. This was followed by a wash and then the cells were resuspended in stain buffer. Data was then acquired via flow cytometry (Attune® Acoustic Focusing Cytometer, Thermo Fisher Scientific, Waltham, Mass.) under high sensitivity mode. Appropriate gating was done while analyzing the data to exclude cell debris and the data was analyzed with gating performed on live events. The results described below are based on mean fluorescence intensity (MFI) data from each group which is plotted as fold increase over the no light controls.

Figure 20B:
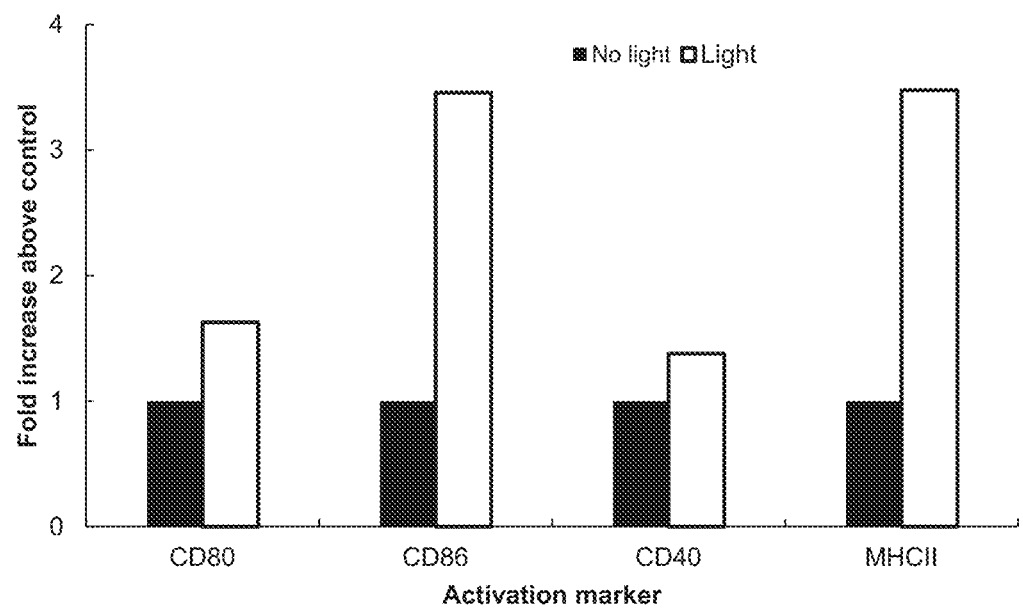
FIG. 20B shows the upregulation of dendritic cell (DC) maturation markers on immature dendric cells (iDCs) co-cultured with tumors subjected to PIT via cetuximab-IRDye 700DX.

FIG. 20B shows the upregulation of dendritic cell (DC) maturation markers on iDCs co-cultured with FaDu tumors subjected to PIT via cetuximab-IRDye 700DX. Co-culture with FaDu caused increased surface CD80, CD86, CD40 and MHCII expression on iDCs as compared to the the no light controls. The Y-axis represents fold increase over respective no light controls C. CD86 Expression in THP1 Cells Upon Co-Culture with PIT and Non-PIT Treated Tumor Cells A431 cell line was grown in complete RPMI and T98G, FaDu and U87 tumor cell lines were grown in complete EMEM media. The cells were plated at 15,000 cells in 100 µL total volume per well in a 96 well tissue culture plate for adherence overnight. The viability of the cells prior to plating was checked via trypan blue exclusion method and >95% cells were viable.

The next day the cells were treated with cetuximab-IR700 at 500 ng/mL for 1 hr at 37° C. in the $CO_2$ incubator and then were treated with light by subjecting the cells to 690 nm laser light fluence of 12 $J/cm^2$. The controls represented wells corresponding to the groups not treated with light (non-PIT treated tumor cells).

THP1 cells (ATCC® TIB202™) were grown in complete RPMI. For co-culture, 15,000 THP1 cells were directly added into the wells with PIT treated tumor cells and control non PIT treated tumor cell wells. The co-cultures were then incubated for 24 hours at 37° C. in the $CO_2$ incubator. On the next day, the cells were then detached using a non-enzymatic detachment solution. The harvested cells from various treatment conditions were then resuspended in PBS only and live/dead discrimination dye Zombie Green (BioLegend) was added (1:500). The cells were incubated for 20 min at room temperature followed by washing with stain buffer.

Cells were resuspended in stain buffer and human Fc blocking reagent (BD Biosciences) was then added and cells were incubated for 20 min at room temperature. Flow cytometry was performed using anti-human CD14 (clone 63D3, BioLegend, San Diego, Calif.) and anti-human CD86 (clone IT2.2, BioLegend, San Diego, Calif.) antibodies, wherein were added to cells at a 1:40 dilution, and then the cells were incubated for 30 min at room temperature. This was followed by a wash and then the cells were resuspended in stain buffer. Data was then acquired via flow cytometry (Attune® Acoustic Focusing Cytometer, Thermo Fisher Scientific, Waltham, Mass.) under high sensitivity mode. Appropriate gating was done while analyzing the data to exclude cell debris and the data was analyzed with gating performed on live events. CD14 marker was used to identify the THP1 cells. The results were based on mean fluorescence intensity (MFI) data from each group which was plotted as fold increase over the no light controls. The data were depicted as fold increase in CD86 surface expression over respective no light controls.

Figure 20C:
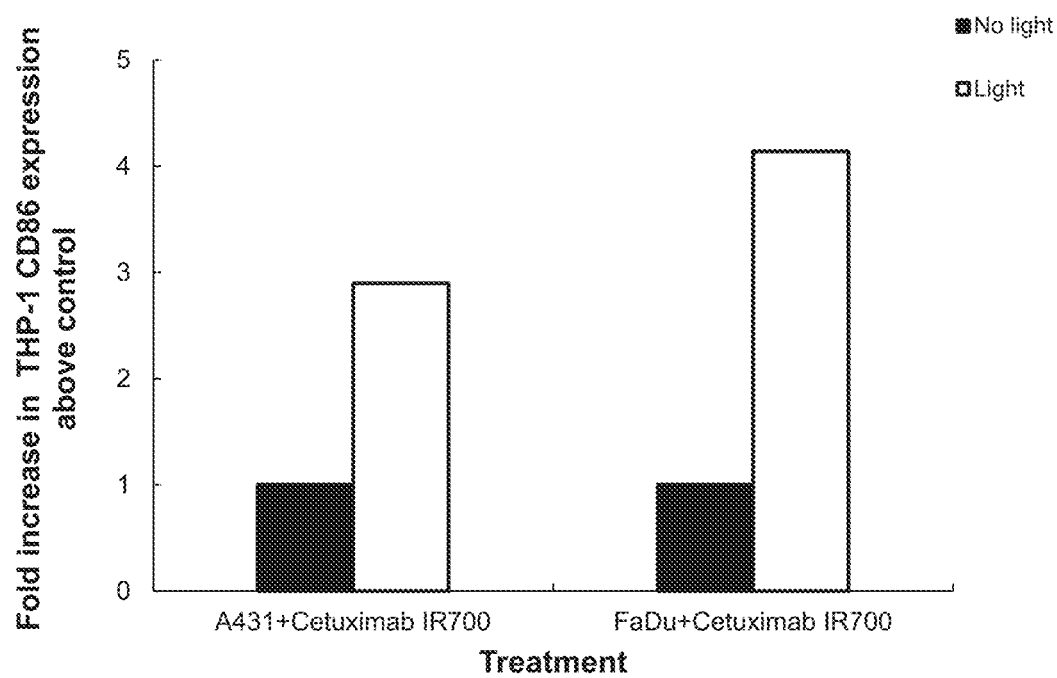
FIG. 20C shows the effect of activating antigen-presenting cells by PIT-treated A431 or FaDu cells (treated using Cetuximab-IRDye 700DX and in the presence of light irradiation) or non-PIT treated A431 or FaDu cells (treated using Cetuximab-IRDye 700DX but with no light irradiation) as assessed by the expression of the exemplary activation marker CD86.

As shown in FIG. 20C, CD86 was upregulated on THP1 cells co-cultured with tumors subjected to PIT via cetuximab-IR700. Co-culture with both A431 and FaDu cells subjected to PIT caused increased surface CD86 expression on THP1 cells as compared to the no light controls.

Example 18: PIT in Combination with Treatment with an Immune-Modulator Enhances Immune Activation Studies were performed to assess whether there is higher immune activation when immune cells are primed with PIT killed tumors and also treated with an immune-modulator. As shown in Example 17, PIT creates an inflammatory environment which leads to activation of immune cells such as dendritic cells (DCs) and monocytes. These PIT primed cells may also exhibit higher potential for further activation when combined with a treatment with an immune-modulator such as Poly I:C (a synthetic double stranded RNA analog). To test this, PIT-treated tumor cells were co-cultured with monocyte derived immature dendritic cells (iDCs) followed by treatment with Poly I:C, and changes in the expression levels of DC activation markers CD80 and CD86 was then assessed. Co-culture of iDCs with non-PIT treated tumor cells was used as controls. Increased CD80 and CD86 expression was seen on DCs that have been previously exposed to an environment where the tumor is killed via PIT versus the condition where the tumor was not treated with PIT.

FaDu cells grown in complete EMEM media were plated in 100 µL total volume per well in a 96 well tissue culture plate for adherence overnight. The viability of the cells prior to plating was checked via the trypan blue exclusion method and >95% cells were found to be viable. The next day the cells were treated with Cetuximab IRDye 700DX (500 ng/mL for 1 hr at 37° C. in an $CO_2$ incubator). PIT cell killing was induced by illumination with a 690 nm laser light at a fluence of 12 $J/cm^2$. The controls represented wells corresponding to the groups not treated with light.

For co-culture, human iDCs (Astarte Biologics) from a healthy donor were directly added into the wells with PIT killed tumor cells and into control wells (non-PIT treated tumor cells). The co-cultures were then incubated for 48 hours at 37° C. in the $CO_2$ incubator. The harvested DCs were then subjected to poly I:C treatment (1 µg/mL) for overnight. The cells were then detached using a non-enzymatic detachment solution.

The harvested cells from various treatment conditions were incubated with live/dead discrimination dye Zombie Green (BioLegend, 1:500) for 20 min at room temperature followed by washing with stain buffer. Cells were resuspended in stain buffer and human Fc blocking reagent (BD) was then added and cells were incubated for 20 min at room temperature. Anti-human CD80 (BioLegend, clone 2D10), anti-human CD86 (BioLegend, clone IT2.2), anti-human CD40 (BioLegend, clone 5C3), anti-human CD11c (BD, clone B-ly6) and anti-human MHCII (BioLegend, clone L243) antibodies were added (1:20) and cells were incubated for 30 min at room temperature. Respective isotype control staining was also performed to assess the background signal. Cells were washed and resuspended in stain buffer. Data was then acquired via flow cytometry (Attune® Acoustic Focusing Cytometer) under high sensitivity mode.

Appropriate gating was performed while analyzing the data to exclude cell debris, and the data was analyzed with gating performed on live events. The results described below are based on median fluorescence intensity (MFI) data from each group which is plotted as fold increase over the no light controls.

Figure 21:
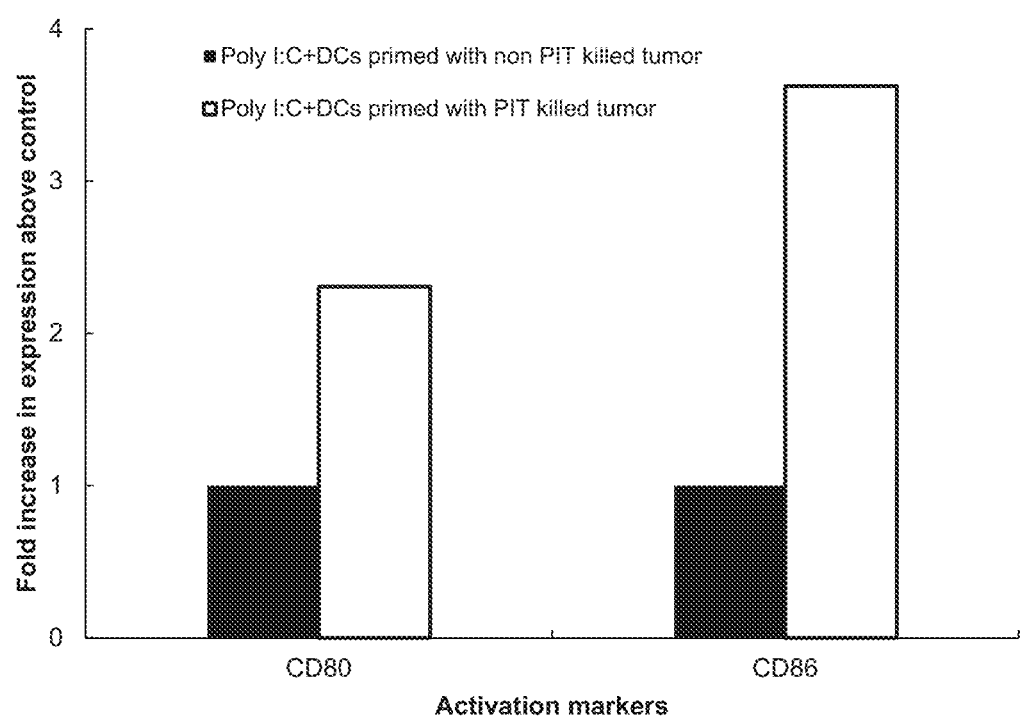
FIG. 21 shows the effect on activation of dendritic cells by priming dendritic cells with PIT-treated tumor cells (treated using Cetuximab-IRDye 700DX) or non-PIT treated tumor cells (treated using Cetuximab-IRDye 700DX but with no light irradiation) followed by their stimulation with an immune modulator (Poly I:C) as assessed by the expression of exemplary activation markers.

The results in FIG. 21 showed that dendritic cells (DCs) treated with PIT in combination with an immune-modulator (Poly I:C) exhibited enhanced immune activation as compared to DCs that were not subjected to PIT treatment in combination with an immune modulator. The pre-treatment of DCs with PIT in combination with an immune-modulator leads to increased CD80 and CD86 expression levels compared to the no light (no PIT) controls.

Thus the data indicated that DCs exposed to an environment created by PIT are inherently more predisposed to activation via an immune-modulator. Therefore, combination treatment with PIT with an immune modulating agent may further enhance the immune activating potential of PIT.

Example 19: Cetuximab Dual Labeled with IRDye 700DX and AlexaFluor488, IRDye 700DX and, DyLight755, IRDye 700DX and IRDye800 CW Similar to the studies described in Example 4, additional studies were performed to assess whether antibodies conjugated to the phthalocyanine photosensitizer IRDye 700DX may also be conjugated to a second fluorescent dye molecule. In some aspects, the dual labeling approach can be used to permit tumor imaging capabilities while maintaining binding to cancer cells and subsequent PIT killing activity.

A. Conjugation Methods

The water-soluble, silicon-phthalocyanine derivative, IRDye 700DX NHS ester and IRDye 800CW-NHS (also called IRDye 800 herein) were obtained from LI-COR Bioscience (Lincoln, Nebr.). Alexa Fluor 488-SDP was obtained from Life Technologies (Carlsbad, Calif.). Dylight 755—NHS was obtained from Thermo Scientific (Waltham, Mass.). Erbitux (cetuximab) was purchased from (Myoderm USA, Norristown, Pa.). Amicon® Ultra Centrifugal Filter Units (Merck Millipore Ltd, Billerica, Mass.). All other chemicals used were of reagent grade.

1. Cetuximab-IR700 (CTX700)

Cetuximab-IRDye 700DX (CTX700) conjugate used to produce all dual conjugates described below was prepared substantially as described in Example 1. Briefly, cetuximab was reacted with 4 molar equivalents of IRDye 700DX NHS ester for 2 hours at pH=8.5, in the dark, at room temperature in a using through Amicon® Ultra Centrifugal Filter Units (Cat #: UFC903024, Merck-Millipore, Billerica, Mass.) for all buffer exchange and UF/DF purification steps taking care to project the conjugate at all times from any unnecessary light exposure.

The conjugate was evaluated by size exclusion chromatography, antibody concentration (conc.) and dye to antibody ratio (DAR) substantially as described in Example 4. The results showed the following characteristics of the conjugate: A690=96.7% monomer; Conc=1.8 mg/mL; DAR=2.4 IRDye 700DX/Ab

2. CTX700-ALX488

Figure 22A:
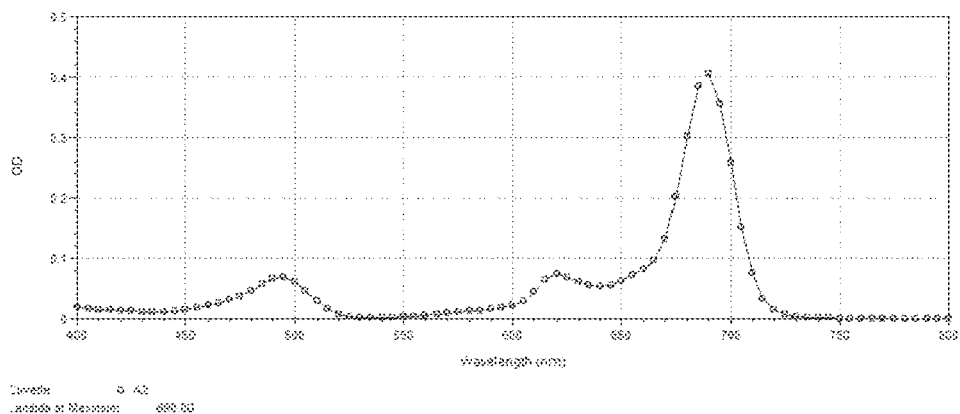
FIG. 22A shows the UV-Vis spectrum of cetuximab-IRDye 700DX-Alexa Flour 488 (CTX700-ALX488).

10 mg of CTX-700 at a concentration of 2 mg/mL in 100 mM phosphate buffer (pH=8.5) was incubated in a light protected container with 2 molar equivalents of Alexa Flour 488-SDP (5 mg/mL DMSO) at room temperature for 2 hours. The reaction was quenched by the addition of 100 µL of 1M glycine solution (pH=8). The conjugate product was exchanged and purified using 10 reaction volumes of 10 mM phosphate buffer saline (PBS) pH=7.1 filtered through Amicon® Ultra Centrifugal Filter Units. The conjugate was characterized by UV-VIS, SE-HPLC, PIT and Dual Emission Flow Cytometry. The UV-Vis Spectrum of CTX700-ALX488 is depicted in FIG. 22A.

3. CTX700-IRDye 800

Figure 22B:
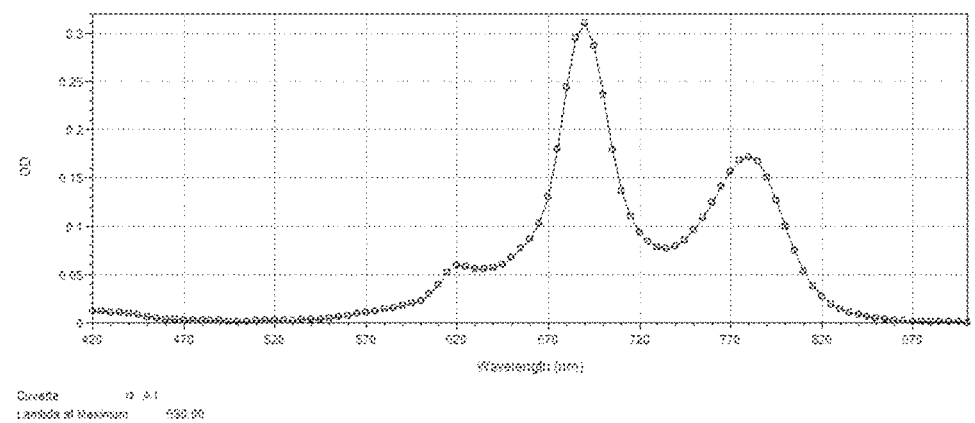
FIG. 22B shows the UV-Vis spectrum of CTX-700-IRDye 800CW.

10 mg of CTX-700 at a concentration of 2 mg/mL in 100 mM phosphate buffer (pH=8.5) was incubated in a light protected container with 2 molar equivalents of IRDye 800CW-NHS (5 mg/mL DMSO) at room temperature for 2 hours. The reaction was quenched by the addition of 100 µL of 1M glycine solution (pH=8). The conjugate product was exchanged and purified using 10 reaction volumes of PBS (pH=7.1) filtered through Amicon® Ultra 15 Centrifugal Filter Units. The conjugate was characterized by UV-VIS, SE-HPLC, PIT and Dual Emission Flow Cytometry. The UV-Vis Spectrum of CTX700-ALX488 is depicted in FIG. 22B.

4. CTX700-Dylight 755

Figure 22C:
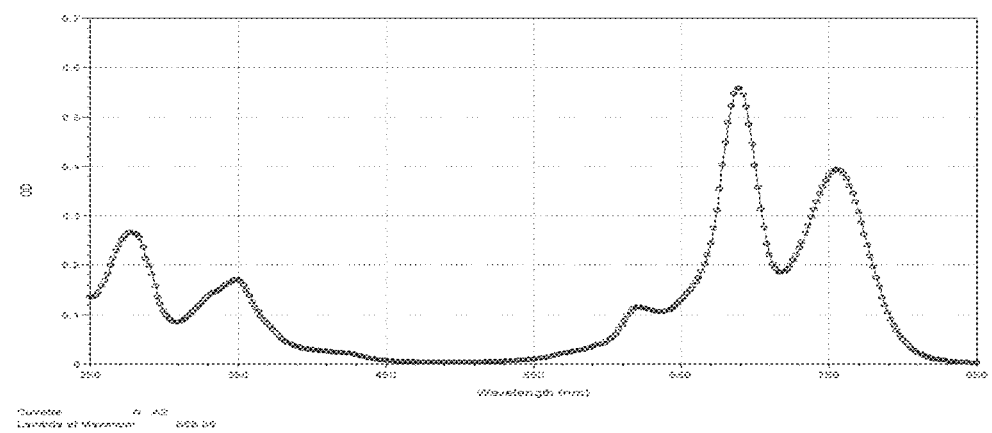
FIG. 22C shows the UV-Vis spectrum of CTX700-Dylight 755.

10 mg of CTX-700 at a concentration of 2 mg/mL in 100 mM phosphate buffer (pH=8.5) was incubated in a light protected container with 4 molar equivalents of Dylight-NHS (10 mg/mL DMSO) at room temperature for 2 hours. The reaction was quenched by the addition of 100 µL of 1M glycine solution (pH=8). The conjugate product was exchanged and purified using 10 reaction volumes of PBS (pH=7.1) filtered through Amicon® Ultra 15 Centrifugal Filter Units. The conjugate was characterized by UV-VIS, SE-HPLC, PIT and Dual Emission Flow Cytometry. The UV-Vis Spectrum of CTX700-ALX488 is depicted in FIG. 22C.

B. Characterization of Conjugates by HPLC-SEC

The conjugates were evaluated by size exclusion chromatography (SEC) on a Shodex KW-803, 8.0×300 mm SEC column using an Agilent 1100 HPLC system equipped with an Agilent G1315A diode array detector (DAD) monitoring the wavelengths of 280, 488, 690, 755 and 778 nm. The running buffer was PBS flowing at a rate of 1 mL/min. The average dye to antibody ratio (DAR) for the imaging dyes were determined using 280, 488, 690, 755 and 778 nm absorbance integration areas for the antibody monomer peak after the appropriate extinction coefficient value correction factors were applied as needed for each respective dye. The CTX-700 used in all the dual conjugation reactions was analyzed by this method prior to conjugation with the imaging dye to have a DAR=2.4 before conjugation and the IRDye 700DX/Ab ratio was assumed to be unchanged after conjugation with the imaging dye. The results are shown in Table 13.

All conjugates demonstrated both the appropriate size exclusion column retention times (8.1-8.2 min for this method) and imaging dye wavelength appropriate absorbance's at those retention times confirming that the imaging dye was incorporated into the CTX-700 antibody conjugate at the measured Dye to Antibody Ratio (DAR) for Dye 2 given in the table.

TABLE 13

HPLC-SEC Determined Purity and PAR Data for Dual Conjugates

| Sample | Purity (A690) | DAR (Dye2) | DAR (IRDye 700DX) |
|---|---|---|---|
| CTX700 | 96.7 | NA | 2.4 |
| CTX700-Alexa Fluor 488 | 97.6 | 1.1 | 2.4 |
| CTX700-IRDye 800 | 98.8 | 1.2 | 2.4 |
| CTX700-Dylt755 | 98.6 | 1.3 | 2.4 |

C. Cell Staining with Dual CTX-IRDye 700DX Conjugates by Flow Cytometry

BxPC3 cells (grown in RPMI containing 10% FBS and 1% Penicillin/Streptomycin) were detached using HyQTase cell detachment reagent. Cells were then checked for viability using trypan blue exclusion dye method and >99% were found to be alive. Cells were counted using hemocytometer and re-suspended in staining buffer (PBS containing 1% BSA and 0.01% sodium azide). Approximately, 45,000 cells were stained per staining condition with individual dye conjugates along with cells only control to assess the background fluorescence in the respective channels. Approximately, 0.25 µg of the dye conjugates/100 µL staining volume containing 45,000 cells was used per staining condition. Cells were then incubated with the dye for an hour at room temperature in dark. The cells were washed once with staining buffer (1800 rpm, 6 min). The stained cells were finally re-suspended in 300 µL of staining buffer.

The cells were read using Applied Biosystems Attune Acoustic Focusing Cytometer (red and blue lasers, 6 channels) in a high sensitivity mode (slower collection mode). All necessary quality control parameters for the machine prior to running the assay were met. The cytometer had 4 fluorescent channels off of 488 nm blue laser namely BL1 (blue laser $1^{st}$ channel), BL2, BL3 and BL4. Their corresponding band pass filters are described in parenthesis in the table above. There are 2 fluorescent channels off of the 638 nm red laser designated RL1 (red laser $1^{st}$ channel) and RL2.

For analysis, the primary Forward Scatter/Side Scatter (FSC/SSC) gate was made so as to avoid getting debris/dead cells into the analysis. The mean fluorescence intensities of the respective channels for the corresponding dye conjugate analyzed was determined. The results are shown in Table 14. The results showed enhanced fluorescence emission intensities of cells labeled with the dual-conjugates relative to CTX700 mono-conjugate. Thus, these results demonstrate that the dual-conjugates may be suitable for imaging applications in addition to photo immunotherapy (PIT).

TABLE 14

Flow Cytometry Fluorescence Emission Data

| Sample | Excitation Wavelength 488 nm (530 nm/30 nm) Emission Wavelength Filter Fluorescence Intensity (AU) | 630 nm (780 nm 760 nm) Fluorescence Intensity (AU) |
| --- | --- | --- |
| Cells only | 95 | 57 |
| CTX700-Alexa Fluor488 | 515* | 1003 |
| CTX-IRDye 800 | 97 | 965 |
| CTX700-IRDye 800 | 88 | 1533* |
| CTX700 | 87 | 1107 |
| CTX700-Dylt755 | 92 | 5311* |

D. Evaluating PIT Killing Activity

BxPC3 cells (#CRL-1687, ATCC, Manassas Va., USA) were seeded in a 96-well, white-walled, clear bottom, tissue culture (TC)-treated polystyrene plate at a concentration of 5,000 cells/well in RPMI-1640 media supplemented with 10% FBS and 1% Penicillin/Streptomycin (complete culture media) and incubated overnight at 37° C. The following day complete culture media was replaced with fresh complete culture media alone or media containing either 500 ng/ml or 100 ng/mL of test agent as indicated, and the plate was incubated for one hour at 37° C.

The cells were then illuminated with a 690 nm laser at a light dose of either 16 J/Cm$^2$ or 32 J/cm$^2$ or protected from light ("no light").

The effect of the different treatment regimens on cell death was measured using the fluorescent stain, CellTox Green (Catalog No: G8731, Promega, Madison, Wis., USA) substantially as described in Example 6. Results were then normalized, setting cell death after incubation with 500 ng/mL cetuximab-IRDye 700DX and PIT treatment with 32 J/cm$^2$ as 100% PIT activity and cell death after incubation with complete culture medium alone and PIT treatment with 32 J/cm$^2$ as 0% PIT activity.

Figure 23A:
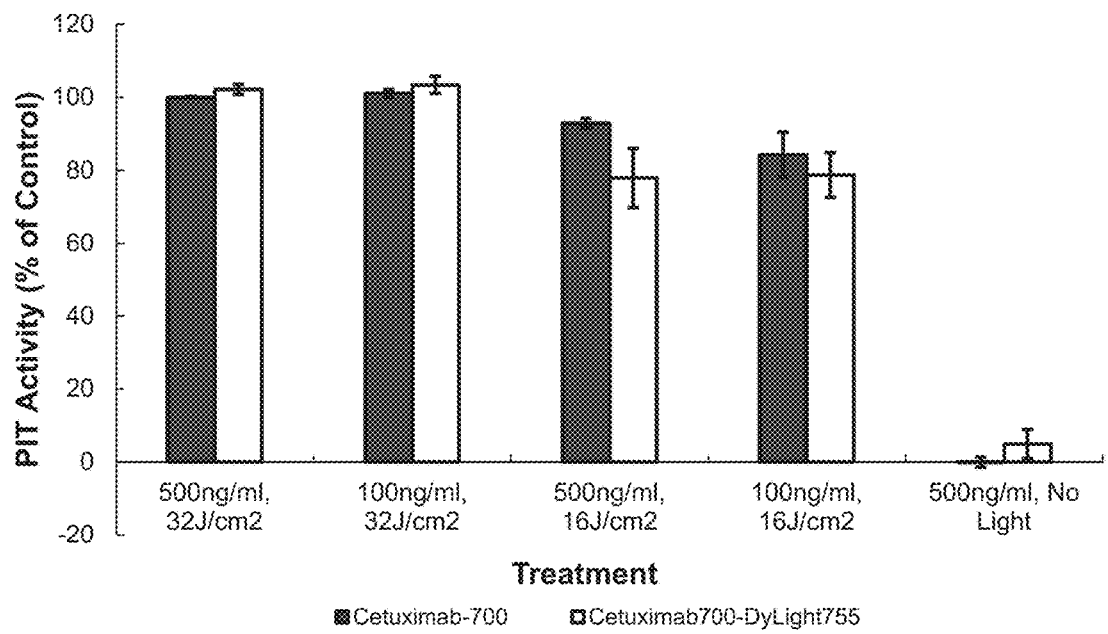
FIG. 23A shows the PIT killing activity of Cetuximab-IRDye 700DX with or without DyLight 755 in BxPC3 cells at various concentrations and light doses.

As shown in FIG. 23A, BxPC3 cells incubated with 100 or 500 ng/mL cetuximab conjugated to IRDye 700DX alone or dual conjugated to IRDye 700DX-DyLight-755 exhibited light-dependent and concentration-dependent killing. The dual conjugate dosed at 500 ng/mL induced at least 90% of the cell killing of the cetuximab-IRDye 700DX solo conjugate control after PIT with 32 J/cm$^2$. When the concentration of conjugate was reduced to 100 ng/mL, cetuximab-IRDye 700DX and the DyLight-755 dual conjugate achieved similar levels of PIT cell killing. Cetuximab-IRDye 700DX and the DyLight-755 dual conjugate maintained a significant level of PIT cell killing at 16 J/cm$^2$, with at least 75% of cell killing at either 100 ng/mL or 500 mg/mL. No PIT cell killing activity was observed with cells incubated with 500 ng/mL of conjugate but not exposed to light. Background cell death (0% activity), as determined with cells incubated with media alone and exposed to 32 J/cm$^2$, was less than 15% of cell population.

Figure 23B:
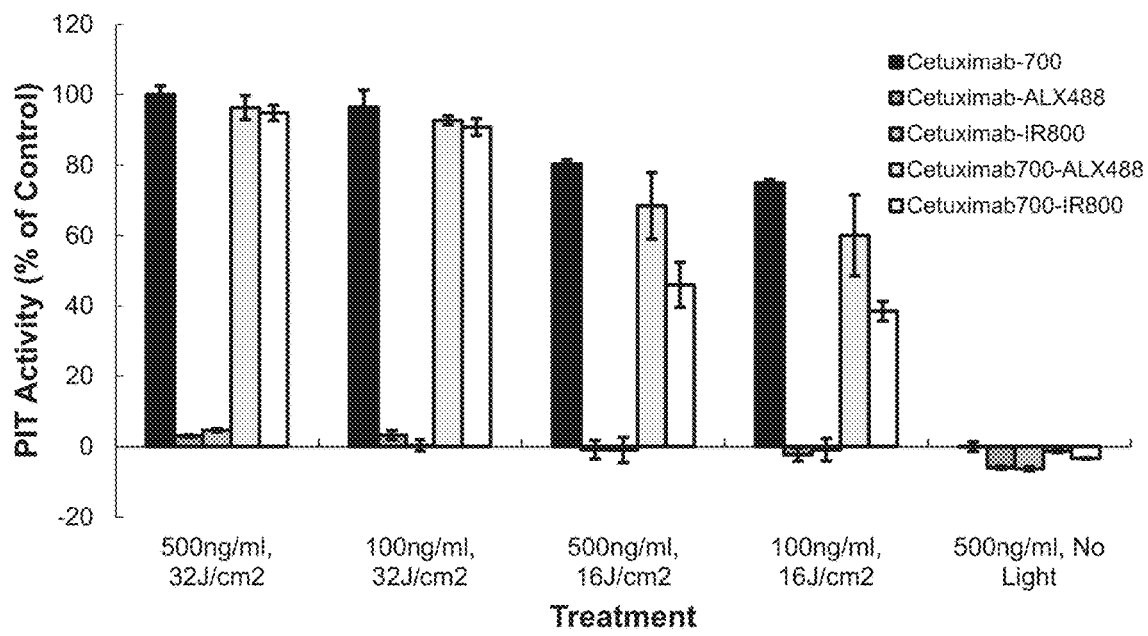
FIG. 23B shows the PIT killing activity of cetuximab-IRDye 800CW, cetuximab-Alexafluor488, or Cetuximab-IRDye 700DX conjugated with or without IRDye 800CW or Alexafluor488 in BxPC3 cells. The results are shown as a percent of PIT activity compared to Cetuximab-IRDye 700DX (control).

As shown in FIG. 23B BxPC3 cells incubated with 100 or 500 ng/mL cetuximab-IRDYE 700DX, alone or dual conjugated to IRDye 700DX and either Alexafluor488 or IRDye 800CW, exhibited light-dependent and concentration-dependent killing. Both dual conjugates, dosed at 500 ng/mL or 100 ng/mL, induced at least 90% of the cell killing of the cetuximab-IRDye 700DX solo conjugate control after PIT with 32 J/cm$^2$. When the light exposure was reduced to 16 J/cm$^2$, at both 100 ng/mL and 500 ng/mL concentrations of cetuximab-IRDye 700DX-Alexafluor488, PIT cell killing was slightly reduced to 60-70% of the control. For cetuximab-IRDye 700DX-IRDye 800, PIT cell killing was reduced to less than 50% of the control for both concentrations. Cetuximab-IRDye 700DX maintained a significant level of PIT cell killing at 16 J/cm$^2$, with at least 75% of cell killing at either 100 ng/mL or 500 mg/mL. The results showed that cetuximab-Alexafluor488 and cetuximab-IRDye 800 solo conjugates were not able to induced PIT cell killing without the presence of IRDye 700DX. No cell killing activity was observed with cells incubated with 500 ng/mL of conjugate but not exposed to light. Background cell death (0% activity), as determined with cells incubated with media alone and exposed to 32 J/cm$^2$, was less than 10% of cell population.

Example 20: Sensitivity of Cetuximab-IRDye 700DX Conjugate, Cetuximab-IRDye 680RD Conjugate, and Cetuximab-IRDye 700+IRDye 680RD Dual Conjugate to White Fluorescent Light Vs. Green LED Light Studies were performed to assess whether protection from light for IRDye 700DX conjugates is a specific property due to the unique sensitivity of IRDye 700DX conjugates to form soluble aggregate formation when exposed to light. Three different conjugates were assessed: (1) a cetuximab-IRDye 700DX conjugate, (2) a cetuximab-IRDye 680RD conjugate, and (3) a cetuximab-IRDye 700+IRDye 680RD dual conjugate.

Although many fluorophores require protection from light because they are not very photostable such that exposure to light results in degradation of the fluorophore and a concomitant decrease in fluorescence properties, IRDye700DX is a uniquely photostable dye (see e.g. Peng et al. Proceedings of SPIE 6097, 2006; www.licor.com/bio/products/reagents/irdye/700dx/photostability.html). Due to the extreme photostability of the dye, this would suggest that IRDye 700DX does not need to be protected from light. However, it was observed that only when IR700 is conjugated to a targeting molecule does IR700 require light protection due to an increased sensitivity for the conjugated molecule to induce soluble aggregate formation.

A. Antibody Conjugation

All antibodies were conjugated to the dyes (i.e., IRDye 700DX, IRDye 600RD, or both) using the same approach.

The cetuximab-IRDye 700DX conjugate was made as described in Example 1.

The cetuximab-IRDye 680RD conjugate was made using the same general protocol as described in Example 1, with the following modifications. A sample of Cetuximab was incubated with 4 molar equivalents of IRDye 680RD (Cat. No. 929-70050; Li-COR, Lincoln, Nebr.) dissolved at 5 mg/mL in DMSO. All other step in the conjugation, purification and characterization process for the conjugate were identical to that described above for the Cetuximab-IR700 conjugate preparation.

The cetuximab-IRDye 700DX+IRDye 680RD dual conjugate was made using the same general protocol as described in Example 1, with the following modifications. To a sample of Cetuximab-IRDye 700DX previously prepared by the protocol described above was added 4 molar equivalents of IRDye 680RD dissolved in DMSO at 5 mg/mL. All other steps in the conjugation, including the purification and characterization process for the conjugate, were identical to that described above for the cetuximab-IRDye 700DX conjugate preparation.

B. Effects of Light Pre-Exposure on Composition of Cetuximab-IRDye 700DX Conjugate, Cetuximab-IRDye 680RD Conjugate, and Cetuximab-IRDye 700+IRDye 680RD Dual Conjugate The conjugates were tested for formation of soluble aggregates under four different conditions with at least 30 µL of conjugate placed in a clear HPLC vial per sample at an antibody conjugate concentration of ~1.8 mg/mL. The samples were exposed to 500 lux white fluorescent lighting at 25° C., 500 lux of green LED lighting (Catalog No: Green-ECS GP19 EcoSmart) at 25° C., no light at 25° C., or no light at 4° C. for 24 hours. After 24 hours under each treatment condition, monomer purity, soluble aggregate formation, and fluorescence was assessed by size exclusion chromatography. The percent soluble aggregate formation was measured using size exclusion chromatography at an absorbance of 280 nm. To evaluate the effect of treatment on fluorescence, the fluorescence at 680 nm (areas for the monomer peak) divided by the area for 280 nm absorbance for the monomer was determined.

Figure 24A:
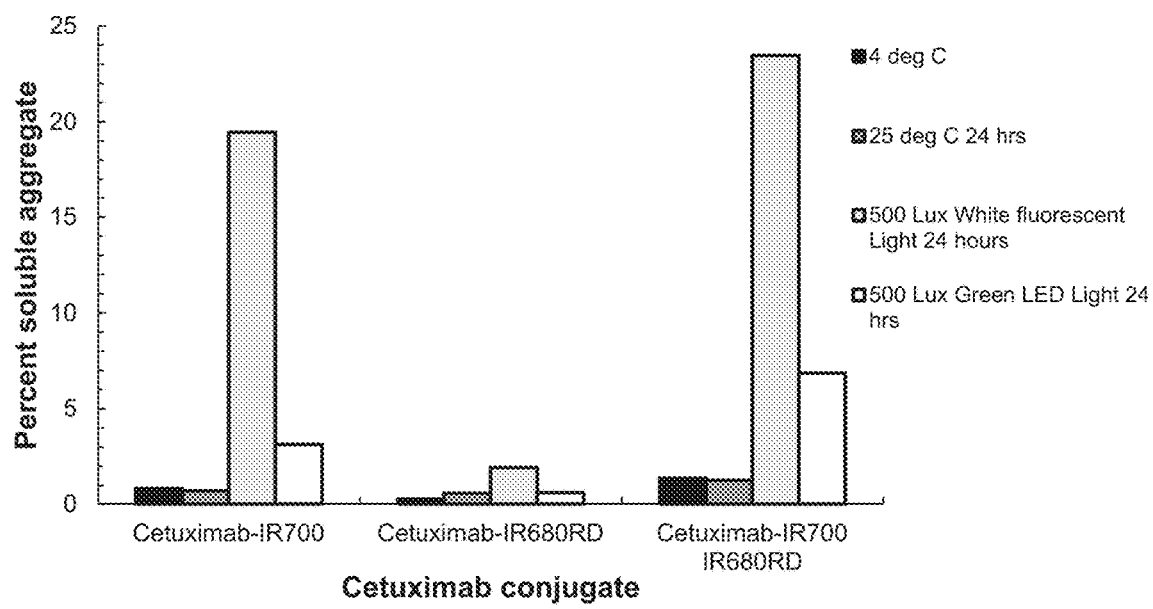
FIG. 24A shows the effect of pre-exposure of cetuximab-IRDye 700DX conjugate, cetuximab-IRDye 680RD conjugate, and cetuximab-IRDye 700+IRDye 680RD dual conjugate to white light or green light on soluble aggregate formation.

The results in FIG. 24A showed that cetuximab conjugated with IRDye 700DX resulted in increased sensitivity to soluble aggregate formation compared to cetuximab conjugated with IRDye 680RD when exposed to white light. Cetuximab-IRDye 700DX exposure to white fluorescent light resulted in a rapid increase in soluble aggregate formation. Cetuximab-IRDye 700DX green light exposure also increased soluble aggregate formation albeit at a rate much slower than that of white light. Less than 1% soluble aggregate formation was observed in samples either incubated at 4° C. or 25° C., but protected from light. In contrast, Cetuximab-IRDye 680RD exposure to white fluorescent light resulted in a very slight increased soluble aggregate formation, which was much less than that of cetuximab-IRDye 700DX. Cetuximab-IRDye 680RD samples incubated at 4° C. or 25° C., but protected from light or exposed to green light did not exhibit any increase in soluble aggregate formation. As shown, the dual conjugate in which IRDye 700DX was conjugated to cetuximab-IRDye 680RD, resulted in sensitivity to white and green light exposure on soluble aggregate formation.

Figure 24B:
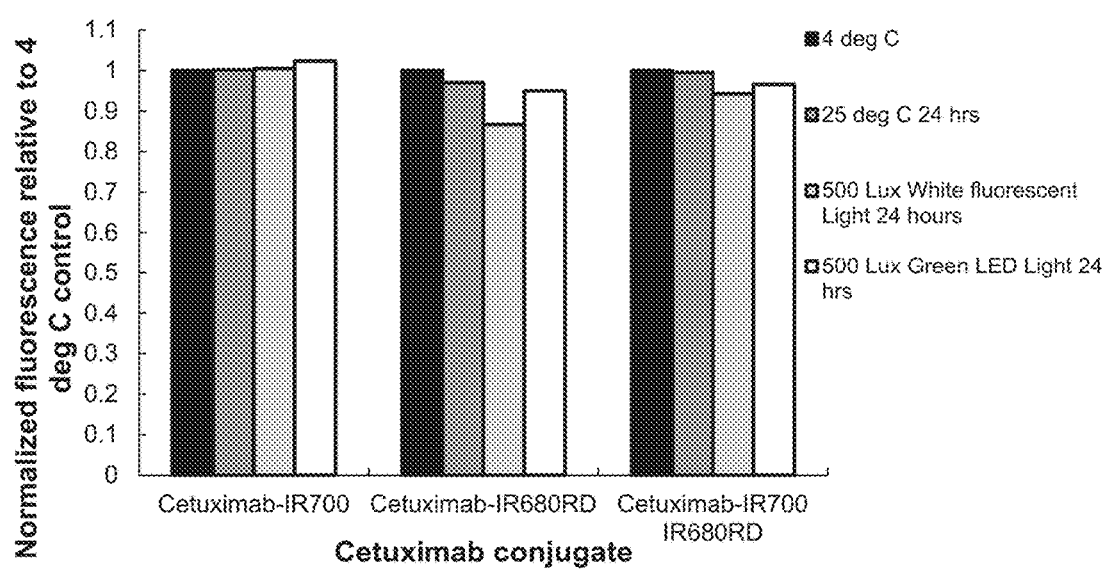
FIG. 24B shows the effect of pre-exposure of cetuximab-IRDye 700DX conjugate, cetuximab-IRDye 680RD conjugate, and cetuximab-IRDye 700+IRDye 680RD dual conjugate to white light or green light on fluorescence normalized to monomer content.

The results in FIG. 24B showed that the cetuximab-IRDye 680RD conjugate was more sensitive to white light exposure than the cetuximab-IRDye 700DX conjugates. For all treatments for cetuximab-IRDye 700DX, the fluorescence of cetuximab-IRDye 700DX conjugate remained stable despite the significant increase in soluble aggregate formation with 500 lux white fluorescent light exposure for 24 hours. Cetuximab-IRDye 680RD exposed to white fluorescent light for 24 hours exhibited the largest decrease in fluorescence of all treatment conditions tested, indicating that some of the IRDye 680RD was likely bleached with white light exposure. A decrease in fluorescence was also observed when IRDye 700DX was dual conjugated with IRDye 680RD. Based on the mono-labeled cetuximab-IRDye 700DX, this decrease in fluorescence was likely due to the IRDye 680RD bleaching for the dual-labeled cetuximab-IRDye 700DX+IRDye 680RD conjugate.

Thus, the results showed that IRDye 700DX conjugates have a unique sensitivity of forming soluble aggregate formation when exposed to light. Despite the increase in soluble aggregate formation in the IRDye 700DX conjugates when exposed to light, the fluorescence properties of IRDye 700DX conjugate did not change, consistent with the reported published findings that IRDye 700DX is a photostable dye. In stark contrast, white light exposure of another conjugate labeled with IRDye 680RD resulted in only a modest increase in soluble aggregate formation when compared to that of IRDye 700DX conjugate. Only when the IRDye 680RD conjugate was labeled with both IRDye 700DX and IRDye 680RD did an increase in soluble aggregate formation occur with the IRDye 680RD conjugate. IRDye 680 conjugate was sensitive to photobleaching with exposure to light.

The data show that cetuximab-IRDye 700DX, cetuximab-IRDye 680RD, and cetuximab-IRDye 700DX+IRDye 680RD conjugates pre-exposed to different wavelengths of light exhibit differential sensitivity to soluble aggregate formation and fluorescence bleaching. The data provided support the need for light protection of conjugates to ensure consistency in product manufacturing. Specifically, for targeting molecule IRDye 700DX conjugates such as antibody-IRDye 700DX conjugates, the fraction of monomer purity and pharmacological activity are essential and changes can lead to a significant impact on the light-activated killing activity.

Example 21: PIT Through Non-Covalent Labeling of Unconjugated, Mono, or Dual-Labeled Primary Antibody with a Secondary Antibody-IRDye 700DX Studies were performed to assess whether antibodies that bind directly to cancer cells require direct conjugation of a phthalocyanine photosensitizer such as IRDye 700DX to mediate PIT killing activity. indirect labeling of anti-cancer antibodies mediated by a secondary antibody conjugated IRDye 700DX can also induce effective PIT killing activity.

Furthermore, in certain situations such as dual-conjugated targeting molecules, dye-dye interactions can result in decreased fluorescence and for IRDye 700DX conjugates, decreased photo-activated killing activity. Indirect labeling of unconjugated, mono, or dual-labeled cetuximab with a secondary IRDye700DX conjugate significantly enhanced fluorescence signal from treated cells and photoactivated killing activity. Taken together, these studies show that increased separation between dual conjugates such as through a secondary antibody or by addition of linkers may enhance fluorescence and photo-activated killing activity of IRDye 700DX conjugates.

A. Antibody Conjugation

All antibodies were conjugated to the dyes (i.e., IRDye 700DX, IRDye 680RD, or sulfo Cy7) using the same approach.

The cetuximab-IRDye 700DX, cetuximab-IRDye 680RD, and cetuximab-IRDye 700DX+IRDye 680RD conjugates were made using the same general protocols as described in Examples 1 and 19.

The cetuximab-sulfo Cy7 conjugate was made using the same general conjugation protocol as described for cetuximab-IRDye 700DX, with the following modifications. To a sample of Cetuximab was added 2 molar equivalents of sulfo-Cyanine7—NHS ester (Cat. No. 15320; Lumiprobe, Hallandale Beach, Fla.) dissolved in DMSO at 10 mg/mL. All other steps in the conjugation, including the purification and characterization process for the conjugate, were identical to that described above for the cetuximab-IRDye 700DX conjugate preparation.

For the cetuximab-donkey anti-human-IRDye 700DX conjugate, the general protocol used to conjugate AffiniPure Donkey Anti-Human IgG, Fcγ Fragment Specific (DxHu) antibody (Catalog number: 709-005-098, Jackson ImmunoResearch Laboratories, West Grove, Pa.) was used. This protocol was similar to the steps used for larger scale conjugation with cetuximab-IRDye 700DX described in Example 1. Modifications to the protocol were made for smaller scale reaction volumes that used 3 mg or less antibody. DxHu antibody was labeled with IRDye 700DX (IR700) to evaluate whether non-covalent labeling of primary antibodies with secondary antibody-IRDye 700DX could be used as for PIT. The DxHu antibody solution was first exchanged with phosphate buffer saline pH 7 using a 30,000 Dalton molecular weight cutoff centrifugal filter, then the antibody solution pH was adjusted to a pH of 8.5 with addition of phosphate buffer at pH=9. Frozen solid aliquots of IRDye 700DX NHS Ester (Cat. No. 929-70011; Li-COR, Lincoln, Nebr.) were thawed at room temperature, then dissolved with DMSO to achieve a 10 mg/mL concentration. In a dark environment, the solubilized IRDye 700DX NHS Ester was then added to the antibody solution at a 4 (IRDye 700DX NHS Ester) to 1 (antibody) molar ratio. The conjugation reaction proceeded at 25° C. for 2 hours protected from light. Glycine (pH 8.2) was added to a final concentration of 10 mM for 15 minutes to quench the reaction. The antibody conjugate solution was then exchanged with 24 mL of PBS pH 7 using a 30,000 Dalton molecular weight cutoff centrifugal filter to remove free dye, glycine, and glycine-IRDye 700DX, and to adjust the pH back to pH 7. The antibody conjugates were analyzed with size exclusion chromatography to evaluate antibody-IRDye 700DX concentration, monomer purity, % soluble aggregate, and dye to antibody ratio.

B. Quantifying Fluorescence Emitted from BxPC3 Cells with Unconjugated, Mono-, or Dual-Conjugated Antibody with or without a Secondary Antibody BxPC3 cells (#CRL-1687, ATCC, Manassas Va.) were incubated for one hour at 4° C. with or without 250 ng/mL anti-EGFR antibody, cetuximab (Myoderm USA, Norristown, Pa.), cetuximab-IRDye 700DX (cetuximab directly conjugated to IRDye 700DX), cetuximab-IRDye 680RD (cetuximab directly conjugated to IRDye 680RD), cetuximab-Cy7-SO3 (cetuximab directly conjugated with sulfonated Cy7), cetuximab-IRDye 700DX+IRDye 680RD (cetuximab directly conjugated with IRDye 700DX and IRDye 680RD), and cetuximab-IR700±sulfo Cy7 (cetuximab directly conjugated with IRDye 700DX and sulfonated Cy7) in RPMI-1640 media supplemented with 10% FBS and 1% Penicillin/Streptomycin (complete culture media). The cells were then washed one time with complete culture media, incubated for 30 minutes at 4° C. with or without 2 μg/mL Donkey anti-Human IRDye 700DX conjugated (DxHu IR700) secondary antibody diluted with complete culture media, and then washed one time with complete culture media. The cells were washed two times with PBS, and incubated with Enzyme Free Cell Dissociation Buffer (Cat No: S-014-C, Millipore, Billerica, Mass.). The cell suspension was transferred to a new tube, and diluted with PBS containing 1% bovine serum albumin.

The fluorescence signal from the fluorescent antibody stained cells was measured with an Attune Flow Cytometer (Thermo Scientific, Waltham, Mass.). A 633 nm laser, and the fluorescence passed through a 645 nm dichroic long pass filter, 740 nm dichroic long pass, and 690/50 nm bandpass filter. The measured fluorescence was normalized to the media only unstained control, to evaluate the fold increase in fluorescence signal.

C. Evaluating PIT Killing Activity: Specificity of PIT Killing Activity

BxPC3 cells (#CRL-1687, ATCC, Manassas Va.) were incubated for one hour at 4° C. with or without 250 ng/mL anti-EGFR antibody, cetuximab (Myoderm USA, Norristown, Pa.), cetuximab-IR700 (cetuximab directly conjugated to IRDye 700DX), Cetuximab-IRDye 680RD (cetuximab directly conjugated to IRDye 680RD), cetuximab-Cy7-SO3 (cetuximab directly conjugated with sulfonated Cy7), Cetuximab-IRDye 700DX+IRDye 680RD (cetuximab directly conjugated with IRDye 700DX and IRDye 680RD), and Cetuximab-IRDye 700DX+sulfo Cy7 (cetuximab directly conjugated with IR700 and sulfonated Cy7) in RPMI-1640 media supplemented with 10% FBS and 1% Penicillin/Streptomycin (complete culture media). The cells were then washed one time with complete culture media, incubated for 30 minutes at 4° C. with or without 2 μg/mL Donkey anti-Human IRDye 700DX conjugated (DxHu IR700) secondary antibody diluted with complete culture media, and then washed one time with complete culture media. The cells were then illuminated with a 690 nm laser at a light dose of 16 J/cm$^2$ or protected from light ("no light").

The effect of different treatment regimens on cell death was measured using the fluorescent stain, CellTox Green (Cat No: G8731, Promega, Madison, Wis.). CellTox Green is a non-permeable fluorescent dye that exhibits increased fluorescence upon binding to DNA. Therefore, only cells that have compromised plasma membranes exhibit strong CellTox Green staining. After the light treatment, all cells were incubated with 1× CellTox Green reagent diluted in complete culture media. Wells that did not include any cells were also incubated with 1× CellTox Green reagent diluted in complete culture media to serve as background subtraction wells during fluorescent signal detection. The CellTox Green fluorescence signal was measured at 24 hours after light treatment using a fluorescence plate reader. The cells were then lysed with detergent, incubated at 37° C. for 30 minutes, and the CellTox Green fluorescence signal was measured again post lysis. The percent dead cells was calculated by taking the ratio between background (lx CellTox Green in complete culture media without cells) subtracted CellTox Green signal per well prior to and post lysis and multiplying the ratio by 100.

Table 15 shows the fluorescence of the BxPC3 cells after treatment with unconjugated, mono-, or dual-labeled cetuximab with a secondary antibody-IRDye 700DX conjugate. The results show that non-covalent labeling of unconjugated, mono-, or dual-labeled cetuximab with a secondary antibody-IRDye 700DX conjugate increases fluorescence of BxPC3 labeled cells. BxPC3 cells incubated with 250 ng/mL cetuximab only or no primary antibody but with 2 μg/mL donkey anti-human-IRDye 700DX, and cetuximab-sulfo Cy7. All treatments in which cells treated with both primary and secondary donkey anti-human-IRDye 700DX resulted in an enhancement in fluorescent signal relative when compared to that of the same treated primary antibody, but without the donkey anti-human-IRDye 700DX secondary antibody. The treatment that yielded the highest fluorescence increase was treatment 8, in which the BxPC3 cells were labeled with cetuximab-IRDye 680RD, followed by donkey anti-human-IRDye 700DX.

TABLE 15

Fluorescence of BxPC3 cells after treatment with unconjugated, mono-, or dual-labeled cetuximab with a secondary antibody IRDye 700DX conjugate

| Treatment | 1st incubation | 2nd incubation | Fluorescence |
|---|---|---|---|
| 1 | 250 ng/mL cetuximab | — | 1,052 |
| 2 | 250 ng/mL cetuximab | 2 µg/mL Don × Hu IRDye 700DX | 55,134 |
| 3 | — | 2 µg/mL Don × Hu IRDye 700DX | 1,087 |
| 4 | Media only | Media only | 1,089 |
| 5 | 250 ng/mL cetuximab-IRDye 700DX (2.5) | — | 36,099 |
| 6 | 250 ng/mL cetuximab-IRDye 700DX (2.5) | 2 µg/mL Don × Hu IRDye 700DX | 74,100 |
| 7 | 250 ng/mL cetuximab-IRDye 680 RD | — | 111,050 |
| 8 | 250 ng/mL cetuximab-IRDye 680 RD | 2 µg/mL Don × Hu IRDye 700DX | 133,216 |
| 9 | 250 ng/mL cetuximab IRDye 700DX (2.5) + IRDye 680 RD | — | 73,511 |
| 10 | 250 ng/mL cetuximab IRDye 700DX (2.5) + IRDye 680 RD | 2 µg/mL Don × Hu IRDye 700DX | 91,705 |
| 11 | 250 ng/mL cetuximab IRDye 700DX (2.5) + Cy7 | — | 4,601 |
| 12 | 250 ng/mL cetuximab IRDye 700DX (2.5) + sulfo Cy7 | 2 µg/mL Don × Hu IRDye 700DX | 22,122 |
| 13 | cetuximab-sulfo Cy7 | — | 1,132 |
| 14 | cetuximab-sulfo Cy7 | 2 µg/mL Don × Hu IRDye 700DX | 39,341 |

As shown in Table 16, the results with exemplary dual conjugates showed that, in some cases, dual-conjugated cetuximab, such as cetuximab-IRDye 700DX+IRDye 680 RD and cetuximab-IRDye 700 DX+sulfo Cy7, exhibited decreased photo-activated killing when compared to that of mono-labeled cetuximab-IRDye 700DX, indicating that the dual conjugates could interfere with the photo-activated killing potency. For Cetuximab-IRDye 700DX+IRDye 680 RD, the reduced killing activity may be due to spectral overlap between IRDye 700DX and IRDye 680, thereby reducing the photons that are absorbed by the IRDye 700DX to mediate the photo-activated killing. For cetuximab-IRDye 700DX+sulfo Cy7, the significant reduction in photo-activated killing relative that of Cetuximab-IRDye 700DX alone is likely due to dye-to-dye interactions resulting in IRDye 700DX quenching, which is consistent with the decrease in fluorescence from BxPC3 cells incubated with cetuximab-IRDye 700DX+sulfo Cy7 when compared to that of cells stained with mono-labeled cetuximab-IRDye 700DX.

However, the extent of cell killing was increased in the presence of a secondary antibody conjugated to IRDye 700Dx, indicating that the dual conjugate did not interfere with the PIT potency when combined with the secondary antibody. The data in Table 16 showed that cetuximab conjugates labeled with donkey anti-human-IRDye 700DX (DxHu IR700) secondary antibody enhanced photo-activated killing of BxPC3 cells. Increased cell death was only observed with cells treated with cetuximab that was either directly conjugated with IRDye 700DX or with a secondary anti-human-IRDye 700DX antibody, and when the cells were illuminated with a 690 nm laser. Background cell death in all treatments not exposed to the 690 nm laser was similar. All treatments in which cells treated with both primary and secondary donkey anti-human-IRDye 700DX resulted in an enhancement in photo-activated cell killing relative when compared to that of the same treated primary antibody, but without the donkey anti-human-IRDye 700DX secondary.

TABLE 16

Effect of cetuximab and donkey anti-human-IR700 (DxHu IR700) secondary antibody on PIT of BxPC3 cells.

| Treatment | 1st incubation | 2nd incubation | % Dead cells 690 nm Light (16 J/cm$^2$) | % Dead cells No Light |
|---|---|---|---|---|
| 1 | 250 ng/mL Cetuximab | — | 5.89% +/− 0.49% | 7.17% +/− 0.86% |
| 2 | 250 ng/mL Cetuximab | 2 µg/mL Don × Hu IRDye700DX | 91.76% +/− 4.2% | 7.66% +/− 0.50% |
| 3 | — | 2 µg/mL Don × Hu IRDye 700DX | 6.62% +/− 0.57% | 8.27% +/−1.14% |
| 4 | Media only | Media only | 6.72% +/− 0.54% | 8.76% +/−1.03% |
| 5 | 250 ng/mL Cetuximab-IRDye 700DX (2.5) | — | 65.76% +/− 5.14% | 7.44% +/−1.10% |
| 6 | 250 ng/mL Cetuximab-IRDye 700DX (2.5) | 2 µg/mL Don × Hu IRDye 700DX | 96.66% +/− 4.24% | 7.89% +/− 0.24% |

TABLE 16-continued

Effect of cetuximab and donkey anti-human-IR700 (DxHu IR700) secondary antibody on PIT of BxPC3 cells.

| Treatment | 1st incubation | 2nd incubation | % Dead cells 690 nm Light (16 J/cm²) | % Dead cells No Light |
|---|---|---|---|---|
| 7 | 250 ng/mL Cetuximab-IRDye 680 RD | — | 7.03% +/− 0.18% | 12.18% +/− 3.16% |
| 8 | 250 ng/mL Cetuximab-IRDye 680 RD | 2 µg/mL Don × Hu IRDye 700DX | 92.51% +/− 0.54% | 10.30% +/− 0.73% |
| 9 | 250 ng/mL Cetuximab IRDye 700DX (2.5) + IRDye 680 RD | — | 38.00% +/− 2.11% | 5.92% +/− 1.08% |
| 10 | 250 ng/mL Cetuximab IRDye 700DX (2.5) + IRDye 680 RD | 2 µg/mL Don × Hu IRDye 700DX | 96.66% +/− 2.49% | 7.00% +/− 1.18% |
| 11 | 250 ng/mL Cetuximab IRDye 700DX (2.5) + Cy7 | — | 12.12% +/− 0.79% | 7.63% +/− 1.35% |
| 12 | 250 ng/mL Cetuximab IRDye 700DX (2.5) + Cy7 | 2 µg/mL Don × Hu IRDye 700DX | 94.09% +/− 1.29% | 8.88% +/− 1.76% |
| 13 | Cetuximab-sulfo Cy7 | — | 4.36% +/− 0.36% | 6.47% +/− 0.53% |
| 14 | Cetuximab-sulfo Cy7 | 2 µg/mL Don × Hu IRDye 700DX | 72.16% +/− 1.86% | 7.33% +/− 0.39% |

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | Sequence |
|---|---|
| 1 | CRGDKGPDC |
| 2 | CCRGDKGPDC |
| 3 | AKPAPPKPEPKPKKAP |
| 4 | AKVKDEPQRRSARLS |
| 5 | CAGALCY |
| 6 | CAGRRSAYC |
| 7 | CARSKNKDC |
| 8 | CDCRGDCFC |
| 9 | CDTRL |
| 10 | CGKRK |
| 11 | CGLIIQKNEC |
| 12 | CGNKRTR |
| 13 | CGNKRTRGC |
| 14 | CGRRAGGSC |
| 15 | CKAAKNK |
| 16 | CKGGRAKDC-GG |
| 17 | CLSDGKRKC |
| 18 | CMYIEALDKYAC |
| 19 | KKCGGGGIRLRG |
| 20 | CNAGESSKNC |
| 21 | CNGRC |
| 22 | CNRRTKAGC |
| 23 | CPGPEGAGC |
| 24 | CPKTRRPVC |
| 25 | CPRECESIC |
| 26 | CRAKSKVAC |
| 27 | CREAGRKAC |
| 28 | CREKA |
| 29 | CRGDKGPDC |
| 30 | CRGRRST |
| 31 | CRKDKC |
| 32 | CRPPR |
| 33 | CRRETAWAC |
| 34 | CRSRKG |
| 35 | CSRPRRSEC |

| SEQ ID NO. | Sequence |
|---|---|
| 36 | CTTHWGFTLC |
| 37 | CVPELGHEC |
| 38 | EKGEGALPTGKSK |
| 39 | FALGEA |
| 40 | GLNGLSSADPSSD |
| 41 | GSMSIARL |
| 42 | GVSFLEYR |
| 43 | IFLLWQR |
| 44 | IFLLWQR-C-RR |
| 45 | PEPHC |
| 46 | PISNDQKVSDDDK |
| 47 | RMWPSSTVNLSAGRR |
| 48 | RPARPAR |
| 49 | SMSIARL |
| 50 | VDEDRASLLKSQE |
| 51 | VSFLEYR |
| 52 | WNAPAEEWGNW |

The invention claimed is:

1. A method of treating a lesion in a subject by photoimmunotherapy, the method comprising:
   (a) intravenously administering to the subject a conjugate comprising IR700 linked to cetuximab, wherein the conjugate is administered in an amount that is between at or about 640 mg/m$^2$ and at or about 2000 mg/m$^2$; and
   (b) after administering the conjugate, irradiating the lesion at a wavelength of 600 nm to 850 nm at a dose of from at or about 25 J cm$^{-2}$ to at or about 400 J cm$^{-2}$ or from at or about 25 J/cm fiber length to at or about 500 J/cm fiber length, thereby treating the lesion.

2. The method of claim 1, wherein the irradiation is carried out between 30 minutes and 96 hours after administering the conjugate.

3. The method of claim 1, wherein the irradiation is carried out 24 hours±3 hours after administering the conjugate.

4. The method of claim 1, wherein the lesion is irradiated at a wavelength of 690±50 nm or at a wavelength of 690±20 nm.

5. The method of claim 1, wherein the lesion is irradiated at a dose of at or about 50 J cm$^{-2}$ or at or about 100 J/cm fiber length.

6. The method of claim 1, wherein the administering is a single injection or single infusion.

7. The method of claim 1, further comprising a dosing schedule whereby steps (a) and (b) are repeated.

8. The method of claim 7, wherein the dosing schedule is repeated if a residual lesion remains at a time that is more than or is at or about 2 weeks, 3 weeks, 4 weeks, 2 months, 6 months or 1 year after initiation of the prior administration of the conjugate.

9. The method of claim 7, wherein the dosing schedule is repeated if a residual lesion remains at or about 4 weeks after initiation of the prior administration of the conjugate.

10. The method of claim 1, wherein the lesion is a tumor that is a superficial tumor.

11. The method of claim 10, wherein the irradiating step is carried out using a microlens-tipped fiber for surface illumination.

12. The method of claim 1, wherein the lesion is a tumor that is a subcutaneous tumor.

13. The method of claim 12, wherein the irradiating step is carried out using cylindrical diffusing fibers.

14. The method of claim 13, wherein the cylindrical diffusing fibers comprise a diffuser length of at or about 0.5 cm to at or about 10 cm and spaced 1.8±0.2 cm apart.

15. The method of claim 1, wherein the conjugate is administered in an amount that is about 1280 mg/m$^2$.

16. The method of claim 1, wherein the conjugate is administered in an amount that is at or about 640 mg/m$^2$.

17. The method of claim 1, wherein the lesion is associated with a disease or condition is selected from the group consisting of a bladder cancer, a cancer of the larynx, a stomach cancer, a lung cancer, a colon cancer, a head or neck cancer, and a pancreatic cancer.

18. The method of claim 17, wherein the disease or condition is a head or neck cancer.

19. The method of claim 18, wherein the disease or condition is a head or neck cancer that cannot be successfully treated with surgery, radiation or chemotherapy.

20. The method of claim 1, wherein the lesion is a squamous cell carcinoma.

21. A method of treating a lesion in a subject by photoimmunotherapy, the method comprising:
 a) intravenously administering to the subject a conjugate comprising IR700 linked to cetuximab, wherein the conjugate is administered in an amount that is at or about 640 mg/m$^2$; and
 b) after administering the conjugate, irradiating the lesion at a wavelength of 690±50 nm at a dose of at or about 50 J cm$^{-2}$ or at or about 100 J/cm of fiber length, thereby treating the lesion.

22. The method of claim 21, wherein the lesion is irradiated at a wavelength of 690±20 nm.

23. The method of claim 21, wherein the lesion is associated with a disease or condition that is a head or neck cancer.

24. The method of claim 23, wherein the disease or condition is a head or neck cancer that cannot be successfully treated with surgery, radiation or chemotherapy.

25. The method of claim 21, wherein the irradiation is carried out 24 hours±3 hours after administering the conjugate.

26. The method of claim 21, further comprising a dosing schedule whereby steps (a) and (b) are repeated if a residual lesion remains at or about 4 weeks after initiation of the prior administration of the conjugate.

27. The method of claim 21, wherein the lesion is a tumor that is a superficial tumor, and wherein the irradiating step is carried out using a microlens-tipped fiber for surface illumination.

28. The method of claim 21, wherein the lesion is a tumor that is a subcutaneous tumor, and wherein the irradiating step is carried out using cylindrical diffusing fibers having a diffuser length of at or about 0.5 cm to at or about 10 cm and spaced 1.8±0.2 cm apart.

29. The method of claim 21, wherein the lesion is a squamous cell carcinoma.

\* \* \* \* \*

SEQUENCE LISTING

```
<160> NUMBER OF SEQ ID NOS: 52

<210> SEQ ID NO 1
<211> LENGTH: 9
<212> TYPE: PRT
<213> ORGANISM: Artificial Sequence
<220> FEATURE:
<223> OTHER INFORMATION: homing peptide

<400> SEQUENCE: 1

Cys Arg Gly Asp Lys Gly Pro Asp Cys
1               5

<210> SEQ ID NO 2
<211> LENGTH: 10
<212> TYPE: PRT
<213> ORGANISM: Artificial Sequence
<220> FEATURE:
<223> OTHER INFORMATION: homing peptide

<400> SEQUENCE: 2

Cys Cys Arg Gly Asp Lys Gly Pro Asp Cys
1               5                   10

<210> SEQ ID NO 3
<211> LENGTH: 16
<212> TYPE: PRT
<213> ORGANISM: Artificial Sequence
<220> FEATURE:
<223> OTHER INFORMATION: homing peptide

<400> SEQUENCE: 3

Ala Lys Pro Ala Pro Pro Lys Pro Glu Pro Lys Pro Lys Lys Ala Pro
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: homing peptide

<400> SEQUENCE: 4

Ala Lys Val Lys Asp Glu Pro Gln Arg Arg Ser Ala Arg Leu Ser
```

```
1               5               10              15
```

<210> SEQ ID NO 5
<211> LENGTH: 7
<212> TYPE: PRT
<213> ORGANISM: Artificial Sequence
<220> FEATURE:
<223> OTHER INFORMATION: homing peptide

<400> SEQUENCE: 5

Cys Ala Gly Ala Leu Cys Tyr
1               5

<210> SEQ ID NO 6
<211> LENGTH: 9
<212> TYPE: PRT
<213> ORGANISM: Artificial Sequence
<220> FEATURE:
<223> OTHER INFORMATION: homing peptide

<400> SEQUENCE: 6

Cys Ala Gly Arg Arg Ser Ala Tyr Cys
1               5

<210> SEQ ID NO 7
<211> LENGTH: 9
<212> TYPE: PRT
<213> ORGANISM: Artificial Sequence
<220> FEATURE:
<223> OTHER INFORMATION: homing peptide

<400> SEQUENCE: 7

Cys Ala Arg Ser Lys Asn Lys Asp Cys
1               5

<210> SEQ ID NO 8
<211> LENGTH: 9
<212> TYPE: PRT
<213> ORGANISM: Artificial Sequence
<220> FEATURE:
<223> OTHER INFORMATION: homing peptide

<400> SEQUENCE: 8

Cys Asp Cys Arg Gly Asp Cys Phe Cys
1               5

<210> SEQ ID NO 9
<211> LENGTH: 5
<212> TYPE: PRT
<213> ORGANISM: Artificial Sequence
<220> FEATURE:
<223> OTHER INFORMATION: homing peptide

<400> SEQUENCE: 9

Cys Asp Thr Arg Leu
1               5

<210> SEQ ID NO 10
<211> LENGTH: 5
<212> TYPE: PRT
<213> ORGANISM: Artificial Sequence
<220> FEATURE:
<223> OTHER INFORMATION: homing peptide

<400> SEQUENCE: 10

Cys Gly Lys Arg Lys
1               5

```
<210> SEQ ID NO 11
<211> LENGTH: 10
<212> TYPE: PRT
<213> ORGANISM: Artificial Sequence
<220> FEATURE:
<223> OTHER INFORMATION: homing peptide

<400> SEQUENCE: 11

Cys Gly Leu Ile Ile Gln Lys Asn Glu Cys
1               5                   10

<210> SEQ ID NO 12
<211> LENGTH: 7
<212> TYPE: PRT
<213> ORGANISM: Artificial Sequence
<220> FEATURE:
<223> OTHER INFORMATION: homing peptide

<400> SEQUENCE: 12

Cys Gly Asn Lys Arg Thr Arg
1               5

<210> SEQ ID NO 13
<211> LENGTH: 9
<212> TYPE: PRT
<213> ORGANISM: Artificial Sequence
<220> FEATURE:
<223> OTHER INFORMATION: homing peptide

<400> SEQUENCE: 13

Cys Gly Asn Lys Arg Thr Arg Gly Cys
1               5

<210> SEQ ID NO 14
<211> LENGTH: 9
<212> TYPE: PRT
<213> ORGANISM: Artificial Sequence
<220> FEATURE:
<223> OTHER INFORMATION: homing peptide

<400> SEQUENCE: 14

Cys Gly Arg Arg Ala Gly Gly Ser Cys
1               5

<210> SEQ ID NO 15
<211> LENGTH: 7
<212> TYPE: PRT
<213> ORGANISM: Artificial Sequence
<220> FEATURE:
<223> OTHER INFORMATION: homing peptide

<400> SEQUENCE: 15

Cys Lys Ala Ala Lys Asn Lys
1               5

<210> SEQ ID NO 16
<211> LENGTH: 11
<212> TYPE: PRT
<213> ORGANISM: Artificial Sequence
<220> FEATURE:
<223> OTHER INFORMATION: homing peptide

<400> SEQUENCE: 16

Cys Lys Gly Gly Arg Ala Lys Asp Cys Gly Gly
1               5                   10
```

<210> SEQ ID NO 17
<211> LENGTH: 9
<212> TYPE: PRT
<213> ORGANISM: Artificial Sequence
<220> FEATURE:
<223> OTHER INFORMATION: homing peptide

<400> SEQUENCE: 17

Cys Leu Ser Asp Gly Lys Arg Lys Cys
1               5

<210> SEQ ID NO 18
<211> LENGTH: 12
<212> TYPE: PRT
<213> ORGANISM: Artificial Sequence
<220> FEATURE:
<223> OTHER INFORMATION: homing peptide

<400> SEQUENCE: 18

Cys Met Tyr Ile Glu Ala Leu Asp Lys Tyr Ala Cys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: homing peptide

<400> SEQUENCE: 19

Lys Lys Cys Gly Gly Gly Gly Ile Arg Leu Arg Gly
1               5                   10

<210> SEQ ID NO 20
<211> LENGTH: 10
<212> TYPE: PRT
<213> ORGANISM: Artificial Sequence
<220> FEATURE:
<223> OTHER INFORMATION: homing peptide

<400> SEQUENCE: 20

Cys Asn Ala Gly Glu Ser Ser Lys Asn Cys
1               5                   10

<210> SEQ ID NO 21
<211> LENGTH: 5
<212> TYPE: PRT
<213> ORGANISM: Artificial Sequence
<220> FEATURE:
<223> OTHER INFORMATION: homing peptide

<400> SEQUENCE: 21

Cys Asn Gly Arg Cys
1               5

<210> SEQ ID NO 22
<211> LENGTH: 9
<212> TYPE: PRT
<213> ORGANISM: Artificial Sequence
<220> FEATURE:
<223> OTHER INFORMATION: homing peptide

<400> SEQUENCE: 22

Cys Asn Arg Arg Thr Lys Ala Gly Cys
1               5

```
<210> SEQ ID NO 23
<211> LENGTH: 9
<212> TYPE: PRT
<213> ORGANISM: Artificial Sequence
<220> FEATURE:
<223> OTHER INFORMATION: homing peptide

<400> SEQUENCE: 23

Cys Pro Gly Pro Glu Gly Ala Gly Cys
1               5

<210> SEQ ID NO 24
<211> LENGTH: 9
<212> TYPE: PRT
<213> ORGANISM: Artificial Sequence
<220> FEATURE:
<223> OTHER INFORMATION: homing peptide

<400> SEQUENCE: 24

Cys Pro Lys Thr Arg Arg Pro Val Cys
1               5

<210> SEQ ID NO 25
<211> LENGTH: 9
<212> TYPE: PRT
<213> ORGANISM: Artificial Sequence
<220> FEATURE:
<223> OTHER INFORMATION: homing peptide

<400> SEQUENCE: 25

Cys Pro Arg Glu Cys Glu Ser Ile Cys
1               5

<210> SEQ ID NO 26
<211> LENGTH: 9
<212> TYPE: PRT
<213> ORGANISM: Artificial Sequence
<220> FEATURE:
<223> OTHER INFORMATION: homing peptide

<400> SEQUENCE: 26

Cys Arg Ala Lys Ser Lys Val Ala Cys
1               5

<210> SEQ ID NO 27
<211> LENGTH: 9
<212> TYPE: PRT
<213> ORGANISM: Artificial Sequence
<220> FEATURE:
<223> OTHER INFORMATION: homing peptide

<400> SEQUENCE: 27

Cys Arg Glu Ala Gly Arg Lys Ala Cys
1               5

<210> SEQ ID NO 28
<211> LENGTH: 5
<212> TYPE: PRT
<213> ORGANISM: Artificial Sequence
<220> FEATURE:
<223> OTHER INFORMATION: homing peptide

<400> SEQUENCE: 28

Cys Arg Glu Lys Ala
1               5

<210> SEQ ID NO 29
```

```
<211> LENGTH: 9
<212> TYPE: PRT
<213> ORGANISM: Artificial Sequence
<220> FEATURE:
<223> OTHER INFORMATION: homing peptide

<400> SEQUENCE: 29

Cys Arg Gly Asp Lys Gly Pro Asp Cys
1               5

<210> SEQ ID NO 30
<211> LENGTH: 7
<212> TYPE: PRT
<213> ORGANISM: Artificial Sequence
<220> FEATURE:
<223> OTHER INFORMATION: homing peptide

<400> SEQUENCE: 30

Cys Arg Gly Arg Arg Ser Thr
1               5

<210> SEQ ID NO 31
<211> LENGTH: 6
<212> TYPE: PRT
<213> ORGANISM: Artificial Sequence
<220> FEATURE:
<223> OTHER INFORMATION: homing peptide

<400> SEQUENCE: 31

Cys Arg Lys Asp Lys Cys
1               5

<210> SEQ ID NO 32
<211> LENGTH: 5
<212> TYPE: PRT
<213> ORGANISM: Artificial Sequence
<220> FEATURE:
<223> OTHER INFORMATION: homing peptide

<400> SEQUENCE: 32

Cys Arg Pro Pro Arg
1               5

<210> SEQ ID NO 33
<211> LENGTH: 9
<212> TYPE: PRT
<213> ORGANISM: Artificial Sequence
<220> FEATURE:
<223> OTHER INFORMATION: homing peptide

<400> SEQUENCE: 33

Cys Arg Arg Glu Thr Ala Trp Ala Cys
1               5

<210> SEQ ID NO 34
<211> LENGTH: 6
<212> TYPE: PRT
<213> ORGANISM: Artificial Sequence
<220> FEATURE:
<223> OTHER INFORMATION: homing peptide

<400> SEQUENCE: 34

Cys Arg Ser Arg Lys Gly
1               5

<210> SEQ ID NO 35
<211> LENGTH: 9
```

<212> TYPE: PRT
<213> ORGANISM: Artificial Sequence
<220> FEATURE:
<223> OTHER INFORMATION: homing peptide

<400> SEQUENCE: 35

Cys Ser Arg Pro Arg Arg Ser Glu Cys
1               5

<210> SEQ ID NO 36
<211> LENGTH: 10
<212> TYPE: PRT
<213> ORGANISM: Artificial Sequence
<220> FEATURE:
<223> OTHER INFORMATION: homing peptide

<400> SEQUENCE: 36

Cys Thr Thr His Trp Gly Phe Thr Leu Cys
1               5                   10

<210> SEQ ID NO 37
<211> LENGTH: 9
<212> TYPE: PRT
<213> ORGANISM: Artificial Sequence
<220> FEATURE:
<223> OTHER INFORMATION: homing peptide

<400> SEQUENCE: 37

Cys Val Pro Glu Leu Gly His Glu Cys
1               5

<210> SEQ ID NO 38
<211> LENGTH: 13
<212> TYPE: PRT
<213> ORGANISM: Artificial Sequence
<220> FEATURE:
<223> OTHER INFORMATION: homing peptide

<400> SEQUENCE: 38

Glu Lys Gly Glu Gly Ala Leu Pro Thr Gly Lys Ser Lys
1               5                   10

<210> SEQ ID NO 39
<211> LENGTH: 6
<212> TYPE: PRT
<213> ORGANISM: Artificial Sequence
<220> FEATURE:
<223> OTHER INFORMATION: homing peptide

<400> SEQUENCE: 39

Phe Ala Leu Gly Glu Ala
1               5

<210> SEQ ID NO 40
<211> LENGTH: 13
<212> TYPE: PRT
<213> ORGANISM: Artificial Sequence
<220> FEATURE:
<223> OTHER INFORMATION: homing peptide

<400> SEQUENCE: 40

Gly Leu Asn Gly Leu Ser Ser Ala Asp Pro Ser Ser Asp
1               5                   10

<210> SEQ ID NO 41
<211> LENGTH: 8
<212> TYPE: PRT

<213> ORGANISM: Artificial Sequence
<220> FEATURE:
<223> OTHER INFORMATION: homing peptide

<400> SEQUENCE: 41

Gly Ser Met Ser Ile Ala Arg Leu
1               5

<210> SEQ ID NO 42
<211> LENGTH: 8
<212> TYPE: PRT
<213> ORGANISM: Artificial Sequence
<220> FEATURE:
<223> OTHER INFORMATION: homing peptide

<400> SEQUENCE: 42

Gly Val Ser Phe Leu Glu Tyr Arg
1               5

<210> SEQ ID NO 43
<211> LENGTH: 7
<212> TYPE: PRT
<213> ORGANISM: Artificial Sequence
<220> FEATURE:
<223> OTHER INFORMATION: homing peptide

<400> SEQUENCE: 43

Ile Phe Leu Leu Trp Gln Arg
1               5

<210> SEQ ID NO 44
<211> LENGTH: 10
<212> TYPE: PRT
<213> ORGANISM: Artificial Sequence
<220> FEATURE:
<223> OTHER INFORMATION: homing peptide

<400> SEQUENCE: 44

Ile Phe Leu Leu Trp Gln Arg Cys Arg Arg
1               5                   10

<210> SEQ ID NO 45
<211> LENGTH: 5
<212> TYPE: PRT
<213> ORGANISM: Artificial Sequence
<220> FEATURE:
<223> OTHER INFORMATION: homing peptide

<400> SEQUENCE: 45

Pro Glu Pro His Cys
1               5

<210> SEQ ID NO 46
<211> LENGTH: 13
<212> TYPE: PRT
<213> ORGANISM: Artificial Sequence
<220> FEATURE:
<223> OTHER INFORMATION: homing peptide

<400> SEQUENCE: 46

Pro Ile Ser Asn Asp Gln Lys Val Ser Asp Asp Lys
1               5                   10

<210> SEQ ID NO 47
<211> LENGTH: 15
<212> TYPE: PRT
<213> ORGANISM: Artificial Sequence

```
<220> FEATURE:
<223> OTHER INFORMATION: homing peptide

<400> SEQUENCE: 47

Arg Met Trp Pro Ser Ser Thr Val Asn Leu Ser Ala Gly Arg Arg
1               5                   10                  15

<210> SEQ ID NO 48
<211> LENGTH: 7
<212> TYPE: PRT
<213> ORGANISM: Artificial Sequence
<220> FEATURE:
<223> OTHER INFORMATION: homing peptide

<400> SEQUENCE: 48

Arg Pro Ala Arg Pro Ala Arg
1               5

<210> SEQ ID NO 49
<211> LENGTH: 7
<212> TYPE: PRT
<213> ORGANISM: Artificial Sequence
<220> FEATURE:
<223> OTHER INFORMATION: homing peptide

<400> SEQUENCE: 49

Ser Met Ser Ile Ala Arg Leu
1               5

<210> SEQ ID NO 50
<211> LENGTH: 13
<212> TYPE: PRT
<213> ORGANISM: Artificial Sequence
<220> FEATURE:
<223> OTHER INFORMATION: homing peptide

<400> SEQUENCE: 50

Val Asp Glu Asp Arg Ala Ser Leu Leu Lys Ser Gln Glu
1               5                   10

<210> SEQ ID NO 51
<211> LENGTH: 7
<212> TYPE: PRT
<213> ORGANISM: Artificial Sequence
<220> FEATURE:
<223> OTHER INFORMATION: homing peptide

<400> SEQUENCE: 51

Val Ser Phe Leu Glu Tyr Arg
1               5

<210> SEQ ID NO 52
<211> LENGTH: 11
<212> TYPE: PRT
<213> ORGANISM: Artificial Sequence
<220> FEATURE:
<223> OTHER INFORMATION: homing peptide

<400> SEQUENCE: 52

Trp Asn Ala Pro Ala Glu Glu Trp Gly Asn Trp
1               5                   10
```